(12) United States Patent
Hoekstra et al.

(10) Patent No.: US 9,309,273 B2
(45) Date of Patent: Apr. 12, 2016

(54) METALLOENZYME INHIBITOR COMPOUNDS

(71) Applicant: Viamet Pharmaceuticals, Inc., Durham, NC (US)

(72) Inventors: William J. Hoekstra, Durham, NC (US); Christopher M. Yates, Raleigh, NC (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 14/364,276

(22) PCT Filed: Dec. 10, 2012

(86) PCT No.: PCT/US2012/068818
§ 371 (c)(1),
(2) Date: Jun. 10, 2014

(87) PCT Pub. No.: WO2013/090210
PCT Pub. Date: Jun. 20, 2013

(65) Prior Publication Data
US 2014/0349973 A1    Nov. 27, 2014

Related U.S. Application Data

(60) Provisional application No. 61/569,279, filed on Dec. 11, 2011, provisional application No. 61/701,370, filed on Sep. 14, 2012.

(51) Int. Cl.
| | |
|---|---|
| A61K 31/675 | (2006.01) |
| A61K 31/535 | (2006.01) |
| A61K 31/50 | (2006.01) |
| A61K 31/501 | (2006.01) |
| A61K 31/4965 | (2006.01) |
| A61K 31/445 | (2006.01) |
| A61K 31/44 | (2006.01) |
| A61K 31/41 | (2006.01) |
| C07D 413/00 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 417/00 | (2006.01) |
| C07D 419/00 | (2006.01) |
| C07F 9/06 | (2006.01) |
| C07F 9/28 | (2006.01) |
| C07D 211/68 | (2006.01) |
| C07D 211/80 | (2006.01) |
| C07D 213/02 | (2006.01) |
| C07D 421/00 | (2006.01) |
| C07D 257/00 | (2006.01) |
| A61K 31/4439 | (2006.01) |
| C07D 401/06 | (2006.01) |
| C07D 409/14 | (2006.01) |
| C07D 401/14 | (2006.01) |
| C07D 405/14 | (2006.01) |
| C07D 413/14 | (2006.01) |
| C07D 403/06 | (2006.01) |
| C07D 403/14 | (2006.01) |
| C07D 409/06 | (2006.01) |
| C07D 417/14 | (2006.01) |
| A01N 43/713 | (2006.01) |
| A01N 43/84 | (2006.01) |
| A01N 57/16 | (2006.01) |

(52) U.S. Cl.
CPC .............. *C07F 9/06* (2013.01); *A01N 43/713* (2013.01); *A01N 43/84* (2013.01); *A01N 57/16* (2013.01); *A61K 31/4439* (2013.01); *C07D 401/06* (2013.01); *C07D 401/14* (2013.01); *C07D 403/06* (2013.01); *C07D 403/14* (2013.01); *C07D 405/14* (2013.01); *C07D 409/06* (2013.01); *C07D 409/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 4,616,026 A | 10/1986 | Richardson et al. | |
| 8,883,797 B2 * | 11/2014 | Hoekstra | A61K 45/06 514/256 |
| 2012/0329802 A1* | 12/2012 | Hoekstra | A61K 45/06 514/249 |
| 2013/0005719 A1* | 1/2013 | Hoekstra | C07D 401/14 514/229.2 |

FOREIGN PATENT DOCUMENTS

| | | |
|---|---|---|
| CN | 103857675 A | 6/2014 |
| CN | 103930418 A | 7/2014 |
| EP | 69442 A1 | 1/1983 |
| WO | WO-2004108684 A1 | 12/2004 |
| WO | WO-2011133875 A2 | 10/2011 |

OTHER PUBLICATIONS

Curtis, RF. et al. Naturally occurring Thiophens. Part V. Acetylenic Thiophens from the Basidiomycete Daedalea juniperina Murr. J. Chem. Soc. 1969, p. 1814.*

(Continued)

*Primary Examiner* — Rita Desai
*Assistant Examiner* — Ben S Michelson
(74) *Attorney, Agent, or Firm* — Wolf, Greenfield & Sacks, P.C.

(57) ABSTRACT

The instant invention describes compounds having metalloenzyme modulating activity, and methods of treating diseases, disorders or symptoms thereof mediated by such metalloenzymes.

21 Claims, No Drawings

(56) References Cited

OTHER PUBLICATIONS

Eto, H. et al., "New Antifungal 1,2,4-Triazoles with Difluoro(heteroaryl) methyl Moiety", Chemical & Pharmaceutical Bulletin 2000, vol. 48, pp. 982-990.
International Search Report of PCT/US2012/068818 dated Mar. 19, 2013.
Chinese Office Actin dated Apr. 29, 2015 for Chinese Application No. 201280069217.7.
Extended European Search Report dated May 8, 2015 for EP Appln. No. 12858190.7.
Eurasian Office Action dated Mar. 12, 2015 for Eurasian Appln. No. 201491151/28.

* cited by examiner

METALLOENZYME INHIBITOR COMPOUNDS

CROSS REFERENCE TO RELATED APPLICATIONS

This application is the U.S. National Stage, pursuant to 35 U.S.C. §371, of U.S. International Application No. PCT/US2012/068818, filed Dec. 10, 2012, designating the United States and published on Jun. 20, 2013 as Publication WO 2013/090210, which claims priority to U.S. Application No. 61/569,279, flied Dec. 11, 2011, and U.S. Application No. 61/701,370, filed Sep. 14, 2012, the entire contents of which are incorporated herein by reference.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

A compound of formula (I), or salt, solvate, hydrate or prodrug thereof, wherein:

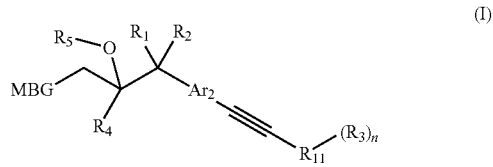

(I)

$R_1$ is halo;

$R_2$ is halo;

each $R_3$ is independently cyano, haloalkyl, alkoxy, halo, haloalkoxy, hydroxy, amino, —$NR_6R_9$, —$SR_{10}$, —$C(O)R_{10}$, optionally substituted haloalkyl, optionally substituted arylalkoxy, —$C(O)NR_6R_7$, —CH(OH)-haloalkyl, optionally substituted alkyl, hydroxyalkyl, optionally substituted alkoxyalkyl, isocyano, cycloalkylaminocarbonyl, optionally substituted aryloxyalkyl, optionally substituted arylalkylthio, haloalkylthio, optionally substituted arylalkylsulfonyl, optionally substituted arylalkylsulfinyl, optionally substituted heteroarylalkoxy, or haloalkylcarbonyl;

n is 0, 1, 2 or 3;

$R_4$ is aryl optionally substituted with 0, 1, 2 or 3 independent $R_8$;

$R_5$ is H, alkyl, phosphato, phosphito, alkoxyphosphato, or —C(O)alkyl optionally substituted with amino;

$R_6$ is independently H or alkyl;

$R_7$ is independently H, optionally substituted alkyl, optionally substituted haloalkyl, or optionally substituted arylalkyl;

each $R_8$ is independently cyano, haloalkyl, alkoxy, halo, or haloalkoxy;

each $R_9$ is independently H, alkyl, —C(O)alkyl, —C(O)H, —C(O)haloalkyl, or optionally substituted haloalkyl;

each $R_{10}$ is independently H, optionally substituted alkyl, optionally substituted aryl, optionally substituted arylalkyl;

Ar$_2$ is

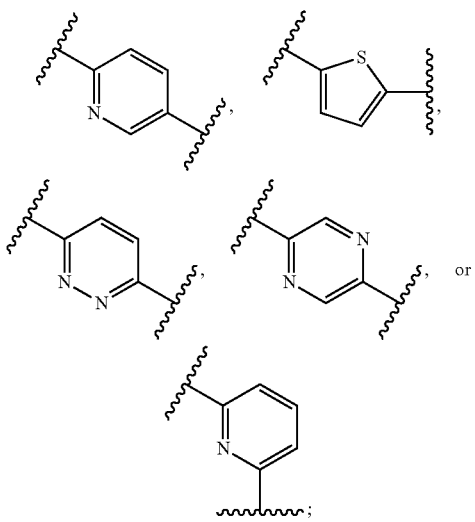

R$_{11}$ is optionally substituted phenyl, optionally substituted alkyl, optionally substituted thienyl, pyrrolyl, furanyl, optionally substituted pyridyl, —CH(OH)-alkyl, —CH(OH)-haloalkyl, optionally substituted arylalkyl, optionally substituted aryloxyalkyl, haloalkyl, haloalkoxyalkyl, optionally substituted indolyl, optionally substituted benzofuranyl, heterocycloalkyl, or

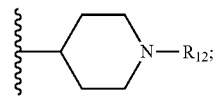

R$_{12}$ is R$_4$, —C(O)R$_4$, —C(O)R$_7$, —SO$_2$R$_4$;

MBG is optionally substituted tetrazolyl, optionally substituted triazolyl, optionally substituted oxazolyl, optionally substituted pyrimidinyl, optionally substituted thiazolyl, or optionally substituted pyrazolyl.

Another aspect is a compound of formula (I), or salt, solvate, hydrate or prodrug thereof, wherein:

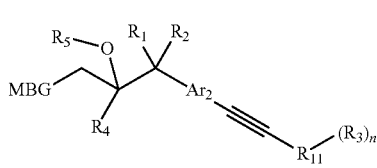

(I)

R$_1$ is halo;
R$_2$ is halo;
each R$_3$ is independently cyano, haloalkyl, alkoxy, halo, haloalkoxy, hydroxy, amino, —NR$_6$R$_9$, —SR$_{10}$, —C(O)R$_{10}$, optionally substituted haloalkyl, optionally substituted arylalkoxy, —C(O)NR$_6$R$_7$, —CH(OH)-haloalkyl, optionally substituted alkyl, hydroxyalkyl, optionally substituted alkoxyalkyl, isocyano, cycloalkylaminocarbonyl, optionally substituted aryloxyalkyl, optionally substituted arylalkylthio, haloalkylthio, optionally substituted arylalkylsulfonyl, optionally substituted arylalkylsulfinyl, optionally substituted heteroarylalkoxy, optionally substituted arylthioalkyl, or haloalkylcarbonyl;

n is 0, 1, 2 or 3;
R$_4$ is aryl optionally substituted with 0, 1, 2 or 3 independent R$_8$;
R$_5$ is H, alkyl, phosphato, phosphito, alkoxyphosphato, or —C(O)alkyl optionally substituted with 1 or 2 amino;
R$_6$ is independently H or alkyl;
R$_7$ is independently H, optionally substituted alkyl, optionally substituted haloalkyl, or optionally substituted arylalkyl;
each R$_8$ is independently cyano, haloalkyl, alkoxy, halo, or haloalkoxy;
each R$_9$ is independently H, alkyl, —C(O)alkyl, —C(O)H, —C(O)haloalkyl, optionally substituted arylalkyl, or optionally substituted haloalkyl;
each R$_{10}$ is independently H, optionally substituted alkyl, optionally substituted aryl, optionally substituted heterocycloalkyl, or optionally substituted arylalkyl;
Ar$_2$ is

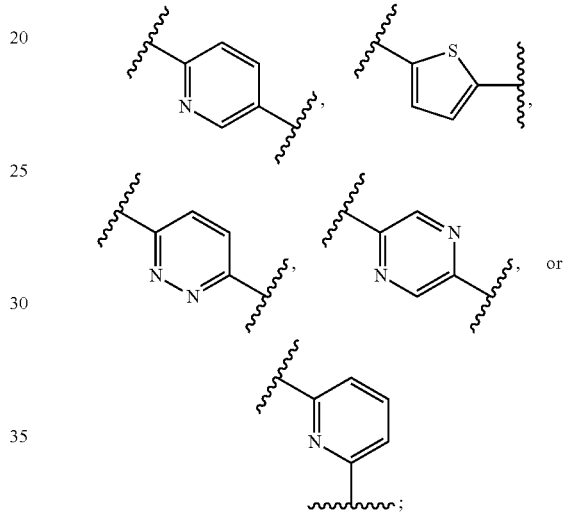

R$_{11}$ is optionally substituted phenyl, optionally substituted alkyl, optionally substituted thienyl, pyrrolyl, furanyl, optionally substituted pyridyl, —CH(OH)-alkyl, —CH(OH)-haloalkyl, optionally substituted arylalkyl, optionally substituted aryloxyalkyl, haloalkyl, haloalkoxyalkyl, optionally substituted indolyl, optionally substituted benzofuranyl, heterocycloalkyl, or

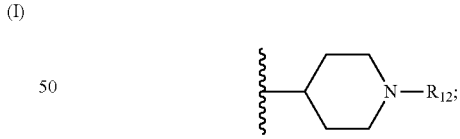

R$_{12}$ is R$_4$, —C(O)R$_4$, —C(O)R$_7$, —SO$_2$R$_4$;
MBG is optionally substituted tetrazolyl, optionally substituted triazolyl, optionally substituted oxazolyl, optionally substituted pyrimidinyl, optionally substituted thiazolyl, or optionally substituted pyrazolyl.

Another aspect is a compound of the formulae herein, wherein R$_1$ is fluoro.

Another aspect is a compound of the formulae herein, wherein R$_2$ is fluoro.

Another aspect is a compound of the formulae herein, wherein R$_1$ and R$_2$ are fluoro.

Another aspect is a compound of the formulae herein, wherein R$_4$ is phenyl optionally substituted with 0, 1, 2 or 3 independent R$_8$.

Another aspect is a compound of the formulae herein, wherein $R_4$ is phenyl optionally substituted with 0, 1, 2 or 3 independent halo.

Another aspect is a compound of the formulae herein, wherein $R_4$ is phenyl optionally substituted with 0, 1, 2 or 3 independent fluoro.

Another aspect is a compound of the formulae herein, wherein $R_4$ is 2,4-difluorophenyl.

Another aspect is a compound of the formulae herein, wherein $R_5$ is H.

Another aspect is a compound of the formulae herein, wherein $R_5$ is amino substituted acyl.

Another aspect is a compound of the formulae herein, wherein $R_5$ is —C(O)alkyl optionally substituted with 1 or 2 amino.

Another aspect is a compound of the formulae herein, wherein $R_5$ is phosphato.

Another aspect is a compound of the formulae herein, wherein:
 $R_1$ is fluoro;
 $R_2$ is fluoro;
 $R_4$ is 2,4-difluorophenyl;
 $R_5$ is H;
 $Ar_2$ is

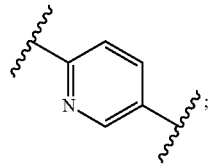 [SMILES: *c1ccc(*)nc1]

and
MBG is 1-tetrazolyl.

Another aspect is a compound of the formulae herein, wherein:
 $R_1$ is fluoro;
 $R_2$ is fluoro;
 $R_4$ is 2,4-difluorophenyl;
 $R_5$ is H;
 $Ar_2$ is

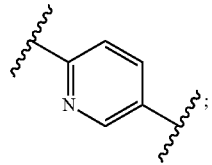 [SMILES: *c1ccc(*)nc1]

MBG is 1-tetrazolyl;
$R_{11}$ is phenyl, thienyl, arylalkyl, aryloxyalkyl, each optionally substituted with 0, 1, 2, or 3 independent $R_3$;
each $R_3$ is independently cyano, haloalkyl, halo, haloalkoxy, optionally substituted arylalkoxy, haloalkylaminocarbonyl, optionally substituted arylalkylaminocarbonyl; and
n is 1 or 2.

Another aspect is a compound of the formulae herein, wherein:
 $R_1$ is fluoro;
 $R_2$ is fluoro;
 $R_4$ is 2,4-difluorophenyl;
 $R_5$ is H;
 $Ar_2$ is

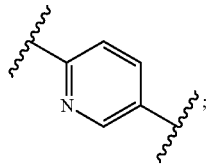 [SMILES: *c1ccc(*)nc1]

MBG is 1-tetrazolyl;
$R_{11}$ is phenyl, thienyl, arylalkyl, aryloxyalkyl, each optionally substituted with 0, 1, 2, or 3 independent $R_3$;
each $R_3$ is independently cyano, haloalkyl, halo, haloalkoxy, arylalkoxy optionally substituted with halo, cyano, haloalkyl, or haloalkoxy, haloalkylaminocarbonyl, arylalkylaminocarbonyl optionally substituted with halo, cyano, or haloalkyl; and
n is 1 or 2.

Another aspect is a compound of the formulae herein, wherein:
 $R_1$ is fluoro;
 $R_2$ is fluoro;
 $R_4$ is 2,4-difluorophenyl;
 $R_5$ is H;
 $Ar_2$ is

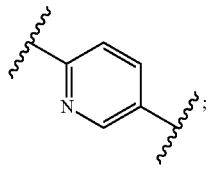 [SMILES: *c1ccc(*)nc1]

MBG is 1-tetrazolyl;
$R_{11}$ is phenyl, thienyl, arylalkyl, aryloxyalkyl, each optionally substituted with 0, 1, 2, or 3 independent $R_3$;
each $R_3$ is independently —$NR_6R_9$, haloalkylcarbonyl, alkoxyalkyl, hydroxyalkyl, acyl, haloalkylthio, —CH(OH)-haloalkyl, alkyl, alkoxy, cyano, haloalkyl, halo, haloalkoxy, arylalkoxy optionally substituted with halo, cyano, haloalkyl, or haloalkoxy, haloalkylaminocarbonyl, arylalkylaminocarbonyl optionally substituted with halo, cyano, haloalkoxy, or haloalkyl; and
n is 1 or 2.

Another aspect is a compound of the formulae herein, wherein:
 $R_1$ is fluoro;
 $R_2$ is fluoro;
 $R_4$ is 2,4-difluorophenyl;
 $R_5$ is H;
 $Ar_2$ is

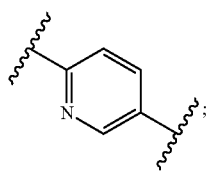 [SMILES: *c1ccc(*)nc1]

MBG is 1-tetrazolyl;
$R_{11}$ is phenyl, thienyl, arylalkyl, aryloxyalkyl, each optionally substituted with 0, 1, 2, or 3 independent $R_3$;

each $R_3$ is independently cyano, haloalkyl, halo, haloalkoxy, optionally substituted arylalkoxy, haloalkylaminocarbonyl, optionally substituted arylalkylaminocarbonyl; and n is 1.

Another aspect is a compound of the formulae herein, wherein:

$R_1$ is fluoro;
$R_2$ is fluoro;
$R_4$ is 2,4-difluorophenyl;
$R_5$ is H;
$Ar_2$ is

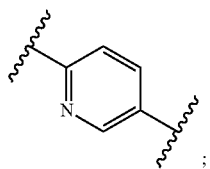 [SMILES: *c1ccc(*)nc1]

MBG is 1-tetrazolyl;
$R_{11}$ is phenyl optionally substituted with 0, 1, 2, or 3 independent $R_3$;
each $R_3$ is independently cyano, haloalkyl, halo; and
n is 1 or 2.

Another aspect is a compound of the formulae herein, wherein:

$R_1$ is fluoro;
$R_2$ is fluoro;
$R_4$ is 2,4-difluorophenyl;
$R_5$ is H;
$Ar_2$ is

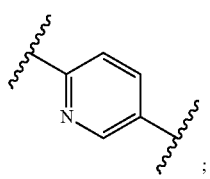 [SMILES: *c1ccc(*)nc1]

MBG is 1-tetrazolyl;
$R_{11}$ is phenyl optionally substituted with 0, 1, 2, or 3 independent $R_3$;
each $R_3$ is independently —$NR_6R_9$, haloalkylcarbonyl, alkoxyalkyl, hydroxyalkyl, acyl, haloalkylthio, —CH(OH)-haloalkyl, alkyl, alkoxy, cyano, haloalkyl, halo, haloalkoxy, arylalkoxy optionally substituted with halo, cyano, haloalkyl, or haloalkoxy, haloalkylaminocarbonyl, arylalkylaminocarbonyl optionally substituted with halo, cyano, haloalkoxy, or haloalkyl; and
n is 1 or 2.

Another aspect is a compound of the formulae herein, wherein:

$R_1$ is fluoro;
$R_2$ is fluoro;
$R_4$ is 2,4-difluorophenyl;
$R_5$ is H;

$Ar_2$ is

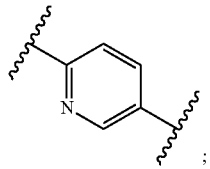 [SMILES: *c1ccc(*)nc1]

MBG is 1-tetrazolyl;
$R_{11}$ is thienyl optionally substituted with 0, 1, 2, or 3 independent $R_3$;
each $R_3$ is independently haloalkylaminocarbonyl, optionally substituted arylalkylaminocarbonyl; and
n is 1 or 2.

Another aspect is a compound of the formulae herein, wherein:

$R_1$ is fluoro;
$R_2$ is fluoro;
$R_4$ is 2,4-difluorophenyl;
$R_5$ is H;
$Ar_2$ is

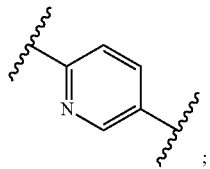 [SMILES: *c1ccc(*)nc1]

MBG is 1-tetrazolyl;
$R_{11}$ is thienyl optionally substituted with 0, 1, 2, or 3 independent $R_3$;
each $R_3$ is independently haloalkylaminocarbonyl or arylalkylaminocarbonyl optionally substituted with halo, cyano, or haloalkyl; and
n is 1 or 2.

Another aspect is a compound of the formulae herein, wherein:

$R_1$ is fluoro;
$R_2$ is fluoro;
$R_4$ is 2,4-difluorophenyl;
$R_5$ is H;
$Ar_2$ is

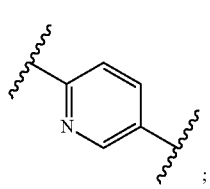 [SMILES: *c1ccc(*)nc1]

MBG is 1-tetrazolyl;
$R_{11}$ is thienyl optionally substituted with 0, 1, 2, or 3 independent $R_3$;
each $R_3$ is independently —$NR_6R_9$, haloalkylcarbonyl, alkoxyalkyl, hydroxyalkyl, acyl, haloalkylthio, —CH(OH)-haloalkyl, alkyl, alkoxy, cyano, haloalkyl, halo, haloalkoxy, arylalkoxy optionally substituted with halo, cyano, haloalkyl, or haloalkoxy, haloalkylaminocarbonyl, arylalkylaminocarbonyl optionally substituted with halo, cyano, haloalkoxy, or haloalkyl; and
n is 1 or 2.

Another aspect is a compound of the formulae herein, wherein:
$R_1$ is fluoro;
$R_2$ is fluoro;
$R_4$ is 2,4-difluorophenyl; and
$R_5$ is H.

Another aspect is a compound of the formulae herein, wherein:
each $R_3$ is independently cyano, haloalkyl, halo, haloalkoxy, optionally substituted arylalkoxy, haloalkylaminocarbonyl, optionally substituted arylalkylaminocarbonyl; and
n is 1 or 2.

Another aspect is a compound of the formulae herein, wherein:
each $R_3$ is independently —$NR_6R_9$, haloalkylcarbonyl, alkoxyalkyl, hydroxyalkyl, acyl, haloalkylthio, —CH(OH)-haloalkyl, alkyl, alkoxy, cyano, haloalkyl, halo, haloalkoxy, arylalkoxy optionally substituted with halo, cyano, haloalkyl, or haloalkoxy, haloalkylaminocarbonyl, arylalkylaminocarbonyl optionally substituted with halo, cyano, haloalkoxy, or haloalkyl; and
n is 1 or 2.

Another aspect is a compound of the formulae herein, wherein:
each $R_3$ is independently cyano, haloalkyl, halo, haloalkoxy, optionally substituted arylalkoxy, haloalkylaminocarbonyl, optionally substituted arylalkylaminocarbonyl; and
n is 1.

Another aspect is a compound of the formulae herein, wherein:
each $R_3$ is independently cyano, haloalkyl, halo, haloalkoxy, optionally substituted arylalkoxy, haloalkylaminocarbonyl, optionally substituted arylalkylaminocarbonyl; and
n is 2.

Another aspect is a compound of the formulae herein, wherein:
each $R_3$ is independently hydroxy, amino, —$NR_6R_9$, —$SR_{10}$, —$C(O)R_{10}$, $C(O)NR_6R_7$, —CH(OH)-haloalkyl, optionally substituted alkyl, hydroxyalkyl, alkoxyalkyl, isocyano, cycloalkylaminocarbonyl, aryloxyalkyl, arylalkylthio, haloalkylthio, arylalkylsulfonyl, arylalkylsulfinyl, optionally substituted heteroarylalkoxy, or haloalkylcarbonyl; and
n is 1 or 2.

Another aspect is a compound of the formulae herein, wherein:
each $R_3$ may be optionally substituted with halo, cyano, haloalkyl, haloalkoxy, alkylaminocarbonyl, heteroaryl, or aryl.

Another aspect is a compound of the formulae herein, wherein:
each arylalkoxy may be optionally substituted with halo, cyano, haloalkyl, haloalkoxy, alkylaminocarbonyl, heteroaryl, or aryl.

Another aspect is a compound of the formulae herein, wherein:
each aryloxyalkyl may be optionally substituted with halo, cyano, haloalkyl, haloalkoxy, or aryl.

Another aspect is a compound of the formulae herein, wherein:
each arylalkylthio may be optionally substituted with halo, haloalkyl, haloalkoxy or cyano.

Another aspect is a compound of the formulae herein, wherein:
each arylalkylsulfonyl may be optionally substituted with halo, haloalkyl, haloalkoxy, or cyano.

Another aspect is a compound of the formulae herein, wherein:
each arylalkylsulfinyl may be optionally substituted with halo, haloalkyl, haloalkoxy, or cyano.

Another aspect is a compound of the formulae herein, wherein:
each heteroarylalkoxy may be optionally substituted with halo, haloalkyl, haloalkoxy, or cyano.

Another aspect is a compound of the formulae herein, wherein:
each arylthioalkyl may be optionally substituted with halo, haloalkyl, haloalkoxy, or cyano.

Another aspect is a compound of the formulae herein, wherein:
each thienyl may be optionally substituted with halo, haloalkyl, alkyl, haloalkylcarbonyl, haloalkylaminocarbonyl, haloarylalkylaminocarbonyl, cyanoarylalkylaminocarbonyl, haloalkylarylalkylaminocarbonyl, heterocycloalkylcarbonyl, methylsulfonylphenylalkylaminocarbonyl, or cyano.

Another aspect is a compound of the formulae herein, wherein:
each pyridyl within the definition of $R_{11}$ may be optionally substituted with halo, cyano, haloalkoxy, or haloalkyl.

Another aspect is a compound of the formulae herein, wherein:
each indolyl may be optionally substituted with halo, cyano, haloalkoxy, or haloalkyl.

Another aspect is a compound of the formulae herein, wherein:
each benzofuranyl may be optionally substituted with halo, cyano, haloalkoxy, or haloalkyl.

Another aspect is a compound of the formulae herein, wherein:
each MBG may be optionally substituted with halo, cyano, haloalkoxy, or haloalkyl.

Another aspect is a compound of the formulae herein, wherein:
each $R_{11}$ may be optionally substituted with halo, cyano, alkyl, haloalkoxy, or haloalkyl.

Another aspect is a compound of the formulae herein, wherein:
each $R_3$ is independently 4-cyano, 4-trifluoromethyl, 3-cyano, 4-isopropoxy, 4-fluoro, 3-trifluoromethoxy, 4-trifluoromethoxy, 3-chloro, 4-chloro, 2-fluoro, 5-fluoro, 4-(2,2,2-trifluoroethoxy), 4-(3,3,3-trifluoro, 2,2-difluoropropoxy), 4-cyano-3-fluorophenylmethoxy, 4-cyanophenylmethoxy, 1-hydroxy-2,2,2-trifluoroethyl, or (4-fluorophenylmethyl)NHC(O)—, 2,4-di-fluoro, 1-methyl, 3,4-di-fluoro, 2-fluoro-4-trifluoromethyl, 3-fluoro, 4-difluoromethyl, 2-fluoro-4-methyl, 5-chloro, 5-trifluoromethyl, 3,5-di-fluoro, 2-fluoro-5-methoxy, 2,6-di-fluoro, 5-methyl, 4-(1,1-difluoroethane), 4-difluoromethoxy, 4-trifluoromethylthio, 3-fluoro-4-chloro, 4-acetyl, 4-hydroxymethyl, 4-methoxymethyl, 5-bromo, 5-difluoromethyl, 5-trifluoroacetyl, 1-(2,2,2-trifluoroethyl), 2-fluoro-4-(methylamino), 4-dimethylamino, 3-fluoro-4-difluoromethyl, 1-difluoromethyl, 2,5-difluoro, 4-formylamino, 4-isocyano, 2-fluoro-4-cyano, 3-fluoro-4-cyano, 2-fluoro-5-cyano, 5-(2,2,2-trifluoroethyl), 4-trifluoroacetylamino, 4-(2,2,2-trifluoroethyl)amino, 4-aminocarbonyl, 2-fluoro-4-amino, 4-acetylamino, 4-(fluorophenyl)methylamino, 4-(2,2,2-trifluoroethyl), (2,2,2-trifluoroethyl)aminocarbonyl, pyrrolidinylcarbonyl, 4-(fluorophenyl)methyloxy, 4-(fluorophenyl)carbonyl, 1-trifluoroacetyl, 3-(2,2,2-trifluoroethyl)oxy, 3-(cyanophenyl)methyloxy, 4-(trifluoromethoxyphenyl)methyloxy, [(2-fluoro-4-cyano)phenyl]methyloxy, [(2-fluoro-5-cyano)phenyl]methyloxy, 3-(trifluoromethoxy)methyloxy, 2,4-(difluorophenyl)methyloxy, 3,4-(di-fluorophenyl)methyloxy, 4-(chlorophenyl)methyloxy, (2-fluoro-4-chlorophenyl)methyloxy, [4-(methylaminocarbonyl)phenyl]methyloxy, (5-cyano-2-pyridyl)methyloxy, (2-thiazole)methyloxy, (3-cyano-4-fluorophenyl)methyloxy, (2,3-di-fluorophenyl)methyloxy, 2-fluoro-4-chloro, (3-cyanophenyl)methylaminocarbonyl, (4-cyanophenyl)methylaminocarbonyl, (4-trifluoromethylphenyl)methylaminocarbonyl, (1-morpholino)carbonyl, [4-(methanesulfonyl)phenyl]methylaminocarbonyl, (2-fluoro-4-cyanophenyl)methyloxy, (3-fluoro-5-cyanophenyl)methyloxy, (4-fluorophenyl)sulfonyl, 1-hydroxy-(2,2,3,3,3-pentafluoro)propyl, (3-fluoro-4-cyanophenyl)methylsulfinyl, (3-fluoro-4-cyanophenyl)methylthio, (3-fluoro-4-cyanophenyl)methylsulfonyl, (2-cyano-5-pyridyl)methyloxy, (3-fluoro-4-cyanophenyl)methyloxy, 1-hydroxyethyl, 2-fluoro-4-methoxy, 4-methylamino, 4-hydroxy, (4-fluorophenyl)methylamino, (3-fluorophenyl)methylaminocarbonyl, (4-fluorophenyl)methylaminocarbonyl, (2-fluoro-3-cyanophenyl)methyloxy, (4-cyanophenyl)methylthio, (3-fluoro-4-chlorophenyl)methyloxy, (4-biphenyl)methyloxy, (4-methylphenyl)methyloxy, (4-ethylphenyl)methyloxy, (4-difluoromethylphenyl)methyloxy, (4-trifluoromethylphenyl)methyloxy, 3-cyano-4-fluoro, (4-(1-pyrrolyl)phenyl)methyloxy, 4-phenyl, (4-(2-oxazolyl)phenyl)methyloxy, 4-(5-cyanothienyl)methyloxy.

Another aspect is a compound of formula (II), or salt, solvate, hydrate or prodrug thereof, wherein:

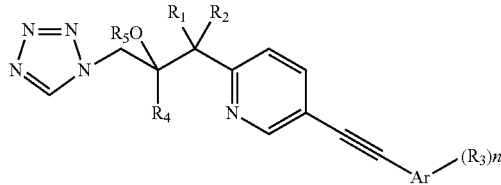

(II)

$R_1$, $R_2$, $R_3$, $R_4$, $R_5$, $R_6$, $R_7$, $R_8$, $R_9$, and $R_{10}$ are defined as described in the above embodiments;
Ar is aryl or heteroaryl;
n is 0, 1, 2 or 3.

In one aspect, the compound of any of the formulae herein (e.g., formula I or formula II) is that wherein the compound inhibits (or is identified to inhibit) lanosterol demethylase (CYP51).

In one aspect, the compound of any of the formulae herein (e.g., formula I or formula II) is that wherein the compound is identified as having an activity range against a target enzyme (e.g., *C. albicans* MIC<1.0 µg/mL and *A. fumigatus* MIC≤64 µg/mL).

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal via the 1-tetrazolyl moiety; in another aspect, the compound is identified as having a bonding interaction with the metal via the N2 of the 1-tetrazolyl moiety; in another aspect, the compound is identified as having a bonding interaction with the metal via the N3 of the 1-tetrazolyl moiety; in another aspect, the compound is identified as having a bonding interaction with the metal via the N4 of the 1-tetrazolyl moiety. In one aspect, the compound is identified as having a bonding interaction with the metal via the 2-tetrazolyl moiety; in another aspect, the compound is identified as having a bonding interaction with the metal via the N1 of the 2-tetrazolyl moiety; in another aspect, the compound is identified as having a bonding interaction with the metal via the N3 of the 2-tetrazolyl moiety; in another aspect, the compound is identified as having a bonding interaction with the metal via the N4 of the 2-tetrazolyl moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of any of the formulae herein (e.g., formula I or formula II) (and pharmaceutically acceptable salts, solvates, or hydrates thereof)

2-(2,4-Difluorophenyl)-1,1-difluoro-1-(5-(phenylethynyl)pyridin-2-yl)-3-(1H-tetrazol-1-yl)propan-2-ol (1);

1-(5-((4-Chlorophenyl)ethynyl)pyridin-2-yl)-2-(2,4-difluorophenyl)-1,1-difluoro-3-(1H-tetrazol-1-yl)propan-2-ol (2);

2-(2,4-Difluorophenyl)-1,1-difluoro-(5-((4-fluorophenyl)ethynyl)pyridin-2-yl)-3-(1H-tetrazol-1-yl)propan-2-ol (3);

2-(2,4-Difluorophenyl)-1-(5-((2,4-difluorophenyl)ethynyl)pyridin-2-yl)-1,1-difluoro-3-(1H-tetrazol-1-yl)propan-2-ol (4);

2-(2,4-Difluorophenyl)-1,1-difluoro-3-(1H-tetrazol-1-yl)-1-(5-((4-(trifluoromethyl)phenyl) ethynyl)pyridin-2-yl)propan-2-ol (5);

5-((6-(2-(2,4-difluorophenyl)-1,1-difluoro-2-hydroxy-3-(1H-tetrazol-1-yl)propyl)pyridin-3-yl) ethynyl)-N-(4-fluorobenzyl)thiophene-2-carboxamide (6);

4-((4-((6-(2-(2,4-difluorophenyl)-1,1-difluoro-2-hydroxy-3-(1H-tetrazol-1-yl) propyl)pyridin-3-yl) ethynyl) phenoxy) methyl)-2-fluorobenzonitrile (7);

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (8);

2-(2,4-difluorophenyl)-1,1-difluoro-3-(1H-tetrazol-1-yl)-1-(5-((4-(2,2,2-trifluoro-1-hydroxyethyl)phenyl) ethynyl)pyridin-2-yl)propan-2-ol (9);

2-(2,4-Difluorophenyl)-1,1-difluoro-1-(5-((1-methyl-1H-pyrrol-3-yl)ethynyl)pyridin-2-yl)-3-(1H-tetrazol-1-yl)propan-2-ol (10);

2-(2,4-Difluorophenyl)-1,1-difluoro-1-(5-((4-fluorophenyl)ethynyl)thiophen-2-yl)-3-(1H-tetrazol-1-yl)propan-2-ol (11);

2-(2,4-Difluorophenyl)-1-(6-((3,4-difluorophenyl)ethynyl)pyridazin-3-yl)-1,1-difluoro-3-(1H-tetrazol-1-yl)propan-2-ol (12);

4-(6-(2-(2,4-Difluorophenyl)-1,1-difluoro-2-hydroxy-3-(1H-tetrazol-1-yl)propyl)pyridin-3-yl)but-3-yn-2-ol (13);

2-(2,4-Difluorophenyl)-1,1-difluoro-3-(1H-tetrazol-1-yl)-1-(5-((5-(2,2,2-trifluoro-1-hydroxyethyl)thiophen-2-yl)ethynyl)pyridin-2-yl)propan-2-ol (14);

2-(2,4-difluorophenyl)-1-(5-((3,4-difluorophenyl)ethynyl)pyrazin-2-yl)-1,1-difluoro-3-(1H-tetrazol-1-yl)propan-2-ol (15);

2-(2,4-Difluorophenyl)-1,1-difluoro-3-(1H-tetrazol-1-yl)-1-(5-((5-(2,2,2-trifluoro-1-hydroxy ethyl)furan-2-yl)ethynyl)pyridin-2-yl)propan-2-ol (16);

2-(2,4-Difluorophenyl)-1,1-difluoro-1-(5-(3-(3-fluorophenyl)prop-1-yn-1-yl)pyridin-2-yl)-3-(1H-tetrazol-1-yl)propan-2-ol (17);

2-(2,4-Difluorophenyl)-1,1-difluoro-1-(5-(3-(4-fluorophenoxy)prop-1-yn-1-yl)pyridin-2-yl)-3-(1H-tetrazol-1-yl)propan-2-ol (18);

2-(2,4-Difluorophenyl)-1,1-difluoro-1-(5-((1-(4-fluorophenyl)piperidin-4-yl)ethynyl)pyridin-2-yl)-3-(1H-tetrazol-1-yl)propan-2-ol (19);

1-(5-((4-((4-Cyanobenzyl)oxy)phenyl)ethynyl)pyridin-2-yl)-2-(2,4-difluorophenyl)-1,1-difluoro-3-(1H-tetrazol-1-yl) propan-2-yl dihydrogen phosphate (20);

1-(5-((3-chlorophenyl)ethynyl)pyridin-2-yl)-2-(2,4-difluorophenyl)-1,1-difluoro-3-(1H-tetrazol-1-yl)propan-2-ol (21);

2-(2,4-difluorophenyl)-1,1-difluoro-1-(5-((2-fluoro-4-(trifluoromethyl)phenyl)ethynyl)pyridin-2-yl)-3-(1H-tetrazol-1-yl)propan-2-ol (22);

2-(2,4-difluorophenyl)-1-(5-(3,3-difluoroprop-1-ynyl)pyridin-2-yl)-1,1-difluoro-3-(1H-tetrazol-1-yl)propan-2-ol (23);

2-(2,4-difluorophenyl)-1,1-difluoro-1-(5-((2-fluorophenyl)ethynyl)pyridin-2-yl)-3-(1H-tetrazol-1-yl)propan-2-ol (24);

2-(2,4-difluorophenyl)-1,1-difluoro-1-(5-((3-fluorophenyl)ethynyl)pyridin-2-yl)-3-(1H-tetrazol-1-yl)propan-2-ol (25);

1-(5-((4-(difluoromethyl)phenyl)ethynyl)pyridin-2-yl)-2-(2,4-difluorophenyl)-1,1-difluoro-3-(1H-tetrazol-1-yl)propan-2-ol (26);

2-(2,4-difluorophenyl)-1,1-difluoro-1-(5-((2-fluoro-4-methylphenyl)ethynyl)pyridin-2-yl)-3-(1H-tetrazol-1-yl)propan-2-ol (27);

2-(2,4-difluorophenyl)-1,1-difluoro-1-(5-((3-fluoropyridin-2-yl)ethynyl)pyridin-2-yl)-3-(1H-tetrazol-1-yl)propan-2-ol (28);

1-(5-((5-chlorothiophen-2-yl)ethynyl)pyridin-2-yl)-2-(2,4-difluorophenyl)-1,1-difluoro-3-(1H-tetrazol-1-yl)propan-2-ol (29);

2-(2,4-difluorophenyl)-1,1-difluoro-3-(1H-tetrazol-1-yl)-1-(5-((5-(trifluoromethyl)thiophen-2-yl)ethynyl)pyridin-2-yl)propan-2-ol (30);

2-(2,4-difluorophenyl)-1-(5-((3,5-difluoropyridin-2-yl)ethynyl)pyridin-2-yl)-1,1-difluoro-3-(1H-tetrazol-1-yl)propan-2-ol (31);

2-(2,4-difluorophenyl)-1,1-difluoro-1-(5-((5-fluoropyridin-2-yl)ethynyl)pyridin-2-yl)-3-(1H-tetrazol-1-yl)propan-2-ol (32);

2-(2,4-difluorophenyl)-1,1-difluoro-1-(5-((6-fluoropyridin-3-yl)ethynyl)pyridin-2-yl)-3-(1H-tetrazol-1-yl)propan-2-ol (33);

2-(2,4-difluorophenyl)-1,1-difluoro-3-(1H-tetrazol-1-yl)-1-(5-((4-(trifluoromethoxy)phenyl)ethynyl)pyridin-2-yl)propan-2-ol (34);

2-(2,4-difluorophenyl)-1,1-difluoro-1-(5-((2-fluoro-4-methoxyphenyl)ethynyl)pyridin-2-yl)-3-(1H-tetrazol-1-yl)propan-2-ol (35);

2-(2,4-difluorophenyl)-1-(5-((2,6-difluorophenyl)ethynyl)pyridin-2-yl)-1,1-difluoro-3-(1H-tetrazol-1-yl)propan-2-ol (36);

2-(2,4-difluorophenyl)-1-(5-((3,4-difluorophenyl)ethynyl)pyridin-2-yl)-1,1-difluoro-3-(1H-tetrazol-1-yl)propan-2-ol (37);

2-(2,4-difluorophenyl)-1,1-difluoro-1-(5-((5-methylthiophen-2-yl)ethynyl)pyridin-2-yl)-3-(1H-tetrazol-1-yl)propan-2-ol (38);

1-(5-((4-(1,1-difluoroethyl)phenyl)ethynyl)pyridin-2-yl)-2-(2,4-difluorophenyl)-1,1-difluoro-3-(1H-tetrazol-1-yl)propan-2-ol (39);

1-(5-((4-(difluoromethoxy)phenyl)ethynyl)pyridin-2-yl)-2-(2,4-difluorophenyl)-1,1-difluoro-3-(1H-tetrazol-1-yl)propan-2-ol (40);

2-(2,4-difluorophenyl)-1,1-difluoro-3-(1H-tetrazol-1-yl)-1-(5-((4-(trifluoromethylthio)phenyl)ethynyl)pyridin-2-yl)propan-2-ol (41);

1-(5-((4-chloro-3-fluorophenyl)ethynyl)pyridin-2-yl)-2-(2,4-difluorophenyl)-1,1-difluoro-3-(1H-tetrazol-1-yl)propan-2-ol (42);

2-(4-chloro-2-fluorophenyl)-1,1-difluoro-1-(5-((4-fluorophenyl)ethynyl)pyridin-2-yl)-3-(1H-tetrazol-1-yl)propan-2-ol (43);

1,1-difluoro-2-(2-fluoro-4-(trifluoromethyl)phenyl)-1-(5-((4-fluorophenyl)ethynyl)pyridin-2-yl)-3-(1H-tetrazol-1-yl)propan-2-ol (44);

2-(2,5-difluorophenyl)-1,1-difluoro-1-(5-((4-fluorophenyl)ethynyl)pyridin-2-yl)-3-(1H-tetrazol-1-yl)propan-2-ol (45);

2-(3,4-difluorophenyl)-1,1-difluoro-1-(5-((4-fluorophenyl)ethynyl)pyridin-2-yl)-3-(1H-tetrazol-1-yl)propan-2-ol (46);

1-(4-((6-(2-(2,4-difluorophenyl)-1,1-difluoro-2-hydroxy-3-(1H-tetrazol-1-yl)propyl)pyridin-3-yl)ethynyl)phenyl)ethanone (47);

2-(2,4-difluorophenyl)-1,1-difluoro-1-(6-((4-fluorophenyl)ethynyl)pyridin-2-yl)-3-(1H-tetrazol-1-yl)propan-2-ol (48);

2-(2,4-difluorophenyl)-1,1-difluoro-1-(6-((4-fluorophenyl)ethynyl)pyridazin-3-yl)-3-(1H-tetrazol-1-yl)propan-2-ol (49);

2-(2,4-difluorophenyl)-1,1-difluoro-1-(5-((4-(hydroxymethyl)phenyl)ethynyl)pyridin-2-yl)-3-(1H-tetrazol-1-yl)propan-2-ol (50);

2-(2,4-difluorophenyl)-1,1-difluoro-1-(5-((4-(methoxymethyl)phenyl)ethynyl)pyridin-2-yl)-3-(1H-tetrazol-1-yl)propan-2-ol (51);

4-(6-(2-(2,4-difluorophenyl)-1,1-difluoro-2-hydroxy-3-(1H-tetrazol-1-yl)propyl)pyridin-3-yl)-1,1,1-trifluorobut-3-yn-2-ol (52);

1-(5-((5-bromothiophen-2-yl)ethynyl)pyridin-2-yl)-2-(2,4-difluorophenyl)-1,1-difluoro-3-(1H-tetrazol-1-yl)propan-2-ol (53);

1-(5-((5-(difluoromethyl)thiophen-2-yl)ethynyl)pyridin-2-yl)-2-(2,4-difluorophenyl)-1,1-difluoro-3-(1H-tetrazol-1-yl)propan-2-ol (54);

1-(5-((6-(2-(2,4-difluorophenyl)-1,1-difluoro-2-hydroxy-3-(1H-tetrazol-1-yl)propyl)pyridin-3-yl)ethynyl)thiophen-2-yl)-2,2,2-trifluoroethanone (55);

2-(2,4-difluorophenyl)-1,1-difluoro-3-(1H-tetrazol-1-yl)-1-(5-((1-(2,2,2-trifluoroethyl)-1H-pyrrol-3-yl)ethynyl)pyridin-2-yl)propan-2-ol (56);

2-(2,4-difluorophenyl)-1,1-difluoro-3-(1H-tetrazol-1-yl)-1-(5-(3-(2,2,2-trifluoroethoxy)prop-1-ynyl)pyridin-2-yl)propan-2-ol (57);

2-(2,4-difluorophenyl)-1,1-difluoro-3-(1H-tetrazol-1-yl)-1-(5-(thiophen-2-ylethynyl)pyridin-2-yl)propan-2-ol (58);

2-(2,4-difluorophenyl)-1,1-difluoro-1-(5-((2-fluoro-4-(methylamino)phenyl)ethynyl)pyridin-2-yl)-3-(1H-tetrazol-1-yl)propan-2-ol (59);

2-(2,4-difluorophenyl)-1,1-difluoro-1-(5-((4-(methylamino)phenyl)ethynyl)pyridin-2-yl)-3-(1H-tetrazol-1-yl)propan-2-ol (60);

2-(2,4-difluorophenyl)-1-(5-((3,4-difluorophenyl)ethynyl)thiophen-2-yl)-1,1-difluoro-3-(1H-tetrazol-1-yl)propan-2-ol (61);

2-(2,4-difluorophenyl)-1-(5-((4-(dimethylamino)phenyl)ethynyl)pyridin-2-yl)-1,1-difluoro-3-(1H-tetrazol-1-yl)propan-2-ol (62);

1-(5-((1H-pyrrol-3-yl)ethynyl)pyridin-2-yl)-2-(2,4-difluorophenyl)-1,1-difluoro-3-(1H-tetrazol-1-yl)propan-2-ol (63);

1-(5-((4-(difluoromethyl)-3-fluorophenyl)ethynyl)pyridin-2-yl)-2-(2,4-difluorophenyl)-1,1-difluoro-3-(1H-tetrazol-1-yl)propan-2-ol (64);

2-(2,4-difluorophenyl)-1,1-difluoro-1-(5-(3-(3-fluorophenyl)prop-1-ynyl)pyridin-2-yl)-3-(1H-tetrazol-1-yl)propan-2-ol (65);

1-(5-((1-(difluoromethyl)-1H-pyrrol-3-yl)ethynyl)pyridin-2-yl)-2-(2,4-difluorophenyl)-1,1-difluoro-3-(1H-tetrazol-1-yl)propan-2-ol (66);

2-(2,4-difluorophenyl)-1-(5-((2,5-difluorophenyl)ethynyl)pyridin-2-yl)-1,1-difluoro-3-(1H-tetrazol-1-yl)propan-2-ol (67);

N-(4-((6-(2-(2,4-difluorophenyl)-1,1-difluoro-2-hydroxy-3-(1H-tetrazol-1-yl)propyl)pyridin-3-yl)ethynyl)phenyl)formamide (68);

4-((6-(2-(2,4-difluorophenyl)-1,1-difluoro-2-hydroxy-3-(1H-tetrazol-1-yl)propyl)pyridin-3-yl)ethynyl)benzonitrile (69);

2-(2,4-difluorophenyl)-1,1-difluoro-1-(5-((4-isocyanophenyl)ethynyl)pyridin-2-yl)-3-(1H-tetrazol-1-yl)propan-2-ol (70);

3-((6-(2-(2,4-difluorophenyl)-1,1-difluoro-2-hydroxy-3-(1H-tetrazol-1-yl)propyl)pyridin-3-yl)ethynyl)benzonitrile (71);

1-(5-((5-bromofuran-2-yl)ethynyl)pyridin-2-yl)-2-(2,4-difluorophenyl)-1,1-difluoro-3-(1H-tetrazol-1-yl)propan-2-ol (72);

4-((6-(2-(2,4-difluorophenyl)-1,1-difluoro-2-hydroxy-3-(1H-tetrazol-1-yl)propyl)pyridin-3-yl)ethynyl)-3-fluorobenzonitrile (73);

4-((6-(2-(2,4-difluorophenyl)-1,1-difluoro-2-hydroxy-3-(1H-tetrazol-1-yl)propyl)pyridin-3-yl)ethynyl)-2-fluorobenzonitrile (74);

3-((6-(2-(2,4-difluorophenyl)-1,1-difluoro-2-hydroxy-3-(1H-tetrazol-1-yl)propyl)pyridin-3-yl)ethynyl)-4-fluorobenzonitrile (75);

1-(5-((5-(difluoromethyl)furan-2-yl)ethynyl)pyridin-2-yl)-2-(2,4-difluorophenyl)-1,1-difluoro-3-(1H-tetrazol-1-yl)propan-2-ol (76);

2-(2,4-difluorophenyl)-1,1-difluoro-3-(1H-tetrazol-1-yl)-1-(5-((5-(2,2,2-trifluoroethyl)thiophen-2-yl)ethynyl)pyridin-2-yl)propan-2-ol (77);

1-(5-((4-aminophenyl)ethynyl)pyridin-2-yl)-2-(2,4-difluorophenyl)-1,1-difluoro-3-(1H-tetrazol-1-yl)propan-2-ol (78);

N-(4-((6-(2-(2,4-difluorophenyl)-1,1-difluoro-2-hydroxy-3-(1H-tetrazol-1-yl)propyl)pyridin-3-yl)ethynyl)phenyl)-2,2,2-trifluoroacetamide (79);

2-(2,4-difluorophenyl)-1,1-difluoro-3-(1H-tetrazol-1-yl)-1-(5-((4-(2,2,2-trifluoroethylamino)phenyl)ethynyl)pyridin-2-yl)propan-2-ol (80);

4-((6-(2-(2,4-difluorophenyl)-1,1-difluoro-2-hydroxy-3-(1H-tetrazol-1-yl)propyl)pyridin-3-yl)ethynyl)phenol (81);

4-((6-(2-(2,4-difluorophenyl)-1,1-difluoro-2-hydroxy-3-(1H-tetrazol-1-yl)propyl)pyridin-3-yl)ethynyl)benzamide (82);

1-(5-((4-amino-2-fluorophenyl)ethynyl)pyridin-2-yl)-2-(2,4-difluorophenyl)-1,1-difluoro-3-(1H-tetrazol-1-yl)propan-2-ol (83);

N-(4-((6-(2-(2,4-difluorophenyl)-1,1-difluoro-2-hydroxy-3-(1H-tetrazol-1-yl)propyl)pyridin-3-yl)ethynyl)phenyl)acetamide (84);

1-(5-(3-(2,4-difluorophenoxy)prop-1-ynyl)pyridin-2-yl)-2-(2,4-difluorophenyl)-1,1-difluoro-3-(1H-tetrazol-1-yl)propan-2-ol (85);

4-(3-(6-(2-(2,4-difluorophenyl)-1,1-difluoro-2-hydroxy-3-(1H-tetrazol-1-yl)propyl)pyridin-3-yl)prop-2-ynyloxy)benzonitrile (86);

1-(5-((1H-indol-5-yl)ethynyl)pyridin-2-yl)-2-(2,4-difluorophenyl)-1,1-difluoro-3-(1H-tetrazol-1-yl)propan-2-ol (87);

2-(2,4-difluorophenyl)-1,1-difluoro-1-(5-((4-(4-fluorobenzylamino)phenyl)ethynyl)pyridin-2-yl)-3-(1H-tetrazol-1-yl)propan-2-ol (88);

1-(5-(benzofuran-5-ylethynyl)pyridin-2-yl)-2-(2,4-difluorophenyl)-1,1-difluoro-3-(1H-tetrazol-1-yl)propan-2-ol (89);

2-(2,4-difluorophenyl)-1,1-difluoro-3-(1H-tetrazol-1-yl)-1-(5-((4-(2,2,2-trifluoroethyl)phenyl)ethynyl)pyridin-2-yl)propan-2-ol (90);

4-((6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)benzamide (91);

(4-((6-(2-(2,4-difluorophenyl)-1,1-difluoro-2-hydroxy-3-(1H-tetrazol-1-yl)propyl)pyridin-3-yl)ethynyl)phenyl)(pyrrolidin-1-yl)methanone (92);

2-(2,4-difluorophenyl)-1,1-difluoro-1-(5-((4-(4-fluorobenzyloxy)phenyl)ethynyl)pyridin-2-yl)-3-(1H-tetrazol-1-yl)propan-2-ol (93);

5-((6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)thiophene-2-carboxamide (94);

(4-((6-(2-(2,4-difluorophenyl)-1,1-difluoro-2-hydroxy-3-(1H-tetrazol-1-yl)propyl)pyridin-3-yl)ethynyl)piperidin-1-yl)(4-fluorophenyl)methanone (95);

1-(4-((6-(2-(2,4-difluorophenyl)-1,1-difluoro-2-hydroxy-3-(1H-tetrazol-1-yl)propyl)pyridin-3-yl)ethynyl)piperidin-1-yl)-2,2,2-trifluoroethanone (96);

2-(2,4-difluorophenyl)-1,1-difluoro-3-(1H-tetrazol-1-yl)-1-(5-((3-(2,2,2-trifluoroethoxy)phenyl)ethynyl)pyridin-2-yl)propan-2-ol (97);

3-((6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)benzamide (98);

1,1-difluoro-2-(4-fluorophenyl)-1-(5-((4-fluorophenyl)ethynyl)pyridin-2-yl)-3-(1H-tetrazol-1-yl)propan-2-ol (99);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (100);

2-(2,4-difluorophenyl)-1,1-difluoro-3-(1H-tetrazol-1-yl)-1-(5-((4-(4-(trifluoromethoxy)benzyloxy)phenyl)ethynyl)pyridin-2-yl)propan-2-ol (101);

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)-3-fluorobenzonitrile (102);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-4-fluorobenzonitrile (103);

2-(2,4-difluorophenyl)-1,1-difluoro-3-(1H-tetrazol-1-yl)-1-(5-((4-(3-(trifluoromethoxy)benzyloxy)phenyl)ethynyl)pyridin-2-yl)propan-2-ol (104);

1-(5-((4-(2,4-difluorobenzyloxy)phenyl)ethynyl)pyridin-2-yl)-2-(2,4-difluorophenyl)-1,1-difluoro-3-(1H-tetrazol-1-yl)propan-2-ol (105);

1-(5-((4-(3,4-difluorobenzyloxy)phenyl)ethynyl)pyridin-2-yl)-2-(2,4-difluorophenyl)-1,1-difluoro-3-(1H-tetrazol-1-yl)propan-2-ol (106);

1-(5-((4-(4-chlorobenzyloxy)phenyl)ethynyl)pyridin-2-yl)-2-(2,4-difluorophenyl)-1,1-difluoro-3-(1H-tetrazol-1-yl)propan-2-ol (107);

1-(5-((4-(4-chloro-2-fluorobenzyloxy)phenyl)ethynyl)pyridin-2-yl)-2-(2,4-difluorophenyl)-1,1-difluoro-3-(1H-tetrazol-1-yl)propan-2-ol (108);

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)-N-methylbenzamide (109);

6-((4-((6-(2-(2,4-difluorophenyl)-1,1-difluoro-2-hydroxy-3-(1H-tetrazol-1-yl)propyl)pyridin-3-yl)ethynyl)phenoxy)methyl)nicotinonitrile (110);

2-(2,4-difluorophenyl)-1,1-difluoro-3-(1H-tetrazol-1-yl)-1-(5-((4-(thiazol-2-ylmethoxy)phenyl)ethynyl)pyridin-2-yl)propan-2-ol (111);

5-((4-((6-(2-(2,4-difluorophenyl)-1,1-difluoro-2-hydroxy-3-(1H-tetrazol-1-yl)propyl)pyridin-3-yl)ethynyl)phenoxy)methyl)-2-fluorobenzonitrile (112);

1-(5-((4-(2,3-difluorobenzyloxy)phenyl)ethynyl)pyridin-2-yl)-2-(2,4-difluorophenyl)-1,1-difluoro-3-(1H-tetrazol-1-yl)propan-2-ol (113);

1-(5-(3-(4-chlorophenoxy)prop-1-ynyl)pyridin-2-yl)-2-(2,4-difluorophenyl)-1,1-difluoro-3-(1H-tetrazol-1-yl)propan-2-ol (114);

4-(3-(6-(2-(2,4-difluorophenyl)-1,1-difluoro-2-hydroxy-3-(1H-tetrazol-1-yl)propyl)pyridin-3-yl)prop-2-ynyloxy)-3-fluorobenzonitrile (115);

4-(3-(6-(2-(2,4-difluorophenyl)-1,1-difluoro-2-hydroxy-3-(1H-tetrazol-1-yl)propyl)pyridin-3-yl)prop-2-ynyloxy)-2-fluorobenzonitrile (116);

1-(5-(3-(4-chloro-2-fluorophenoxy)prop-1-ynyl)pyridin-2-yl)-2-(2,4-difluorophenyl)-1,1-difluoro-3-(1H-tetrazol-1-yl)propan-2-ol (117);

1-(5-(3-(4-(difluoromethyl)phenoxy)prop-1-ynyl)pyridin-2-yl)-2-(2,4-difluorophenyl)-1,1-difluoro-3-(1H-tetrazol-1-yl)propan-2-ol (118);

5-((6-(2-(2,4-difluorophenyl)-1,1-difluoro-2-hydroxy-3-(1H-tetrazol-1-yl)propyl)pyridin-3-yl)ethynyl)-N-(3-fluorobenzyl)thiophene-2-carboxamide (119);

N-(3-cyanobenzyl)-5-((6-(2-(2,4-difluorophenyl)-1,1-difluoro-2-hydroxy-3-(1H-tetrazol-1-yl)propyl)pyridin-3-yl)ethynyl)thiophene-2-carboxamide (120);

N-(4-cyanobenzyl)-5-((6-(2-(2,4-difluorophenyl)-1,1-difluoro-2-hydroxy-3-(1H-tetrazol-1-yl)propyl)pyridin-3-yl)ethynyl)thiophene-2-carboxamide (121);

5-((6-(2-(2,4-difluorophenyl)-1,1-difluoro-2-hydroxy-3-(1H-tetrazol-1-yl)propyl)pyridin-3-yl)ethynyl)-N-(4-(trifluoromethyl)benzyl)thiophene-2-carboxamide (122);

(5-((6-(2-(2,4-difluorophenyl)-1,1-difluoro-2-hydroxy-3-(1H-tetrazol-1-yl)propyl)pyridin-3-yl)ethynyl)thiophen-2-yl)(morpholino)methanone (123);

(5-((6-(2-(2,4-difluorophenyl)-1,1-difluoro-2-hydroxy-3-(1H-tetrazol-1-yl)propyl)pyridin-3-yl)ethynyl)thiophen-2-yl)(pyrrolidin-1-yl)methanone (124);

5-((6-(2-(2,4-difluorophenyl)-1,1-difluoro-2-hydroxy-3-(1H-tetrazol-1-yl)propyl)pyridin-3-yl)ethynyl)-N-(4-(methylsulfonyl)benzyl)thiophene-2-carboxamide (125);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-2-fluorobenzonitrile (126);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-5-fluorobenzonitrile (127);

2-(2,4-difluorophenyl)-1,1-difluoro-1-(5-(piperidin-4-ylethynyl)pyridin-2-yl)-3-(1H-tetrazol-1-yl)propan-2-ol (128);

2-(2,4-difluorophenyl)-1,1-difluoro-1-(5-((1-(4-fluorophenylsulfonyl)piperidin-4-yl)ethynyl)pyridin-2-yl)-3-(1H-tetrazol-1-yl)propan-2-ol (129);

1-(4-((6-(2-(2,4-difluorophenyl)-1,1-difluoro-2-hydroxy-3-(1H-tetrazol-1-yl)propyl)pyridin-3-yl)ethynyl)phenyl)-2,2,3,3,3-pentafluoropropan-1-ol (130);

4-((4-((6-(2-(2,5-difluorophenyl)-1,1-difluoro-2-hydroxy-3-(1H-tetrazol-1-yl)propyl)pyridin-3-yl)ethynyl)phenoxy)methyl)-2-fluorobenzonitrile (131);

4-((4-((6-(2-(4-chloro-2-fluorophenyl)-1,1-difluoro-2-hydroxy-3-(1H-tetrazol-1-yl)propyl)pyridin-3-yl)ethynyl)phenoxy)methyl)-2-fluorobenzonitrile (132);

4-((4-((6-(2-(2,4-difluorophenyl)-1,1-difluoro-2-hydroxy-3-(1H-tetrazol-1-yl)propyl)pyridin-3-yl)ethynyl)phenylthio)methyl)-2-fluorobenzonitrile (133);

4-((4-((6-(2-(2,4-difluorophenyl)-1,1-difluoro-2-hydroxy-3-(1H-tetrazol-1-yl)propyl)pyridin-3-yl)ethynyl)phenylsulfinyl)methyl)-2-fluorobenzonitrile (134);

4-((4-((6-(2-(2,4-difluorophenyl)-1,1-difluoro-2-hydroxy-3-(1H-tetrazol-1-yl)propyl)pyridin-3-yl)ethynyl)phenylsulfonyl)methyl)-2-fluorobenzonitrile (135);

4-((4-((6-(2-(2,5-difluorophenyl)-1,1-difluoro-2-hydroxy-3-(1H-tetrazol-1-yl)propyl)pyridin-3-yl)ethynyl)phenoxy)methyl)benzonitrile (136);

4-((4-((6-(2-(4-chloro-2-fluorophenyl)-1,1-difluoro-2-hydroxy-3-(1H-tetrazol-1-yl)propyl)pyridin-3-yl)ethynyl)phenoxy)methyl)benzonitrile (137);

4-((4-((6-(2-(2,4-difluorophenyl)-1,1-difluoro-2-hydroxy-3-(1H-tetrazol-1-yl)propyl)pyridin-3-yl)ethynyl)phenylthio)methyl)benzonitrile (138);

5-((4-((6-(2-(2,4-difluorophenyl)-1,1-difluoro-2-hydroxy-3-(1H-tetrazol-1-yl)propyl)pyridin-3-yl)ethynyl)phenoxy)methyl)picolinonitrile (139);

1-(5-((4-(4-cyanobenzyloxy)phenyl)ethynyl)pyridin-2-yl)-2-(2,4-difluorophenyl)-1,1-difluoro-3-(1H-tetrazol-1-yl)propan-2-yl dihydrogen phosphate (140);

5-((6-(2-(2,4-difluorophenyl)-1,1-difluoro-2-hydroxy-3-(2H-tetrazol-2-yl)propyl)pyridin-3-yl)ethynyl)-N-(4-fluorobenzyl)thiophene-2-carboxamide (141);

4-((4-((6-(2-(2,4-difluorophenyl)-1,1-difluoro-2-hydroxy-3-(2H-tetrazol-2-yl)propyl)pyridin-3-yl)ethynyl)phenoxy)methyl)benzonitrile (142);

4-((4-((6-(2-(2,4-difluorophenyl)-1,1-difluoro-2-hydroxy-3-(2H-tetrazol-2-yl)propyl)pyridin-3-yl)ethynyl)phenoxy)methyl)-2-fluorobenzonitrile (143);

2-(2,4-difluorophenyl)-1,1-difluoro-1-(5-((4-fluorophenyl)ethynyl)pyridin-2-yl)-3-(1H-tetrazol-1-yl)propan-2-yl 2-aminoacetate hydrochloride (144);

(2S)-2-(2,4-Difluorophenyl)-1,1-difluoro-1-(5-((4-fluorophenyl)ethynyl)pyridin-2-yl)-3-(1H-tetrazol-1-yl)propan-2-yl 2,6-diaminohexanoate dihydrochloride (145);

1-(5-((4-(4-chloro-3-fluorobenzyloxy)phenyl)ethynyl)pyridin-2-yl)-2-(2,4-difluorophenyl)-1,1-difluoro-3-(1H-tetrazol-1-yl)propan-2-ol (146);

1-(5-((4-(biphenyl-4-ylmethoxy)phenyl)ethynyl)pyridin-2-yl)-2-(2,4-difluorophenyl)-1,1-difluoro-3-(1H-tetrazol-1-yl)propan-2-ol (147);

2-(2,4-difluorophenyl)-1,1-difluoro-1-(5-((4-(4-methylbenzyloxy)phenyl)ethynyl)pyridin-2-yl)-3-(1H-tetrazol-1-yl)propan-2-ol (148);

2-(2,4-difluorophenyl)-1-(5-((4-(4-ethylbenzyloxy)phenyl)ethynyl)pyridin-2-yl)-1,1-difluoro-3-(1H-tetrazol-1-yl)propan-2-ol (149);

1-(5-((4-(4-(difluoromethyl)benzyloxy)phenyl)ethynyl)pyridin-2-yl)-2-(2,4-difluorophenyl)-1,1-difluoro-3-(1H-tetrazol-1-yl)propan-2-ol (150);

(+)-1-(5-((4-(4-(difluoromethyl)benzyloxy)phenyl)ethynyl)pyridin-2-yl)-2-(2,4-difluorophenyl)-1,1-difluoro-3-(1H-tetrazol-1-yl)propan-2-ol ((+)-150);

2-(2,4-difluorophenyl)-1,1-difluoro-3-(1H-tetrazol-1-yl)-1-(5-((4-(4-(trifluoromethyl)benzyloxy)phenyl)ethynyl)pyridin-2-yl)propan-2-ol (151);

4-(4-((6-(2-(2,4-difluorophenyl)-1,1-difluoro-2-hydroxy-3-(1H-tetrazol-1-yl)propyl)pyridin-3-yl)ethynyl)benzyloxy)-3-fluorobenzonitrile (152);

5-(4-((6-(2-(2,4-difluorophenyl)-1,1-difluoro-2-hydroxy-3-(1H-tetrazol-1-yl)propyl)pyridin-3-yl)ethynyl)benzyloxy)-2-fluorobenzonitrile (153);

1-(5-((4-(4-(1H-pyrazol-1-yl)benzyloxy)phenyl)ethynyl)pyridin-2-yl)-2-(2,4-difluorophenyl)-1,1-difluoro-3-(1H-tetrazol-1-yl)propan-2-ol (154);

4-(4-((6-(2-(2,4-difluorophenyl)-1,1-difluoro-2-hydroxy-3-(1H-tetrazol-1-yl)propyl)pyridin-3-yl)ethynyl)benzyloxy)benzonitrile (155);

1-(5-((4-((4-chlorophenoxy)methyl)phenyl)ethynyl)pyridin-2-yl)-2-(2,4-difluorophenyl)-1,1-difluoro-3-(1H-tetrazol-1-yl)propan-2-ol (156);

1-(5-((4-((biphenyl-4-yloxy)methyl)phenyl)ethynyl)pyridin-2-yl)-2-(2,4-difluorophenyl)-1,1-difluoro-3-(1H-tetrazol-1-yl)propan-2-ol (157);

2-(2,4-difluorophenyl)-1,1-difluoro-1-(5-((4-(4-(oxazol-2-yl)benzyloxy)phenyl)ethynyl)pyridin-2-yl)-3-(1H-tetrazol-1-yl)propan-2-ol (158);

2-(2,4-difluorophenyl)-1,1-difluoro-1-(5-((4-((4-fluorophenoxy)methyl)phenyl)ethynyl)pyridin-2-yl)-3-(1H-tetrazol-1-yl)propan-2-ol (159);

1-(5-((4-((3,4-difluorophenoxy)methyl)phenyl)ethynyl)pyridin-2-yl)-2-(2,4-difluorophenyl)-1,1-difluoro-3-(1H-tetrazol-1-yl)propan-2-ol (160);

1-(5-((4-((4-(difluoromethyl)phenoxy)methyl)phenyl)ethynyl)pyridin-2-yl)-2-(2,4-difluorophenyl)-1,1-difluoro-3-(1H-tetrazol-1-yl)propan-2-ol (161);

4-(4-((6-(2-(2,4-difluorophenyl)-1,1-difluoro-2-hydroxy-3-(1H-tetrazol-1-yl)propyl)pyridin-3-yl)ethynyl)benzylthio)benzonitrile (162);

5-(4-((6-(2-(2,4-difluorophenyl)-1,1-difluoro-2-hydroxy-3-(1H-tetrazol-1-yl)propyl)pyridin-3-yl)ethynyl)phenoxy)methyl)thiophene-2-carbonitrile (163);

4-(4-((6-(2-(2,4-difluorophenyl)-1,1-difluoro-2-hydroxy-3-(1H-tetrazol-1-yl)propyl)pyridin-3-yl)ethynyl)benzyloxy)-2-fluorobenzonitrile (164);

1-(5-((4-((4-chloro-3-fluorophenoxy)methyl)phenyl)ethynyl)pyridin-2-yl)-2-(2,4-difluorophenyl)-1,1-difluoro-3-(1H-tetrazol-1-yl)propan-2-ol (165);

4-((3-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (166).

In another aspect, the invention provides a pharmaceutical composition comprising the compound of any of the formulae herein (e.g., formula I or formula II) and a pharmaceutically acceptable carrier.

In other aspects, the invention provides a method of modulating metalloenzyme activity in a subject, comprising contacting the subject with a compound of any of the formulae herein (e.g., formula I or formula II), in an amount and under conditions sufficient to modulate metalloenzyme activity.

In another aspect, the invention provides a method of treating a subject suffering from or susceptible to a disorder or disease, wherein the subject has been identified as in need of treatment for the disorder or disease, comprising administering to said subject in need thereof, an effective amount of a compound or pharmaceutical composition of any of the formulae herein (e.g., formula I or formula II), such that said subject is treated for said disorder.

In another aspect the subject is an animal other than a human

The methods herein include those wherein the disorder or disease is associated with one or more of the following pathogenic fungi: *Absidia corymbifera, Ajellomyces dermatitidis, Arthroderma benhamiae, Arthroderma fulvum, Arthroderma gypseum, Arthroderma incurvaturn, Arthroderma otae, Arthroderma vanbreuseghemii, Aspergillus flavus, Aspergillus fumigates, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Fusarium solani, Geotrichum candidum, Histoplasma capsulaturn, Hortaea werneckii, Issatschenkia orientalis, Madurella grisae, Malassezia fur fur, Malassezia globosa, Malassezia obtusa, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium marneffei, Pichia anomala, Pichia guilliermondii, Pneumocystis carinii, Pseudallescheria boydii, Rhizopus oryzae, Rhodotorula rubra, Scedosporium apiospernium, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin, Trichosporon mucoides.*

The methods herein include those wherein the disorder or disease is Aspergillosis, Blastomycosis, Candidiasis, Chromomycosis, Coccidioidomycosis, Cryptococcosis, Dermatophytoses, Histoplasmosis, Keratomycosis, Lobomycosis, *Malassezia* infection, Mucormycosis, Paracoccidioidomycosis, *Penicillium marneffei* infection, Phaeohyphomycosis, Pneumocystis pneumonia, or Rhinosporidiosis.

The methods herein include those wherein the disorder or disease is Chagas disease (Genus *Trypanosoma*), African trypanosomiasis (Genus *Trypanosoma*), leishmaniasis (Genus *Leishmania*), tuberculosis (Genus *Mycobacterium*), leprosy (Genus *Mycobacterium*), malaria (Genus *Plasmodium*), or tinea (capitis, corporis, pedis, tonsurans, versicolor).

In one aspect, the invention provides a method of treating a subject suffering from or susceptible to a metalloenzyme-related disorder or disease, comprising administering to the subject an effective amount of a compound or pharmaceutical composition of any of the formulae herein (e.g., formula I or formula II).

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any of the formulae herein (e.g., formula I or formula II), such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formula I or formula II), such that metalloenzyme activity in said subject is modulated (e.g., down regulated, inhibited).

The methods herein include those wherein the disease or disorder is mediated by any of 4-hydroxyphenyl pyruvate dioxygenase, 5-lipoxygenase, adenosine deaminase, alcohol dehydrogenase, aminopeptidase N, angiotensin converting enzyme, aromatase (CYP19), calcineurin, carbamoyl phosphate synthetase, carbonic anhydrase family, catechol o-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is mediated by any of 1-deoxy-d-xylulose-5-phosphate reductoisomerase (DXR), 17-alpha hydroxylase (CYP17), aldosterone synthase (CYP11B2), aminopeptidase P, anthrax lethal factor, arginase, beta-lactamase, cytochrome P450 2A6, d-ala d-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesterase VII, relaxase, retinoic acid hydroxylase (CYP26), TNF-alpha converting enzyme (TACE), UDP-(3-O—(R-3-hydroxymyristoyl))-N-acetyl-glucosamine deacetylase (LpxC), vascular adhesion protein-1 (VAP-1), or vitamin D hydroxylase (CYP24).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic fungal infection, skin structure fungal infection, mucosal fungal infection, or onychomycosis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another aspect of the invention is a composition comprising a compound of a formulae herein (e.g., formula (I) or formula (II)) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "arylalkenyl" refers to an unsaturated hydrocarbon chain that may be a straight chain or branched chain, containing 2 to 12 carbon atoms and at least one carbon-carbon double bond wherein one or more of the $sp^2$ hybridized carbons of the alkenyl unit attaches to an aryl moiety. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of treating a subject suffering from or susceptible to a disorder or disease, comprising administering to the subject an effective amount of a compound or pharmaceutical composition of any of the formulae herein (e.g., formula I or formula II).

In other aspects, the invention provides a method of treating a subject suffering from or susceptible to a disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formula I or formula II), such that said subject is treated for said disorder.

In one aspect, the invention provides a method of modulating the metalloenzyme activity of a cell in a subject, comprising contacting the subject with a compound of any of the formulae herein (e.g., formula I or formula II), in an amount and under conditions sufficient to modulate metalloenzyme activity.

In one embodiment, the modulation is inhibition.

In another aspect, the invention provides a method of treating a subject suffering from or susceptible to a metalloenzyme-mediated disorder or disease, comprising administering to the subject an effective amount of a compound or pharmaceutical composition of any of the formulae herein (e.g., formula I or formula II).

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formula I or formula II), such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is prostate cancer, breast cancer, inflammatory bowel disease, psoriasis, systemic fungal infection, skin structure fungal infection, mucosal fungal infection, and onychomycosis.

In certain embodiments, the subject is a mammal, preferably a primate or human.

In another embodiment, the invention provides a method as described above, wherein the effective amount of the compound of any of the formulae herein (e.g., formula I or formula II) is as described above.

In another embodiment, the invention provides a method as described above, wherein the compound of any of the formulae herein (e.g., formula I or formula II) is administered intravenously, intramuscularly, subcutaneously, intracerebroventricularly, orally or topically.

In another embodiment, the invention provides a method as described herein wherein the compound of any of the formulae herein (e.g., formula I or formula II) demonstrates selectivity for an activity range against a target enzyme (e.g., $C.$ $albicans$ MIC<1.0 µg/mL and $A.$ $fumigatus$ MIC≤64 µg/mL).

In other embodiments, the invention provides a method as described above, wherein the compound of any of the formulae herein (e.g., formula I or formula II) is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease.

Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of any of the formulae herein (e.g., formula I or formula II) and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of any of the formulae herein (e.g., formula I or formula II), in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

The compounds and compositions herein can be used in methods of modulating metalloenzyme activity in a microorganism on a plant comprising contacting a compound herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

One aspect is a method of treating or preventing a fungal disease or disorder in or on a plant comprising contacting a compound of any of the formulae herein with the plant. Another aspect is a method of treating or preventing fungi growth in or on a plant comprising contacting a compound of any of the formulae herein with the plant. Another aspect is a method of inhibiting microorganisms in or on a plant comprising contacting a compound of any of the formulae herein with the plant.

The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound any of the formulae herein (e.g., formula I or formula II); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Azoles

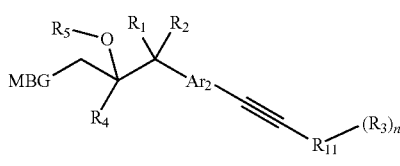

Syntheses of alkyne targets (I) may be accomplished using the example synthesis that is shown below (Scheme 1). A broad range of arenes and heterocycles ($R_{11}$=aryl or heteroaryl), may be prepared starting from aryl-bromides starting materials (e.g. 1). For the purpose of this example, $R_4$ is a halogenated benzene moiety. An example synthesis of targets (I) commences with condensation of 2,5-dibromo-pyridine with copper-activated ethyl α-bromo-acetate followed by condensation of the incipient ethyl ester product with lithiated bromodifluorobenzene to furnish ketone B (Scheme 1). The ketone is epoxidized with diazomethane to afford C. The 1-tetrazole product D (and 2-tetrazole isomer) is obtained by opening the epoxide C with tetrazole in the presence of potassium carbonate. The resultant pyridyl-bromide D is treated with phenyl-acetylenes to give coupled products (e.g. 1).

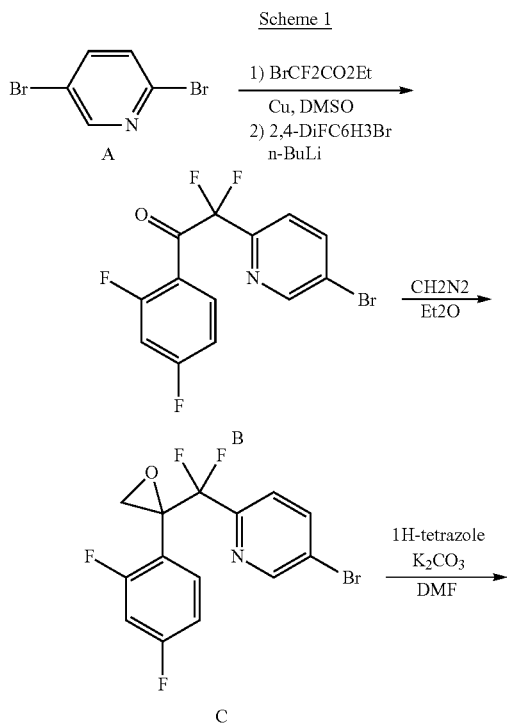

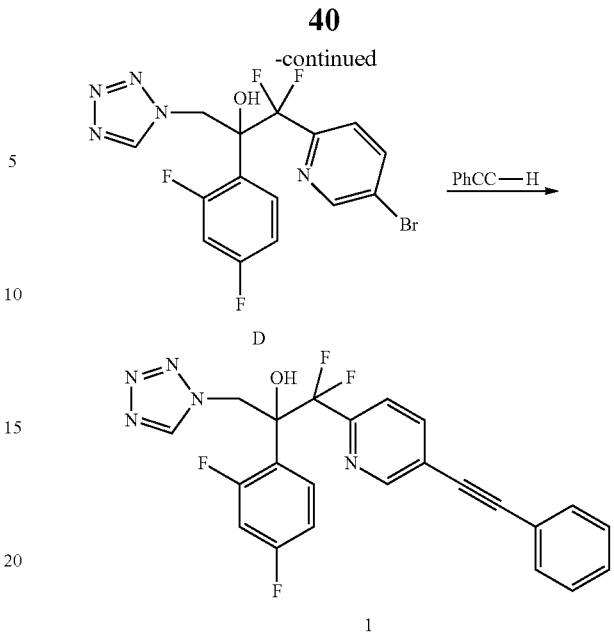

In embodiments, the invention provides for the intermediate compounds of the formulae delineated herein and methods of converting such compounds to compounds of the formulae herein (e.g., in Scheme 1, A to B; B to D; C to 1; or D to 1) comprising reacting a compound herein with one or more reagents in one or more chemical transformations (including those provided herein) to thereby provide the compound of any of the formulae herein or an intermediate compound thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula (e.g., in Scheme 1, A to B; B to D; C to 1; or D to 1). The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Example 1

2-(2,4-Difluorophenyl)-1,1-difluoro-1-(5-(phenylethynyl)pyridin-2-yl)-3-(1H-tetrazol-yl)propan-2-ol (1)

To a suspension of copper powder (2.68 g, 42.2 mmol) in DMSO (35 mL) was added ethyl bromodifluoroacetate (2.70 mL, 21.10 mmol), and the mixture was stirred for 1 h at RT. 2,5-Dibromopyridine (2.50 g, 10.55 mmol) was then added and continued stirring for 15 h at RT. The reaction was quenched with aqueous NH₄Cl and extracted with DCM (3×25 mL). The combined organic layers were washed with water, washed with brine, dried over anhydrous Na₂SO₄, and concentrated under reduced pressure to afford crude product mixture which upon column purification using EtOAc/hexane afforded the ethyl ester intermediate (2.40 g, 8.57 mmol, 81%) as a pale yellow oil. $^1$H NMR (500 MHz, CDCl$_3$): δ 8.71 (s, 1H), 8.00 (d, J=9.0 Hz, 1H), 7.64 (d, J=9.0 Hz, 1H), 4.42-4.35 (m, 2H), 1.39-1.31 (m, 3H).

To a stirred solution of 2,4-difluoro-bromobenzene (1.65 g, 8.57 mmol) in diethyl ether (10 mL) was added n-BuLi (3.70 mL, 8.57 mmol) at −70° C. followed by addition of ester (2.40 g, 8.57 mmol) in diethyl ether (5 mL) after 15 minutes. The reaction mixture was stirred for 1 h at −70° C. and warmed to room temperature at which point another 2 h stirring was employed. The reaction was quenched with aqueous NH$_4$Cl solution and extracted with ethyl acetate (3×20 mL). The combined organic layers were washed with water, washed with brine, dried over anhydrous Na$_2$SO$_4$, and concentrated under reduced pressure. The crude compound was purified by column chromatography to afford ketone B (1.30 g, 3.73 mmol, 43%) as yellow liquid. $^1$H NMR (500 MHz, CDCl$_3$): δ 8.62 (s, 1H), 8.08-8.04 (m, 2H), 7.74-7.70 (m, 1H), 7.05-6.95 (m, 1H), 6.88-6.78 (m, 1H). MS (ESI): 347, 349 [(M$^+$+1)+2].

To a stirred solution of ketone B (1.30 g, 3.73 mmol) in diethyl ether (300 mL) was added freshly prepared diazomethane at 0° C. followed by warming to RT. The reaction mixture was stirred for 2 h. The volatiles were removed under reduced pressure to afford a crude product mixture which upon column chromatography using EtOAc/hexane as the eluent afforded oxirane C (800 mg, 2.20 mmol, 59%) as light yellow solid. $^1$H NMR (500 MHz, CDCl$_3$): δ 8.72 (s, 1H), 7.89 (d, J=9.0 Hz, 1H), 7.39-7.35 (m, 2H), 6.86-6.83 (m, 1H), 6.77-6.74 (m, 1H), 3.44 (s, 1H), 2.98 (s, 1H). MS (ESI): 362, 364 [(M$^+$+1)+2].

To a stirred solution of epoxide C (5 g, 13.8 mmol) in DMF (15 mL) was added K$_2$CO$_3$ (1.9 g, 13.87 mmol) followed by 1H-tetrazole (1.55 g, 20.72 mmol) at RT. The resulting reaction mixture was heated to 70° C. and stirred for 16 h. The progress of the reaction was monitored by TLC. The reaction was quenched with ice-cold water (50 mL) and extracted with ethyl acetate (3×50 mL). The combined organic layer was washed with water (30 mL), brine (30 mL) and dried over anhydrous Na$_2$SO$_4$ to obtain a crude product which was purified by silica gel column chromatography eluting with 40% EtOAc/hexane to afford 1-tetrazole product D (2.7 g, 6.24 mmol, 45.3%) as white solid. $^1$H NMR (500 MHz, CDCl$_3$): 8.73 (s, 1H), 8.62 (s, 1H), 7.95 (dd, J=2.0 Hz, 8.0 Hz, 1H), 7.46 (d, J=8.5 Hz, 1H), 7.31-7.28 (m, 1H), 6.86 (s, 1H), 6.77-6.73 (m, 1H), 6.70-6.66 (m, 1H), 5.60 (d, J=14.5 Hz, 1H), 5.11 (d, J=14.5 Hz, 1H).

Mass: m/z 433.3 [M$^+$+2]

To a stirred solution of compound D (100 mg, 0.23 mmol) in DMF (2 mL) were added phenyl acetylene (35 mg, 0.34 mmol) followed by TPP (6 mg, 0.023 mmol), Pd(PPh$_3$)$_2$Cl$_2$ (16 mg, 0.023 mmol), CuI (4 mg, 0.023 mmol) and Et$_3$N (5 mL) at RT and purged with argon for a period of 30 min and the stirring was continued for 16 h at RT. The reaction mixture was cooled to RT, filtered through a pad of celite and the filtrate was concentrated under reduced pressure. Thus obtained residue was diluted with water (50 mL) and extracted with ethyl acetate (2×50 mL). The combined organic layer was washed with water (15 mL), brine (15 mL), dried over anhydrous Na$_2$SO$_4$ and concentrated under reduced pressure to afford the crude product. The crude product was purified by silica gel column chromatography eluting with gradients of EtOAc/hexane to afford 1 (30 mg, 0.06 mmol, 28%) as off-white solid. $^1$H NMR (500 MHz, CDCl$_3$): δ 8.75 (s, 1H), 8.65 (s, 1H), 7.88 (dd, J=2.0 Hz, 8.5 Hz, 1H), 7.55-7.53 (m, 3H), 7.41-7.37 (m, 3H), 7.31-7.26 (m, 2H), 6.76-6.75 (m, 1H), 6.66-6.64 (m, 1H), 5.61 (d, J=14.0 Hz, 1H), 5.12 (d, J=14.0 Hz, 1H). HPLC: 96.4%. MS (ESI): m/z 453 [M$^+$+1].

Example 2

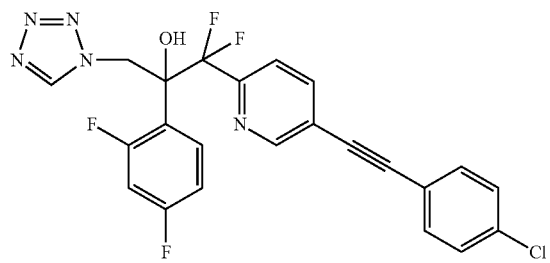

1-(5-((4-Chlorophenyl)ethynyl)pyridin-2-yl)-2-(2,4-difluorophenyl)-1,1-difluoro-3-(1H-tetrazol-1-yl)propan-2-ol (2)

To a stirred solution of compound D (100 mg, 0.231 mmol) in THF (5 mL) were added 4-chloro phenyl acetylene (47 mg, 0.345 mmol) followed by Pd(PPh$_3$)$_2$Cl$_2$ (16 mg, 0.023 mmol), CuI (4.4 mg, 0.023 mmol) and diisopropyl ethylamine (0.08 mL, 0.462 mmol) at RT under argon atmosphere. The resulting reaction mixture was stirred for 16 h at reflux temperature under argon atmosphere. The progress of the reaction was monitored by TLC and LC-MS. The reaction mixture was cooled to RT, filtered through a pad of celite and filtrate was concentrated under reduced pressure. The obtained residue was diluted with water (15 mL) and extracted with ethyl acetate (4×30 mL). The combined organic layer was washed with water (10 mL), dried over anhydrous Na$_2$SO$_4$ and concentrated under reduced pressure to afford the crude product. The crude product was purified by prep HPLC (mobile phase: CH$_3$CN:0.1% TFA in H$_2$O, gradient; flow Rate: 15.0 mL/min) to afford 2 (14 mg, 0.028 mmol, 12.5%) as pale yellow solid. $^1$H NMR (500 MHz, CDCl$_3$): δ 8.75 (s, 1H), 8.64 (s, 1H), 7.88 (d, J=8.5 Hz, 1H), 7.55 (d, J=8.5 Hz, 2H), 7.47 (d, J=9.0 Hz, 1H), 7.37 (d, J=8.5 Hz, 2H), 7.33-7.28 (m, 1H), 6.78-6.74 (m, 1H), 6.68-6.65 (m, 1H), 5.60 (d, J=14.5 Hz, 1H), 5.13 (d, J=14.5 Hz, 1H). HPLC: 99.5%. MS (ESI): m/z 488 [M$^+$+1].

Example 3

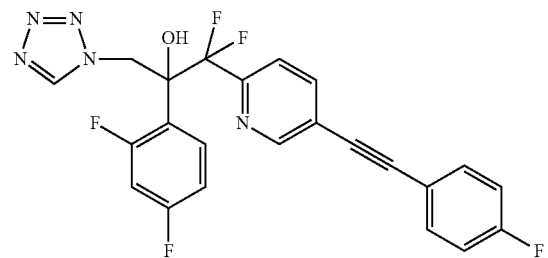

2-(2,4-Difluorophenyl)-1,1-difluoro-1-(5-((4-fluorophenyl)ethynyl)pyridin-2-yl)-3-(1H-tetrazol-1-yl)propan-2-ol (3)

To a stirred solution of compound D (250 mg, 0.578 mmol) in DMF (5 mL) were added 4-fluoro phenyl acetylene (104 mg, 0.868 mmol) followed by TPP (15 mg, 0.0578 mmol), CuI (11 mg, 0.0578 mmol) and Et₃N (16 mL) at RT and purged with argon for a period of 20 min. To the resulting reaction mixture was added Pd(PPh₃)₂Cl₂ (40 mg, 0.0578 mmol), again purged with argon for 20 min and stirred at RT. After 16 h, only 0.87% conversion was observed by LC-MS; the reaction mixture was then slowly heated to 60° C. and stirred for 6 h. After 6 h, the reaction mixture was cooled to RT, filtered through a pad of celite and filtrate was concentrated under reduced pressure. The obtained residue was diluted with water (50 mL) and extracted with ethyl acetate (3×40 mL). The combined organic layer was washed with water (2×15 mL), dried over anhydrous Na₂SO₄ and concentrated under reduced pressure to afford the crude product. The crude product was purified by silica gel column chromatography eluting with 35% EtOAc/hexane to afford 3 (25 mg, 0.053 mmol, 9.2%) as off-white solid. ¹H NMR (500 MHz, CDCl₃): δ 8.75 (s, 1H), 8.63 (s, 1H), 7.88 (d, J=8.0 Hz, 1H), 7.55-7.51 (m, 2H), 7.33-7.27 (m, 2H), 7.09 (t, J=8.0 Hz, 2H), 6.78-6.74 (m, 1H), 6.68-6.65 (m, 1H), 5.61 (d, J=14.5 Hz, 1H), 5.13 (d, J=14.5 Hz, 1H). HPLC: 92.97%. MS (ESI): m/z 472.4 [M⁺+1].

Example 4

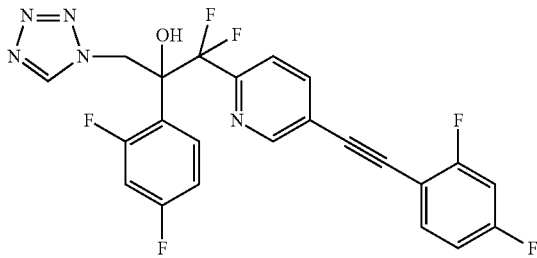

2-(2,4-Difluorophenyl)-1-(5-((2,4-difluorophenyl)ethynyl)pyridin-2-yl)-1,1-difluoro-3-(1H-tetrazol-1-yl)propan-2-ol (4)

To a stirred solution of compound D (100 mg, 0.231 mmol) in DMF (3 mL) were added 2,4-difluoro phenyl acetylene (47.9 mg, 0.347 mmol) followed by TPP (6 mg, 0.023 mmol), CuI (4.39 mg, 0.023 mmol) at RT and purged with argon for a period of 20 min. To the resulting reaction mixture was added Pd(PPh₃)₂Cl₂ (16.24 mg, 0.023 mmol) again purged with argon for 15 min and stirred for 16 h at RT. The reaction mixture was cooled to RT, filtered through a pad of celite and filtrate was concentrated under reduced pressure. The obtained residue was diluted with water (20 mL) and extracted with ethyl acetate (4×20 mL). The combined organic layer was washed with water (2×10 mL), dried over anhydrous Na₂SO₄ and concentrated under reduced pressure to afford the crude product. The crude product was purified by prep HPLC (mobile phase: (A) CH₃CN (B) 0.1% TFA in H₂O, isocratic: A:B=70:30; flow Rate: 15.0 mL/min) to afford 4 (18 mg, 0.036 mmol, 15.9%) as off-white solid. ¹H NMR (500 MHz, CDCl₃): δ 8.75 (s, 1H), 8.66 (s, 1H), 7.91 (dd, J=1.5 Hz, 8.0 Hz, 1H), 7.56 (d, J=8.0 Hz, 1H), 7.53-7.49 (m, 1H), 7.32-7.27 (m, 1H), 6.94-6.88 (m, 2H), 6.78-6.74 (m, 1H), 6.69-6.65 (m, 1H), 5.61 (d, J=14.0 Hz, 1H), 5.13 (d, J=14.0 Hz, 1H). HPLC: 99.7%. MS (ESI): m/z 490 [M⁺+1].

Example 5

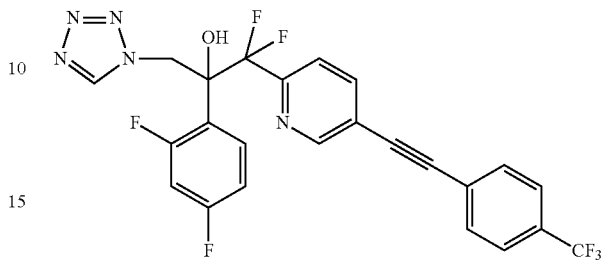

2-(2,4-Difluorophenyl)-1,1-difluoro-3-(1H-tetrazol-1-yl)-1-(5-((4-(trifluoromethyl)phenyl)ethynyl)pyridin-2-yl)propan-2-ol (5)

To a stirred solution of compound D (300 mg, 0.69 mmol) in DMF (5 mL) were added 4-(trifluoromethyl)phenyl acetylene (177 mg, 1.0 mmol) followed by TPP (18 mg, 0.069 mmol), CuI (13 mg, 0.069 mmol), Pd(PPh₃)₂Cl₂ (48 mg, 0.069 mmol) and Et₃N (10 mL) at RT and purged with argon for a period of 30 min. The resulting reaction mixture was stirred for 16 h at RT. The reaction mixture was cooled to RT, filtered through a pad of celite and the filtrate was concentrated under reduced pressure. The obtained residue was diluted with water (50 mL) and extracted with ethyl acetate (3×40 mL). The combined organic layer was washed with water (2×20 mL), brine (20 mL), dried over anhydrous Na₂SO₄ and concentrated under reduced pressure to afford the crude product. The crude product was purified by prep HPLC (mobile phase: CH₃CN:0.1% TFA in H₂O, gradient; flow Rate: 15.0 mL/min) to afford 5 (18 mg, 0.034 mmol, 5%) as pale yellow solid. ¹H NMR (500 MHz, CDCl₃): δ 8.75 (s, 1H), 8.66 (s, 1H), 7.92 (d, J=8.5 Hz, 1H), 7.65 (s, 3H), 7.53 (d, J=8.5 Hz, 1H), 7.34-7.29 (m, 1H), 6.78-6.74 (m, 1H), 6.69-6.66 (m, 1H), 5.61 (d, J=14.5 Hz, 1H), 5.15 (d, J=14.5 Hz, 1H). HPLC: 99.3%. MS (ESI): m/z 522.3 [M⁺+1].

Scheme 2

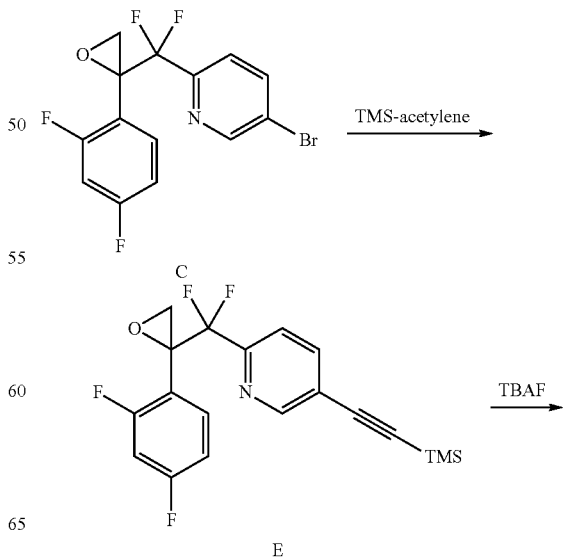

-continued

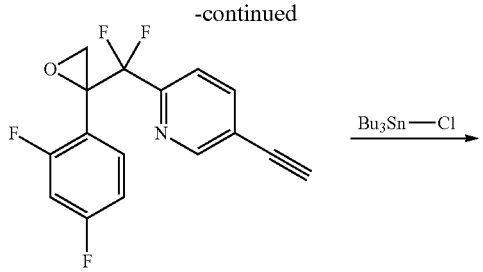

F

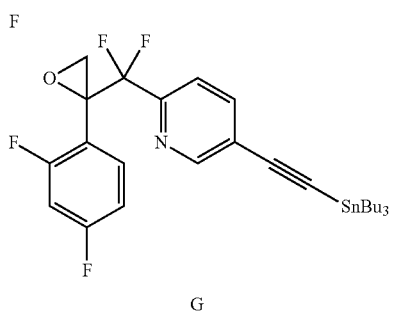

G

Preparation of Tributyltin Intermediate G

To a stirred solution of compound C (20.0 g, 55.24 mmol) in THF (300 mL) were added TMS-acetylene (10.3 mL, 82.87 mmol) followed by CuI (525 mg, 2.76 mmol), Pd(PPh$_3$)$_2$Cl$_2$ (1.93 g, 2.76 mmol) and Et$_3$N (20 mL) at RT under inert atmosphere and stirred for 16 h; progress of the reaction was monitored by TLC. The reaction mixture was filtered through a pad of celite and washed with EtOAc (3×100 mL). The filtrate was washed with water (150 mL), brine (150 mL), dried over anhydrous Na$_2$SO$_4$ and concentrated under reduced pressure to obtain the crude. The crude material was purified by silica gel column chromatography (eluent: 7% EtOAc/hexanes) to afford compound E (18.0 g, 47.5 mmol, 85%) as pale yellow solid. $^1$H NMR (400 MHz, CDCl$_3$): δ 8.69 (s, 1H), 7.78 (d, J=10.0 Hz, 1H), 7.76 (d, J=10.0 Hz, 1H), 7.37-7.31 (m, 1H), 6.85-6.80 (m, 1H), 6.76-6.71 (m, 1H), 3.45 (d, J=5.0 Hz, 1H), 2.96 (d, J=5.0 Hz, 1H), 0.26 (s, 9H). To a stirred solution of E (18.0 g, 47.5 mmol) in THF (200 mL) was added TBAF (52.2 mL, 52.25 mmol; 1M solution in THF) at 0° C. under inert atmosphere and stirred for 1 h; progress of the reaction was monitored by TLC. The volatiles were then evaporated under reduced pressure; the obtained residue was diluted with EtOAc (500 mL), washed with water (250 mL), brine (250 mL), dried over anhydrous Na$_2$SO$_4$ and concentrated under reduced pressure to obtain the crude. The crude material was purified by silica gel column chromatography (eluent: 8-10% EtOAc/hexanes) to afford compound F (9.0 g, 29.31 mmol, 61.7%) as pale yellow solid. $^1$H NMR (400 MHz, CDCl$_3$): δ 8.73 (d, J=1.5 Hz, 1H), 7.82 (dd, J=8.0, 1.5 Hz, 1H), 7.44 (d, J=8.0 Hz, 1H), 7.38-7.34 (m, 1H), 6.85-6.81 (m, 1H), 6.76-6.72 (m, 1H), 3.44 (d, J=5.0 Hz, 1H), 3.31 (s, 1H), 2.97 (d, J=5.0 Hz, 1H).

To a stirred solution of compound F (9.0 g, 29.31 mmol) in Et$_2$O (200 mL) was added n-BuLi (22.0 mL, 35.18 mmol; 1.6M in hexane) at −78° C. under inert atmosphere. After being stirred at −78° C. for 30 min, n-Bu$_3$SnCl (11.9 mL, 43.97 mmol) was added. The reaction mixture was allowed to warm to RT and stirred for 16 h. The progress of the reaction was monitored by TLC. The reaction mixture was quenched with saturated NH$_4$Cl solution, extracted with EtOAc (2×200 mL). The combined organic extracts were washed with water (150 mL), brine (150 mL), dried over anhydrous Na$_2$SO$_4$ and concentrated under reduced pressure to obtain the crude-G (20.0 g). The crude was used for the next reaction without further purification.

Scheme 3

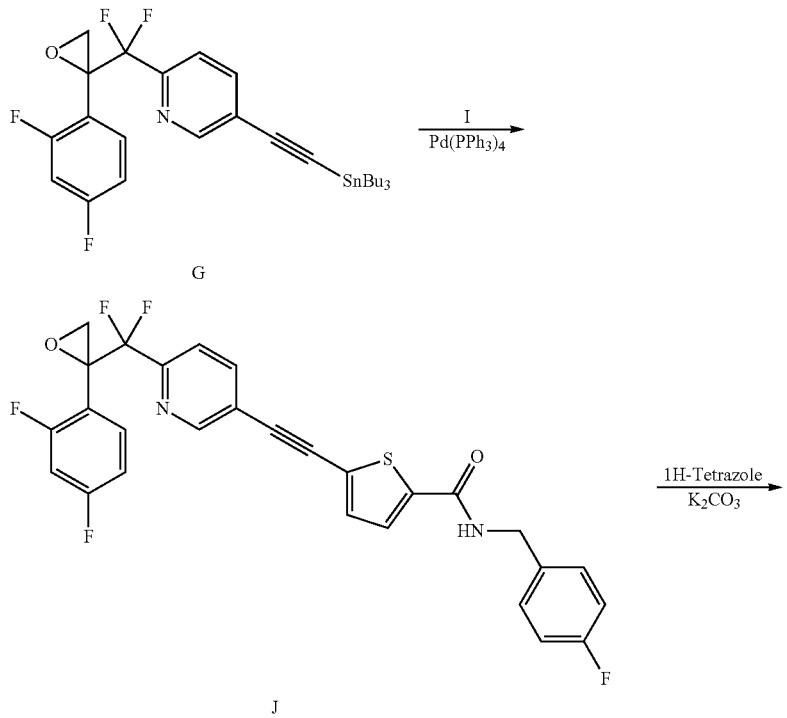

-continued

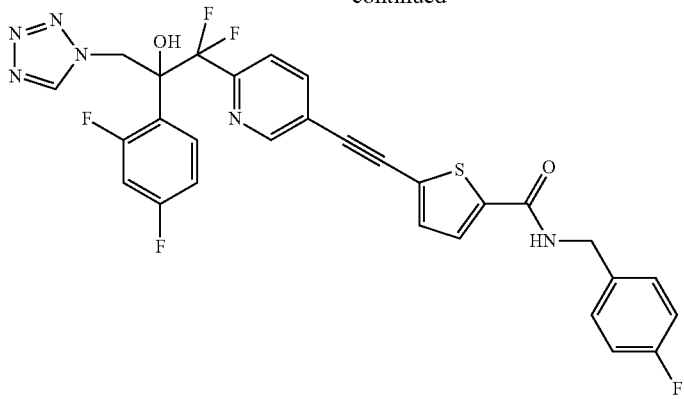

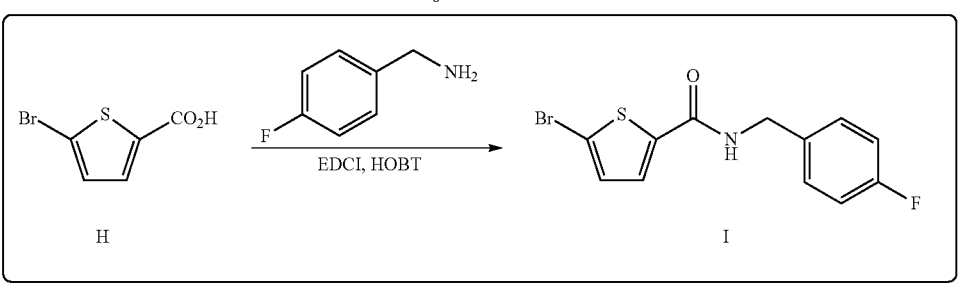

Example 6

5-((6-(2-(2,4-difluorophenyl)-1,1-difluoro-2-hydroxy-3-(1H-tetrazol-1-yl)propyl)pyridin-3-yl)ethynyl)-N-(4-fluorobenzyl)thiophene-2-carboxamide (6)

To a stirred solution of acid-H (1.50 g, 7.24 mmol) in DMF (20 mL) was added 4-fluoro benzyl amine (1.35 g, 10.84 mmol) followed by HOBt (1.08 g, 7.95 mmol) and DIPEA (3 mL, 18.07 mmol) under inert atmosphere at RT and stirred for 5 min. Then, EDCI (1.52 g, 7.96 mmol) was added to the reaction mixture and continued stirring for 16 h; progress of the reaction was monitored by TLC. The reaction mixture was then diluted with EtOAc (100 mL) and washed with 0.1N HCl (100 mL). The separated organic layer was washed with saturated $NaHCO_3$ solution (100 mL), brine (100 mL), dried over anhydrous $Na_2SO_4$ and concentrated under reduced pressure to obtain the crude. The crude material was purified by silica gel column chromatography (eluent: 20% EtOAc/hexane) to afford the amide-I (1.5 g, 4.77 mmol, 66%) as colorless oil. $^1$H NMR (400 MHz, $CDCl_3$): δ 7.31-7.28 (m, 2H), 7.23 (d, J=4.0 Hz, 1H), 7.05-6.99 (m, 3H), 6.21 (bs, 1H), 4.55 (d, J=5.6 Hz, 2H).

To a stirred solution of compound G (4.0 g, crude) in 1,4-dioxane (20 mL) was added compound I (600 mg, 1.91 mmol) followed by purge with argon for 20 min. $Pd(PPh_3)_4$ (434 mg, 0.37 mmol) was then added to the mixture at RT and purged with argon for another 20 min. The reaction mixture was gradually heated up to 80° C. and stirred for 3 h; progress of the reaction was monitored by TLC. The reaction mixture was allowed to cool to RT and the volatiles were evaporated under reduced pressure to afford the compound J (1.0 g, crude). The crude compound was used for the next reaction without further purification. $^1$H NMR (400 MHz, $CDCl_3$): δ 8.76 (s, 1H), 7.85 (dd, J=8.0, 2.0 Hz, 1H), 7.47 (d, J=8.0, Hz, 1H), 7.40-7.31 (m, 4H), 7.27 (d, J=4.0 Hz, 1H), 7.06-7.02 (m, 2H), 6.86-6.81 (m, 1H), 6.77-6.71 (m, 1H), 6.25 (t, J=5.6 Hz, 1H), 4.59 (d, J=5.6 Hz, 2H), 3.47 (d, J=5.0 Hz, 1H), 2.98 (d, J=5.0 Hz, 1H). LC-MS (ESI): m/z 540.0 [M]$^+$ at 4.28 RT (86% pure).

To a stirred solution of epoxide J (1.0 g, crude) in dry DMF (10 mL) was added 1H-tetrazole (194 mg, 2.77 mmol) followed by $K_2CO_3$ (255 mg, 1.85 mmol) at RT under inert atmosphere. The resulting reaction mixture was gradually heated up to 65° C. and stirred for 16 h; progress of the reaction was monitored by TLC. The reaction mixture was diluted with ice-cold water (100 mL) and extracted with EtOAc (2×100 mL). The combined organic extracts were washed with water (50 mL), brine (50 mL), dried over anhydrous $Na_2SO_4$ and concentrated under reduced pressure to obtain the crude. The crude material was purified by silica gel column chromatography (eluted with 45-50% EtOAc/hexanes) to afford 6 (500 mg, 0.82 mmol) as pale yellow solid. $^1$H-NMR (400 MHz, $CDCl_3$): δ 8.74 (s, 1H), 8.64 (s, 1H), 7.89 (dd, J=8.4, 2.0 Hz, 1H), 7.56 (d, J=8.4 Hz, 1H), 7.38 (d, J=4.0 Hz, 1H), 7.35-7.27 (m, 4H), 7.14 (bs, OH), 7.05 (t, J=8.4 Hz, 2H), 6.79-6.73 (m, 1H), 6.69-6.64 (m, 1H), 6.22 (t, J=5.6 Hz, 1H), 5.59 (d, J=14.0 Hz, 1H), 5.14 (d, J=14.0 Hz, 1H), 4.60 (d, J=5.6 Hz, 2H).

Chiral Preparative HPLC Method for the Separation of 6-Enantiomers:

The racemate-6 (303 mg, 0.49 mmol) was separated by preparative high performance liquid chromatography (CHIRALPAK IA, 250×20 mm, 5μ; using (A) n-Hexane, (B) EtOH (A:B, 75:25) as a mobile phase; Flow rate: 15 mL/min) to obtain 6-(+) (100 mg) as off-white solid.

Analytical Data for 6-(+):

Chiral HPLC Purity: 98.5% ee $R_t$=20.22 min (CHIRALPAK IA, 250×4.6 mm, 5μ; mobile phase (A) n-Hexane, (B) EtOH (A:B::75:25); flow Rate: 1.00 mL/min).

Optical rotation $[α]_D^{20}$: +19.76° (c=0.1% in MeOH).

$^1$H-NMR (400 MHz, $CDCl_3$): δ 8.74 (s, 1H), 8.64 (s, 1H), 7.89 (dd, J=8.4, 2.0 Hz, 1H), 7.56 (d, J=8.4 Hz, 1H), 7.38 (d, J=4.0 Hz, 1H), 7.35-7.27 (m, 4H), 7.14 (bs, OH), 7.05 (t, J=8.4 Hz, 2H), 6.79-6.73 (m, 1H), 6.69-6.64 (m, 1H), 6.22 (t,

J=5.6 Hz, 1H), 5.59 (d, J=14.0 Hz, 1H), 5.14 (d, J=14.0 Hz, 1H), 4.60 (d, J=5.6 Hz, 2H). Mass: m/z 611 [M+H]$^+$. HPLC: 98.5%.

3 h; progress of the reaction was monitored by TLC. The reaction mixture was cooled to RT, diluted with ice-cold water (100 mL) and extracted with EtOAc (2×100 mL). The

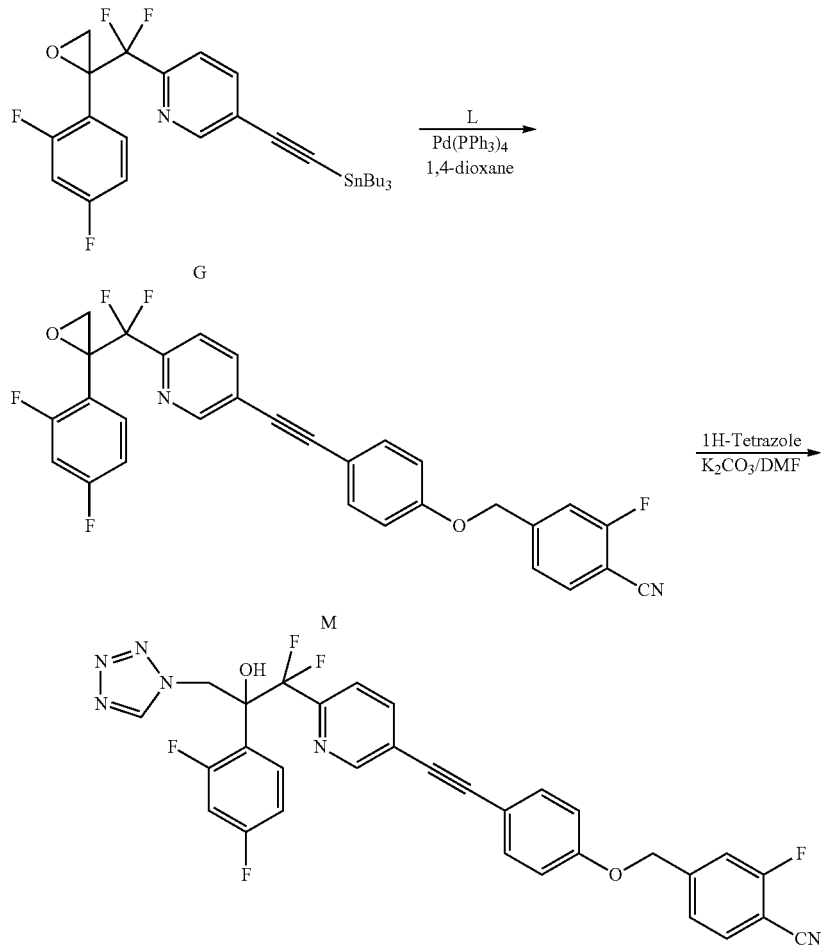

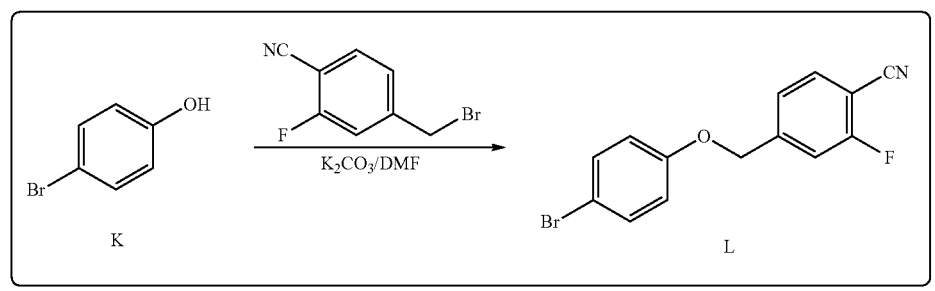

Example 7

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)-2-fluorobenzonitrile (7)

To a stirred solution of 4-bromophenol (K) (1.0 g, 5.78 mmol) in DMF (10 mL) were added K$_2$CO$_3$ (1.6 g, 11.56 mmol) followed by 4-cyano-3-fluoro benzyl bromide (1.36 g, 6.36 mmol) at RT under inert atmosphere. The resulting reaction mixture was gradually heated up to 70° C. and stirred for combined organic layers were washed with water (2×50 mL), brine (100 mL), dried over anhydrous Na$_2$SO$_4$ and concentrated under reduced pressure to obtain the crude. The crude compound was purified by silica gel column chromatography (eluent: 15% EtOAc/Hexanes) to afford L (1.2 g, 3.93 mmol, 68%) as brown solid. $^1$H NMR (400 MHz, CDCl$_3$): δ 7.66-7.62 (m, 1H), 7.41 (d, J=6.8 Hz, 2H), 7.32-7.29 (m, 2H), 6.82 (d, J=6.8 Hz, 2H), 5.09 (s, 2H). LC-MS: m/z 304.7 [M−H]$^-$ at 4.80 RT (75.9% pure).

To a stirred solution of compound G (3.0 g, crude) in 1,4-dioxane (15 mL) was added L (1.2 g, 3.93 mmol) and purged with inert gas for 15 min. To the resulting reaction mixture was added Pd(PPh$_3$)$_4$ (291 mg, 0.25 mmol) and purged for another 10 min. The reaction mixture was then gradually heated up to 90° C. and stirred for 3 h; progress of the reaction was monitored by TLC. The reaction mixture was then cooled to RT; volatiles were evaporated under reduced pressure to obtain the crude. The crude material was purified by silica gel column chromatography (eluent: 18% EtOAc/hexanes) to afford M (0.7 g, crude) as yellow solid. $^1$H NMR (400 MHz, CDCl$_3$): δ 8.77 (s, 1H), 7.85 (d, J=8.0 Hz, 1H), 7.68 (dd, J=8.4, 1.6 Hz, 1H), 7.53 (d, J=6.8 Hz, 2H), 7.46 (d, J=8.0 Hz, 1H), 7.41-7.33 (m, 3H), 6.97 (d, J=6.8 Hz, 2H), 6.88-6.83 (m, 1H), 6.77-6.71 (m, 1H), 5.17 (s, 2H), 3.48 (d, J=5.2 Hz, 1H), 3.00 (d, J=5.2 Hz, 1H). LCMS: m/z 533.9 [M+H]$^+$ at 5.29 RT (89.0% pure).

To a stirred solution of M (0.7 g, crude) in DMF (7 mL) were added 1H-tetrazole (138 mg, 1.97 mmol) followed by K$_2$CO$_3$ (181 mg, 1.31 mmol) at RT under inert atmosphere. The resulting reaction mixture was gradually heated up to 65° C. and stirred for 7 h; progress of the reaction was monitored by TLC. The reaction mixture was cooled to RT; diluted with ice-cold water (50 mL) and extracted with EtOAc (2×50 mL). The combined organic layers were washed with water (2×50 mL), brine (50 mL), dried over anhydrous Na$_2$SO$_4$ and concentrated under reduced pressure to obtain the crude. The crude compound was purified by silica gel column chromatography (eluent: 40% EtOAc/hexanes) to afford 7 (350 mg, 0.58 mmol) as yellow solid. $^1$H NMR (500 MHz, CDCl$_3$): δ 8.75 (s, 1H), 8.62 (s, 1H), 7.86 (d, J=8.0 Hz, 1H), 7.67 (t, J=8.0 Hz, 1H), 7.53 (d, J=8.0 Hz, 1H), 7.50 (d, J=9.0 Hz, 2H), 7.34-7.32 (m, 4H), 6.95 (d, J=9.0 Hz, 2H), 6.77-6.75 (m, 1H), 6.67-6.65 (m, 1H), 5.59 (d, J=14.0 Hz, 1H), 5.15 (s, 2H), 5.12 (d, J=14.0 Hz, 1H).

Chiral Preparative HPLC Method for the Separation of Enantiomers of 7:

The enantiomers of 7 (35 mg) were separated by normal-phase preparative high performance liquid chromatography (CHIRALPAK IC, 250×20 mm, 5μ; using (A) 0.1% TEA in n-hexane, (B) Ethanol (A:B::70:30) as a mobile phase; Flow rate: 15 mL/min) to obtain 7-(+) (15 mg) as off-white solid.

Analytical Data for 7-(+):

Chiral HPLC: 100% ee R$_t$=27.72 min (Chiralpak IC, 250× 4.6 mm, 5μ; mobile phase (A) 0.1% TEA in n-Hexane, (B) Ethanol (A:B::70:30); flow Rate: 1.00 mL/min)

Optical rotation [α]$_D^{20}$: +29.80° (c=0.1% in MeOH).

$^1$H NMR (500 MHz, CDCl$_3$): δ 8.75 (s, 1H), 8.62 (s, 1H), 7.86 (d, J=8.0 Hz, 1H), 7.67 (t, J=8.0 Hz, 1H), 7.53 (d, J=8.0 Hz, 1H), 7.50 (d, J=9.0 Hz, 2H), 7.34-7.32 (m, 4H), 6.95 (d, J=9.0 Hz, 2H), 6.77-6.75 (m, 1H), 6.67-6.65 (m, 1H), 5.59 (d, J=14.0 Hz, 1H), 5.15 (s, 2H), 5.12 (d, J=14.0 Hz, 1H). MS (ESI): 603 [M+H]$^+$. HPLC: 99.0%.

Scheme 5

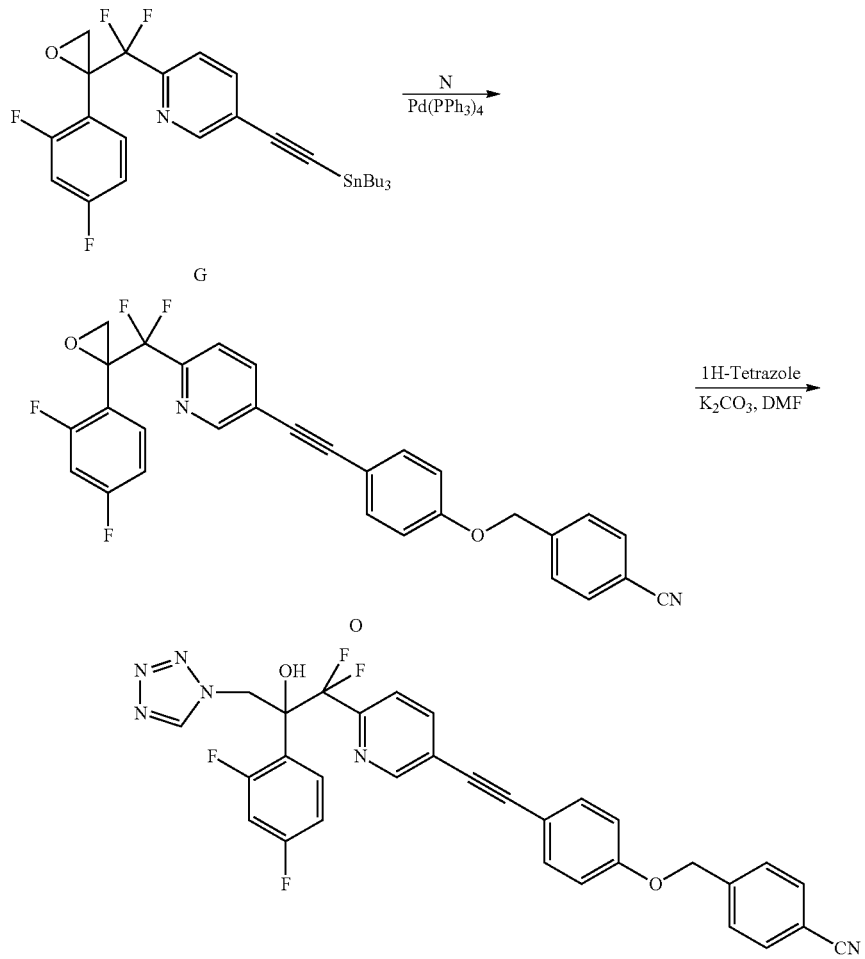

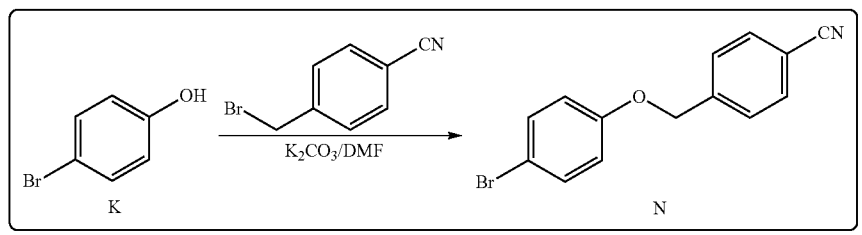

Example 8

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (8)

To a stirred solution of 4-bromophenol (K) (2.9 g, 14.45 mmol) in DMF (20 mL) was added $K_2CO_3$ (4.0 g, 28.90 mmol) followed by 4-cyano benzyl bromide (3.4 g, 17.34 mmol) under inert atmosphere at RT. The mixture was gradually heated up to 80° C. and stirred for 1 h; progress of the reaction was monitored by TLC. The reaction mixture was cooled to RT, quenched with ice-cold water (100 mL), extracted with EtOAc (2×100 mL). The combined organic layers were washed with water (100 mL), brine (100 mL), dried over anhydrous $Na_2SO_4$ and concentrated under reduced pressure to obtain the crude. The crude material was purified by silica gel column chromatography (eluent: 5% EtOAc/hexane) to afford the compound N (2.9 g, 10.06 mmol, 71%) as colorless liquid. $^1H$ NMR (400 MHz, $CDCl_3$): δ 7.68 (d, J=8.4 Hz, 2H), 7.52 (d, J=8.4 Hz, 2H), 7.39 (d, J=9.2 Hz, 2H), 6.83 (d, J=9.2 Hz, 2H), 5.09 (s, 2H).

To a stirred solution of compound G (3.5 g, crude) in 1,4-dioxane (20 mL) was added compound N (2.7 g, 9.39 mmol) and purged with argon for 20 min. $Pd(PPh_3)_4$ (678 mg, 0.58 mmol) was added to the mixture at RT and purged with argon for another 20 min. The reaction mixture was gradually heated up to 80° C. and stirred for 3 h; progress of the reaction was monitored by TLC. The reaction mixture was allowed to cool to RT and the volatiles were evaporated under reduced pressure to afford the compound O (800 mg, crude). The crude was used for the next reaction without further purification. $^1H$ NMR (500 MHz, $CDCl_3$): δ 8.74 (s, 1H), 7.81 (d, J=8.0 Hz, 1H), 7.69 (d, J=8.0 Hz, 2H), 7.55 (d, J=8.0 Hz, 2H), 7.51 (d, J=9.0 Hz, 2H), 7.44 (d, J=8.0 Hz, 1H), 7.39-7.35 (m, 1H), 6.96 (d, J=9.0 Hz, 2H), 6.85-6.82 (m, 1H), 6.76-6.72 (m, 1H), 5.16 (s, 2H), 3.47 (d, J=5.0 Hz, 1H), 2.98 (d, J=5.0 Hz, 1H). Mass (ESI): m/z 515 $[M+H]^+$.

To a stirred solution of epoxide O (800 mg, crude) in dry DMF (10 mL) was added 1H-tetrazole (163 mg, 2.33 mmol) followed by $K_2CO_3$ (215 mg, 1.55 mmol) at RT under inert atmosphere. The resulting reaction mixture was gradually heated up to 65° C. and stirred for 16 h; the progress of the reaction was monitored by TLC. The reaction mixture was diluted with ice-cold water (50 mL) and extracted with EtOAc (2×50 mL). The combined organic extracts were washed with water (50 mL), brine (50 mL), dried over anhydrous $Na_2SO_4$ and concentrated under reduced pressure to obtain the crude. The crude material was purified by silica gel column chromatography (eluted with 40-45% EtOAc/hexanes) to afford 8 (360 mg, 0.61 mmol, 39.5%) as yellow solid. $^1H$-NMR (400 MHz, $CDCl_3$): δ 8.76 (s, 1H), 8.62 (s, 1H), 7.84 (d, J=8.0 Hz, 1H), 7.70 (d, J=8.0 Hz, 2H), 7.69-7.51 (m, 3H), 7.47 (d, J=7.5 Hz, 2H), 7.33-7.27 (m, 2H), 6.96 (d, J=7.5 Hz, 2H), 6.78-6.73 (m, 1H), 6.69-6.64 (m, 1H), 5.60 (d, J=14.0 Hz, 1H), 5.16 (s, 2H), 5.12 (d, J=14.0 Hz, 1H).

Chiral Preparative HPLC Method for the Separation of 8 Enantiomers (Preparation of 8 (+)):

The enantiomers of 8 (300 mg, 0.51 mmol) were separated by preparative high performance liquid chromatography (CHIRALPAK IC®, 250×20 mm, 5µ; using (A) 0.1% DEA in n-Hexane, (B) EtOH (A:B::60:40) as a mobile phase; Flow rate: 15 mL/min) to obtain 8-(+) (115 mg) as off-white solid.

Analytical Data for 8-(+):

$^1H$-NMR (400 MHz, $CDCl_3$): δ 8.76 (s, 1H), 8.62 (s, 1H), 7.84 (d, J=8.0 Hz, 1H), 7.70 (d, J=8.0 Hz, 2H), 7.69-7.51 (m, 3H), 7.47 (d, J=7.5 Hz, 2H), 7.33-7.27 (m, 2H), 6.96 (d, J=7.5 Hz, 2H), 6.78-6.73 (m, 1H), 6.69-6.64 (m, 1H), 5.60 (d, J=14.0 Hz, 1H), 5.16 (s, 2H), 5.12 (d, J=14.0 Hz, 1H).

Chiral HPLC Purity: 99.74% ee $R_t$=18.11 min (CHIRALPAK IC®, 250×4.6 mm, 5µ; mobile phase (A) 0.1% DEA in n-hexane, (B) EtOH (A:B::60:40); flow Rate: 1.00 mL/min).

Optical rotation $[α]_D^{20}$: +27.00° (c=0.1% in MeOH). Mass: m/z 585 $[M+H]^+$. HPLC: 98.7%.

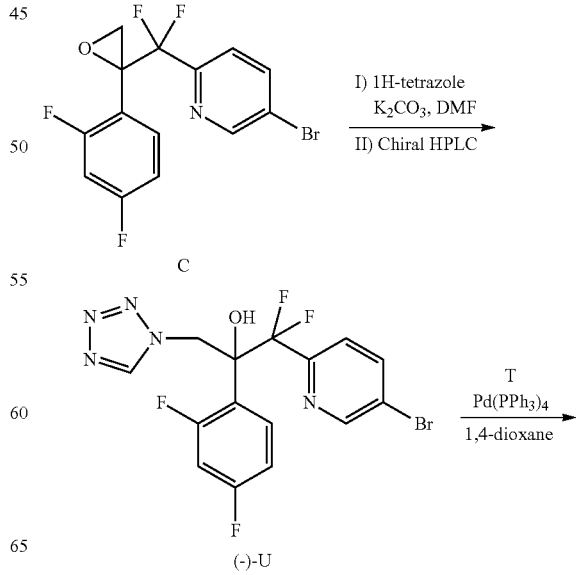

Scheme 6

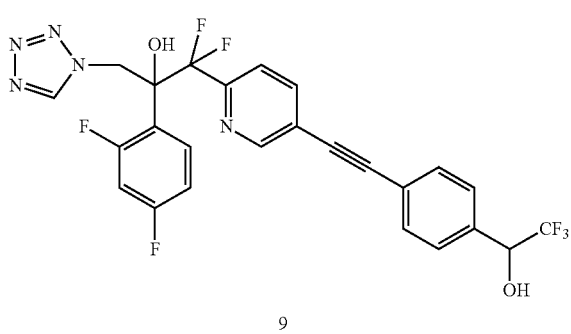

9

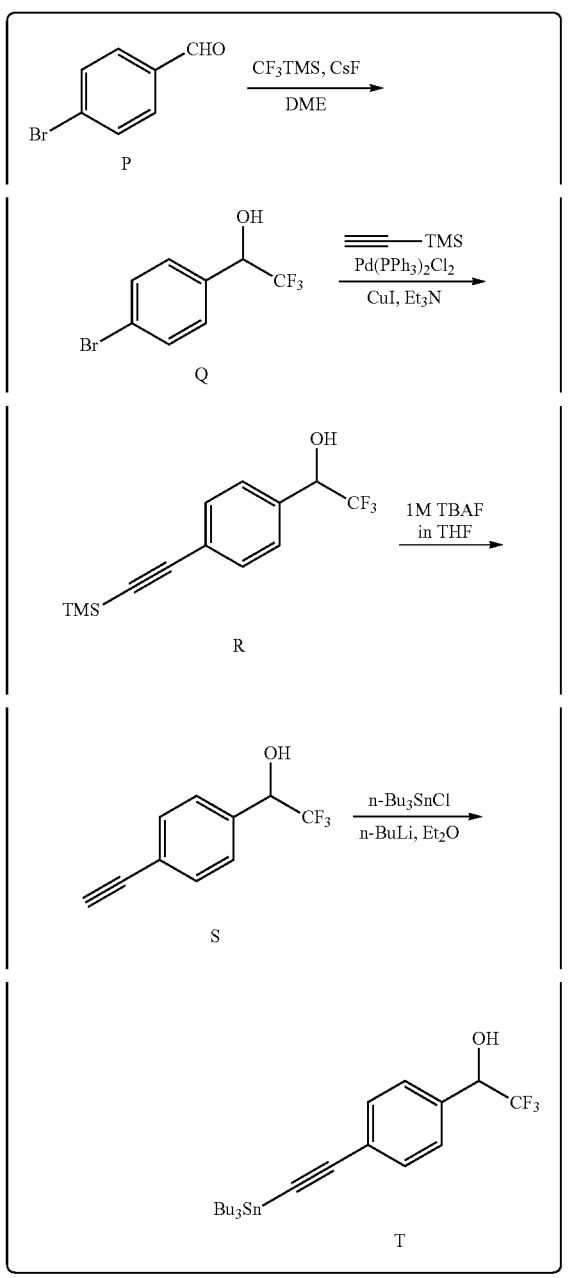

Example 9

2-(2,4-difluorophenyl)-1,1-difluoro-3-(1H-tetrazol-1-yl)-1-(5-((4-(2,2,2-trifluoro-1-hydroxyethyl)phenyl)ethynyl)pyridin-2-yl)propan-2-ol (9)

To a stirred solution of 4-bromobenzaldehyde (P) (2.0 g, 10.81 mmol) in DME (20 mL) were added CF$_3$TMS (1.4 mL, 16.2 mmol) and CsF (1.64 g, 10.81 mmol) at 0° C. under inert atmosphere. The resulting reaction mixture was stirred for 16 h at RT; progress of the reaction was monitored by TLC. The reaction mixture was then quenched with 1N aq. HCl (8 mL) and stirring was continued for another 1 h at RT. The volatiles were evaporated under reduced pressure; the residue was diluted with water (100 mL) and extracted with DCM (2×100 mL). The combined organic layer was washed with water (100 mL), dried over anhydrous Na$_2$SO$_4$ and concentrated under reduced pressure to obtain the crude. The crude compound was purified by silica gel column chromatography (eluent: 5-6% EtOAc/hexanes) to afford Q (0.65 g, 2.54 mmol, 23.5%) as yellow syrup. $^1$H NMR (500 MHz, CDCl$_3$): δ 7.54 (d, J=9.0 Hz, 2H), 7.36 (d, J=9.0 Hz, 2H), 5.01-4.98 (m, 1H), 2.87 (bs, OH).

To a stirred solution of Q (0.45 g, 1.76 mmol) in Et$_3$N (5 mL) were added TMS-acetylene (0.33 mL, 2.65 mmol), Pd(PPh$_3$)$_2$Cl$_2$ (41 mg, 0.035 mmol) and CuI (11 mg, 0.053 mmol) at RT under inert atmosphere. The resulting reaction mixture was gradually heated up to 75° C. stirred for 16 h; progress of the reaction was monitored by TLC. The reaction mixture was then cooled to RT, diluted with water (50 mL) and extracted with Et$_2$O (2×50 mL). The combined organic layer was washed with brine (50 mL), dried over anhydrous Na$_2$SO$_4$ and concentrated under reduced pressure to obtain the crude. The crude material was purified by silica gel column chromatography (eluent: 5% EtOAc/hexane) to afford R (0.4 g, 1.47 mmol, 83%) as brown syrup. $^1$H NMR (400 MHz, CDCl$_3$): δ 7.56 (d, J=8.8 Hz, 2H), 7.37 (d, J=8.8 Hz, 2H), 5.04-5.01 (m, 1H), 2.68 (bs, OH), 0.26 (s, 9H).

To a stirred solution of compound R (0.4 g, 1.47 mmol) in THF (3 mL) was added TBAF (1.5 mL, 1.47 mmol, 1M in THF) drop wise at 0° C. and stirred for 1 h; progress of the reaction was monitored by TLC. The volatiles were evaporated under reduced pressure to obtain the crude. The crude material was purified by silica gel column chromatography (eluent: 5% EtOAc/Hexane) to afford S (0.25 g, 1.25 mmol, 85%) as brown syrup. $^1$H NMR (500 MHz, CDCl$_3$): δ 7.53 (d, J=8.0 Hz, 2H), 7.36 (d, J=8.0 Hz, 2H), 5.04-5.02 (m, 1H), 3.11 (s, 1H), 2.62 (bs, OH).

To a stirred solution of S (0.1 g, 0.5 mmol) in Et$_2$O (6 mL) was added n-BuLi (0.7 mL, 1.1 mmol; 1.6 M in hexane) at −78° C. under inert atmosphere. After being stirred for 45 min, n-Bu$_3$SnCl (0.27 mL, 1.0 mmol) was added drop wise and stirred for another 10 min at −78° C. The resulting reaction mixture was allowed to warm to RT and continued stirring for another 2 h; progress of the reaction was monitored by TLC. The reaction was then quenched with aqueous NH$_4$Cl (20 mL) and extracted with EtOAc (2×25 mL). The combined organic layers were washed with water (20 mL), brine (20 mL), dried over anhydrous Na$_2$SO$_4$ and concentrated under reduced pressure to afford T (0.3 g, crude) as yellow syrup. This was used for the next step without further purification.

To a stirred solution of compound C (10.0 g, 27.62 mmol) in DMF (20 mL) was added 1H-tetrazole (2.85 g, 41.43 mmol) followed by K$_2$CO$_3$ (3.81 g, 27.62 mmol) at RT. The resulting reaction mixture was gradually heated to 65° C. and stirred for 16 h; the progress of the reaction was monitored by TLC. The reaction was diluted with ice-cold water (250 mL) and extracted with EtOAc (2×250 mL). The combined organic layer was washed with water (200 mL), brine (200 mL), dried over anhydrous Na$_2$SO$_4$ and concentrated under reduced pressure to obtain a crude product. The crude material was purified by silica gel column chromatography (eluent: 40% EtOAc/hexanes) to afford U (5.20 g, 12.03 mmol, 43.5%) as pale yellow solid. $^1$H NMR (500 MHz, CDCl$_3$): δ 8.73 (s, 1H), 8.62 (s, 1H), 7.95 (dd, J=8.0, 2.0 Hz, 1H), 7.46 (d, J=8.0 Hz, 1H), 7.31-7.27 (m, 1H), 6.86 (s, OH), 6.77-6.73 (m, 1H), 6.70-6.66 (m, 1H), 5.60 (d, J=14.5 Hz, 1H), 5.11 (d, J=14.5 Hz, 1H).

Chiral Preparative HPLC Method for Separation of Enantiomers of U (Preparation of U (−)).

The enantiomers of U (5.20 g, 12.03 mmol) were separated by normal-phase preparative high performance liquid chromatography (CHIRALPAK IA, 250×20 mm, 5μ; using (A) n-Hexane, (B) EtOH (A:B::90:10) as a mobile phase; Flow rate: 15 mL/min) to obtain U-(−) (2.5 g) as off-white solid.

Analytical Data for U-(−):

Chiral HPLC: 99.46% ee R$_t$=20.05 min (Chiralpak IA, 250×4.6 mm, 5μ; mobile phase (A) n-hexane-(B) Ethanol (A:B:90:10); flow Rate: 1.00 mL/min).

Optical rotation $[\alpha]_D^{25}$: −16.48° (c=0.1% in MeOH).

$^1$H NMR (500 MHz, CDCl$_3$): δ 8.73 (s, 1H), 8.62 (s, 1H), 7.95 (dd, J=8.0, 2.0 Hz, 1H), 7.46 (d, J=8.0 Hz, 1H), 7.31-7.27 (m, 1H), 6.86 (s, OH), 6.77-6.73 (m, 1H), 6.70-6.66 (m, 1H), 5.60 (d, J=14.5 Hz, 1H), 5.11 (d, J=14.5 Hz, 1H). Mass: m/z 430 [M-2]$^-$. HPLC: 99.7%.

To a stirred solution of T (0.43 g, crude) in 1,4-dioxane (5 mL) was added U-(−) (0.18 g, 0.42 mmol) at RT and purged with argon for 5 min. To the resulting reaction mixture was added Pd(PPh$_3$)$_4$ (24 mg, 0.03 mmol) and purged with argon for another 10 min at RT. The resulting reaction mixture was gradually heated up to 90° C. and stirred for 2 h; progress of the reaction was monitored by TLC. The reaction mixture was then cooled to RT; the volatiles were evaporated under reduced pressure to obtain the crude. The crude material was purified by silica gel column chromatography (eluent: 40% EtOAc/hexane) to afford 9 (90 mg, crude) as brown solid.

Chiral Preparative HPLC Method for Separation of Enantiomers of U (Preparation of 9 (−)):

The enantiomers of 9 (35 mg) were separated by normal-phase preparative high performance liquid chromatography (CHIRALPAK IA, 250×20 mm, 5μ; using (A) 0.1% DEA in n-Hexane, (B) EtOH:MeOH (80:20) (A:B::80:20) as a mobile phase; Flow rate: 15 mL/min) to obtain 9 (−) (15 mg) as off-white solid.

Analytical Data for 9-(−):

Chiral HPLC: 100% ee R$_t$=19.56 min (Chiralpak IA, 250×4.6 mm, 5μ; mobile phase (A) 0.1% DEA in n-hexane-(B) EtOH:MeOH (80:20) (A:B::80:20); flow Rate: 1.00 mL/min)

Optical rotation $[\alpha]_D^{20}$: +2.16° (c=0.1% in MeOH).

$^1$H NMR (400 MHz, CDCl$_3$): δ 8.75 (s, 1H), 8.66 (s, 1H), 7.90 (d, J=8.4 Hz, 1H), 7.60-7.51 (m, 5H), 7.34-7.28 (m, 1H), 6.79-6.73 (m, 1H), 6.67-6.65 (m, 1H), 5.61 (d, J=14.4 Hz, 1H), 5.13 (d, J=14.4 Hz, 1H), 5.09-5.06 (m, 1H), 2.98 (bs, OH). Mass: m/z 552.1 [M+H]$^+$. HPLC: 99.5%.

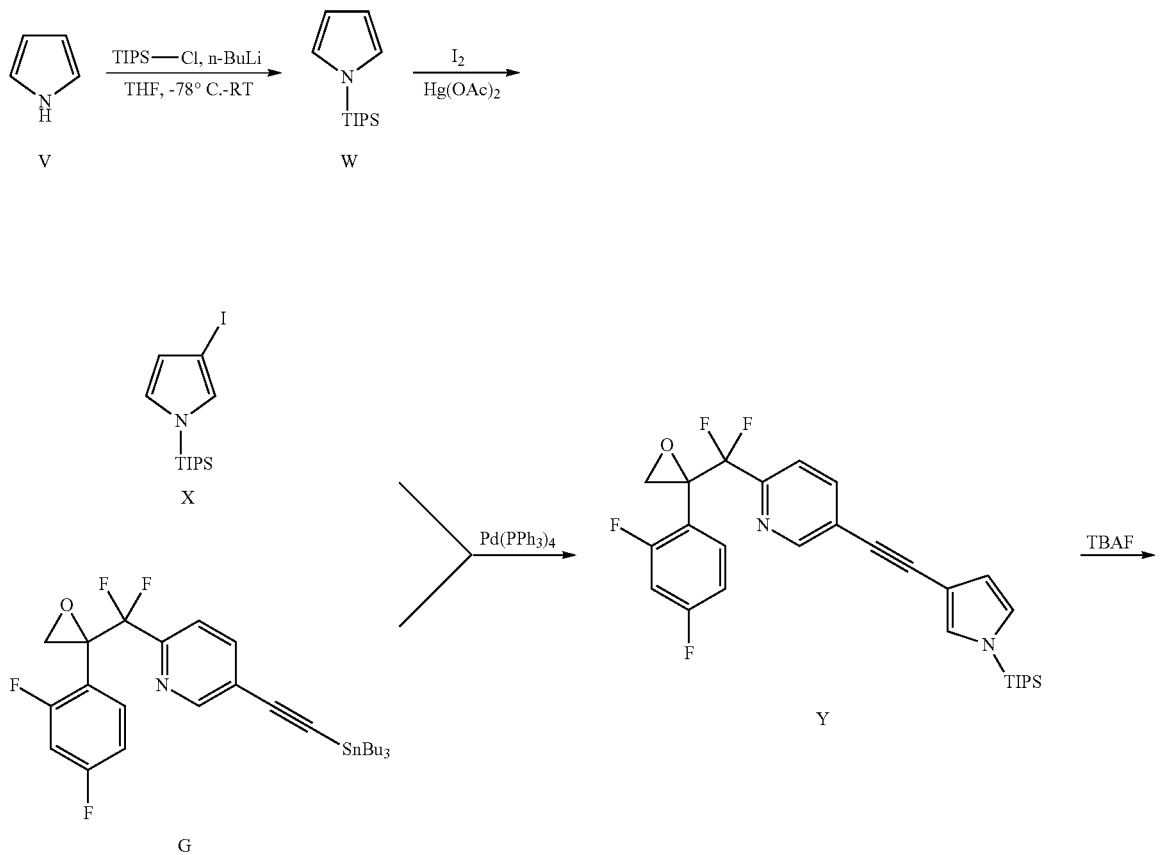

Scheme 7

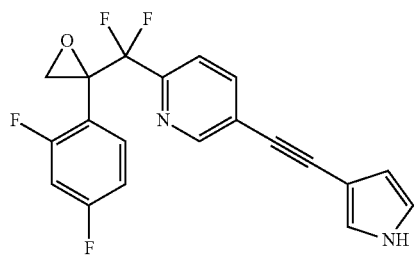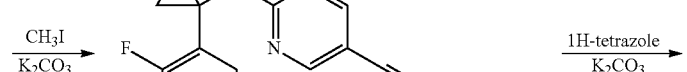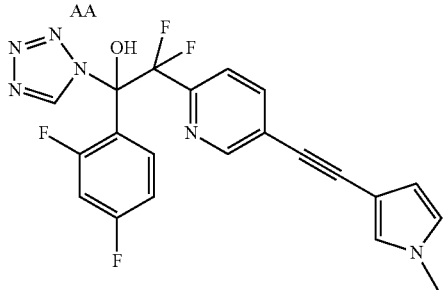

Example 10

2-(2,4-Difluorophenyl)-1,1-difluoro-1-(5-((1-methyl-1H-pyrrol-3-yl)ethynyl)pyridin-2-yl)-3-(1H-tetrazol-1-yl)propan-2-ol (10)

To a stirred solution of 1H-pyrrole (V) (3.0 g, 44.7 mmol) in THF (100 mL) was added n-BuLi (30.7 mL, 49.1 mmol; 1.6M solution in hexane) at −78° C. and maintained for 30 min at the same temperature under argon atmosphere. To the reaction mixture was added triisopropylsilyl chloride (9.56 mL, 44.7 mmol) at −78° C. and the resulting reaction mixture was allowed to warm to RT and then stirred for additional 30 min. After complete consumption of the starting material (monitored by TLC), the reaction mixture was quenched with saturated aq. NH$_4$Cl solution and then extracted with EtOAc (2×100 mL). The combined organic extracts were washed with water (100 mL), dried over anhydrous Na$_2$SO$_4$ and concentrated under reduced pressure to obtain W (6.5 g, 29.14 mmol, 65%) as a colorless syrup. $^1$H NMR (500 MHz, CDCl$_3$): δ 6.79 (s, 2H), 6.31 (s, 2H), 1.52-1.42 (m, 3H), 1.09 (d, J=7.5 Hz, 18H).

To a stirred solution of compound W (3.0 g, 13.45 mmol) and Hg(OAc)$_2$ (4.7 g, 14.84 mmol) in DCM (200 mL) was added a solution of Iodine (3.41 g, 13.45 mmol) in DCM (300 mL) drop wise over a period of 45 min at −25° C. and then maintained for 5 h at the same temperature under argon atmosphere. After complete consumption of the starting material (monitored by TLC), the reaction mixture was concentrated under reduced pressure to obtain crude X. The crude material was triturated with hexane (15 mL) and the obtained material (2.1 g) was directly taken for the next reaction without further purification. $^1$H NMR (500 MHz, CDCl$_3$): δ 6.64 (s, 1H), 6.36 (s, 1H), 6.31 (s, 1H), 1.53-1.25 (m, 3H), 1.09 (d, J=7.5 Hz, 18H).

To a stirred solution of epoxy tin compound G (1.0 g, crude) in 1,4-dioxane (20 mL) were added compound X (936 mg, crude) followed by Pd(PPh$_3$)$_4$ (193 mg, 0.167 mmol) at RT under intert atmosphere. The resulting solution was purged with argon gas for 15 min. The reaction mixture was slowly heated up to 90° C. and then maintained for 3 h. After complete consumption of the starting material (monitored by TLC), the reaction mixture was cooled to RT and concentrated under reduced pressure to obtain the crude. The crude material was purified by silica gel column chromatography (eluent: 5% EtOAc/hexane) to afford Y (90 mg) as a colorless semi solid. This compound contained some amount of tin impurities, which was directly taken for the next step without any further purification. LC-MS (ESI): m/z 529 [M+H]$^+$ at RT 6.06 min with 67.2% purity.

To a stirred solution of compound Y (600 mg, mixture) in THF (20 mL) was added TBAF (1.1 mL, 1.13 mmol) at 0° C. under inert atmosphere. The reaction mixture was allowed to warm to RT and maintained for 30 min. After complete consumption of the starting material (monitored by TLC), the reaction mixture was diluted with water (20 mL) and extracted with EtOAc (2×30 mL). The combined organic extracts were washed with water (40 mL), brine (40 mL), dried over anhydrous Na$_2$SO$_4$ and concentrated under reduced pressure to obtain the crude. The crude material was purified by silica gel column chromatography (15-20% EtOAc in Hexane gradient) to afford compound Z (200 mg, 0.53 mmol) as a pale yellow solid. $^1$H NMR (500 MHz, CDCl$_3$): δ 8.72 (s, 1H), 8.38 (s, NH), 7.78 (dd, J=8.5, 1.5 Hz, 1H), 7.40 (d, J=8.5 Hz, 1H), 7.38-7.33 (m, 1H), 7.13 (s, 1H), 6.84-6.71 (m, 3H), 6.43 (s, 1H), 3.46 (d, J=5.0 Hz, 1H), 2.97 (d, J=5.0 Hz, 1H). MS (EI): m/z 373 [M+H]$^+$.

To a stirred solution of compound Z (100 mg, 0.26 mmol) in ACN (10 mL) was added K$_2$CO$_3$ (111 mg, 0.80 mmol) at RT under inert atmosphere. After being stirred for 30 min, iodomethane (0.1 mL, 1.3 mmol) was added to the reaction mixture slowly at RT and the resulting reaction mixture was heated up to 80° C. and then stirred for 6 h. After complete consumption of the starting material (monitored by TLC), the reaction mixture was cooled to RT and concentrated under reduced pressure. The obtained residue was dissolved in EtOAc (25 mL), washed with water (20 mL), brine (20 mL), dried over anhydrous Na$_2$SO$_4$ and concentrated under reduced pressure to obtain the crude. The crude material was purified by silica gel column chromatography (10-15%

EtOAc in Hexane gradient) to afford compound AA (50 mg, 0.12 mmol, 48%) as a brown syrup. $^1$H NMR (500 MHz, CDCl$_3$): δ 8.70 (s, 1H), 7.76 (d, J=8.0 Hz, 1H), 7.39 (d, J=8.0 Hz, 1H), 7.36-7.33 (m, 1H), 6.93 (s, 1H), 6.84-6.81 (m, 1H), 6.75-6.71 (m, 1H), 6.56 (s, 1H), 6.33 (s, 1H), 3.67 (s, 3H), 3.46 (d, J=5.0 Hz, 1H), 2.97 (d, J=5.0 Hz, 1H). To a stirred solution of compound AA (100 mg, 0.25 mmol) in DMF (5 mL) was added K$_2$CO$_3$ (35 mg, 0.25 mmol) followed by 1H-tetrazole (27 mg, 0.38 mmol) at RT under inert atmosphere. The reaction mixture was then heated up to 65° C. and then stirred for 16 h. After complete consumption of the starting material (monitored by TLC), the reaction mixture was cooled to RT and concentrated under reduced pressure. The obtained residue was dissolved in EtOAc (30 mL), washed with water (20 mL), brine (20 mL), dried over anhydrous Na$_2$SO$_4$ and concentrated under reduced pressure to obtain the crude. The crude material was purified by silica gel column chromatography (eluent: 30-35% EtOAc in Hexane gradient) to afford 10 (23 mg, 0.05 mmol, 20%) as a colorless solid. $^1$H NMR (500 MHz, CDCl$_3$): δ 8.75 (s, 1H), 8.57 (s, 1H), 7.79 (dd, J=8.5, 1.5 Hz, 1H), 7.49 (s, OH), 7.48 (d, J=8.5 Hz, 1H), 7.30-7.27 (m, 1H), 6.92 (s, 1H), 6.76-6.72 (m, 1H), 6.66-6.63 (m, 1H), 6.56 (s, 1H), 6.31 (s, 1H), 5.63 (d, J=14.0 Hz, 1H), 5.08 (d, J=14.0 Hz, 1H), 3.67 (s, 3H). MS (EI): m/z 457 [M+H]$^+$. HPLC: 97.17%.

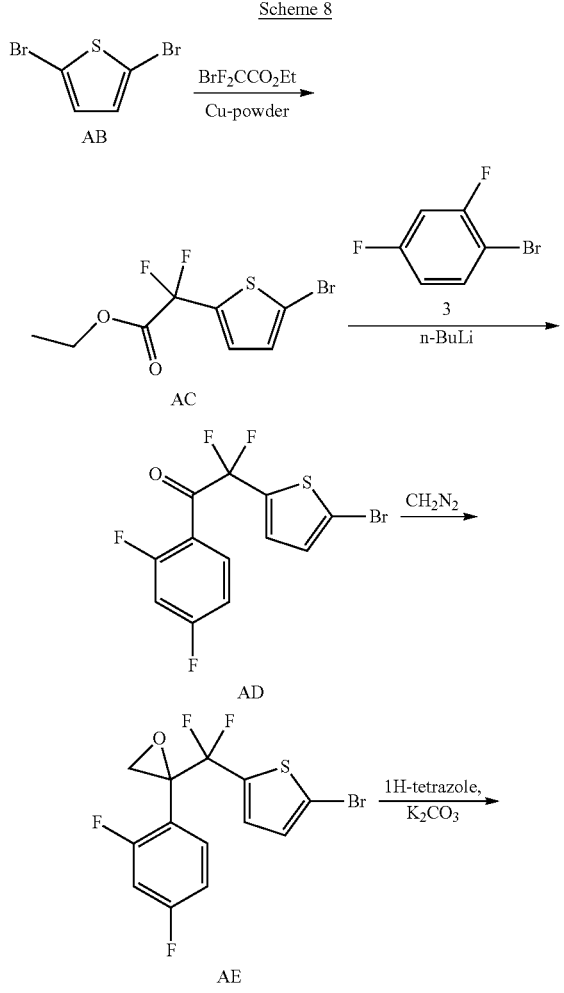

Scheme 8

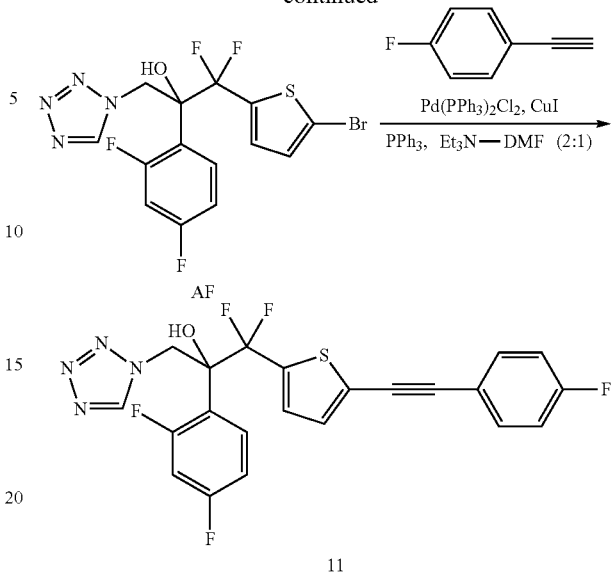

Example 11

2-(2,4-Difluorophenyl)-1,1-difluoro-1-(5-((4-fluorophenyl)ethynyl)thiophen-2-yl)-3-(1H-tetrazol-1-yl)propan-2-ol (11)

To a stirred suspension of copper powder (2.07 g, 33.0 mmol) in DMSO (5 mL) was added ethyl bromodifluoroacetate (2.0 mL, 16.52 mmol) at RT and then stirring was maintained for 1 h under inert atmosphere. To this, compound AB (2.0 g, 8.26 mmol) was added and stirred at RT for 10 h. After completion of reaction (monitored by TLC), the reaction was quenched with saturated aqueous NH$_4$Cl solution (30 mL) and extracted with DCM (3×50 mL). The combined organic extracts were washed with water (50 mL), brine (50 mL), dried over anhydrous Na$_2$SO$_4$ and concentrated under reduced pressure to obtain the crude. The crude material was purified by silica gel column chromatography (0-2% EtOAc in Hexane gradient) to afford compound AC (0.56 g, 1.96 mmol, 23.7%) as a brown syrup. $^1$H NMR (500 MHz, CDCl$_3$): δ 7.17 (d, J=4.0 Hz, 1H), 7.02 (d, J=4.0 Hz, 1H), 4.39 (q, J=7.0 Hz, 2H), 1.38 (t, J=7.0 Hz, 3H).

To a stirred solution of 1-bromo-2,4-difluorobenzene AC (0.25 ml, 1.96 mmol) in Et$_2$O (10 mL) was added n-BuLi (1.3 mL, 1.96 mmol; 1.6M in hexane) at −78° C. and stirred for 30 min under inert atmosphere. A solution of ester AC (560 mg, 1.96 mmol) in Et$_2$O (2 mL) was added to the reaction mixture at −78° C. and stirring was continued for another 2 h. After completion of the reaction (monitored by TLC), the reaction mixture was quenched with saturated NH$_4$Cl solution (15 mL) and extracted with EtOAc (3×20 mL). The combined organic extracts were washed with water (30 mL), brine (30 mL), dried over anhydrous Na$_2$SO$_4$ and concentrated under reduced pressure to obtain crude. The crude material was purified by silica gel column chromatography (15-20% EtOAc in hexane gradient) to afford the ketone AD (400 mg, 1.13 mmol, 57.6%) as a brown syrup. $^1$H NMR (500 MHz, CDCl$_3$): δ 7.86-7.81 (m, 1H), 7.10 (d, J=4.0 Hz, 1H), 7.04 (d, J=4.0 Hz, 1H), 7.01-6.98 (m, 1H), 6.91-6.84 (m, 1H). MS (EI): m/z 354 [M+H]$^+$.

To a stirred solution of ketone AD (430 mg, 1.218 mmol) in Et$_2$O (10 mL) was added freshly prepared diazomethane [prepared by dissolving NMU (627 mg, 6.09 mmol) in 1:1 mixture of 10% aq. KOH solution (40 mL) and Et$_2$O (40 mL) at 0° C. followed by separation and drying of the organic layer using KOH pellets] at −5° C. and stirred for 2 h. The resulting reaction mixture was allowed to warm to RT and stirring was continued for additional 3 h. The progress of the reaction was monitored by TLC. The reaction mixture was concentrated under reduced pressure and the obtained crude material was purified by silica gel column chromatography (20-25% EtOAc in hexane gradient) to afford the epoxide AE (320 mg, 0.87 mmol, 71.5%) as a brown syrup. $^1$H NMR (500 MHz, CDCl$_3$): δ 7.36-7.29 (m, 1H), 6.98 (d, J=4.0 Hz, 1H), 6.94 (d, J=4.0 Hz, 1H), 6.87-6.76 (m, 2H), 3.36 (d, J=5.0 Hz, 1H), 2.98 (d, J=5.0 Hz, 1H). MS (EI): m/z 368 [M]$^+$.

To a stirred solution of epoxide AE (320 mg, 0.87 mmol) in DMF (5 mL) was added 1H-tetrazole (92 mg, 1.3 mmol) followed by K$_2$CO$_3$ (120 mg, 0.87 mmol) at RT under inert atmosphere. The reaction mixture was gradually heated up to 65° C. and maintained for 8 h. The progress of the reaction was monitored by TLC. After complete consumption of starting material, the reaction mixture was diluted with ice-cold water (20 mL) and then extracted with EtOAc (3×30 mL). The combined organic extracts were washed with water (30 mL), brine (30 mL), dried over anhydrous Na$_2$SO$_4$ and concentrated under reduced pressure to obtain the crude. The crude material was purified by silica gel column chromatography (40-45% EtOAc in Hexane gradient) to afford AF (120 mg, 0.27 mmol, 31.5%) as a brown solid. $^1$H NMR (500 MHz, CDCl$_3$): δ 8.61 (s, 1H), 7.39-7.35 (m, 1H), 6.93 (d, J=4.0 Hz, 1H), 6.83 (d, J=4.0 Hz, 1H), 6.79-6.75 (m, 2H), 5.60 (d, J=14.0 Hz, 1H), 5.00 (d, J=15.0 Hz, 1H), 4.39 (s, OH). MS (EI): m/z 435 [M−H]$^−$. HPLC: 91.2%.

1-Ethynyl-4-fluorobenzene (22 mg, 0.18 mmol), CuI (2 mg, 0.01 mmol), PPh$_3$ (3 mg, 0.01 mmol) were added successively to a stirred solution of AF (50 mg, 0.114 mmol) in Et$_3$N-DMF (2:1; 6 mL) at RT under inert atmosphere. The resulting mixture was degassed by purging with argon for 15 min. To this, Pd(PPh$_3$)$_2$Cl$_2$ (8 mg, 0.01 mmol) was added and again purged with argon for 15 min. The resulting mixture was then heated to 90° C. and maintained for 16 h at the same temperature. After complete consumption of starting material (monitored by TLC), the reaction mixture was cooled to RT, diluted with water (10 mL) and extracted with EtOAc (3×25 mL). The combined organic extracts were washed with water (30 mL), brine (30 mL), dried over anhydrous Na$_2$SO$_4$ and concentrated under reduced pressure to obtain the crude. The crude product was purified by silica gel column chromatography (40-45% EtOAc in Hexane gradient) to afford 11 (35 mg) with 79% HPLC purity.

Note: The above reaction was conducted in two batches (50 mg×2) and then purified. The obtained product (70 mg) as a mixture was further purified by preparative HPLC to afford 11 (35 mg, 0.073 mmol, 32%). $^1$H NMR (500 MHz, CDCl$_3$): δ 8.64 (s, 1H), 7.50-7.47 (m, 2H), 7.36-7.29 (m, 1H), 7.09-7.03 (m, 3H), 6.97 (d, J=5.0 Hz, 1H), 6.80-6.74 (m, 2H), 5.63 (d, J=15.0 Hz, 1H), 5.03 (d, J=15.0 Hz, 1H), 4.41 (s, OH). MS (EI): m/z 475 [M−H]$^−$. HPLC: 98.43%.

Scheme 9

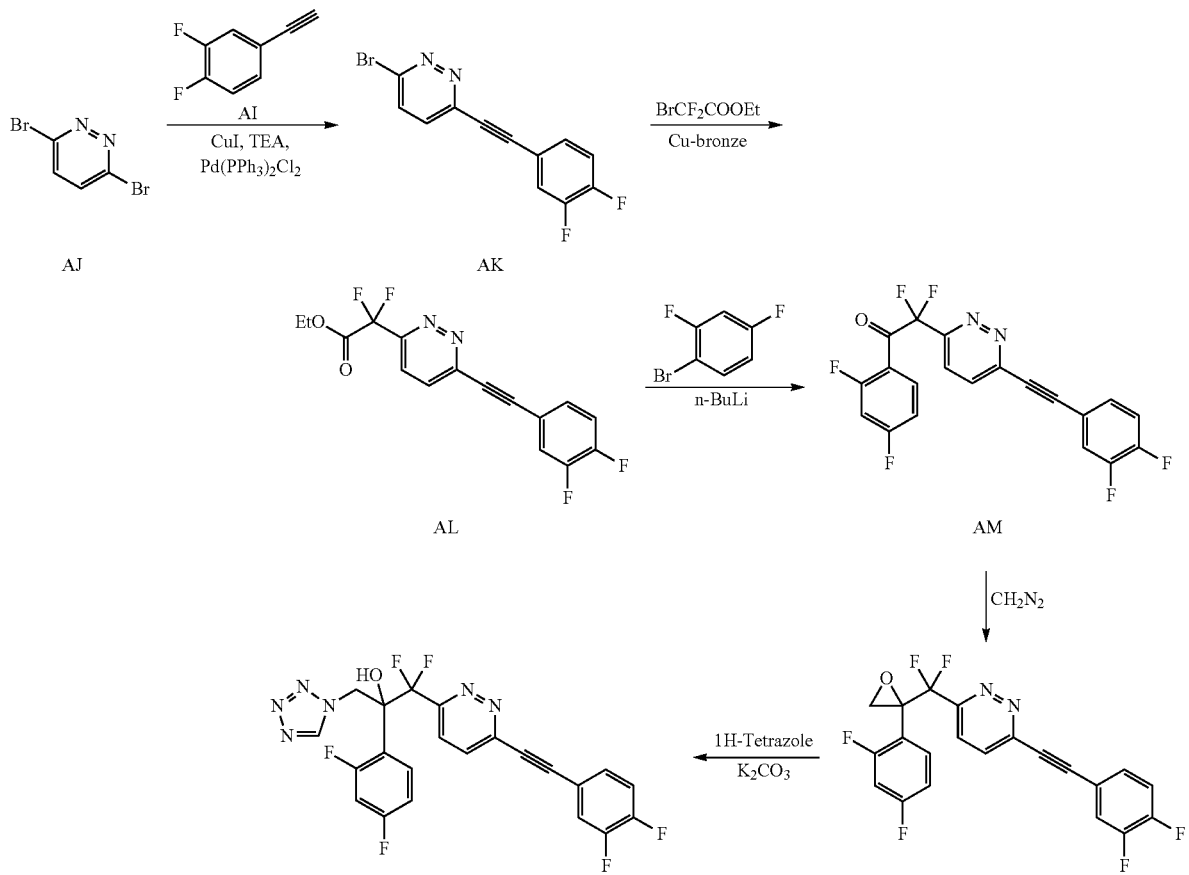

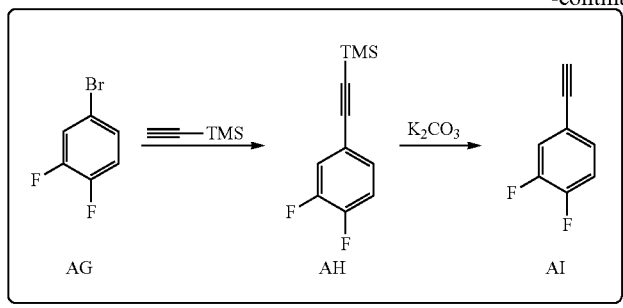

Example 12

2-(2,4-Difluorophenyl)-1-(6-((3,4-difluorophenyl)ethynyl)pyridazin-3-yl)-1,1-difluoro-3-(1H-tetrazol-1-yl)propan-2-ol (12)

To a stirred solution of compound AG (6.0 g, 31.08 mmol) in THF (20 mL), were added trimethylsilyl acetylene (6 mL, 42.4 mmol), Et$_3$N (6.0 mL, 43.2 mmol) followed by CuI (344 mg, 1.81 mmol) at RT and purged with argon for 10 min. To this mixture, Pd(PPh$_3$)$_2$Cl$_2$ (1.3 g, 1.85 mmol) was added at RT and stirring was continued for 16 h under inert atmosphere. After complete consumption of the starting material (monitored by TLC), the reaction mixture was filtered through a pad of celite and washed celite cake with EtOAc (3×75 mL). The filtrate was washed with water (75 mL), brine (75 mL), dried over anhydrous Na$_2$SO$_4$ and concentrated under reduced pressure to obtain the crude. The crude material was purified by silica gel column chromatography (eluent: hexanes) to afford compound AH (5.8 g, 27.61 mmol, 88.8%) as a dark brown liquid.

$^1$H NMR (500 MHz, CDCl$_3$): δ 7.28-7.20 (m, 1H), 7.20-7.17 (m, 1H), 7.10-7.05 (m, 1H), 0.22 (s, 9H)

To a stirred solution of compound AH (5.8 g, 27.61 mmol) in THF (50 mL) was added TBAF (27 mL, 27.61 mmol; 1M solution in THF) at 0° C. under inert atmosphere and stirred at same temperature for 1 h. After complete consumption of the starting material (by TLC), volatiles were concentrated under reduced pressure; the obtained residue was diluted with Et$_2$O (100 mL), washed with water (100 mL), brine (100 mL), dried over anhydrous Na$_2$SO$_4$ and concentrated under reduced pressure to obtain the crude AI (3.4 g) as a brown liquid. The crude product was used in the next step without further purification. $^1$H NMR (500 MHz, CDCl$_3$): δ 7.31-7.21 (m, 2H), 7.13-7.08 (m, 1H), 3.06 (s, 1H)

To a stirred solution of compound AJ (3.0 g, 12.61 mmol) in THF (30 mL) were added compound AI (2.78 g, crude) followed by CuI (0.12 g, 0.63 mmol), Pd(PPh$_3$)$_2$Cl$_2$ (0.44 g, 0.63 mmol) and Et$_3$N (3 mL) at RT under inert atmosphere and stirred for 16 h. After complete consumption of the starting material (by TLC), the reaction mixture was filtered through a pad of celite and washed the celite cake with EtOAc (3×75 mL). The filtrate was washed with water (75 mL), brine (75 mL), dried over anhydrous Na$_2$SO$_4$ and concentrated under reduced pressure to obtain the crude. The crude compound was purified by silica gel column chromatography (eluent: 5% EtOAc/Hexanes) to afford compound AK (1.3 g, 4.40 mmol, 35%) as a brown solid. $^1$H NMR (500 MHz, CDCl$_3$): δ 7.67 (d, J=8.5 Hz, 1H), 7.48 (d, J=8.5 Hz, 1H), 7.46-7.42 (m, 1H), 7.39-7.37 (m, 1H), 7.22-7.17 (m, 1H).

To a stirred suspension of copper-bronze (3.23 g, 17.62 mmol) in DMSO (20 mL) was added ethyl bromodifluoroacetate (1.13 mL, 8.81 mmol) at RT and stirred for 1 h under inert atmosphere. A solution of compound AK (1.3 g, 4.40 mmol) in DMSO (5 mL) was added to the reaction mixture and stirring was continued for another 16 h at RT. After the consumption of starting material (monitored by TLC), the reaction was diluted with aqueous NH$_4$Cl solution (20 mL), filtered through a pad of celite and washed celite cake with DCM (3×55 mL). The collected filtrate was washed with water (30 mL), brine (30 mL), dried over anhydrous Na$_2$SO$_4$ and concentrated under reduced pressure to obtain the crude. The crude material was purified by column chromatography (eluent: 20% EtOAc/Hexanes) to afford ester AL (550 mg, 1.62 mmol, 37%) as a brown solid. $^1$H NMR (500 MHz, CDCl$_3$): δ 7.88 (d, J=8.5 Hz, 1H), 7.78 (d, J=8.5 Hz, 1H), 7.42-7.39 (m, 2H), 7.24-7.20 (m, 1H), 4.43 (q, J=7.0 Hz, 2H), 1.36 (t, J=7.0 Hz, 3H) To a stirred solution of 1-bromo-2,4-difluorobenzene (0.19 mL, 1.62 mmol) in Et$_2$O (20 mL) was added n-BuLi (1.6 mL, 2.43 mmol; 1.6M in hexane) drop wise at −78° C. and stirred for 30 min. A solution of compound AL (550 mg, 1.62 mmol) in Et$_2$O (10 mL) was added to the reaction mixture at −78° C. and stirring was continued for another 5 min. After consumption of the starting material (monitored by TLC), the reaction mixture was quenched with saturated aqueous NH$_4$Cl solution (20 mL) and extracted with EtOAc (3×25 mL). The combined organic extracts were washed with water (50 mL), brine (50 mL), dried over anhydrous Na$_2$SO$_4$ and concentrated under reduced pressure to obtain the crude. The crude compound was purified by column chromatography (eluent: 10% EtOAc/Hexanes) to afford ketone AM (420 mg, 1.03 mmol, 64%) as an off white solid. $^1$H NMR (500 MHz, CDCl$_3$): δ 8.18-8.14 (m, 1H), 7.90 (d, J=9.0 Hz, 1H), 7.80 (d, J=9.0 Hz, 1H), 7.46-7.39 (m, 2H), 7.24-7.18 (m, 1H), 7.05-7.02 (m, 1H), 6.83-6.79 (m, 1H).

To a stirred solution of compound AM (420 mg, 1.03 mmol) in Et$_2$O (10 mL) was added freshly prepared diazomethane [prepared by dissolving NMU (527 mg, 5.17 mmol) in 10% aqueous KOH (100 mL) and Et$_2$O (100 mL) at 0° C. followed by separation and drying of the organic layer using KOH pellets] at 0° C. and stirring was continued for 30 min at 0° C. The resulting reaction mixture was allowed to warm to RT and stirred for 16 h. The progress of the reaction was monitored by TLC. The reaction mixture was concentrated under reduced pressure to obtain the crude. The crude material was purified by silica gel column chromatography (eluent: 20% EtOAc/Hexanes) to afford compound AN (350 mg) as an off-white solid. $^1$H-NMR showed all characteristic peaks along with other minor impurities. This material was directly taken for next reaction without further purification. $^1$H NMR (400 MHz, CDCl$_3$): δ 8.09 (d, J=8.0 Hz, 1H), 7.67 (d, J=8.0 Hz, 1H), 7.45-7.40 (m, 3H), 7.24-7.19 (m, 1H), 6.88-6.85 (m, 1H), 6.79-6.76 (m, 1H), 3.51 (d, J=5.0 Hz, 1H), 3.04 (d, J=5.0 Hz, 1H).

To a stirred solution of compound AN (300 mg, mixture) in DMF (5 mL) were added 1H-tetrazole (75 mg, 1.07 mmol) followed by K$_2$CO$_3$ (99 mg, 0.71 mmol) at RT under inert atmosphere. The resulting reaction mixture was gradually heated up to 65° C. and stirred for 16 h; progress of the reaction was monitored by TLC. The reaction mixture was cooled to RT; diluted with ice-cold water (50 mL) and extracted with EtOAc (2×50 mL). The combined organic layers were washed with water (2×50 mL), brine (50 mL), dried over anhydrous $Na_2SO_4$ and concentrated under reduced pressure to obtain the crude. The crude compound was purified by prep HPLC to afford 12 (25 mg, 0.05 mmol) as a brown solid. $^1$H NMR (500 MHz, $CD_3OD$): δ 8.98 (s, 1H), 7.95 (d, J=8.5 Hz, 1H), 7.78 (d, J=8.5 Hz, 1H), 7.64-7.60 (m, 1H), 7.51-7.49 (m, 1H), 7.40-7.35 (m, 1H), 7.17-7.12 (m, 1H), 6.98-6.95 (m, 1H), 6.76-6.73 (m, 1H), 5.82 (d, J=14.5 Hz, 1H), 5.25 (d, J=14.5 Hz, 1H). MS (ESI): 491 [M+H]$^+$. HPLC: 97.19%

Example 13

4-(6-(2-(2,4-Difluorophenyl)-1,1-difluoro-2-hydroxy-3-(1H-tetrazol-1-yl)propyl)pyridin-3-yl)but-3-yn-2-ol (13)

To a stirred solution of alkyne F (800 mg, 2.6 mmol) in $Et_2O$ (50 mL) was added n-BuLi (1.63 mL, 2.6 mmol; 1.6M solution in hexane) at −78° C. and maintained for 30 min at the same temperature. To the resulting reaction mixture, freshly distilled acetaldehyde (0.14 mL, 3.1 mmol) was added at −78° C. After being stirred for 2 h at −78° C., the reaction mixture was allowed to warm to RT and stirred for additional 2 h. The progress of the reaction was monitored by TLC. After complete consumption of the starting material, the reaction mixture was quenched with saturated $NH_4Cl$ solution (10 mL) and then extracted with EtOAc (2×50 mL). The combined organic extracts were washed with water (50 mL), brine (50 mL), dried over anhydrous $Na_2SO_4$ and concentrated under reduced pressure to obtain the crude. The crude material was purified by silica gel column chromatography (10-15% EtOAc in hexane gradient) to afford compound AO (600 mg, 1.7 mmol, 65%) as a colorless semi solid. $^1$H NMR (500 MHz, $CDCl_3$): δ 8.68 (s, 1H), 7.75 (dd, J=8.5, 1.5 Hz, 1H), 7.42 (d, J=8.5 Hz, 1H), 7.37-7.33 (m, 1H), 6.84-6.81 (m, 1H), 6.75-6.71 (m, 1H), 4.81-4.76 (m, 1H), 3.45 (d, J=5.0 Hz, 1H), 2.97 (d, J=5.0 Hz, 1H), 2.04 (s, OH), 1.58 (d, J=7.0 Hz, 3H). MS (EI): m/z 353 [M+2]$^+$.

To a stirred solution of compound AO (500 mg, 1.4 mmol) in DMF (25 mL) was added $K_2CO_3$ (196 mg, 1.4 mmol) followed by 1H-tetrazole (150 mg, 2.1 mmol) at RT under inert atmosphere. The reaction mixture was then heated up to 65° C. and stirred for 16 h. After complete consumption of the starting material (monitored by TLC), the reaction mixture was cooled to RT and concentrated under reduced pressure. The obtained residue was dissolved in EtOAc (40 mL), washed with water (20 mL), brine (20 mL), dried over anhydrous $Na_2SO_4$ and concentrated under reduced pressure to obtain the crude. The crude material was purified by silica gel column chromatography (30-35% EtOAc in hexane gradient) to afford 13 (250 mg, 0.59 mmol, 41%) as a white solid. $^1$H NMR (500 MHz, $CDCl_3$): δ 8.74 (s, 1H), 8.54 (s, 1H), 7.80 (d, J=8.0 Hz, 1H), 7.51 (d, J=8.0 Hz, 1H), 7.30-7.27 (m, 1H), 7.22 (s, OH), 6.77-6.73 (m, 1H), 6.67-6.64 (m, 1H), 5.58 (d, J=14.5 Hz, 1H), 5.12 (d, J=14.5 Hz, 1H), 4.79-4.76 (m, 1H), 1.93 (s, OH), 1.56 (d, J=7.0 Hz, 3H). MS (EI): m/z 421 [M]$^+$. HPLC: 98.02%.

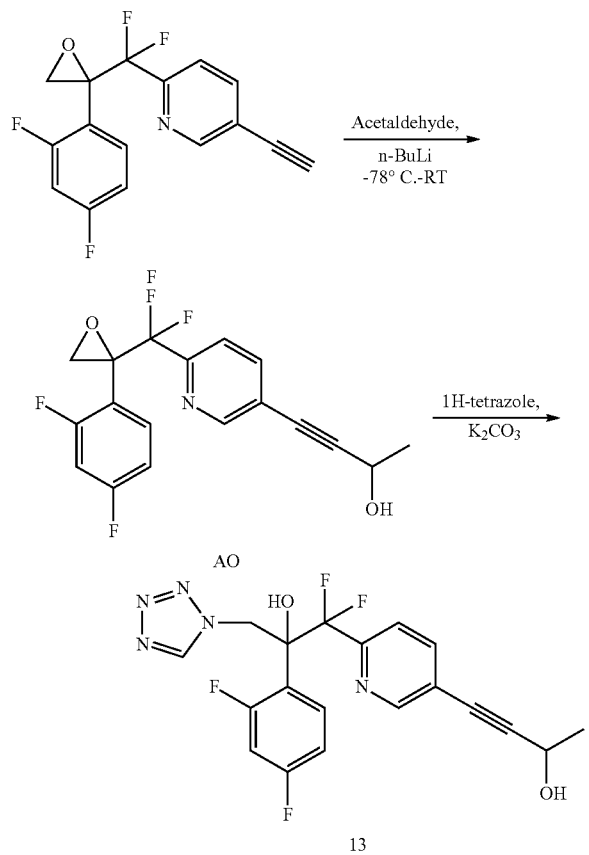

Scheme 10

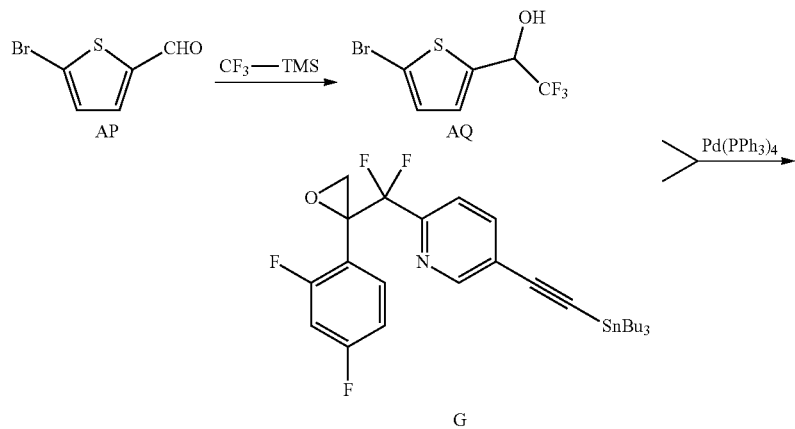

Scheme 11

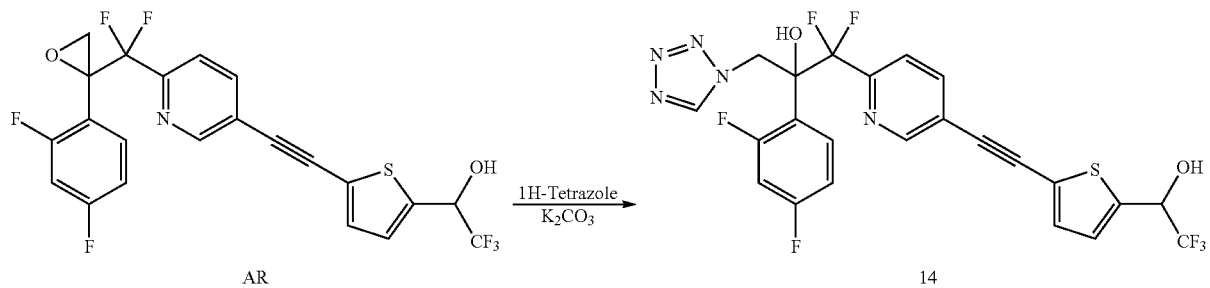

Example 14

2-(2,4-Difluorophenyl)-1,1-difluoro-3-(1H-tetrazol-1-yl)-1-(5-((5-(2,2,2-trifluoro-1-hydroxyethyl)thiophen-2-yl)ethynyl)pyridin-2-yl)propan-2-ol (14)

To a stirred solution of 5-bromothiophene-2-carboxaldehyde AP (5.0 g, 26.1 mmol) in DME (30 mL) was added CsF (3.9 g, 26.1 mmol) at 0° C. and stirred for 10 min under inert atmosphere. $CF_3TMS$ (6.2 mL, 39 mmol) was added to the reaction mixture at 0° C. and stirring was continued for another 18 h at RT. The progress of the reaction was monitored by TLC. The reaction mixture was quenched with 1N HCl solution (20 mL) and extracted with EtOAc (3×100 mL). The combined organic extracts were washed with water (100 mL), brine (100 mL), dried over anhydrous $Na_2SO_4$ and concentrated under reduced pressure to obtain the crude product. The crude material was purified by silica gel column chromatography (eluent: 4-5% EtOAc/Hexanes) to afford compound AQ (5.0 g, 19.15 mmol, 73.3%) as a brown oil. $^1$H NMR (500 MHz, $CDCl_3$): δ 6.99 (d, J=4.0 Hz, 1H), 6.93 (d, J=4.0 Hz, 1H), 5.21-5.16 (m, 1H), 3.16 (d, J=4.5 Hz, OH)

To a stirred solution of compound G (1.5 g, crude) in 1,4-dioxane (10 mL) was added compound AQ (985 mg, 3.77 mmol) at RT and purged with argon for 20 min. To the resulting reaction mixture was added $Pd(PPh_3)_4$ (288 mg, 0.25 mmol) and further degassed for 15 min at RT. The resulting reaction mixture was gradually heated up to 90° C. and stirred for 5 h; the progress of the reaction was monitored by TLC. The reaction mixture was cooled to RT, filtered through a pad of celite and the celite cake was washed with EtOAc (3×30 mL); the filtrate was concentrated under reduced pressure to obtain the crude. The crude material was purified by silica gel column chromatography (eluent: 12% EtOAc/Hexanes) to afford compound AR (800 mg) as a colorless liquid. This compound contained some amount of tin impurities, which was directly taken for the next step without any further purification. $^1$H NMR (500 MHz, $CDCl_3$): δ 8.74 (s, 1H), 7.83 (d, J=7.5 Hz, 1H), 7.46 (d, J=7.5 Hz, 1H), 7.39-7.34 (m, 1H), 7.27 (d, J=3.5 Hz, 1H), 7.12 (d, J=3.5 Hz, 1H), 6.85-6.82 (m, 1H), 6.76-6.73 (m, 1H), 5.28 (d, J=6.0 Hz, 1H), 3.47 (d, J=5.0 Hz, 1H), 2.98 (d, J=5.0 Hz, 1H), 2.91 (s, OH).

To a stirred solution of compound AR (800 mg, crude) in DMF (8 mL) was added $K_2CO_3$ (224 mg, 1.63 mmol) followed by 1H-tetrazole (172 mg, 2.45 mmol) at RT under inert atmosphere. The reaction mixture was then heated up to 65° C. and then stirred for 16 h. After complete consumption of the starting material (monitored by TLC), the reaction mixture was cooled to RT and concentrated under reduced pressure. The obtained residue was dissolved in EtOAc (50 mL), washed with water (50 mL), brine (50 mL), dried over anhydrous $Na_2SO_4$ and concentrated under reduced pressure to obtain the crude. The crude material was purified by silica gel column chromatography (eluent: 35% EtOAc/Hexanes) to afford 14 (280 mg, 0.50 mmol) a pale yellow solid. $^1$H NMR (500 MHz, $CDCl_3$): δ 8.76 (s, 1H), 8.63 (s, 1H), 7.87 (d, J=8.5 Hz, 1H), 7.55 (d, J=8.5 Hz, 1H), 7.32-7.27 (m, 2H), 7.21 (s, OH), 7.13 (d, J=4.0 Hz, 1H), 6.78-6.74 (m, 1H), 6.68-6.65 (m, 1H), 5.61 (d, J=14.0 Hz, 1H), 5.30-5.28 (m, 1H), 5.13 (d, J=14.0 Hz, 1H), 3.08 (s, OH). MS (EI): m/z 558 [M+H]$^+$. HPLC: 97.43%.

Scheme 12

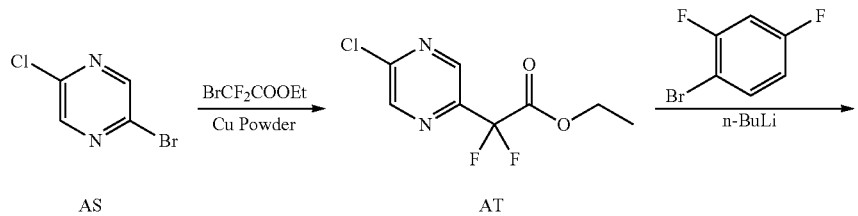

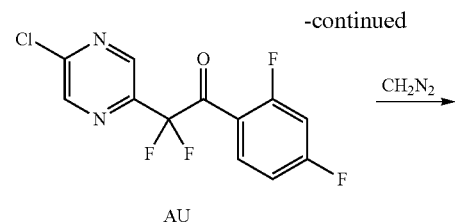

AU

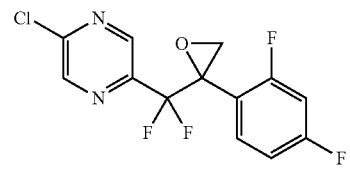

AV

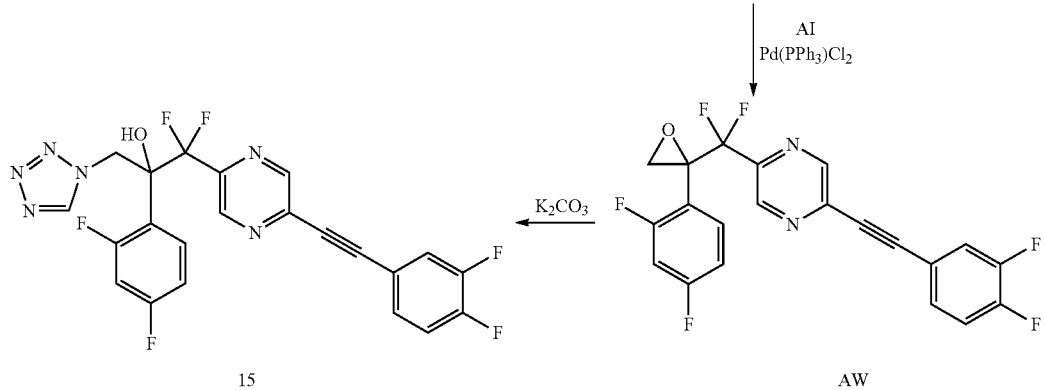

Example 15

2-(2,4-difluorophenyl)-1-(5-((3,4-difluorophenyl) ethynyl)pyrazin-2-yl)-1,1-difluoro-3-(1H-tetrazol-1-yl)propan-2-ol (15)

To a stirred suspension of copper powder (1.48 g, 23.30 mmol) in DMSO (20 mL) was added ethyl bromodifluoroacetate (1.6 mL, 11.65 mmol) at RT and stirred at RT for 1 h under inert atmosphere. A solution of 2-bromo-5-chloropyrazine AS (1.5 g, 7.77 mmol) in DMSO (5 mL) was added to the reaction mixture and stirring was continued for another 16 h at RT. After complete consumption of the starting material (by TLC), the reaction was diluted with saturated aqueous NH$_4$Cl solution (100 mL), filtered through a pad of celite and washed celite cake with DCM (3×75 mL). The collected filtrate was washed with water (100 mL), brine (50 mL), dried over anhydrous Na$_2$SO$_4$ and concentrated under reduced pressure to obtain the crude. The crude material was purified by silica gel column chromatography (eluent: 5% EtOAc/Hexane) to afford ester AT (1.0 g, 4.23 mmol, 54.5%) as a pale yellow syrup. $^1$H NMR (500 MHz, CDCl$_3$): δ 8.78 (s, 1H), 8.62 (s, 1H), 4.38 (q, J=7.0 Hz, 2H), 1.34 (t, J=7.0 Hz, 3H).

To a stirred solution of 1-bromo-2,4-difluorobenzene (0.816 g, 4.23 mmol) in Et$_2$O (20 mL) was added n-BuLi (2.64 mL, 4.23 mmol; 1.6M in hexane) drop wise at −78° C. and stirred for 30 min. A solution of compound AT (1.0 g, 4.23 mmol) in Et$_2$O (10 mL) was added to the reaction mixture at −78° C. and stirring was continued for another 2 h. After complete consumption of the starting material (by TLC), the reaction mixture was quenched with saturated aqueous NH$_4$Cl solution (50 mL) and extracted with EtOAc (3×50 mL). The combined organic extracts were washed with water (50 mL) and brine (50 mL), dried over anhydrous Na$_2$SO$_4$ and concentrated under reduced pressure to obtain the crude. The crude material was purified by silica gel column chromatography (eluent: 5% EtOAc/Hexanes) to afford ketone AU (1.0 g, 3.28 mmol, 77.6%) as a pale yellow syrup. $^1$H NMR (500 MHz, CDCl$_3$): δ 8.86 (s, 1H), 8.56 (s, 1H), 8.06-8.02 (m, 1H), 7.05-7.01 (m, 1H), 6.88-6.84 (m, 1H).

To a stirred solution of compound AU (1.0 g, 3.28 mmol) in Et$_2$O (10 mL) was added freshly prepared diazomethane [prepared by dissolving NMU (1.7 g, 16.49 mmol) in 10% aqueous KOH (30 mL) and Et$_2$O (30 mL) at 0° C. followed by separation and drying of the organic layer using KOH pellets] at 0° C. and stirring was continued for 30 min at the same temperature. The resulting reaction mixture was allowed to warm to RT and stirred for 16 h; progress of the reaction was monitored by TLC. The reaction mixture was concentrated under reduced pressure to obtain the crude. The crude material was purified by silica gel column chromatography (eluent: 5% EtOAc/Hexanes) to afford the epoxide AV (0.8 g, 2.51 mmol, 76.5%) as a brown solid. $^1$H NMR (500 MHz, CDCl$_3$): δ 8.62 (s, 1H), 8.51 (s, 1H), 7.42-7.37 (m, 1H), 6.90-6.86 (m, 1H), 6.79-6.75 (m, 1H), 3.43 (d, J=5.0 Hz, 1H), 3.00 (d, J=5.0 Hz, 1H).

To a stirred solution of compound AI (400 mg, 1.25 mmol), compound AV (277 mg, 2.0 mmol), Et$_3$N (0.4 mL, 3.12 mmol) in DMF (10 mL) was added CuI (12 mg, 0.08 mmol) at RT and then purged with argon for 10 min. To this, Pd(PPh$_3$)$_2$Cl$_2$ (44 mg, 0.08 mmol) was added and the resultant mixture was gradually heated up to 80° C. and stirred for 4 h. After complete consumption of the starting material (monitored by TLC); the reaction mixture was cooled to RT; filtered through a pad of celite and washed celite cake with EtOAc (4×50 mL). The filtrate was washed with water (50 mL), brine (50 mL), dried over anhydrous Na$_2$SO$_4$ and concentrated under reduced pressure to obtain the crude. The crude material was purified by silica gel column chromatography (eluent: 10% EtOAc/Hexanes) to afford compound AW (180 mg, 0.42 mmol, 34%) as a brown solid. $^1$H NMR (500 MHz, CDCl$_3$): δ 8.74 (s, 1H), 8.70 (s, 1H), 7.47-7.39 (m, 3H), 7.23-7.18 (m, 1H) 6.89-6.86 (m, 1H), 6.79-6.74 (m, 1H), 3.46 (d, J=5.0 Hz, 1H), 3.01 (d, J=5.0 Hz, 1H). MS (EI): m/z 421 [M+H]$^+$.

To a stirred solution of compound AW (180 mg, 0.42 mmol) in DMF (5 mL) was added K$_2$CO$_3$ (59 mg, 0.42 mmol) followed by 1H-tetrazole (45 mg, 0.64 mmol) at RT under inert atmosphere. The reaction mixture gradually heated to 65° C. and then maintained for 16 h. The progress of the reaction was monitored by TLC. After complete consumption of staring material, the reaction mixture was cooled to RT, diluted with ice-cold water (50 mL) and extracted with EtOAc (2×50 mL). The combined organic extracts were washed with water (50 mL), brine (50 mL), dried over anhydrous $Na_2SO_4$ and concentrated under reduced pressure to obtain the crude. The crude material was purified by silica gel column chromatography (eluent: 35% EtOAc/hexanes) to afford 15 (25 mg, 0.05 mmol, 12%) as a brown solid. $^1$H NMR (500 MHz, $CDCl_3$): δ 8.75 (s, 1H), 8.71 (s, 1H), 8.62 (s, 1H), 7.46-7.38 (m, 2H), 7.38-7.18 (m, 2H), 6.81-6.77 (m, 1H), 6.74-6.71 (m, 1H), 5.64 (d, J=15.0 Hz, 1H), 5.56 (s, OH), 5.17 (d, J=15.0 Hz, 1H). MS (EI): 491[M+H]$^+$. HPLC: 92.9%.

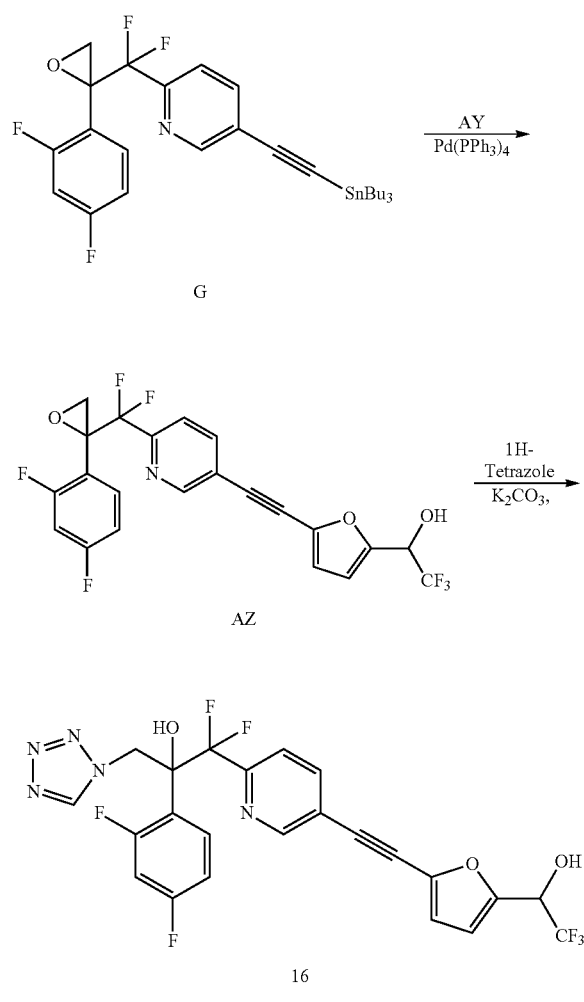

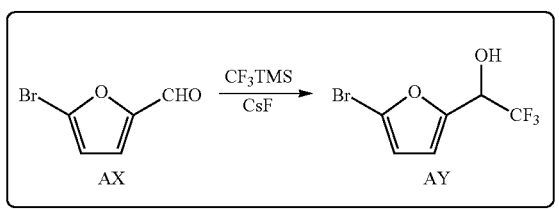

Example 16

2-(2,4-Difluorophenyl)-1,1-difluoro-3-(1H-tetrazol-1-yl)-1-(5-((5-(2,2,2-trifluoro-1-hydroxy ethyl)furan-2-yl)ethynyl)pyridin-2-yl)propan-2-ol (16)

To a stirred solution of 5-bromofuran-2-carbaldehyde AX (250 mg, 1.43 mmol) in DME (10 mL) was added CsF (108 mg, 0.71 mmol) at 0° C. and stirred for 10 min under inert atmosphere. $CF_3$TMS (0.27 mL, 1.71 mmol) was added to the reaction mixture at 0° C. and stirring was continued art 0° C.-RT for 18 h. The progress of the reaction was monitored by TLC. The reaction mixture was quenched with 1N HCl (10 mL) and extracted with EtOAc (2×50 mL). The combined organic extracts were washed with water (50 mL), brine (50 mL), dried over anhydrous $Na_2SO_4$ and concentrated under reduced pressure to obtain the crude AY (200 mg), which was directly taken for next reaction without being purified. $^1$H NMR (500 MHz, $CDCl_3$): δ 6.51 (d, J=3.0 Hz, 1H), 6.35 (d, J=3.0 Hz, 1H), 5.03-4.99 (m, 1H), 2.78 (bs, OH).

To a stirred solution of compound G (500 mg, crude) in 1,4-dioxane (20 mL) was added compound AY (309 mg, crude) at RT and purged with argon for 15 min. To this, Pd(PPh$_3$)$_4$ (97 mg, 0.08 mmol) was added and further degassed for 15 min. The resulting reaction mixture was gradually heated up to 80° C. and stirred for 3 h; the progress of the reaction was monitored by TLC. The reaction mixture was cooled to RT, filtered through a pad of celite and washed celite cake with EtOAc (2×50 mL) and the filtrate was concentrated under reduced pressure to obtain the crude. The crude material was purified by silica gel column chromatography (eluent: 10-12% EtOAc/Hexanes) to afford epoxide AZ (200 mg, mixture) as a colorless oil. $^1$H-NMR showed all the characteristic peaks along with little tin-impurity peaks. The product was directly taken for next reaction without further purification. $^1$H-NMR (500 MHz, $CDCl_3$): δ 8.77 (s, 1H), 7.81 (d, J=8.5 Hz, 1H), 7.42 (d, J=8.5 Hz, 1H), 7.37-7.32 (m, 1H), 6.79-6.75 (m, 3H), 6.60 (d, J=3.5 Hz, 1H), 4.90-5.10 (m, 1H), 3.46 (d, J=5.0 Hz, 1H), 2.98 (d, J=5.0 Hz, 1H), 2.75 (d, J=7.0 Hz, OH).

To a stirred solution of epoxide AZ (200 mg, crude) in DMF (10 mL) was added 1H-tetrazole (44.5 mg, 0.63 mmol) followed by $K_2CO_3$ (58.6 mg, 0.42 mmol) at RT under inert atmosphere. The resulting reaction mixture was gradually heated up to 65° C. and stirred for 16 h; progress of the reaction was monitored by TLC. The reaction mixture was diluted with ice-cold water (50 mL) and extracted with EtOAc (2×50 mL). The combined organic extracts were washed with water (50 mL), brine (50 mL), dried over anhydrous $Na_2SO_4$ and concentrated under reduced pressure to obtain the crude. The crude material was purified by silica gel column chromatography (eluent: 40% EtOAc/hexanes) to afford 16 (20 mg, 0.037 mmol) as an off-white solid. $^1$H-NMR (500 MHz, $CDCl_3$): δ 8.75 (s, 1H), 8.64 (s, 1H), 7.89 (d, J=8.5 Hz, 1H), 7.56 (d, J=8.5 Hz, 1H), 7.32-7.29 (m, 1H), 7.10 (s, OH), 6.78-6.65 (m, 3H), 6.60 (d, J=3.5 Hz, 1H), 5.59 (d, J=14.5 Hz, 1H), 5.13 (d, J=14.5 Hz, 1H), 5.10-5.07 (m, 1H), 2.78 (d, J=7.0 Hz, OH) Mass: m/z 542 [M+H]$^+$. HPLC: 95.59%.

Scheme 14

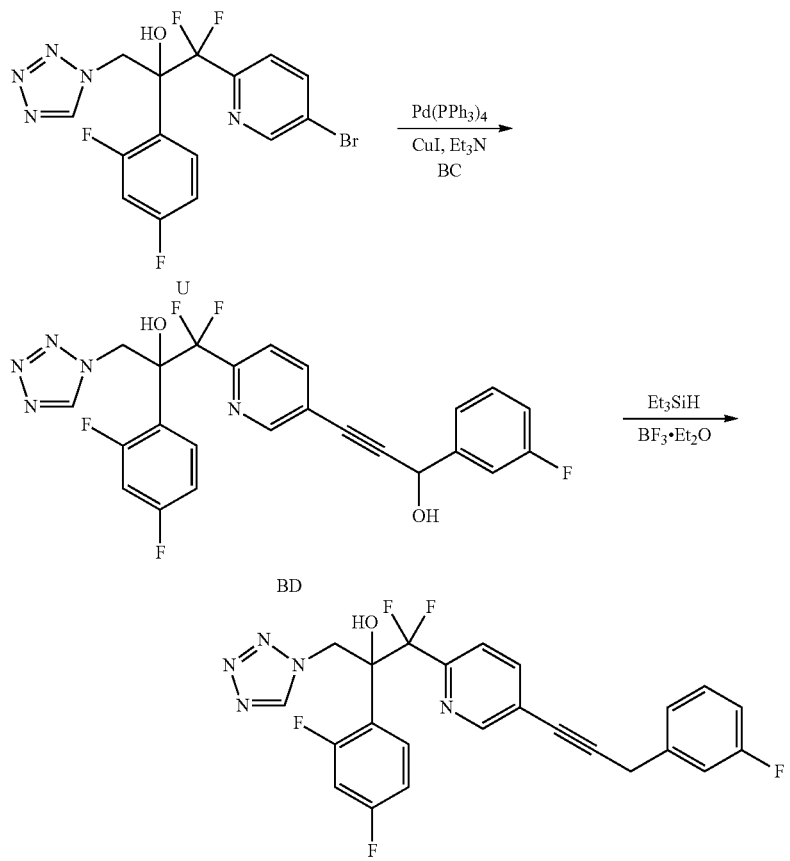

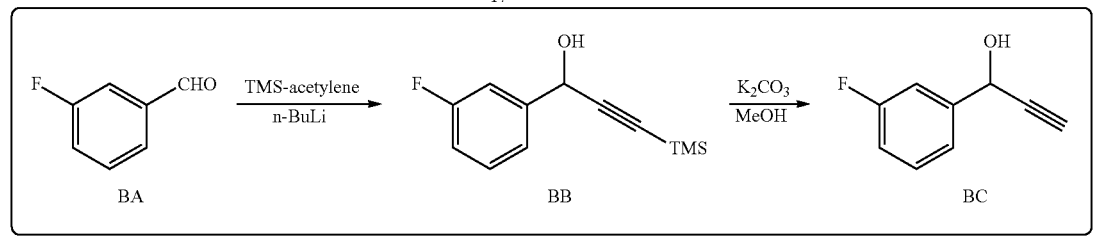

Example 17

2-(2,4-Difluorophenyl)-1,1-difluoro-1-(5-(3-(3-fluorophenyl)prop-1-yn-1-yl)pyridin-2-yl)-3-(1H-tetrazol-1-yl)propan-2-ol (17)

To a stirred solution of trimethylsilylacetylene (1.49 mL, 10.47 mmol) in THF (20 mL) was added n-BuLi (6 mL, 9.67 mmol, 1.6M in Hexane) at 0° C. under inert atmosphere. After being stirred for 1 h, 3-fluorobenzaldehyde BA (1.0 g, 8.06 mmol) was added at 0° C. and stirring was continued for additional 2 h. The progress of the reaction was monitored by TLC. The reaction was quenched with saturated aqueous NH$_4$Cl solution and extracted with DCM (2×50 mL). The combined organic extracts were washed with water (50 mL), brine (50 mL), dried over anhydrous Na$_2$SO$_4$ and concentrated under reduced pressure to obtain the crude. The crude material was purified by silica gel column chromatography (5-10% EtOAc in Hexane gradient) to afford compound BB (1.1 g, 4.95 mmol, 61.5%) as a yellow syrup. $^1$H NMR (400 MHz, CDCl$_3$): δ 7.37-7.28 (m, 3H), 7.04-6.99 (m, 1H), 5.44 (d, J=6.4 Hz, 1H), 2.23 (d, J=6.4 Hz, 1H), 0.21 (s, 9H).

To a stirred solution of compound BB (1.1 g, 4.95 mmol) in MeOH (12 mL) was added K$_2$CO$_3$ (1.02 g, 7.43 mmol) at 0° C. under inert atmosphere. After being stirred for 1 h, the progress of the reaction was monitored by TLC. The reaction was quenched with water (10 mL) and extracted with Et$_2$O (2×50 mL). The combined organic extracts were washed with water (50 mL), brine (50 mL), dried over anhydrous Na$_2$SO$_4$ and concentrated under reduced pressure to obtain the crude BC (600 mg). The crude material was used for the next step without further purification. $^1$H NMR (500 MHz, CDCl$_3$): δ 7.38-7.26 (m, 3H), 7.05-7.02 (m, 1H), 5.47 (dd, J=4.5, 2.0 Hz, 1H), 2.69 (d, J=2.0 Hz, 1H), 2.33 (d, J=4.5 Hz, 1H).

To a stirred solution of compound U (250 mg, 0.578 mmol) in DMF (5 mL) was added compound BC (140 mg, 1.5 eq) and purged with argon gas for 20 min. To this, CuI (11 mg, 0.05 mmol), Pd(PPh$_3$)$_4$ (34 mg, 0.03 mmol) followed by Et$_3$N (0.1 mL, 0.69 mmol) were added at RT and then purged again with argon gas for 15 min. The resultant mixture was gradually heated up to 90° C. and maintained for 5 h. After complete consumption of the starting material (monitored by TLC), the reaction mixture was cooled to RT, diluted with water (20 mL) and extracted with EtOAc (3×40 mL). The combined organic extracts were washed with water (50 mL), brine (50 mL), dried over anhydrous $Na_2SO_4$ and concentrated under reduced pressure to obtain crude. The crude product was purified by silica gel column chromatography (40-45% EtOAc in Hexane gradient) to afford compound BD (180 mg, 0.35 mmol, 62%) as a pale yellow syrup. $^1$H NMR (500 MHz, $CDCl_3$): δ 8.74 (s, 1H), 8.58 (s, 1H), 7.85 (d, J=8.0 Hz, 1H), 7.67-7.64 (m, 1H), 7.54-7.28 (m, 4H) 7.16 (s, OH), 7.08-7.04 (m, 1H), 6.78-6.72 (m, 1H), 6.68-6.63 (m, 1H), 5.71 (d, J=5.2 Hz, 1H), 5.59 (d, J=14.5 Hz, 1H), 5.12 (d, J=14.5 Hz, 1H), 2.74 (d, J=5.2 Hz, 1H). MS (EI): m/z 502 [M+H]$^+$.

To a stirred solution of compound BD (110 mg, 0.22 mmol) in ACN (10 mL) were added $Et_3SiH$ (0.052 mL, 0.33 mmol) followed by $BF_3.Et_2O$ (0.04 mL, 0.33 mmol) at 0° C. under inert atmosphere and maintained for 5 h at the same temperature. The progress of the reaction was monitored by TLC. The reaction was quenched with ice-cold water (10 mL) and extracted with EtOAc (2×30 mL). The combined organic extracts were washed with water (40 mL), brine (40 mL), dried over anhydrous $Na_2SO_4$ and concentrated under reduced pressure to obtain the crude. The crude product was purified by silica gel column chromatography (eluent with 40-45% EtOAc/hexanes 25-30% EtOAc in hexane gradient) to afford 17 (8.0 mg) as an off-white solid. $^1$H NMR (400 MHz, $CDCl_3$): δ 8.76 (s, 1H), 8.48 (s, 1H), 7.73 (d, J=7.2 Hz, 1H), 7.48 (d, J=7.2 Hz, 1H), 7.38-7.24 (m, 2H), 7.14-7.09 (m, 1H), 7.02-6.92 (m, 2H), 6.78-6.72 (m, 1H), 6.67-6.62 (m, 1H), 6.41 (s, OH), 5.60 (d, J=14.5 Hz, 1H), 5.09 (d, J=14.5 Hz, 1H), 3.53 (s, 2H). HPLC: 79.36%. LC-MS (ESI): m/z 488 at RT 4.01 min with 88% purity.

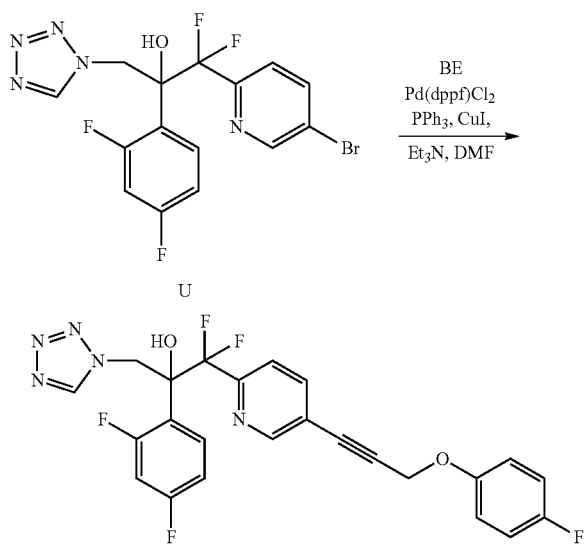

Scheme 15

18

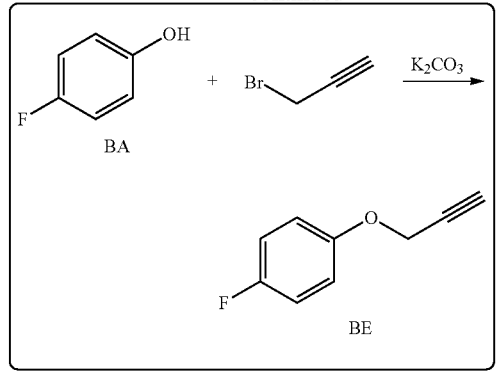

Example 18

2-(2,4-Difluorophenyl)-1,1-difluoro-1-(5-(3-(4-fluorophenoxy)prop-1-yn-1-yl)pyridin-2-yl)-3-(1H-tetrazol-1-yl)propan-2-ol (18)

To a stirred solution of 4-fluorophenol (1.0 g, 8.9 mmol) in DMF (25 mL) was added $K_2CO_3$ (1.84 g, 13.3 mmol) followed by a drop wise addition of propargyl bromide (1.1 mL, 9.8 mmol; 80 wt. % in toluene) at 0° C. under inert atmosphere. The resulting reaction mixture was allowed to warm to RT and then stirred for 8 h; progress of the reaction was monitored by TLC. The reaction mixture was quenched with ice-cold water (40 mL) and extracted with EtOAc (2×40 mL). The combined organic extracts were washed with water (40 mL), brine (40 mL), dried over anhydrous $Na_2SO_4$ and concentrated under reduced pressure to obtain the crude. The crude material was purified by silica gel column chromatography (0-5% EtOAc in hexane gradient) to afford compound BE (0.6 g, 4.0 mmol, 45%) as a colorless syrup. $^1$H NMR (500 MHz, $CDCl_3$): δ 7.00-6.91 (m, 4H), 4.65 (d, J=2.5 Hz, 2H), 2.51 (t, J=2.5 Hz, 1H). MS (EI): m/z 151 [M+H]$^+$. A stirring mixture of compound U (50 mg, 0.11 mmol), compound BE (28 mg, 0.18 mmol), Pd(dppf)$Cl_2.CH_2Cl_2$ complex (8.1 mg, 0.011 mmol), triphenylphosphine (3.0 mg, 0.011 mmol) and CuI (2.2 mg, 0.011 mmol) in $Et_3$N-DMF (2:1; 6 mL) was degassed by purging with argon for 15 min. The resulting reaction mixture was slowly heated up to 90° C. and stirring was continued for 8 h. After complete consumption of the starting material (by TLC), the reaction mixture was cooled to RT, filtered through a pad of celite and washed celite cake with EtOAc (3×20 mL). The filtrate was diluted with water (40 mL) and extracted with EtOAc (2×30 mL). The combined organic extracts were washed with water (30 mL), brine (30 mL), dried over anhydrous $Na_2SO_4$ and concentrated under reduced pressure to obtain the crude. The crude material was purified by silica gel column chromatography (25-30% EtOAc in hexane gradient) to afford 18 (25 mg, 0.049 mmol, 45%) as a brown semi solid. $^1$H NMR (500 MHz, $CDCl_3$): δ 8.73 (s, 1H), 8.54 (s, 1H), 7.80 (d, J=8.0 Hz, 1H), 7.51 (d, J=8.0 Hz, 1H), 7.30-7.28 (m, 1H), 7.14 (s, OH), 7.03-6.99 (m, 2H), 6.96-6.93 (m, 2H), 6.76-6.73 (m, 1H), 6.67-6.64 (m, 1H), 5.58 (d, J=14.0 Hz, 1H), 5.11 (d, J=14.0 Hz, 1H), 4.89 (s, 2H). MS (EI): m/z 502 [M+H]$^+$. HPLC: 97.55%.

Scheme 16

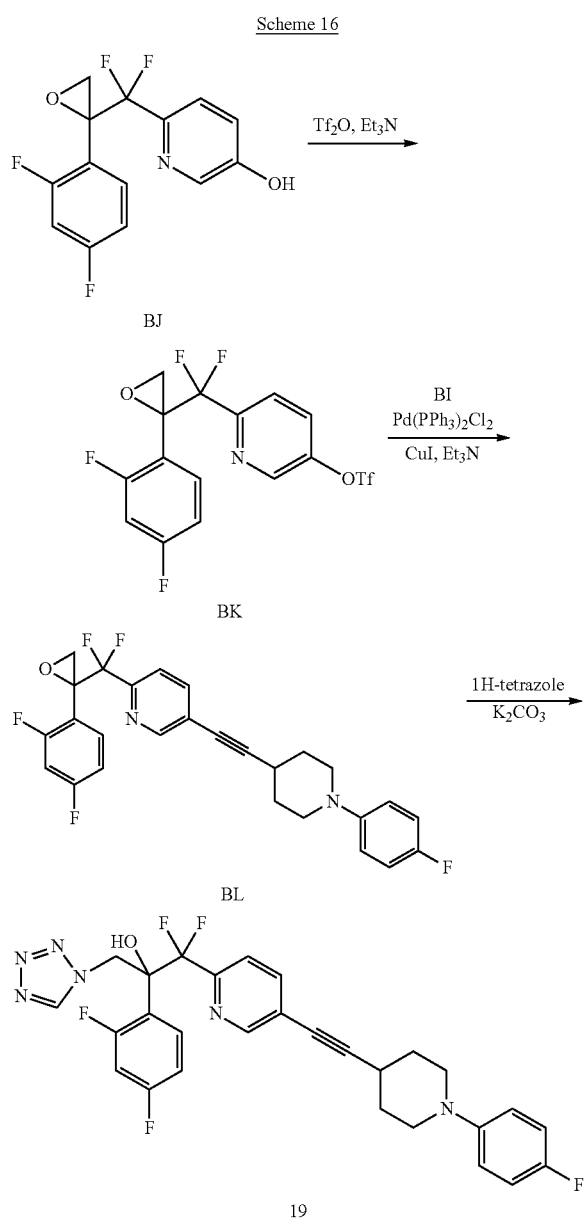

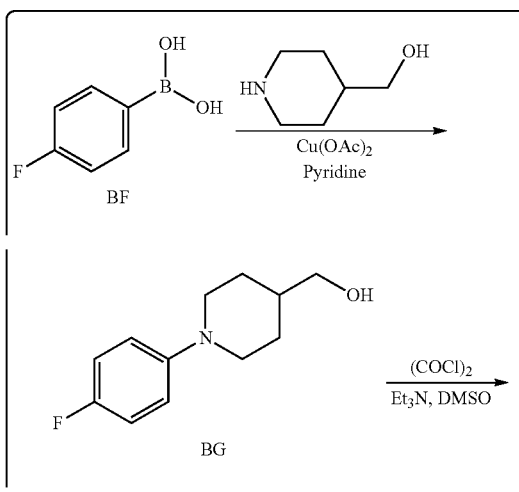

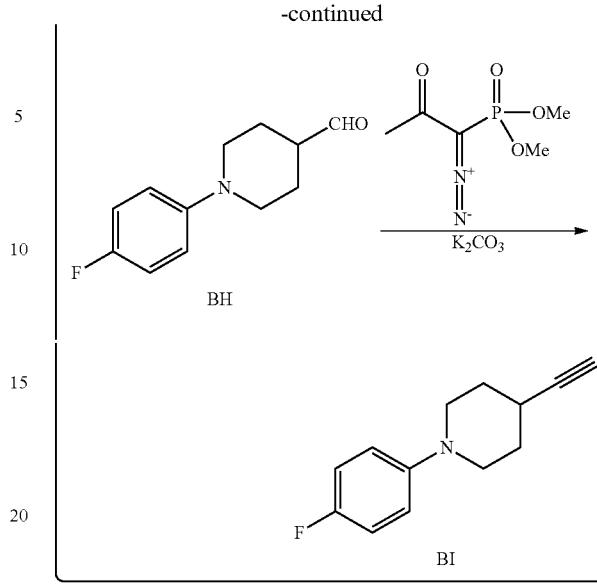

Example 19

2-(2,4-Difluorophenyl)-1,1-difluoro-1-(5-((1-(4-fluorophenyl)piperidin-4-yl)ethynyl)pyridin-2-yl)-3-(1H-tetrazol-1-yl)propan-2-ol (19)

To a suspension of piperidin-4-ylmethanol (750 mg, 6.51 mmol) in DCM (20 mL) were added 4-fluorophenylboronic acid BF (794 mg, 6.51 mmol), Cu(OAc)$_2$ (1.18 g, 6.51 mmol), pyridine (2.6 mL, 32.55 mmol), powdered 4 Å molecular sieves and the reaction was stirred at RT for 16 h under oxygen atmosphere. After consumption of the starting material (monitored by TLC), the reaction mixture was filtered through a pad of celite and washed celite cake with DCM (2×100 mL). The filtrate was washed with water (50 mL), brine (50 mL), dried over anhydrous Na$_2$SO$_4$ and concentrated under reduced pressure to obtain the crude. The crude material was purified by silica gel column chromatography (eluent: 40% EtOAc/hexanes) to afford compound BG (500 mg, mixture) as a colorless thick syrup. This material was taken for next reaction without further purification.

To a stirred solution of oxalyl chloride (0.42 mL, 4.78 mmol) in DCM (50 mL) was cooled to −78° C., and DMSO (0.74 mL, 9.47 mmol) was added drop wise under nitrogen atmosphere. After stirring for 15 min, a solution of compound BG (500 mg, crude) in DCM (10 mL) was added slowly at −78° C. and then maintained at same temperature for 15 min. To this, Et$_3$N (1.25 mL, 9.47 mmol) was added and stirring was continued at −78° C. for another 30 min. The resulting mixture was allowed to warm to RT; progress of the reaction was monitored by TLC. The reaction mixture was diluted with water (50 mL) and extracted with DCM (2×50 mL). The combined organic extracts were washed with saturated aqueous Na$_2$CO$_3$ solution (50 mL), water (50 mL), brine (30 mL), dried over anhydrous Na$_2$SO$_4$ and concentrated under reduced pressure to obtain the crude BH (500 mg). The crude material was used in next step without further purification. $^1$H NMR (400 MHz, CDCl$_3$): δ 9.71 (s, 1H), 6.98-6.91 (m, 4H), 3.50-3.45 (m, 2H), 2.84-2.78 (m, 2H), 2.39-2.36 (m, 1H), 2.07-2.04 (m, 2H), 1.87-1.77 (m, 2H).

To a stirred solution of compound BH (500 mg, crude) in MeOH (15 mL) was added K$_2$CO$_3$ (833 mg, 6.03 mmol) followed by Bestmann reagent (695 mg, 3.62 mmol) at RT under inert atmosphere. The reaction mixture was stirred at RT for 30 min. After completion of the reaction (by TLC), the volatiles were removed under reduced pressure to obtain the crude. The crude material was purified by silica gel column chromatography (eluent: 10% EtOAc/Hexanes) to afford compound BI (320 mg, 1.58 mmol) as a white solid. $^1$H NMR (400 MHz, CDCl$_3$): δ 6.94-6.87 (m, 4H), 3.38-3.33 (m, 2H), 2.92-2.86 (m, 2H), 2.57-2.53 (m, 1H), 2.10 (s, 1H), 2.00-1.96 (m, 2H), 1.85-1.79 (m, 2H). MS (EI): m/z 204 [M+H]$^+$ To a stirred solution of compound BJ (300 mg, crude) in DCM (20 mL) was added Et$_3$N (0.28 ml, 1.20 mmol) followed by Tf$_2$O (0.24 ml, 1.46 mmol) at 0° C. and stirred for 20 min; progress of the reaction was monitored by TLC. The reaction mixture was quenched with ice-cold water (20 mL) and extracted with DCM (2×50 mL). The combined organic extracts were washed with water (50 mL), brine (50 mL), dried over anhydrous Na$_2$SO$_4$ and concentrated under reduced pressure to obtain the crude BK (360 mg, crude). The crude material was used in next step without further purification.

To a stirred solution of compound BK (150 mg, crude), compound BI (84.3 mg, 0.417 mmol), Et$_3$N (0.15 mL, 0.62 mmol) in DMF (10 mL) were added CuI (3.3 mg, 0.017 mmol), and Pd(PPh$_3$)$_2$Cl$_2$ (24.4 mg, 0.034 mmol) under inert atmosphere. The reaction mixture was gradually heated up to 120° C. under Microwave for 20 min. After complete consumption of the starting material (by TLC), the reaction mixture was allowed to cool to RT; filtered through a pad of celite and washed celite cake with EtOAc (4×25 mL). The filtrate was washed with water (40 mL), dried over anhydrous Na$_2$SO$_4$ and concentrated under reduced pressure to obtain the crude. The crude material was purified by silica gel column chromatography (eluent: 10% EtOAc/Hexanes) to afford compound BL (200 mg, crude) as a pale-yellow solid.

To a stirred solution of compound BL (200 mg, crude) in DMF (10 mL) was added 1H-tetrazole (43.4 mg, 0.619 mmol) followed by K$_2$CO$_3$ (57 mg, 0.413 mmol) at RT under inert atmosphere. The resulting reaction mixture was gradually heated up to 65° C. and stirred for 16 h. The progress of the reaction was monitored by TLC. The reaction mixture was diluted with ice-cold water (50 mL) and extracted with EtOAc (2×50 mL). The combined organic extracts were washed with water (40 mL), brine (40 mL), dried over anhydrous Na$_2$SO$_4$ and concentrated under reduced pressure to obtain the crude. The crude material was purified by silica gel column chromatography (eluent: 40% EtOAc/hexanes) to afford 19 (60 mg, 0.108 mmol) as a light-yellow solid. $^1$H NMR (400 MHz, CDCl$_3$): δ 8.75 (s, 1H), 8.52 (s, 1H), 7.77 (dd, J=8.4, 2.0 Hz, 1H), 7.49 (d, J=8.4 Hz, 1H), 7.49 (s, OH), 7.32-7.27 (m, 1H), 6.99-6.85 (m, 4H), 6.81-6.72 (m, 1H), 6.70-6.60 (m, 1H), 5.59 (d, J=14.4 Hz, 1H), 5.10 (d, J=14.4 Hz, 1H), 3.42-3.36 (m, 2H), 2.97-2.91 (m, 2H), 2.81-2.76 (m, 1H), 2.06-2.04 (m, 2H), 1.93-1.87 (m, 2H). MS (ESI): m/z 555 [M+H]$^+$. HPLC: 97.52%.

Scheme 17

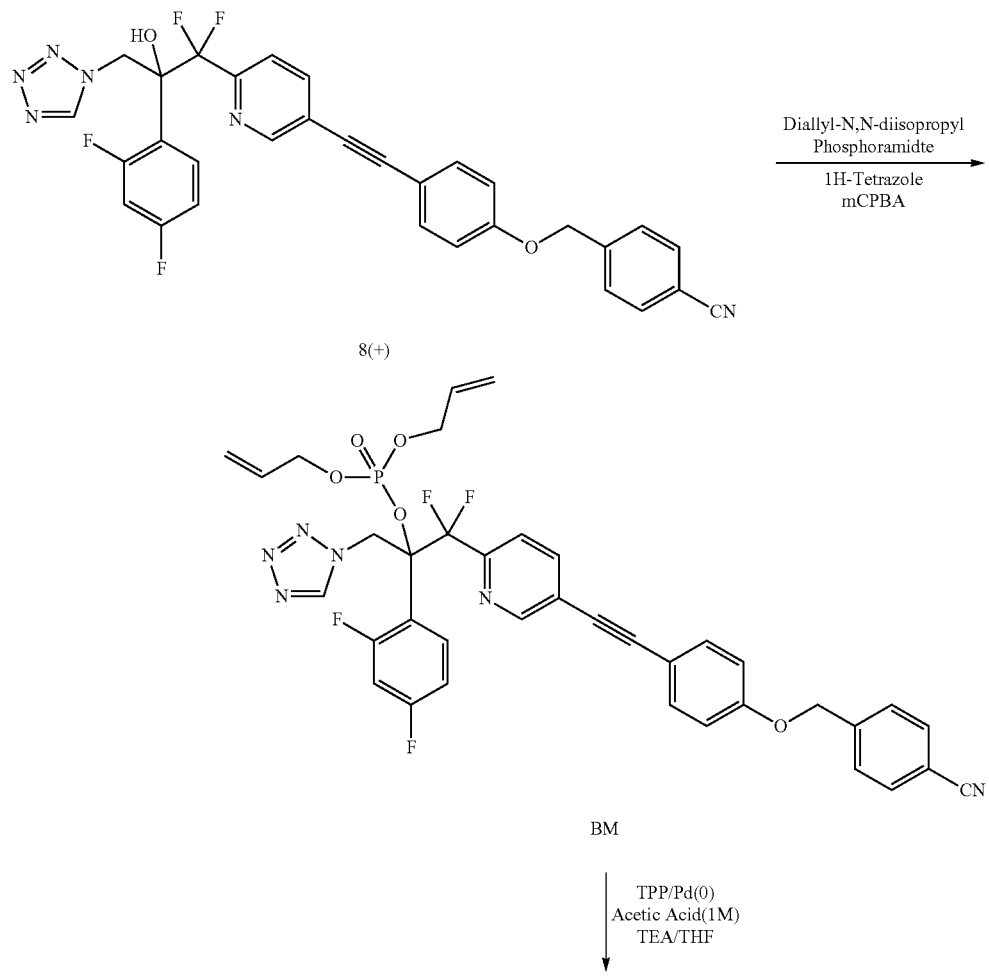

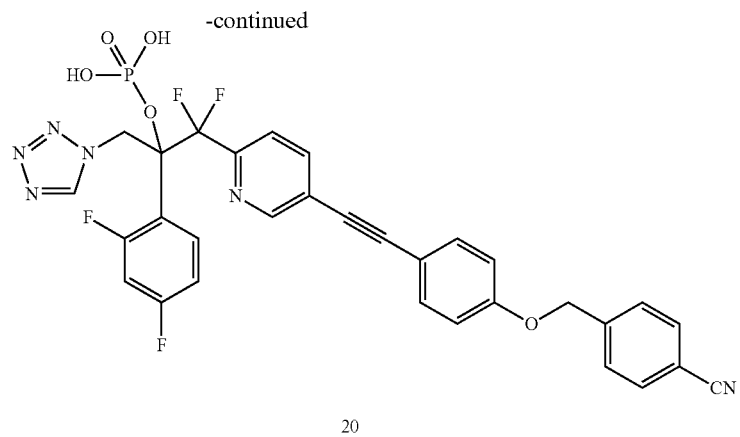

20

Example 20

1-(5-((4-((4-Cyanobenzyl)oxy)phenyl)ethynyl)pyridin-2-yl)-2-(2,4-difluorophenyl)-1,1-difluoro-3-(1H-tetrazol-1-yl) propan-2-yl dihydrogen phosphate (20)

To a stirred suspension of 8(+) (400 mg, 0.686 mmol) and 1H-tetrazole (236 mg, 3.43 mmol) in DCM (25 mL) was added a solution of diallyl-N, N-diisopropylphosphoramidite (0.72 mL, 2.74 mmol) in DCM (5 mL) at RT and stirred for 2 h. A solution of mCPBA (472 mg, 2.74 mmol) in DCM (5 mL) was added slowly at −5° C. and stirred for 1 h. After complete consumption of the starting material, the reaction mixture was diluted with DCM (50 mL), washed with 5% aqueous $Na_2S_2O_5$ (2×40 mL), 10% aqueous $NaHCO_3$ (2×40 mL), brine (50 mL), dried over anhydrous $Na_2SO_4$ and concentrated under reduced pressure to obtain the crude. The residue was purified by mass based preparative HPLC to afford compound BM (250 mg, 0.336 mmol, 49%) as a colorless semi-solid. $^1$H NMR (500 MHz, $CDCl_3$): δ 9.10 (s, 1H), 8.75 (s, 1H), 7.76 (d, J=8.0 Hz, 1H), 7.70 (d, J=8.0 Hz, 2H), 7.56-7.50 (m, 4H), 7.46-7.42 (m, 1H), 7.17 (d, J=8.0 Hz, 1H), 6.96 (d, J=8.0 Hz, 2H), 6.83-6.80 (m, 1H), 6.66-6.62 (m, 1H), 6.19 (d, J=16.0 Hz, 1H), 6.02-5.97 (m, 1H), 5.91 (d, J=16.0 Hz, 1H), 5.85-5.79 (m, 1H), 5.44 (d, J=17.0 Hz, 1H), 5.33-5.22 (m, 3H), 5.16 (s, 2H), 4.74 (d, J=4.0 Hz, 2H), 4.49-4.39 (m, 2H). HPLC: 98.46%.

To a stirred solution of compound BM (220 mg, 0.295 mmol) in THF (10 mL) were added TPP (58 mg, 0.221 mmol) followed by $Pd(PPh_3)_4$ (27 mg, 0.023 mmol), $Et_3N$ (0.08 mL, 0.59 mmol) and 1M Acetic acid solution (1.47 mL, 1.47 mmol) at 0° C. The resulting mixture was stirred at RT for 16 h; progress of the reaction was monitored by TLC. The reaction mixture was filtered through a pad of celite and washed the celite cake with DCM (3×30 mL) and EtOH (3×10 mL). The filtrate was concentrated under reduced pressure to obtain the crude. The crude material was purified by mass based preparative HPLC to afford 20 (70 mg, 0.105 mmol, 35.60%) as a white solid. $^1$H NMR (400 MHz, $CD_3OD$): δ 9.33 (s, 1H), 8.70 (s, 1H), 7.92 (d, J=8.0 Hz, 1H), 7.75 (d, J=8.4 Hz, 2H), 7.64 (d, J=8.4 Hz, 2H), 7.51 (d, J=8.0 Hz, 2H), 7.45-7.39 (m, 1H), 7.34-7.27 (m, 1H), 7.05 (d, J=8.0 Hz, 2H), 6.95-6.89 (m, 1H), 6.83-6.78 (m, 1H), 6.21 (d, J=15.2 Hz, 1H), 5.94 (d, J=15.2 Hz, 1H), 5.21 (s, 2H). $^{31}$P NMR (500 MHz, $CD_3OD$): δ −6.98 (s). MS (ESI): m/z 665 [M]$^+$. HPLC: 97.83%.

Scheme 18

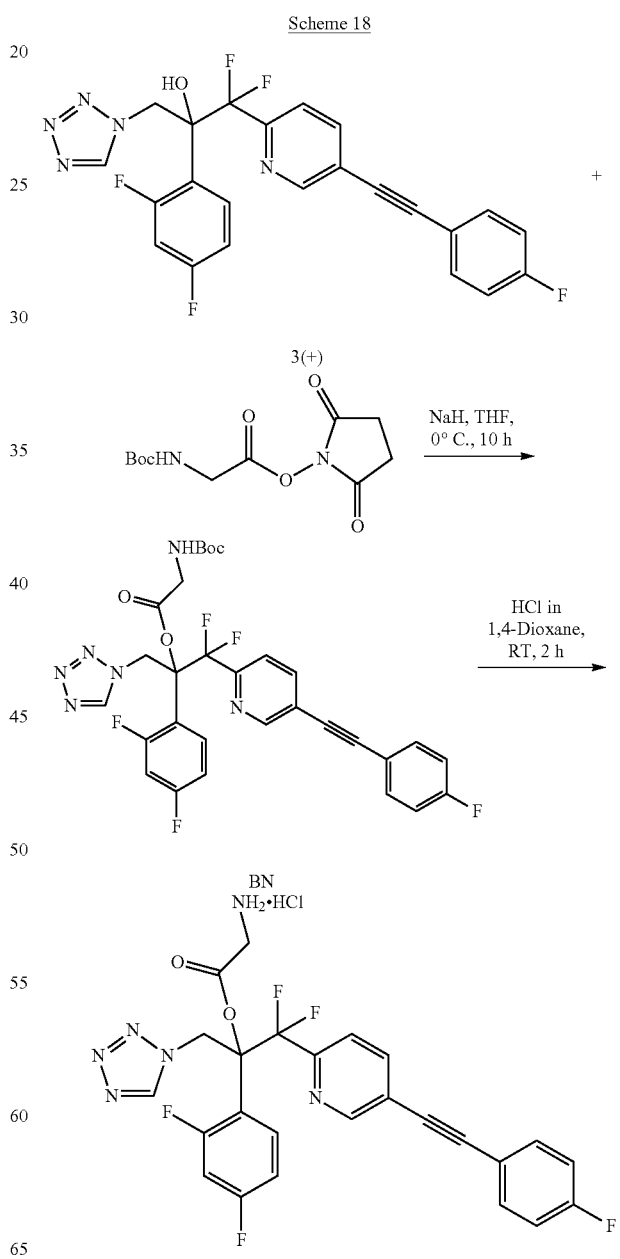

144

Example 144

2-(2,4-Difluorophenyl)-1,1-difluoro-1-(5-((4-fluorophenyl)ethynyl)pyridin-2-yl)-3-(1H-tetrazol-1-yl)propan-2-yl 2-aminoacetate hydrochloride (144)

To a stirred solution of 3 (+) (25 mg, 0.053 mmol) in dry THF (3 mL) was added NaH (5 mg, 0.21 mmol) at 0° C. and stirred at 0° C. for 2 h under inert atmosphere. A solution of N-Boc-Gly-OSu (28.8 mg, 0.10 mmol) in dry THF (2 mL) was added to the reaction mixture at 0° C. and the stirring was continued at same temperature for another 10 h. The progress of the reaction was monitored by TLC. The reaction was quenched with ice-cold water (10 mL) and then extracted with EtOAc (2×15 mL). The combined organic layers were washed with water (10 mL), brine (10 mL), dried over anhydrous $Na_2SO_4$ and concentrated under reduced pressure to obtain the crude product.

Note: The reaction was conducted in 2×25 mg batches and the obtained crude product was combined and purified by preparative TLC to afford BN (12 mg, 0.019 mmol, 18%) as pale yellow semi-solid. $^1$H NMR (500 MHz, $CDCl_3$): δ 9.27 (s, 1H), 8.82 (s, 1H), 7.75 (d, J=8.5 Hz, 1H), 7.57-7.54 (m, 2H), 7.40-7.39 (m, 1H), 7.11-7.08 (m, 2H), 6.99 (d, J=8.0 Hz, 1H), 6.93-6.91 (m, 1H), 6.67-6.63 (m, 1H), 6.05 (d, J=15.0 Hz, 1H), 5.68 (d, J=15.0 Hz, 1H), 5.09 (bs, 1H), 4.19-4.14 (m, 1H), 3.97-3.93 (m, 1H), 1.45 (s, 9H). MS (ESI): m/z 629 $[M+H]^+$.

To a stirred solution of compound BN (18 mg, 0.028 mmol) in 1,4-dioxane (1 mL) was added 4M HCl solution in 1,4-dioxane (0.5 mL) drop-wise at RT and maintained for 2 h. The progress of the reaction was monitored by TLC. The volatiles were evaporated under reduced pressure. The obtained crude was triturated with diethyl ether (3×3 mL) to afford 144 (10 mg, 0.017 mmol, 62%) as a pale yellow solid. $^1$H NMR (400 MHz, DMSO-$d_6$): δ 9.66 (s, 1H), 8.82 (s, 1H), 8.59 (bs, 3H), 8.03 (d, J=7.6 Hz, 1H), 7.69-7.67 (m, 2H), 7.44-7.42 (m, 1H), 7.34-7.30 (m, 4H), 7.12-7.10 (m, 1H), 6.15 (d, J=15.6 Hz, 1H), 5.56 (d, J=15.6 Hz, 1H), 4.13 (d, J=17.6 Hz, 1H), 3.90 (d, J=17.6 Hz, 1H). MS (ESI): m/z 529 $[(M-HCl)+H]^+$. HPLC: 97.9%.

Scheme 19

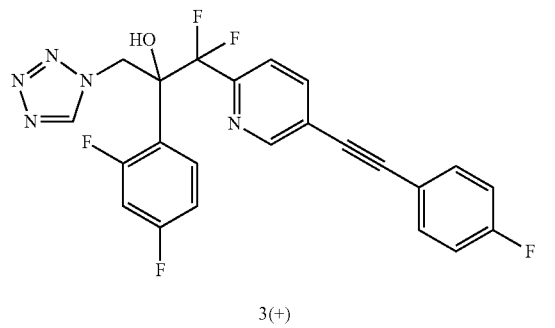

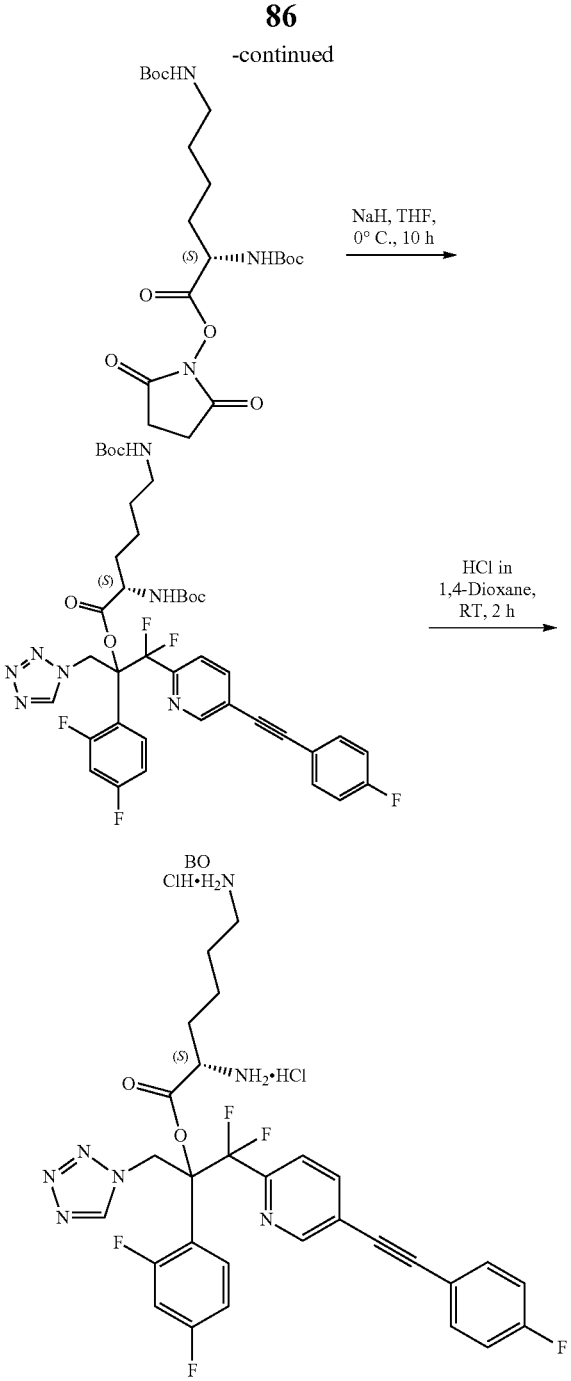

Example 145

(2S)-2-(2,4-Difluorophenyl)-1,1-difluoro-1-(5-((4-fluorophenyl)ethynyl)pyridin-2-yl)-3-(1H-tetrazol-1-yl)propan-2-yl 2,6-diaminohexanoate dihydrochloride (145)

$^1$H NMR (400 MHz, DMSO-$d_6$): δ 9.69 (s, 1H), 8.86 (s, 1H), 8.73 (bs, 3H), 8.07 (d, J=8.0 Hz, 1H), 7.97 (bs, 3H), 7.71-7.69 (m, 3H), 7.33-7.21 (m, 4H), 7.18-7.12 (m, 1H), 6.15 (d, J=15.6 Hz, 1H), 5.63 (d, J=15.6 Hz, 1H), 4.25-4.20 (m, 1H), 2.76-2.72 (m, 2H), 1.90-1.83 (m, 2H), 1.61-1.22 (m, 4H). MS (ESI): m/z 600 $[(M-2HCl)+H]^+$. HPLC: 96.5%.

Examples 21-166 were prepared essentially according to the above synthetic procedures. The following table contains compound information and analytical data for Examples 1-166.

| Example Number | HPLC Method | HPLC (RT) | MS (ESI) (M + H) | Stereochem./ Optical Rotation | Structure |
|---|---|---|---|---|---|
| 1 | Method A: Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.808 | 454 | Racemic | 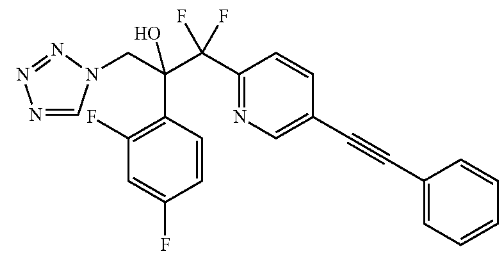 [SMILES: OC(Cn1cnnn1)(c1ccc(F)cc1F)C(F)(F)c1ccc(C#Cc2ccccc2)cn1] |
| 2 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.005 | 488 | Racemic | 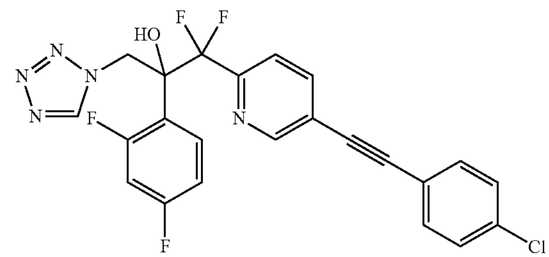 [SMILES: OC(Cn1cnnn1)(c1ccc(F)cc1F)C(F)(F)c1ccc(C#Cc2ccc(Cl)cc2)cn1] |
| 3 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.797 | 472 | Racemic | 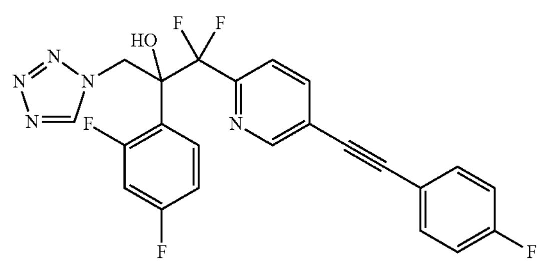 |
| 3(+) | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.700 | 472 | (+) 28.7 | 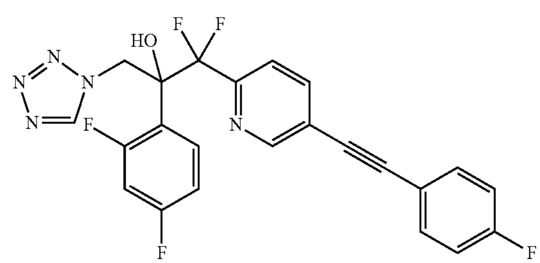 [SMILES: OC(Cn1cnnn1)(c1ccc(F)cc1F)C(F)(F)c1ccc(C#Cc2ccc(F)cc2)cn1] |
| | Method B Column, Type, Size: ChiralPak IC, 250 × 4.6 mm, 5μ Mobile Phase A: n-Hexane Mobile Phase B: IPA A:B:: 50:50 Flow Rate: 1.0 mL/min | 17.397 | | | |

| Example Number | HPLC Method | HPLC (RT) | MS (ESI) (M + H) | Stereochem./ Optical Rotation | Structure |
|---|---|---|---|---|---|
| 4 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.813 | 490 | Racemic | 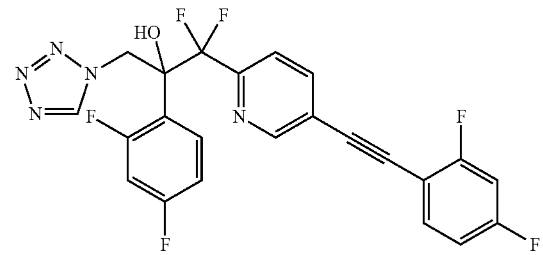 |
| 5 | Method C Column, Type, Size: Acquity UPLC BEH C-18 (2.1 × 50 mm, 1.7µ) Mobile Phase: Solvent A: Acetonitrile Solvent B: 0.025% TFA (Aq) Flow Rate: 0.50 mL/min | 2.918 | 522 | Racemic | 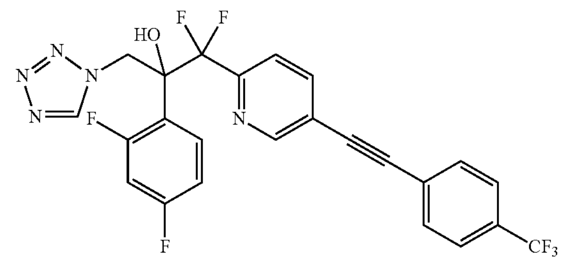 [SMILES: OC(Cn1cnnn1)(c1ccc(F)cc1F)C(F)(F)c1ccc(C#Cc2ccc(C(F)(F)F)cc2)cn1] |
| 6 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.69 | 611.5 | Racemic | 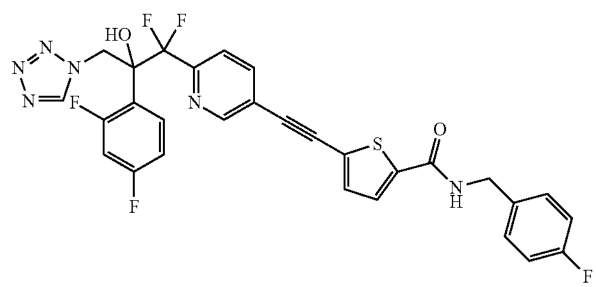 [SMILES: O=C(NCc1ccc(F)cc1)c1ccc(C#Cc2ccc(C(F)(F)C(O)(Cn3cnnn3)c3ccc(F)cc3F)nc2)s1] |
| 6(+) | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min Method J Column, Type, Size: ChiralPak IA, 250 × 4.6 mm, 5µ Mobile Phase A: n-Hexane Mobile Phase B: Ethanol A:B:: 75:25 Flow Rate: 1.0 mL/min | 2.725 20.224 | 611 | (+) 19.76 | 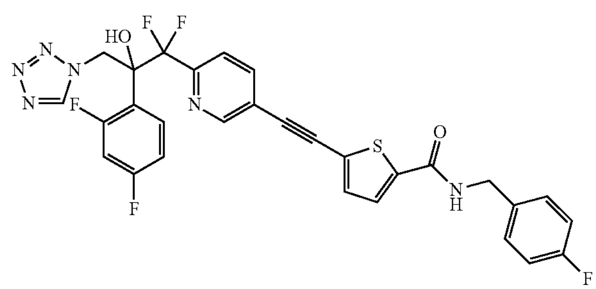 [SMILES: O=C(NCc1ccc(F)cc1)c1ccc(C#Cc2ccc(C(F)(F)C(O)(Cn3cnnn3)c3ccc(F)cc3F)nc2)s1] |
| 7 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.95 | 603.4 | Racemic | 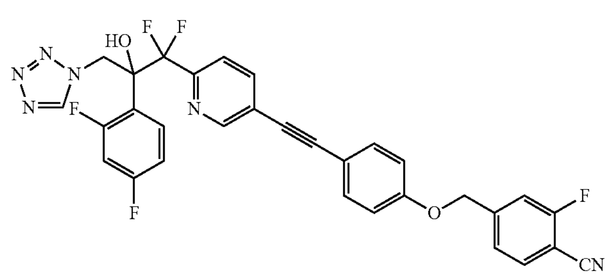 |

| Example Number | HPLC Method | HPLC (RT) | MS (ESI) (M + H) | Stereo-chem./ Optical Rotation | Structure |
|---|---|---|---|---|---|
| 7(+) | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min Method G Column, Type, Size: ChiralPak IC, 250 × 4.6 mm, 5 μm Mobile Phase A: 0.1 % TEA in n-Hexane Mobile Phase B: Ethanol A:B:: 70:30 Flow Rate: 1.0 mL/min | 3.022  28.550 | 603 | (+) 23.12 | 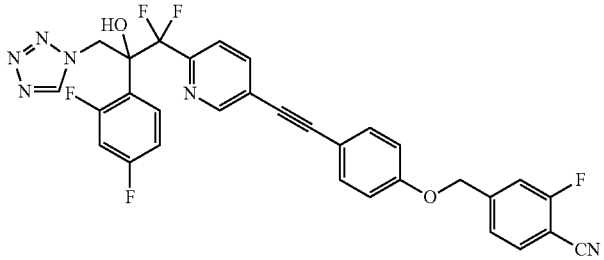 [SMILES: N#Cc1ccc(COc2ccc(C#Cc3ccc(C(F)(F)C(O)(Cn4cnnn4)c4ccc(F)cc4F)nc3)cc2)cc1F] |
| 8 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.919 | 585 | Racemic | 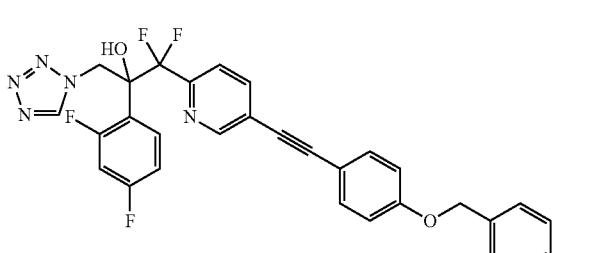 |
| 8(+) | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min Method L Column, Type, Size: ChiralPak IC, 250 × 4.6 mm, 5 μm Mobile Phase A: 0.1% DEA in n-Hexane Mobile Phase B: Ethanol A:B:: 60:40 Flow Rate: 1.0 mL/min | 2.990  16.681 | 585 | (+) 29.0 | 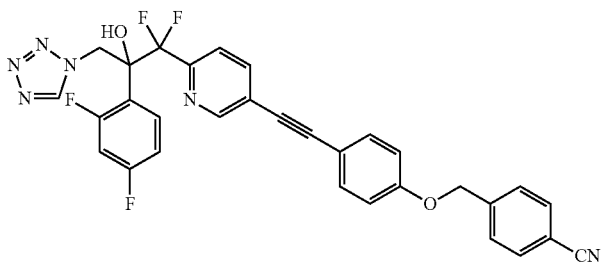 [SMILES: N#Cc1ccc(COc2ccc(C#Cc3ccc(C(F)(F)C(O)(Cn4cnnn4)c4ccc(F)cc4F)nc3)cc2)cc1] |
| 9 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.60 | 552 | Racemic | 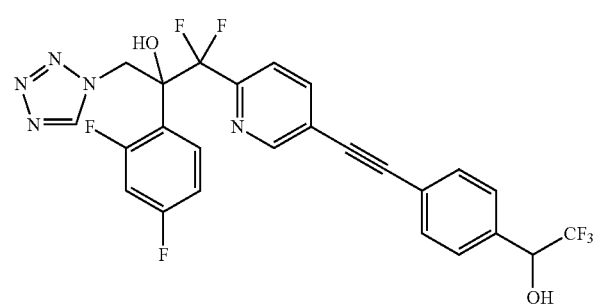 [SMILES: OC(c1ccc(C#Cc2ccc(C(F)(F)C(O)(Cn3cnnn3)c3ccc(F)cc3F)nc2)cc1)C(F)(F)F] |

-continued

| Example Number | HPLC Method | HPLC (RT) | MS (ESI) (M + H) | Stereochem./ Optical Rotation | Structure |
|---|---|---|---|---|---|
| 9(−) | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min Method K Column, Type, Size: ChiralPak IA, 250 × 4.6 mm, 5μ Mobile Phase A: 0.1% DEA in n-Hexane Mobile Phase B: Methanol A:B:: 80:20 Flow Rate: 1.0 mL/min | 2.604<br><br>19.563 | 552 | (−) 2.160 | 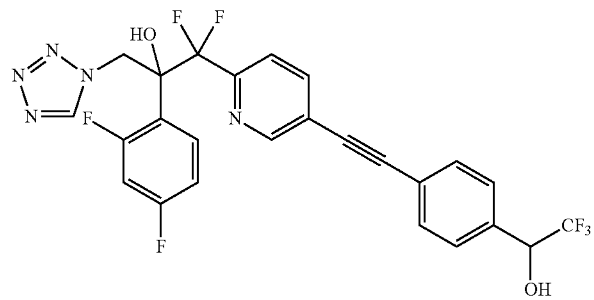 [SMILES: OC(c1ccc(C#Cc2ccc(C(F)(F)C(O)(Cn3cnnn3)c3ccc(F)cc3F)nc2)cc1)C(F)(F)F] |
| 10 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.525 | 457 | Racemic | 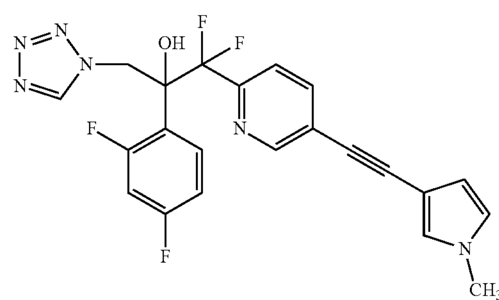 [SMILES: Cn1ccc(C#Cc2ccc(C(F)(F)C(O)(Cn3cnnn3)c3ccc(F)cc3F)nc2)c1] |
| 11 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.997 | 475 (M − H)− | Racemic | 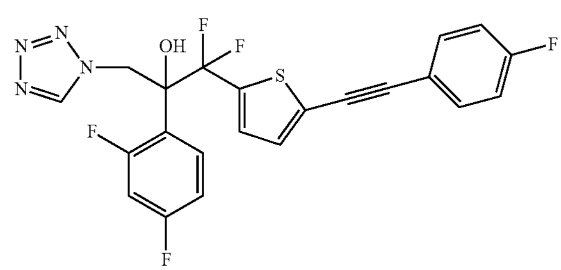 [SMILES: OC(Cn1cnnn1)(c1ccc(F)cc1F)C(F)(F)c1ccc(C#Cc2ccc(F)cc2)s1] |
| 12 | Method F Column, Type, Size: Eclipse XDB C-18 (150 × 4.63 mm, 5 μm) Mobile Phase A: ACN Mobile Phase B: 5 mM NH4OAC Flow Rate: 1.0 mL/min | 10.567 | 491 | Racemic | 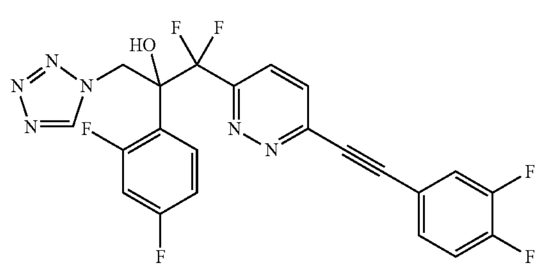 [SMILES: OC(Cn1cnnn1)(c1ccc(F)cc1F)C(F)(F)c1ccc(C#Cc2ccc(F)c(F)c2)nn1] |

-continued

| Example Number | HPLC Method | HPLC (RT) | MS (ESI) (M + H) | Stereochem./ Optical Rotation | Structure |
|---|---|---|---|---|---|
| 13 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.056 | 420 (M − H)⁻ | Racemic | 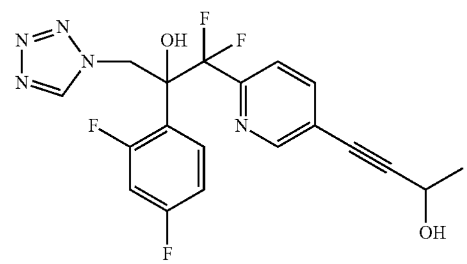 [SMILES: CC(O)C#Cc1ccc(C(F)(F)C(O)(Cn2cnnn2)c2ccc(F)cc2F)nc1] |
| 14 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.626 | 558 | Racemic | 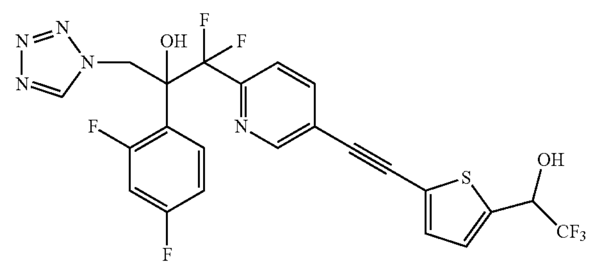 |
| 15 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.732 | 491 | Racemic | 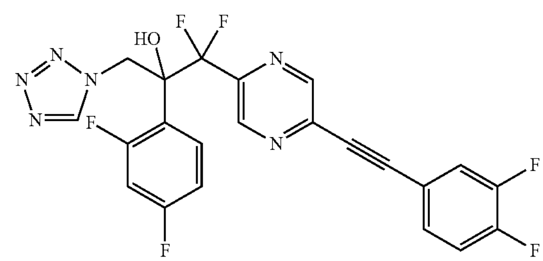 [SMILES: OC(Cn1cnnn1)(c1ccc(F)cc1F)C(F)(F)c1cnc(C#Cc2ccc(F)c(F)c2)cn1] |
| 16 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.474 | 542 | Racemic | 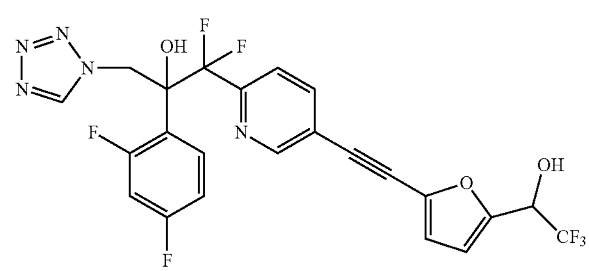 [SMILES: OC(c1ccc(C#Cc2ccc(C(F)(F)C(O)(Cn3cnnn3)c3ccc(F)cc3F)nc2)o1)C(F)(F)F] |
| 17 | Method A Column, Type, Size: Acquity BEH C-18 (50 × 2.1 mm, 1.7μ) Mobile Phase: Solvent A: Acetonitrile Solvent B: 0.025% TEA (Aq) Flow Rate: 0.50 mL/min | 2.830 | 486 | Racemic | 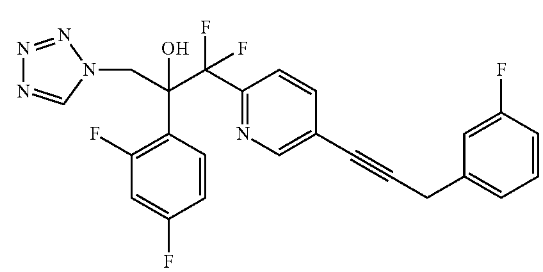 [SMILES: OC(Cn1cnnn1)(c1ccc(F)cc1F)C(F)(F)c1ccc(C#CCc2cccc(F)c2)cn1] |

-continued

| Example Number | HPLC Method | HPLC (RT) | MS (ESI) (M + H) | Stereochem./ Optical Rotation | Structure |
|---|---|---|---|---|---|
| 18 | Method F Column, Type, Size: Eclipse XDB C-18 (150 × 4.6 mm, 5 μm) Mobile Phase A: ACN Mobile Phase B: 5 mM NH₄OAC Flow Rate: 1.0 mL/min | 8.753 | 502 | Racemic | 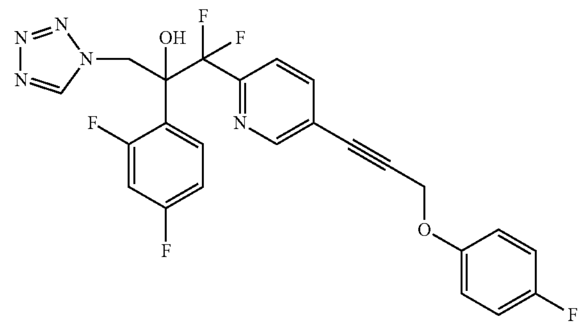 [SMILES: OC(Cn1cnnn1)(c1ccc(F)cc1F)C(F)(F)c1ccc(C#CCOc2ccc(F)cc2)cn1] |
| 19 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.426 | 555 | Racemic | 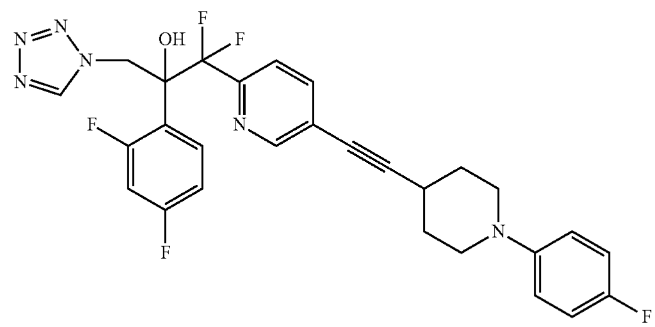 [SMILES: OC(Cn1cnnn1)(c1ccc(F)cc1F)C(F)(F)c1ccc(C#CC2CCN(c3ccc(F)cc3)CC2)cn1] |
| 20 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.574 | 509 | Racemic | 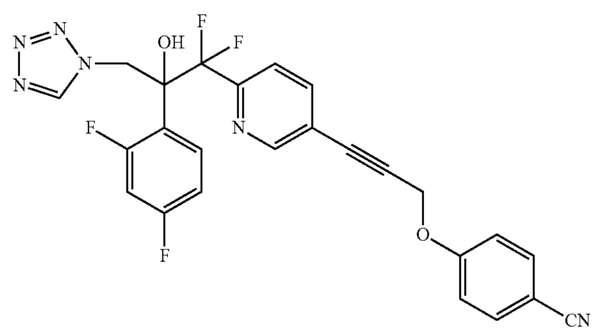 [SMILES: N#Cc1ccc(OCC#Cc2ccc(C(F)(F)C(O)(Cn3cnnn3)c3ccc(F)cc3F)nc2)cc1] |
| 21 | Method C (Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.931 | 488 | Racemic | 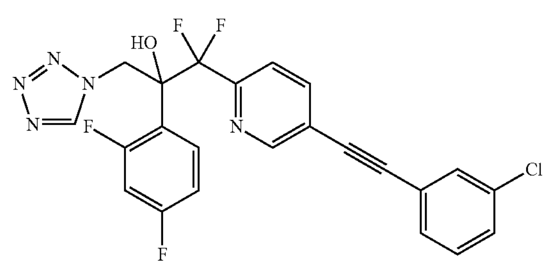 [SMILES: OC(Cn1cnnn1)(c1ccc(F)cc1F)C(F)(F)c1ccc(C#Cc2cccc(Cl)c2)cn1] |
| 22 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.015 | 540 | Racemic | 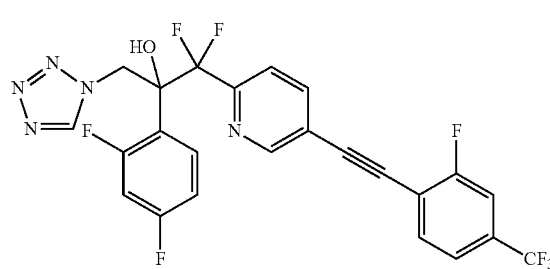 [SMILES: OC(Cn1cnnn1)(c1ccc(F)cc1F)C(F)(F)c1ccc(C#Cc2ccc(C(F)(F)F)cc2F)cn1] |

-continued

| Example Number | HPLC Method | HPLC (RT) | MS (ESI) (M + H) | Stereochem./ Optical Rotation | Structure |
|---|---|---|---|---|---|
| 23 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.401 | 428 | Racemic | 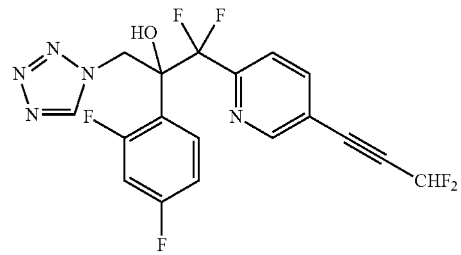 [SMILES: OC(Cn1cnnn1)(c1ccc(F)cc1F)C(F)(F)c1ccc(C#CC(F)F)cn1] |
| 24 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.754 | 472 | Racemic | 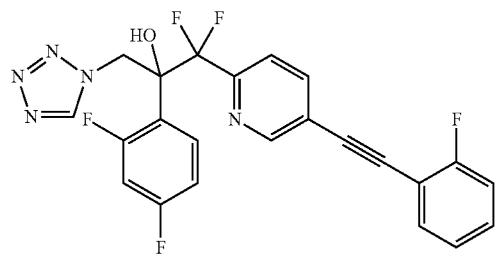 |
| 25 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.788 | 472 | Racemic | 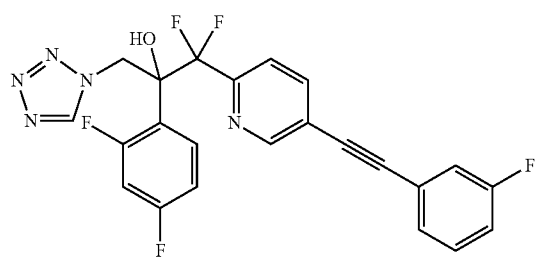 [SMILES: OC(Cn1cnnn1)(c1ccc(F)cc1F)C(F)(F)c1ccc(C#Cc2cccc(F)c2)cn1] |
| 26 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.751 | 504 | Racemic | 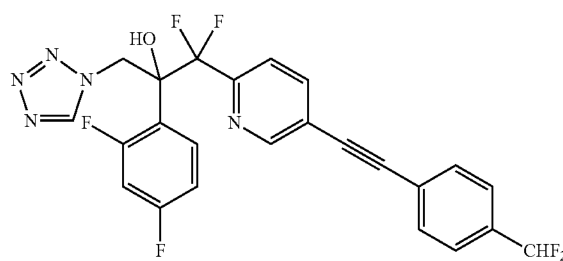 |
| 27 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.910 | 486 | Racemic | 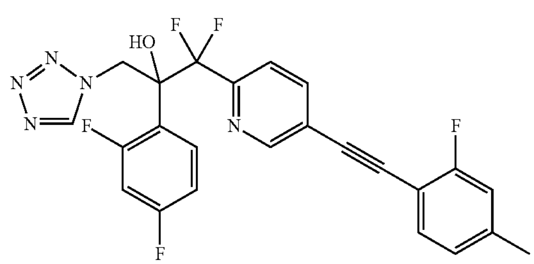 [SMILES: Cc1ccc(C#Cc2ccc(C(F)(F)C(O)(Cn3cnnn3)c3ccc(F)cc3F)nc2)c(F)c1] |

| Example Number | HPLC Method | HPLC (RT) | MS (ESI) (M + H) | Stereo-chem./ Optical Rotation | Structure |
| --- | --- | --- | --- | --- | --- |
| 28 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.336 | 473 | Racemic | 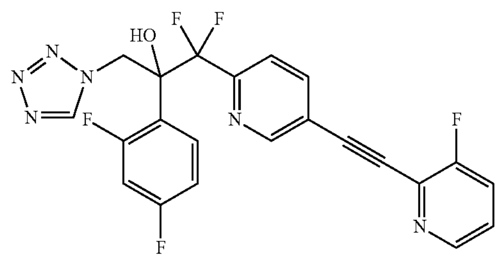 [SMILES: OC(Cn1cnnn1)(c1ccc(F)cc1F)C(F)(F)c1ccc(C#Cc2ncccc2F)cn1] |
| 29 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.013 | 494 | Racemic | 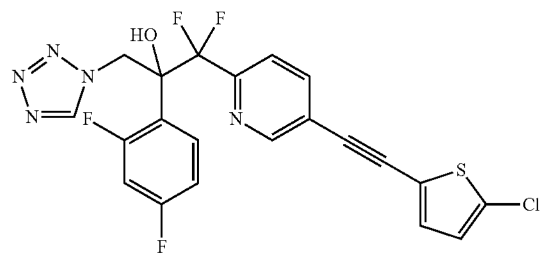 [SMILES: OC(Cn1cnnn1)(c1ccc(F)cc1F)C(F)(F)c1ccc(C#Cc2ccc(Cl)s2)cn1] |
| 30 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.002 | 528 | Racemic | 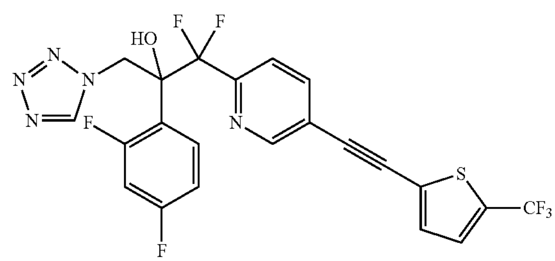 [SMILES: OC(Cn1cnnn1)(c1ccc(F)cc1F)C(F)(F)c1ccc(C#Cc2ccc(C(F)(F)F)s2)cn1] |
| 31 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.480 | 491 | Racemic | 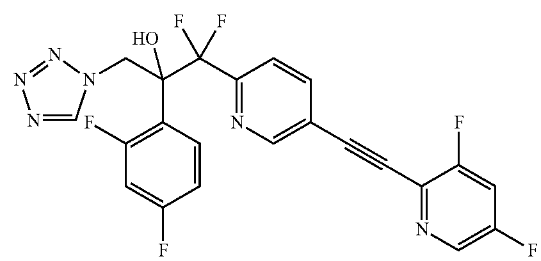 [SMILES: OC(Cn1cnnn1)(c1ccc(F)cc1F)C(F)(F)c1ccc(C#Cc2ncc(F)cc2F)cn1] |
| 32 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.401 | 473 | Racemic | 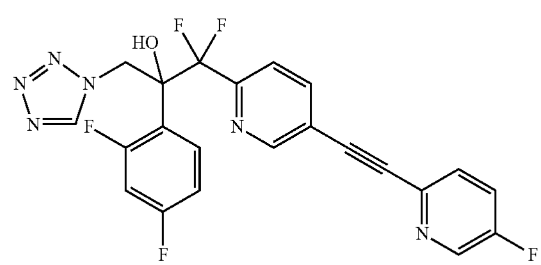 |

| Example Number | HPLC Method | HPLC (RT) | MS (ESI) (M + H) | Stereo-chem./ Optical Rotation | Structure |
|---|---|---|---|---|---|
| 33 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.508 | 473 | Racemic | 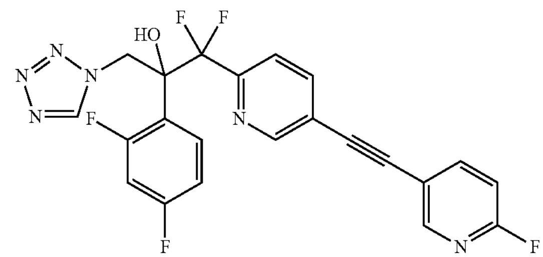 [SMILES: OC(Cn1cnnn1)(c1ccc(F)cc1F)C(F)(F)c1ccc(C#Cc2ccc(F)nc2)cn1] |
| 34 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.007 | 538 | Racemic | 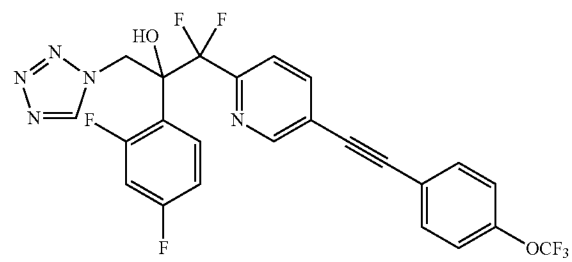 [SMILES: OC(Cn1cnnn1)(c1ccc(F)cc1F)C(F)(F)c1ccc(C#Cc2ccc(OC(F)(F)F)cc2)cn1] |
| 35 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.777 | 502 | Racemic | 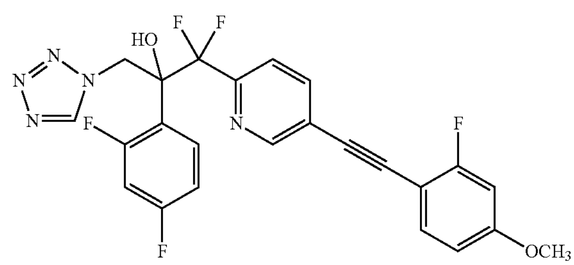 [SMILES: COc1ccc(C#Cc2ccc(C(F)(F)C(O)(Cn3cnnn3)c3ccc(F)cc3F)nc2)c(F)c1] |
| 36 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.739 | 490 | Racemic | 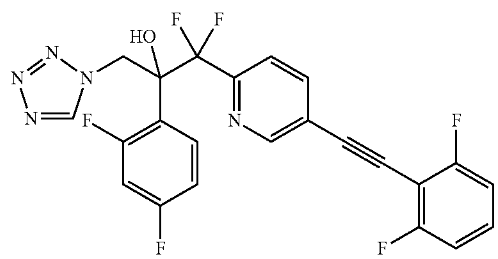 [SMILES: OC(Cn1cnnn1)(c1ccc(F)cc1F)C(F)(F)c1ccc(C#Cc2c(F)cccc2F)cn1] |
| 37 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.820 | 490 | Racemic | 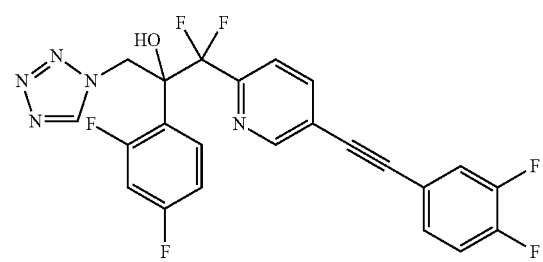 [SMILES: OC(Cn1cnnn1)(c1ccc(F)cc1F)C(F)(F)c1ccc(C#Cc2ccc(F)c(F)c2)cn1] |

-continued

| Example Number | HPLC Method | HPLC (RT) | MS (ESI) (M + H) | Stereochem./ Optical Rotation | Structure |
|---|---|---|---|---|---|
| 38 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.896 | 474 | Racemic | 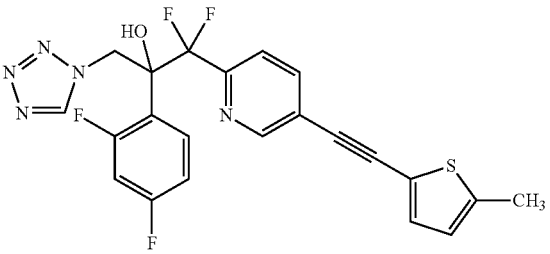 [SMILES: Cc1ccc(C#Cc2ccc(C(F)(F)C(O)(Cn3cnnn3)c3ccc(F)cc3F)nc2)s1] |
| 39 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.908 | 518 | Racemic | 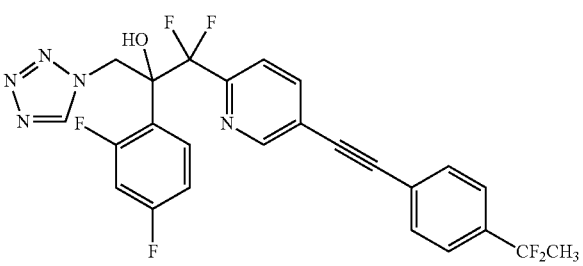 |
| 40 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.799 | 520 | Racemic | 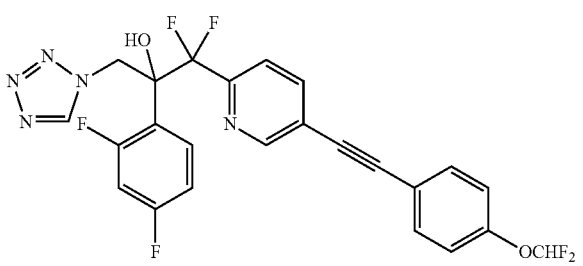 [SMILES: OC(Cn1cnnn1)(c1ccc(F)cc1F)C(F)(F)c1ccc(C#Cc2ccc(OC(F)F)cc2)cn1] |
| 41 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.165 | 554 | Racemic | 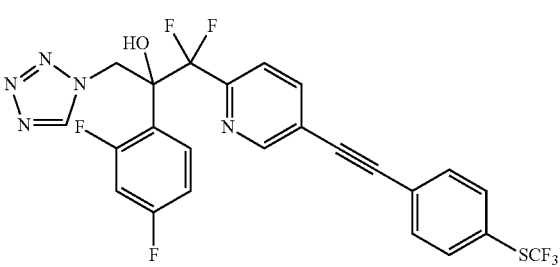 |
| 42 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.015 | 506 | Racemic | 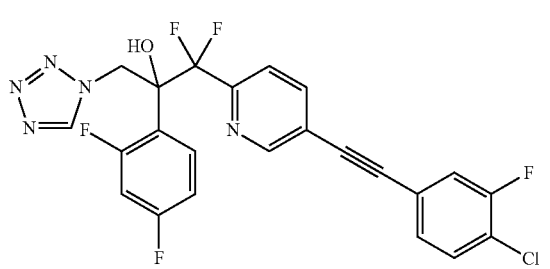 [SMILES: OC(Cn1cnnn1)(c1ccc(F)cc1F)C(F)(F)c1ccc(C#Cc2ccc(Cl)c(F)c2)cn1] |

| Example Number | HPLC Method | HPLC (RT) | MS (ESI) (M + H) | Stereochem./ Optical Rotation | Structure |
|---|---|---|---|---|---|
| 43 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.939 | 489 | Racemic | 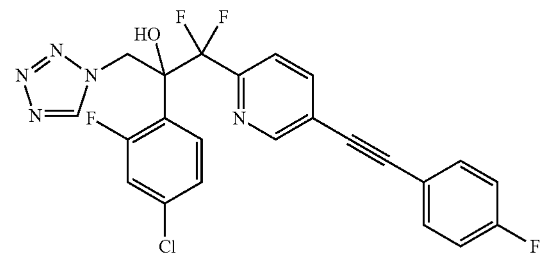 [SMILES: OC(Cn1cnnn1)(c1ccc(Cl)cc1F)C(F)(F)c1ccc(C#Cc2ccc(F)cc2)cn1] |
| 44 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.995 | 522 | Racemic | 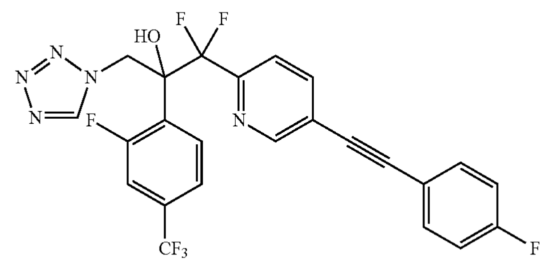 [SMILES: OC(Cn1cnnn1)(c1ccc(C(F)(F)F)cc1F)C(F)(F)c1ccc(C#Cc2ccc(F)cc2)cn1] |
| 45 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.802 | 472 | Racemic | 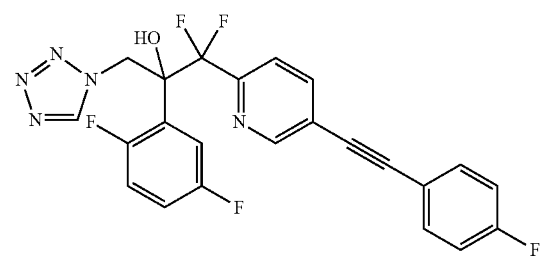 [SMILES: OC(Cn1cnnn1)(c1cc(F)ccc1F)C(F)(F)c1ccc(C#Cc2ccc(F)cc2)cn1] |
| 46 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.829 | 472 | Racemic | 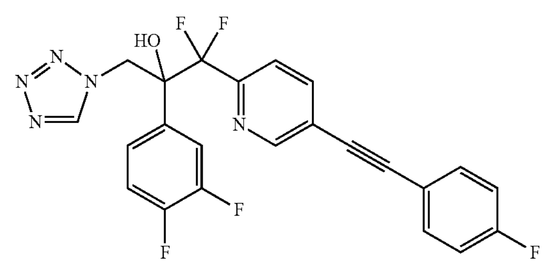 [SMILES: OC(Cn1cnnn1)(c1ccc(F)c(F)c1)C(F)(F)c1ccc(C#Cc2ccc(F)cc2)cn1] |
| 47 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.565 | 496 | Racemic | 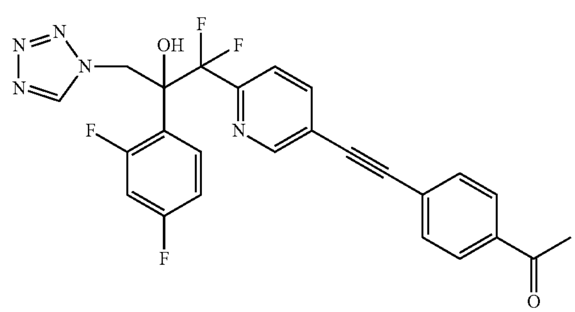 [SMILES: CC(=O)c1ccc(C#Cc2ccc(C(F)(F)C(O)(Cn3cnnn3)c3ccc(F)cc3F)nc2)cc1] |

-continued

| Example Number | HPLC Method | HPLC (RT) | MS (ESI) (M + H) | Stereochem./ Optical Rotation | Structure |
|---|---|---|---|---|---|
| 48 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.726 | 472 | Racemic | 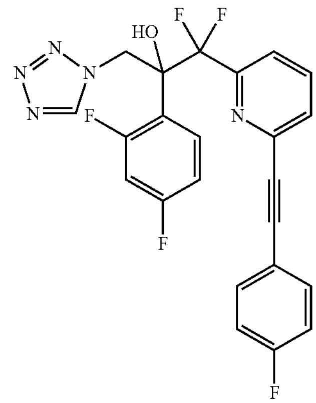 [SMILES: OC(Cn1cnnn1)(c1ccc(F)cc1F)C(F)(F)c1cccc(C#Cc2ccc(F)cc2)n1] |
| 49 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.538 | 473 | Racemic | 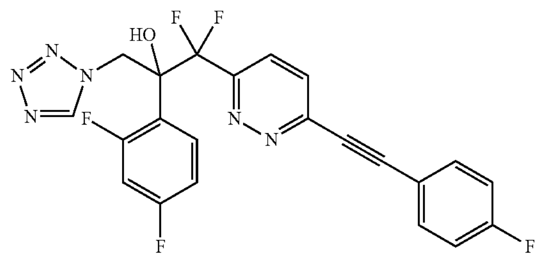 [SMILES: OC(Cn1cnnn1)(c1ccc(F)cc1F)C(F)(F)c1ccc(C#Cc2ccc(F)cc2)nn1] |
| 50 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.309 | 484 | Racemic | 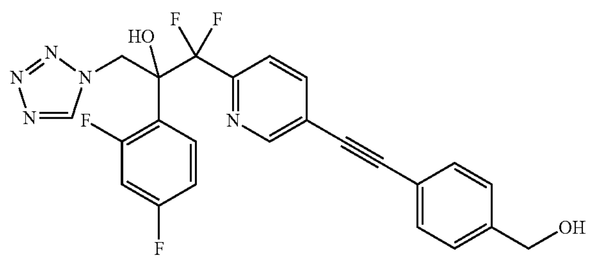 [SMILES: OCc1ccc(C#Cc2ccc(C(F)(F)C(O)(Cn3cnnn3)c3ccc(F)cc3F)nc2)cc1] |
| 51 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.751 | 498 | Racemic | 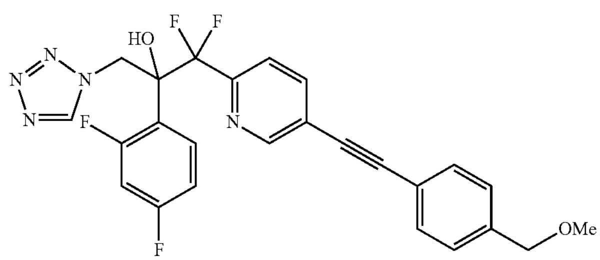 [SMILES: COCc1ccc(C#Cc2ccc(C(F)(F)C(O)(Cn3cnnn3)c3ccc(F)cc3F)nc2)cc1] |
| 52 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.300 | 476 | Racemic | 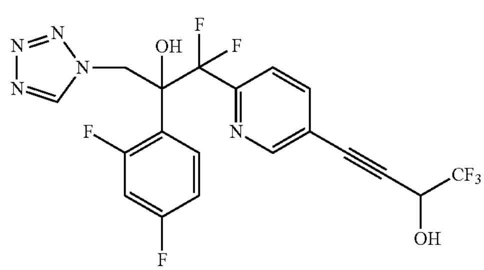 [SMILES: OC(C#Cc1ccc(C(F)(F)C(O)(Cn2cnnn2)c2ccc(F)cc2F)nc1)C(F)(F)F] |

-continued

| Example Number | HPLC Method | HPLC (RT) | MS (ESI) (M + H) | Stereo-chem./ Optical Rotation | Structure |
|---|---|---|---|---|---|
| 53 | Method A Column, Type, Size: Acquity BEH C-18 (50 × 2.1 mm, 1.7μ) Mobile Phase: Solvent A: Acetonitrile Solvent B: 0.025% TEA (Aq) Flow Rate: 0.50 mL/min | 3.040 | 539 | Racemic | 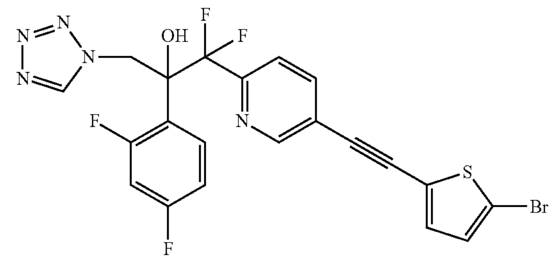 |
| 54 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.790 | 510 | Racemic | 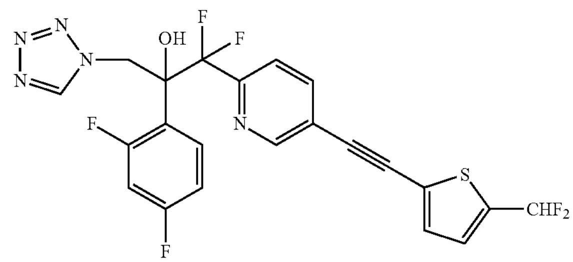 |
| 55 | Method D Column, Type, Size: X-Terra RP-18 (50 × 4.6 mm, 5 μm) Mobile Phase A: ACN: THF (80:20) Mobile Phase B: 0.1% TFA in water Flow Rate: 1.0 mL/min | 6.429 | 556 | Racemic | 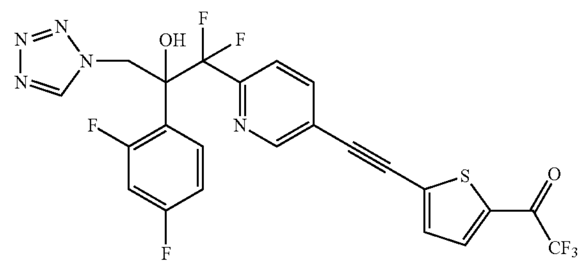 [SMILES: O=C(c1ccc(C#Cc2ccc(C(F)(F)C(O)(Cn3cnnn3)c3ccc(F)cc3F)nc2)s1)C(F)(F)F] |
| 56 | Method E Column, Type, Size: Eclipse XDB C-18 (150 × 4.6 mm, 5.0 μm) Mobile Phase A: ACN Mobile Phase B: 0.1% Aq TFA Flow Rate: 1.0 mL/min | 11.270 | 525 | Racemic | 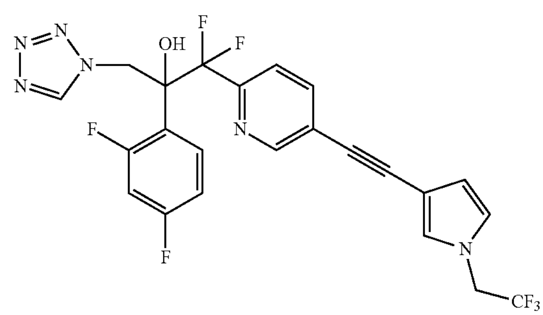 [SMILES: OC(Cn1cnnn1)(c1ccc(F)cc1F)C(F)(F)c1ccc(C#Cc2ccn(CC(F)(F)F)c2)cn1] |
| 57 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.371 | 490 | Racemic | 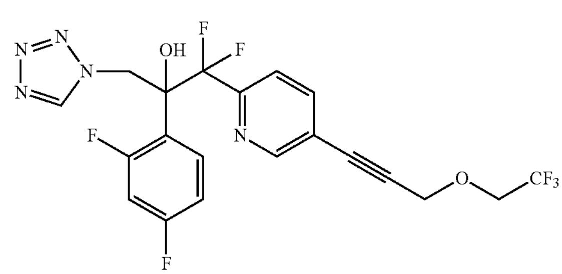 [SMILES: OC(Cn1cnnn1)(c1ccc(F)cc1F)C(F)(F)c1ccc(C#CCOCC(F)(F)F)cn1] |

-continued

| Example Number | HPLC Method | HPLC (RT) | MS (ESI) (M + H) | Stereochem./ Optical Rotation | Structure |
|---|---|---|---|---|---|
| 58 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.731 | 460 | Racemic | 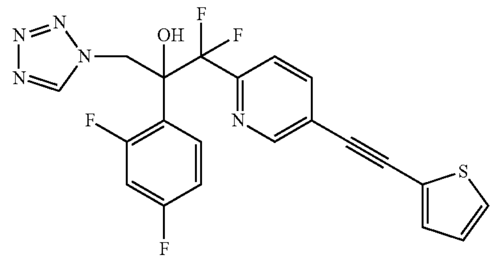 [SMILES: OC(Cn1cnnn1)(c1ccc(F)cc1F)C(F)(F)c1ccc(C#Cc2cccs2)cn1] |
| 59 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.613 | 501 | Racemic | 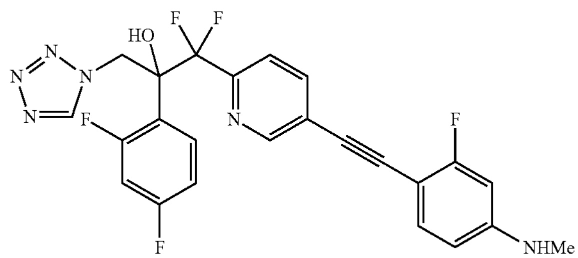 [SMILES: CNc1ccc(C#Cc2ccc(C(F)(F)C(O)(Cn3cnnn3)c3ccc(F)cc3F)nc2)c(F)c1] |
| 60 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.55 | 483 | Racemic | 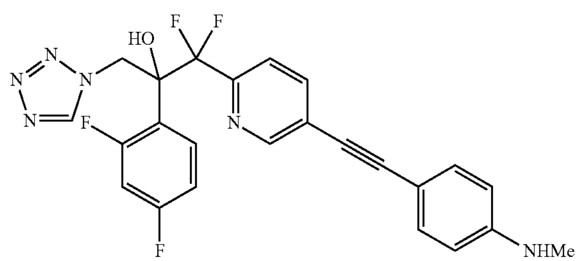 [SMILES: CNc1ccc(C#Cc2ccc(C(F)(F)C(O)(Cn3cnnn3)c3ccc(F)cc3F)nc2)cc1] |
| 60(+) | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.647 | 483 | (+) 51.72 | 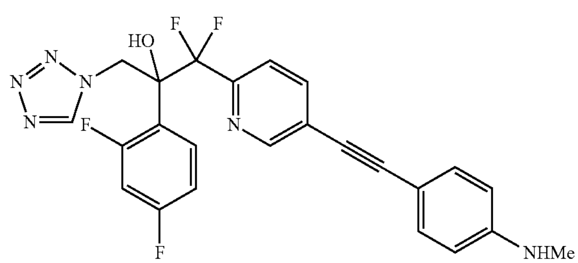 [SMILES: CNc1ccc(C#Cc2ccc(C(F)(F)C(O)(Cn3cnnn3)c3ccc(F)cc3F)nc2)cc1] |
| | Method G Column, Type, Size: ChiralPak IC, 250 × 4.6 mm, 5 µ Mobile Phase A: 0.1% TEA in n-Hexane Mobile Phase B: Ethanol A:B:: 70:30 Flow Rate: 1.0 mL/min | 10.965 | | | |

-continued

| Example Number | HPLC Method | HPLC (RT) | MS (ESI) (M + H) | Stereochem./ Optical Rotation | Structure |
|---|---|---|---|---|---|
| 61 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.017 | 493 (M − H)⁻ | Racemic | 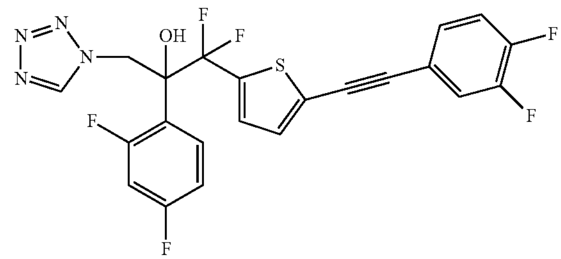 [SMILES: OC(Cn1cnnn1)(c1ccc(F)cc1F)C(F)(F)c1ccc(C#Cc2ccc(F)c(F)c2)s1] |
| 62 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.714 | 497 | Racemic | 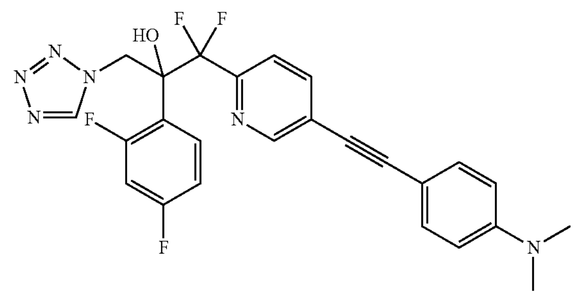 [SMILES: CN(C)c1ccc(C#Cc2ccc(C(F)(F)C(O)(Cn3cnnn3)c3ccc(F)cc3F)nc2)cc1] |
| 63 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.373 | 441 (M − H)⁻ | Racemic | 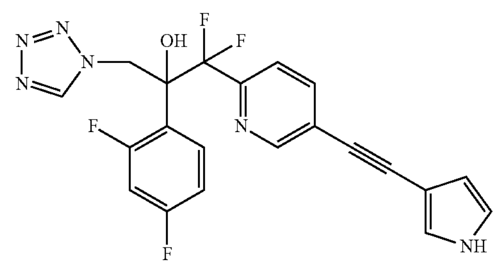 [SMILES: OC(Cn1cnnn1)(c1ccc(F)cc1F)C(F)(F)c1ccc(C#Cc2cc[nH]c2)cn1] |
| 64 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.821 | 522 | Racemic | 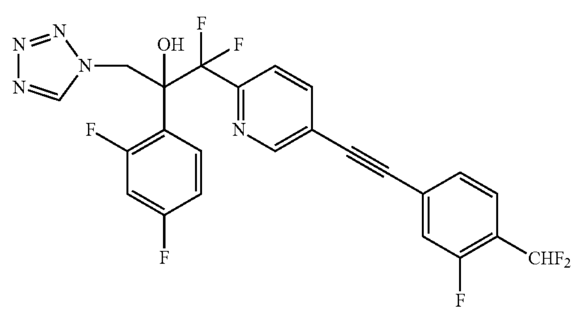 [SMILES: OC(Cn1cnnn1)(c1ccc(F)cc1F)C(F)(F)c1ccc(C#Cc2ccc(C(F)F)c(F)c2)cn1] |
| 65 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.770 | 486 | Racemic | 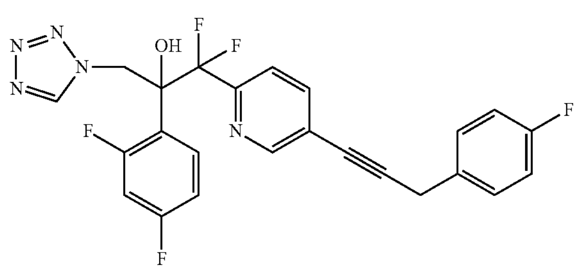 [SMILES: OC(Cn1cnnn1)(c1ccc(F)cc1F)C(F)(F)c1ccc(C#CCc2ccc(F)cc2)cn1] |

| Example Number | HPLC Method | HPLC (RT) | MS (ESI) (M + H) | Stereochem./ Optical Rotation | Structure |
|---|---|---|---|---|---|
| 66 | Method A<br>Column, Type, Size: Acquity BEH C-18 (50 × 2.1 mm, 1.7μ)<br>Mobile Phase:<br>Solvent A: Acetonitrile<br>Solvent B: 0.025% TFA (Aq)<br>Flow Rate: 0.50 mL/min | 2.656 | 493 | Racemic | 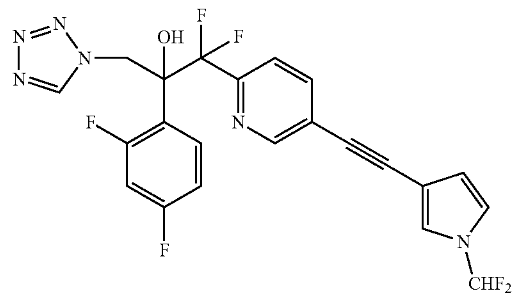 [SMILES: OC(Cn1cnnn1)(c1ccc(F)cc1F)C(F)(F)c1ccc(C#Cc2ccn(C(F)F)c2)cn1] |
| 67 | Method C<br>Column, Type, Size: Acquity UPLC BEH C-18 (2.1 × 50 mm, 1.7μ)<br>Mobile Phase:<br>Solvent A: Acetonitrile<br>Solvent B: 0.025% TFA (Aq)<br>Flow Rate: 0.50 mL/min | 2.708 | 490 | Racemic | 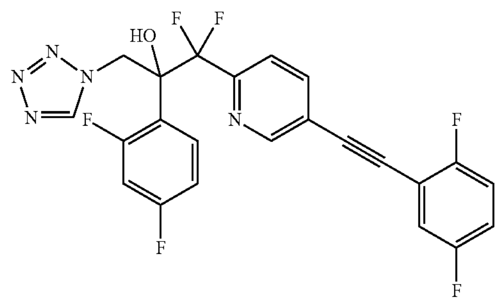 [SMILES: OC(Cn1cnnn1)(c1ccc(F)cc1F)C(F)(F)c1ccc(C#Cc2cc(F)ccc2F)cn1] |
| 68 | Method A<br>Column, Type, Size: Acquity BEH C-18 (50 × 2.1 mm, 1.7μ)<br>Mobile Phase:<br>Solvent A: Acetonitrile<br>Solvent B: 0.025% TFA (Aq)<br>Flow Rate: 0.50 mL/min | 2.332 | 497 | Racemic | 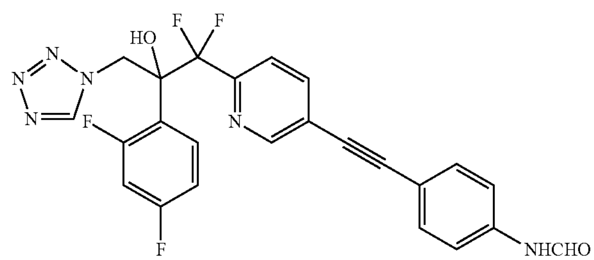 |
| 69 | Method A<br>Column, Type, Size: Acquity BEH C-18 (50 × 2.1 mm, 1.7μ)<br>Mobile Phase:<br>Solvent A: Acetonitrile<br>Solvent B: 0.025% TFA (Aq)<br>Flow Rate: 0.50 mL/min | 2.560 | 479 | Racemic | 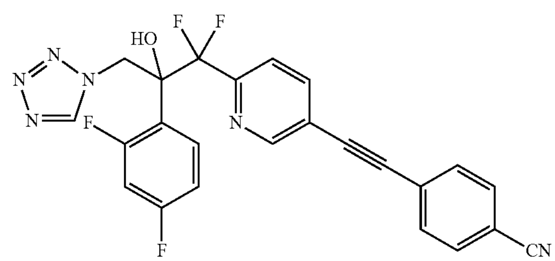 |
| 70 | Method A<br>Column, Type, Size: Acquity BEH C-18 (50 × 2.1 mm, 1.7μ)<br>Mobile Phase:<br>Solvent A: Acetonitrile<br>Solvent B: 0.025% TFA (Aq)<br>Flow Rate: 0.50 mL/min | 2.740 | 479 | Racemic | 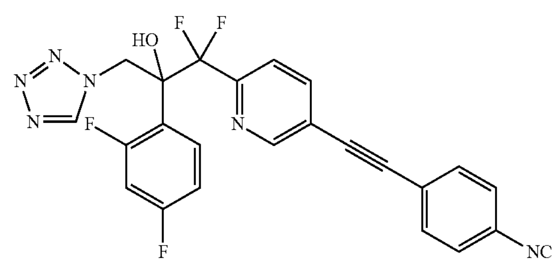 [SMILES: N#Cc1ccc(C#Cc2ccc(C(F)(F)C(O)(Cn3cnnn3)c3ccc(F)cc3F)nc2)cc1] |

| Example Number | HPLC Method | HPLC (RT) | MS (ESI) (M + H) | Stereochem./ Optical Rotation | Structure |
| --- | --- | --- | --- | --- | --- |
| 71 | Method H Column, Type, Size: Luna C-18 (150 × 2.0 mm, 5.0 μm) Mobile Phase A: ACN Mobile Phase B: 0.1% TFA in water Flow Rate: 1.0 mL/min | 6.840 | 479 | Racemic | 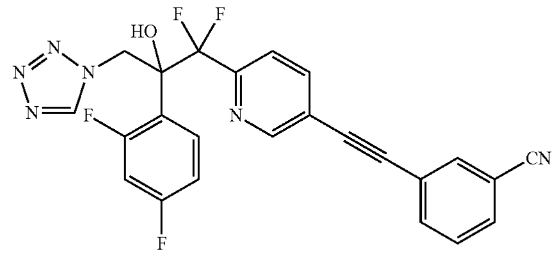 [SMILES: N#Cc1cccc(C#Cc2ccc(C(F)(F)C(O)(Cn3cnnn3)c3ccc(F)cc3F)nc2)c1] |
| 72 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.873 | 521 (M − H)⁻ | Racemic | 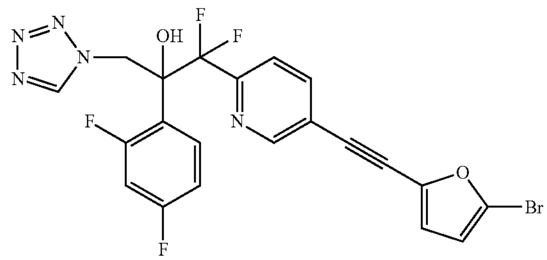 [SMILES: OC(Cn1cnnn1)(c1ccc(F)cc1F)C(F)(F)c1ccc(C#Cc2ccc(Br)o2)cn1] |
| 73 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.681 | 495 (M − H)⁻ | Racemic | 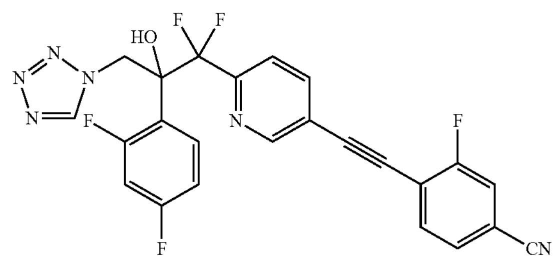 [SMILES: N#Cc1ccc(C#Cc2ccc(C(F)(F)C(O)(Cn3cnnn3)c3ccc(F)cc3F)nc2)c(F)c1] |
| 74 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.699 | 497 | Racemic | 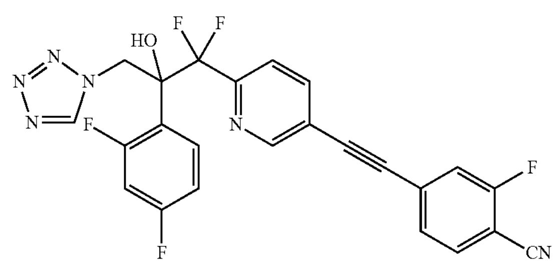 [SMILES: N#Cc1ccc(C#Cc2ccc(C(F)(F)C(O)(Cn3cnnn3)c3ccc(F)cc3F)nc2)cc1F] |
| 75 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.597 | 497 | Racemic | 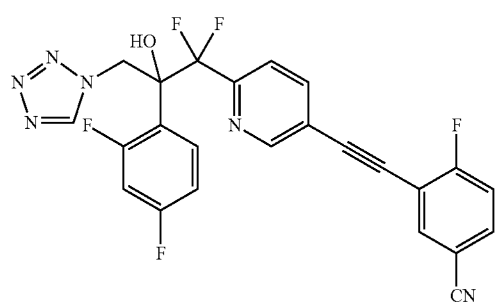 [SMILES: N#Cc1ccc(F)c(C#Cc2ccc(C(F)(F)C(O)(Cn3cnnn3)c3ccc(F)cc3F)nc2)c1] |

-continued

| Example Number | HPLC Method | HPLC (RT) | MS (ESI) (M + H) | Stereo-chem./ Optical Rotation | Structure |
|---|---|---|---|---|---|
| 76 | Method E Column, Type, Size: Eclipse XDB C-18 (150 × 4.6 mm, 5.0 μm) Mobile Phase A: ACN Mobile Phase B: 0.1% Aq TFA Flow Rate: 1.0 mL/min | 8.55 | 494 | Racemic | 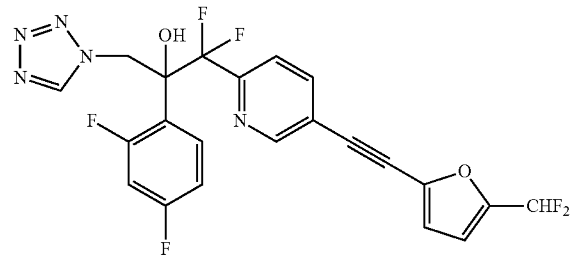 |
| 77 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.87 | 542 | Racemic | 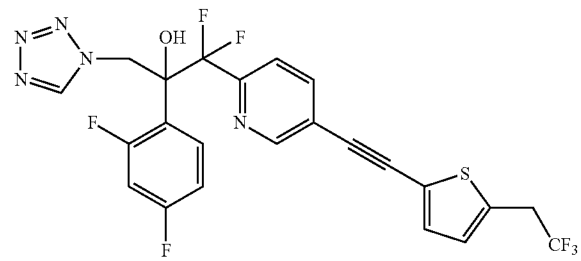 [SMILES: OC(Cn1cnnn1)(c1ccc(F)cc1F)C(F)(F)c1ccc(C#Cc2ccc(CC(F)(F)F)s2)cn1] |
| 77(+) | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.904 | 542 | (+) 33.24 | 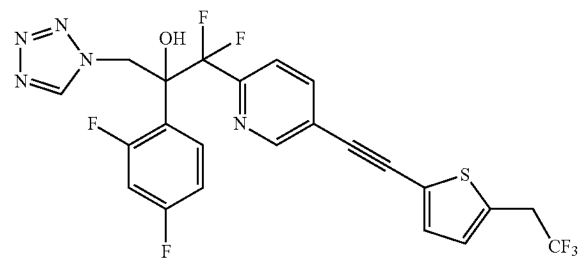 [SMILES: OC(Cn1cnnn1)(c1ccc(F)cc1F)C(F)(F)c1ccc(C#Cc2ccc(CC(F)(F)F)s2)cn1] |
| | Method I Column, Type, Size: ChiralPak IC, 250 × 4.6 mm, 5μ Mobile Phase A: n-Hexane Mobile Phase B: Ethanol A:B:: 80:20 Flow Rate: 1.0 mL/min | 13.045 | | | |
| 78 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.382 | 469 | Racemic | 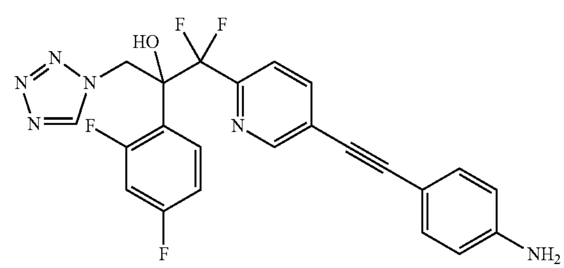 [SMILES: Nc1ccc(C#Cc2ccc(C(F)(F)C(O)(Cn3cnnn3)c3ccc(F)cc3F)nc2)cc1] |
| 79 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.763 | 563 (M − H)⁻ | Racemic | 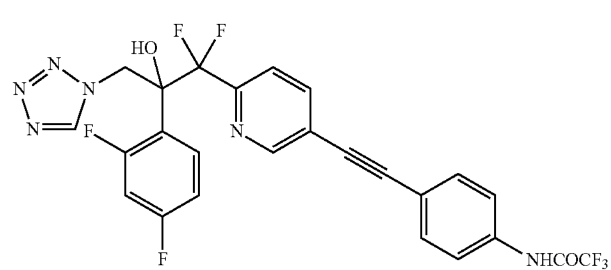 |

| Example Number | HPLC Method | HPLC (RT) | MS (ESI) (M + H) | Stereochem./ Optical Rotation | Structure |
|---|---|---|---|---|---|
| 80 | Method F Column, Type, Size: Eclipse XDB C-18 (150 × 4.6 mm, 5 μm) Mobile Phase A: ACN Mobile Phase B: 5 mM NH₄OAC Flow Rate: 1.0 mL/min | 8.760 | 551 | Racemic | 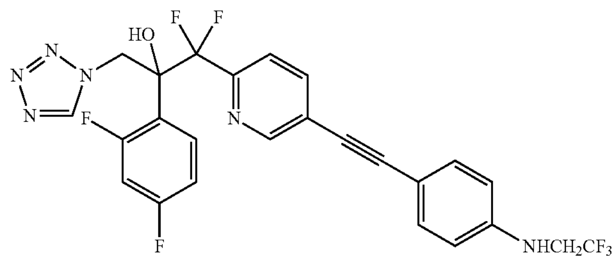 |
| 81 | Method F Column, Type, Size: Eclipse XDB C-18 (150 × 4.6 mm, 5 μm) Mobile Phase A: ACN Mobile Phase B: 5 mM NH₄OAC Flow Rate: 1.0 mL/min | 7.960 | 470 | Racemic | 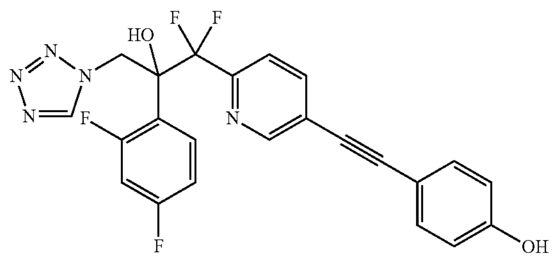 |
| 82 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.094 | 495 (M − H)⁻ | Racemic | 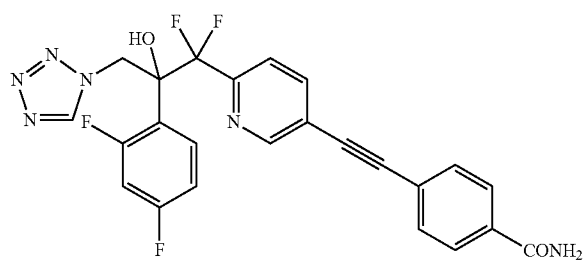 |
| 83 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.536 | 487 | Racemic | 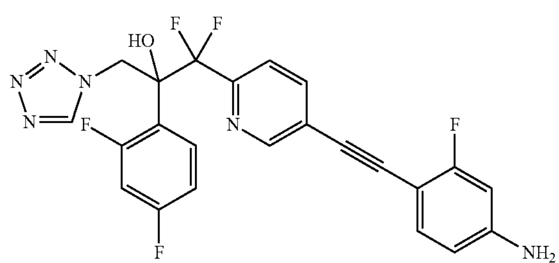 |
| 84 | Method F Column, Type, Size: Eclipse XDB C-18 (150 × 4.6 mm, 5 μm) Mobile Phase A: ACN Mobile Phase B: 5 mM NH₄OAC Flow Rate: 1.0 mL/min | 7.833 | 511 | Racemic | 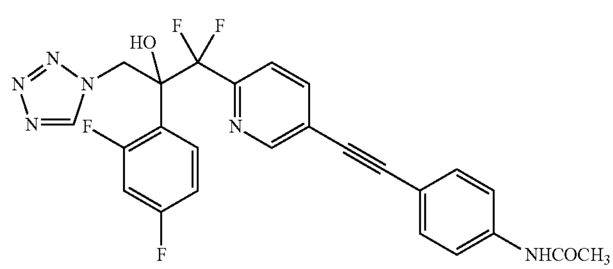 |

| Example Number | HPLC Method | HPLC (RT) | MS (ESI) (M + H) | Stereochem./ Optical Rotation | Structure |
| --- | --- | --- | --- | --- | --- |
| 85 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.797 | 520 | Racemic | 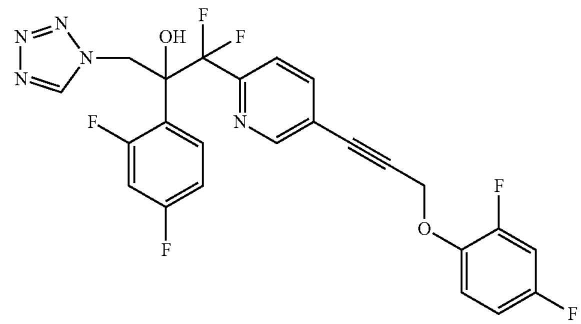 [SMILES: OC(Cn1cnnn1)(c1ccc(F)cc1F)C(F)(F)c1ccc(C#CCOc2ccc(F)cc2F)cn1] |
| 86 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.876 | 550 (M − H)− | Racemic | 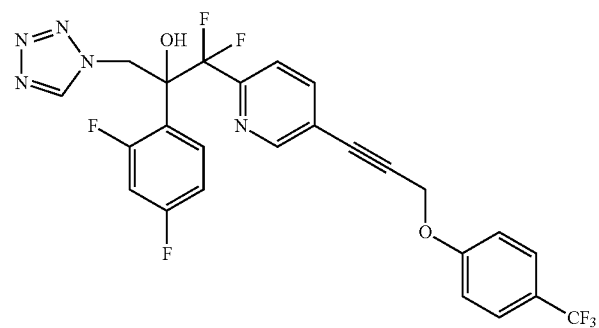 [SMILES: OC(Cn1cnnn1)(c1ccc(F)cc1F)C(F)(F)c1ccc(C#CCOc2ccc(C(F)(F)F)cc2)cn1] |
| 87 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.591 | 493 | Racemic | 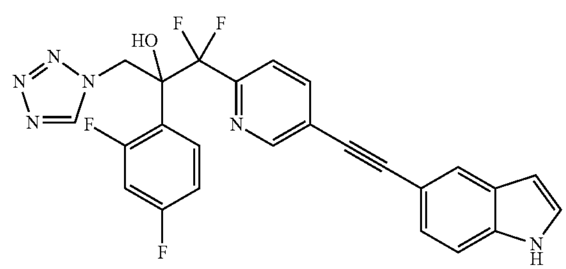 [SMILES: OC(Cn1cnnn1)(c1ccc(F)cc1F)C(F)(F)c1ccc(C#Cc2ccc3[nH]ccc3c2)cn1] |
| 88 | Method C Column, Type, Size: Acquity UPLC BEH C-18 (2.1 × 50 mm, 1.7μ) Mobile Phase: Solvent A: Acetonitrile Solvent B: 0.025% TFA (Aq) Flow Rate: 0.50 mL/min | 2.923 | 577 | Racemic | 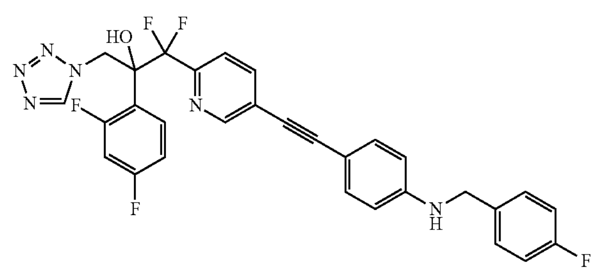 [SMILES: OC(Cn1cnnn1)(c1ccc(F)cc1F)C(F)(F)c1ccc(C#Cc2ccc(NCc3ccc(F)cc3)cc2)cn1] |
| 89 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.857 | 492 (M − H)− | Racemic | 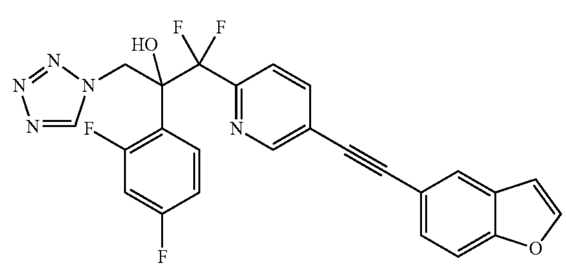 [SMILES: OC(Cn1cnnn1)(c1ccc(F)cc1F)C(F)(F)c1ccc(C#Cc2ccc3occc3c2)cn1] |

-continued

| Example Number | HPLC Method | HPLC (RT) | MS (ESI) (M + H) | Stereochem./ Optical Rotation | Structure |
|---|---|---|---|---|---|
| 90 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.910 | 536 | Racemic | 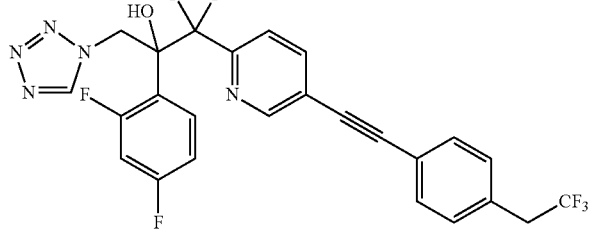 |
| 91 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.555 | 579 | Racemic | 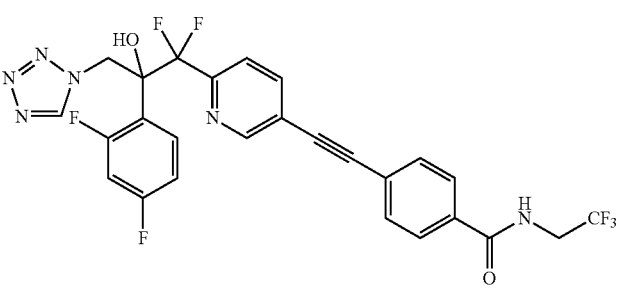 [SMILES: O=C(NCC(F)(F)F)c1ccc(C#Cc2ccc(C(F)(F)C(O)(Cn3cnnn3)c3ccc(F)cc3F)nc2)cc1] |
| 92 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.451 | 551 | Racemic | 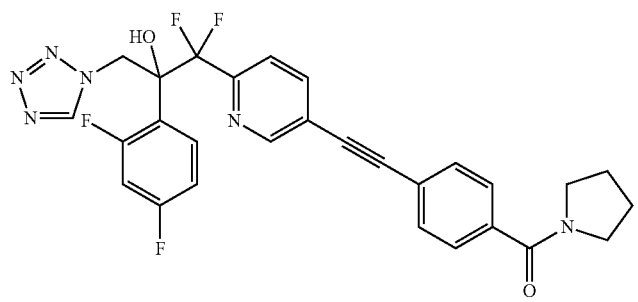 [SMILES: O=C(c1ccc(C#Cc2ccc(C(F)(F)C(O)(Cn3cnnn3)c3ccc(F)cc3F)nc2)cc1)N1CCCC1] |
| 93 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.096 | 578 | Racemic | 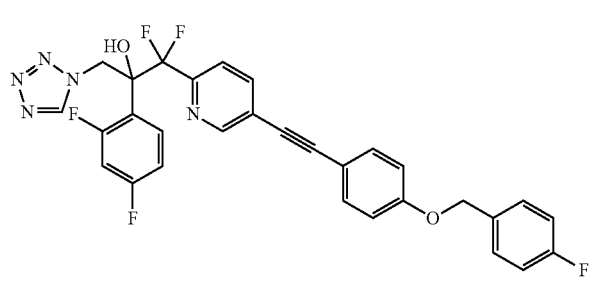 [SMILES: OC(Cn1cnnn1)(c1ccc(F)cc1F)C(F)(F)c1ccc(C#Cc2ccc(OCc3ccc(F)cc3)cc2)cn1] |
| 94 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.568 | 585 | Racemic | 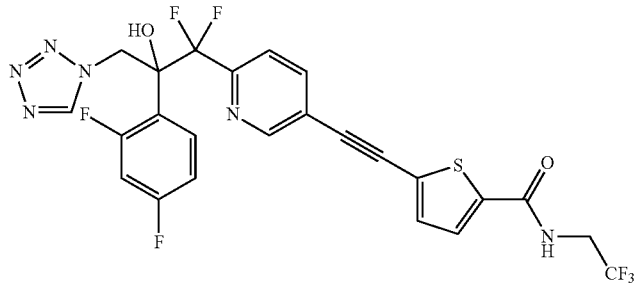 [SMILES: O=C(NCC(F)(F)F)c1ccc(C#Cc2ccc(C(F)(F)C(O)(Cn3cnnn3)c3ccc(F)cc3F)nc2)s1] |

| Example Number | HPLC Method | HPLC (RT) | MS (ESI) (M + H) | Stereochem./ Optical Rotation | Structure |
|---|---|---|---|---|---|
| 95 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.591 | 583 | Racemic | 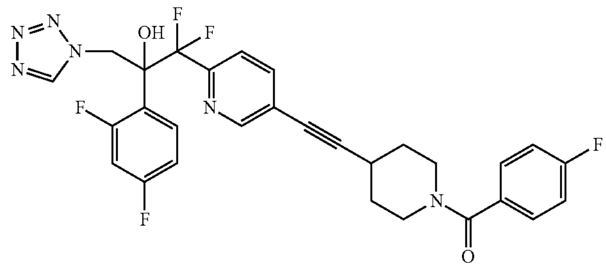 [SMILES: O=C(c1ccc(F)cc1)N1CCC(C#Cc2ccc(C(F)(F)C(O)(Cn3cnnn3)c3ccc(F)cc3F)nc2)CC1] |
| 96 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.682 | 557 | Racemic | 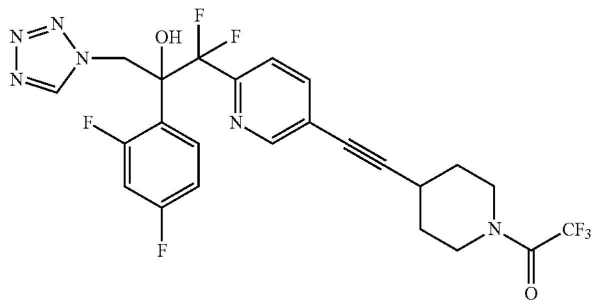 [SMILES: O=C(N1CCC(C#Cc2ccc(C(F)(F)C(O)(Cn3cnnn3)c3ccc(F)cc3F)nc2)CC1)C(F)(F)F] |
| 97 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.910 | 552 | Racemic | 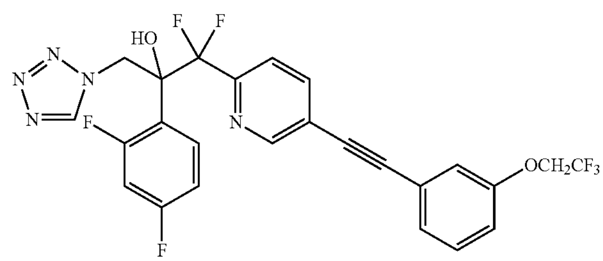 |
| 98 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.571 | 579 | Racemic | 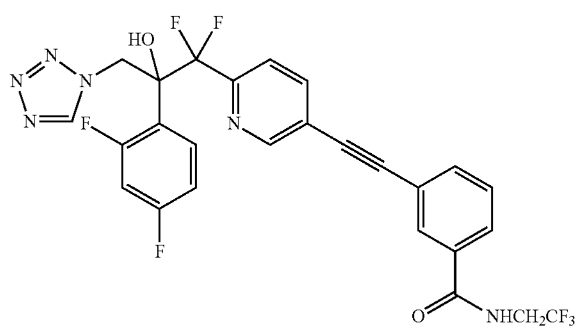 |
| 99 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.792 | 454 | Racemic | 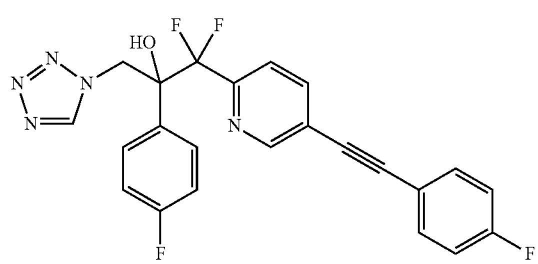 [SMILES: OC(Cn1cnnn1)(c1ccc(F)cc1)C(F)(F)c1ccc(C#Cc2ccc(F)cc2)cn1] |

| Example Number | HPLC Method | HPLC (RT) | MS (ESI) (M + H) | Stereo-chem./ Optical Rotation | Structure |
|---|---|---|---|---|---|
| 100 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.932 | 585 | Racemic | 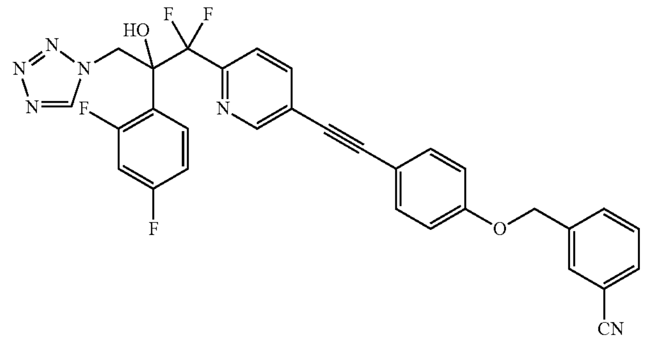 [SMILES: N#Cc1cccc(COc2ccc(C#Cc3ccc(C(F)(F)C(O)(Cn4cnnn4)c4ccc(F)cc4F)nc3)cc2)c1] |
| 101 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.236 | 644 | Racemic | 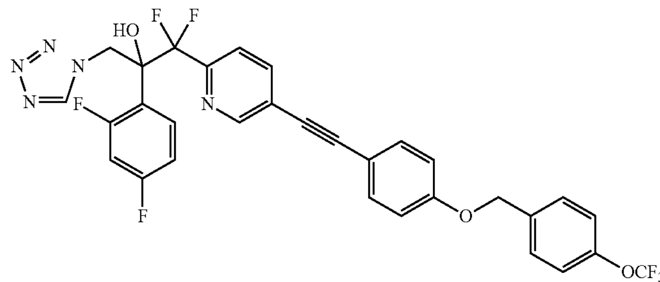 [SMILES: N=N/N=C\NCC(O)(c1ccc(F)cc1F)C(F)(F)c1ccc(C#Cc2ccc(OCc3ccc(OC(F)(F)F)cc3)cc2)cn1] |
| 102 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.987 | 603 | Racemic | 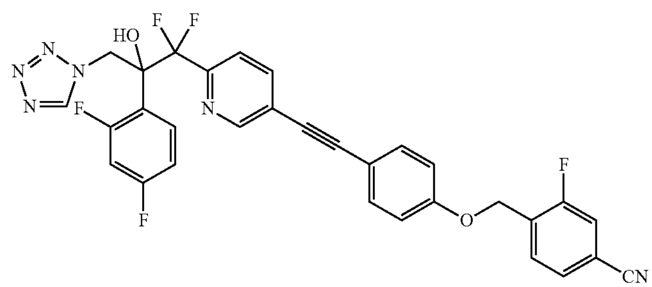 [SMILES: N#Cc1ccc(COc2ccc(C#Cc3ccc(C(F)(F)C(O)(Cn4cnnn4)c4ccc(F)cc4F)nc3)cc2)c(F)c1] |
| 103 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.924 | 603 | Racemic | 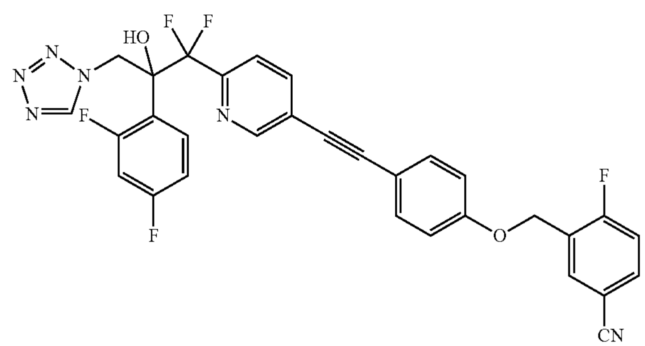 [SMILES: N#Cc1ccc(F)c(COc2ccc(C#Cc3ccc(C(F)(F)C(O)(Cn4cnnn4)c4ccc(F)cc4F)nc3)cc2)c1] |
| 104 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.283 | 644 | Racemic | 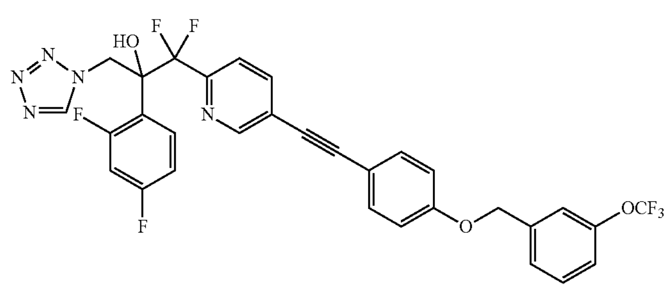 [SMILES: OC(Cn1cnnn1)(c1ccc(F)cc1F)C(F)(F)c1ccc(C#Cc2ccc(OCc3cccc(OC(F)(F)F)c3)cc2)cn1] |

| Example Number | HPLC Method | HPLC (RT) | MS (ESI) (M + H) | Stereochem./ Optical Rotation | Structure |
|---|---|---|---|---|---|
| 105 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.128 | 596 | Racemic | 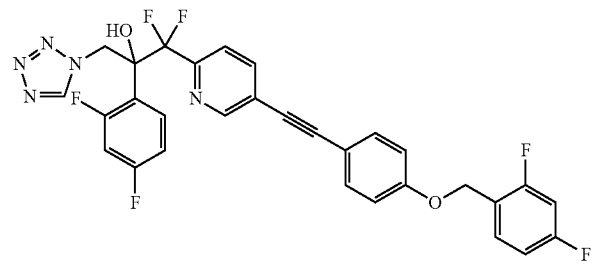 [SMILES: OC(Cn1cnnn1)(c1ccc(F)cc1F)C(F)(F)c1ccc(C#Cc2ccc(OCc3ccc(F)cc3F)cc2)cn1] |
| 106 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.123 | 596 | Racemic | 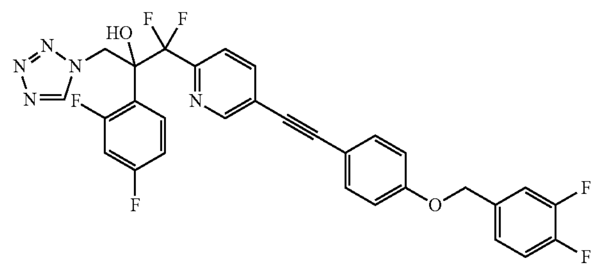 [SMILES: OC(Cn1cnnn1)(c1ccc(F)cc1F)C(F)(F)c1ccc(C#Cc2ccc(OCc3ccc(F)c(F)c3)cc2)cn1] |
| 107 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.252 | 594 | Racemic | 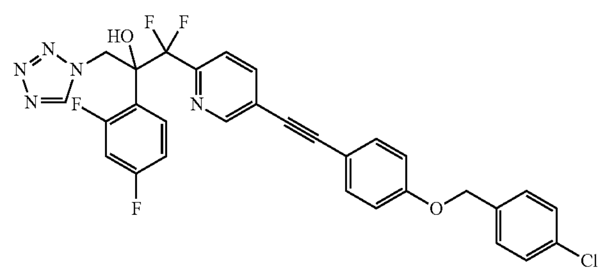 [SMILES: OC(Cn1cnnn1)(c1ccc(F)cc1F)C(F)(F)c1ccc(C#Cc2ccc(OCc3ccc(Cl)cc3)cc2)cn1] |
| 108 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.264 | 612 | Racemic | 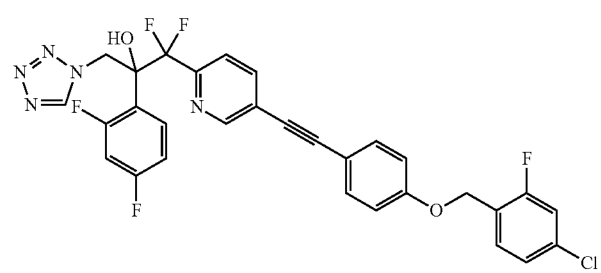 [SMILES: OC(Cn1cnnn1)(c1ccc(F)cc1F)C(F)(F)c1ccc(C#Cc2ccc(OCc3ccc(Cl)cc3F)cc2)cn1] |
| 109 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.605 | 617 | Racemic | 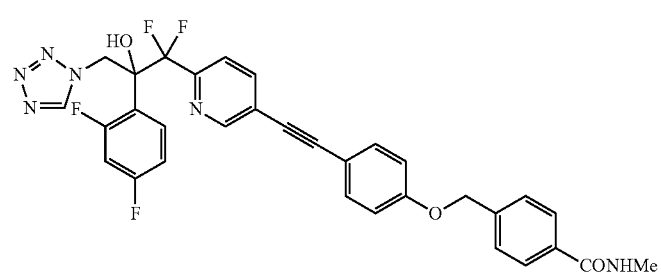 |

| Example Number | HPLC Method | HPLC (RT) | MS (ESI) (M + H) | Stereochem./ Optical Rotation | Structure |
|---|---|---|---|---|---|
| 110 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.781 | 586 | Racemic | 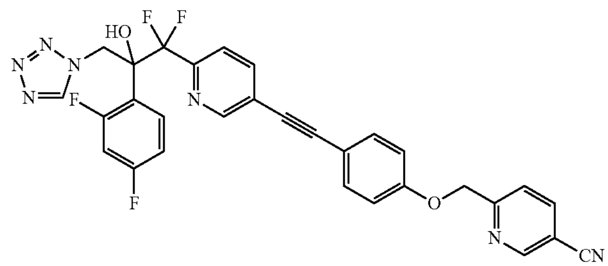 |
| 111 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.749 | 567 | Racemic | 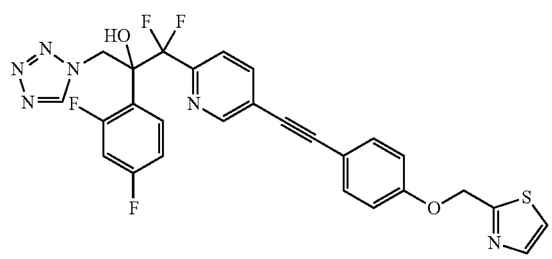 [SMILES: OC(Cn1cnnn1)(c1ccc(F)cc1F)C(F)(F)c1ccc(C#Cc2ccc(OCc3nccs3)cc2)cn1] |
| 112 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.002 | 603 | Racemic | 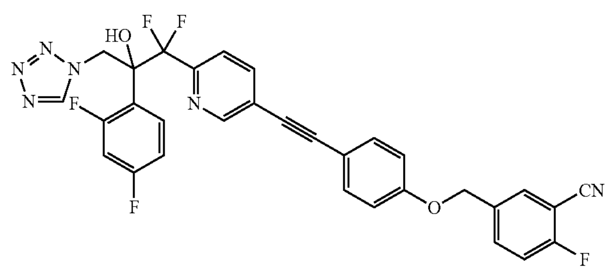 [SMILES: N#Cc1cc(COc2ccc(C#Cc3ccc(C(F)(F)C(O)(Cn4cnnn4)c4ccc(F)cc4F)nc3)cc2)ccc1F] |
| 113 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.129 | 596 | Racemic | 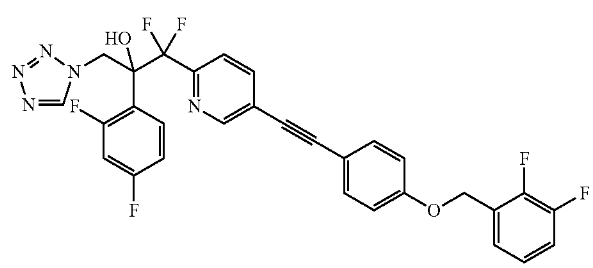 [SMILES: OC(Cn1cnnn1)(c1ccc(F)cc1F)C(F)(F)c1ccc(C#Cc2ccc(OCc3cccc(F)c3F)cc2)cn1] |
| 114 | Method F Column, Type, Size: Eclipse XDB C-18 (150 × 4.6 mm, 5 μm) Mobile Phase A: ACN Mobile Phase B: 5 mM NH$_4$OAC Flow Rate: 1.0 mL/min | 11.687 | 518 | Racemic | 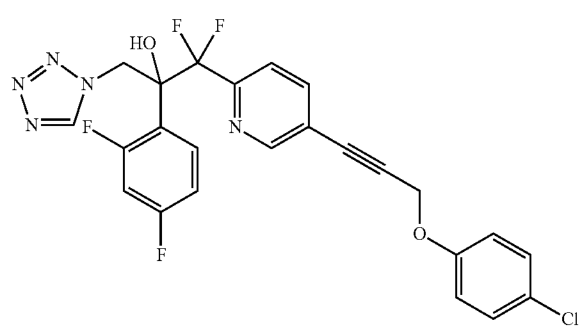 [SMILES: OC(Cn1cnnn1)(c1ccc(F)cc1F)C(F)(F)c1ccc(C#CCOc2ccc(Cl)cc2)cn1] |

-continued

| Example Number | HPLC Method | HPLC (RT) | MS (ESI) (M + H) | Stereo-chem./ Optical Rotation | Structure |
|---|---|---|---|---|---|
| 115 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.685 | 527 | Racemic | 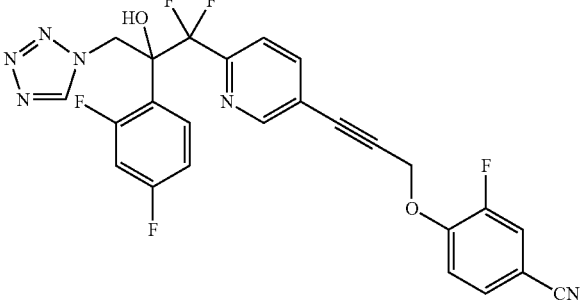 |
| 116 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.656 | 527 | Racemic | 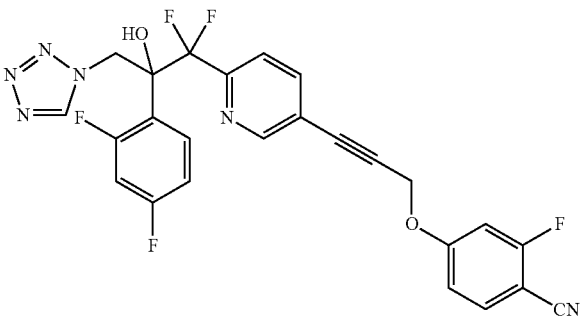 [SMILES: N#Cc1ccc(OCC#Cc2ccc(C(F)(F)C(O)(Cn3cnnn3)c3ccc(F)cc3F)nc2)cc1F] |
| 117 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.925 | 536 | Racemic | 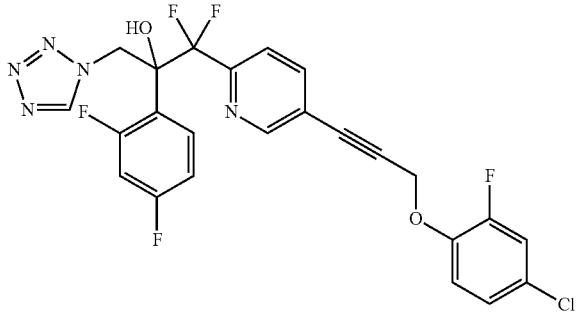 [SMILES: OC(Cn1cnnn1)(c1ccc(F)cc1F)C(F)(F)c1ccc(C#CCOc2ccc(Cl)cc2F)cn1] |
| 118 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.913 | 534 | Racemic | 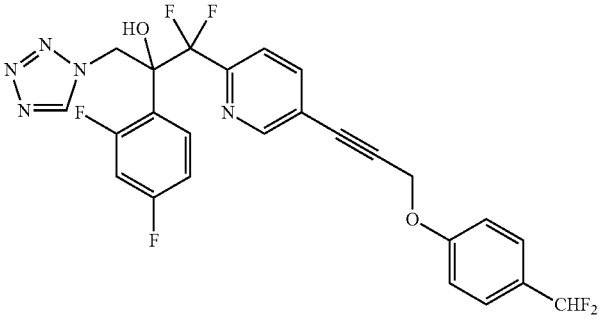 [SMILES: OC(Cn1cnnn1)(c1ccc(F)cc1F)C(F)(F)c1ccc(C#CCOc2ccc(C(F)F)cc2)cn1] |
| 119 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.711 | 611 | Racemic | 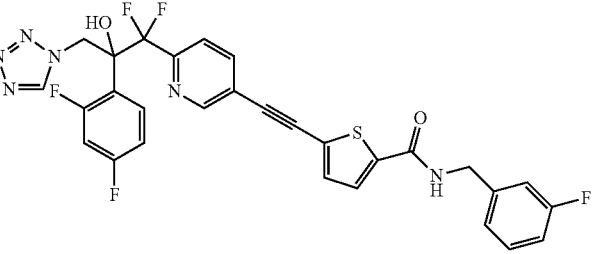 |

-continued

| Example Number | HPLC Method | HPLC (RT) | MS (ESI) (M + H) | Stereochem./ Optical Rotation | Structure |
|---|---|---|---|---|---|
| 120 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.674 | 618 | Racemic | 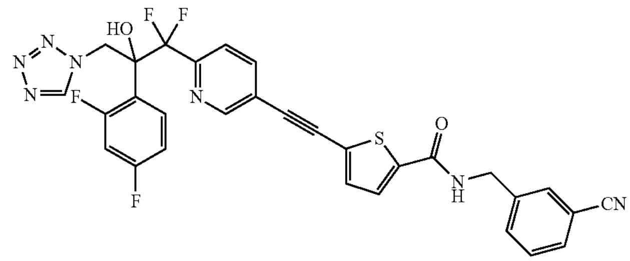 [SMILES: N#Cc1cccc(CNC(=O)c2ccc(C#Cc3ccc(C(F)(F)C(O)(Cn4cnnn4)c4ccc(F)cc4F)nc3)s2)c1] |
| 121 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.624 | 616 (M − H)⁻ | Racemic | 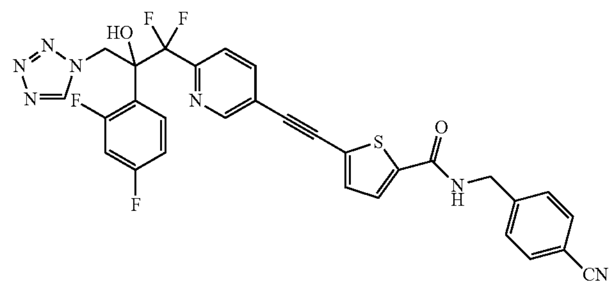 [SMILES: N#Cc1ccc(CNC(=O)c2ccc(C#Cc3ccc(C(F)(F)C(O)(Cn4cnnn4)c4ccc(F)cc4F)nc3)s2)cc1] |
| 122 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.831 | 661 | Racemic | 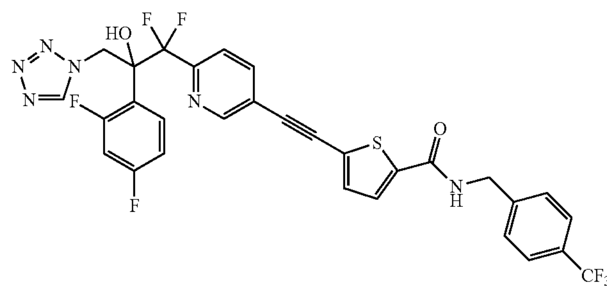 [SMILES: O=C(NCc1ccc(C(F)(F)F)cc1)c1ccc(C#Cc2ccc(C(F)(F)C(O)(Cn3cnnn3)c3ccc(F)cc3F)nc2)s1] |
| 123 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.414 | 573 | Racemic | 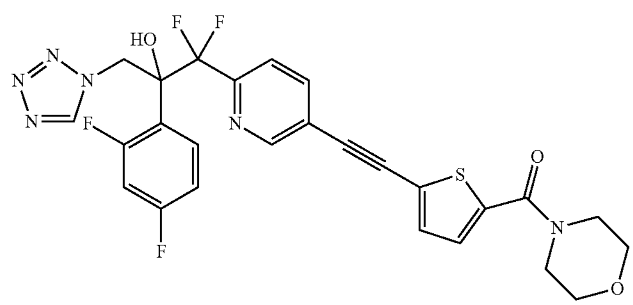 [SMILES: O=C(c1ccc(C#Cc2ccc(C(F)(F)C(O)(Cn3cnnn3)c3ccc(F)cc3F)nc2)s1)N1CCOCC1] |
| 124 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.509 | 557 | Racemic | 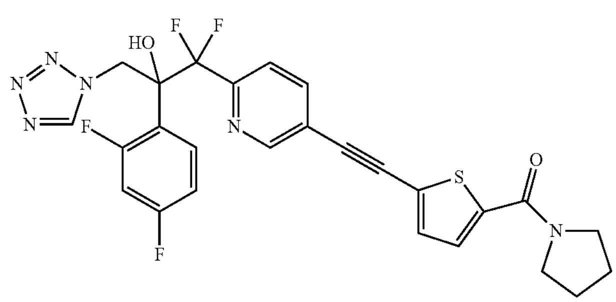 [SMILES: O=C(c1ccc(C#Cc2ccc(C(F)(F)C(O)(Cn3cnnn3)c3ccc(F)cc3F)nc2)s1)N1CCCC1] |

| Example Number | HPLC Method | HPLC (RT) | MS (ESI) (M + H) | Stereochem./ Optical Rotation | Structure |
| --- | --- | --- | --- | --- | --- |
| 125 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.532 | 671 | Racemic | 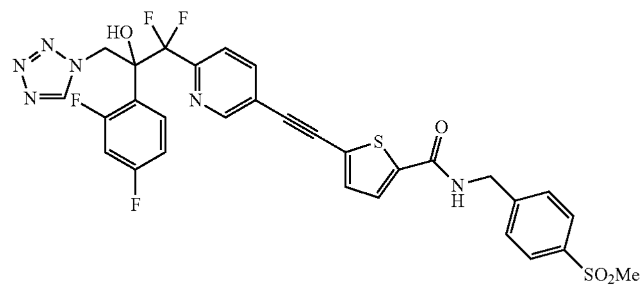 [SMILES: CS(=O)(=O)c1ccc(CNC(=O)c2ccc(C#Cc3ccc(C(F)(F)C(O)(Cn4cnnn4)c4ccc(F)cc4F)nc3)s2)cc1] |
| 126 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.243 | 603 | Racemic | 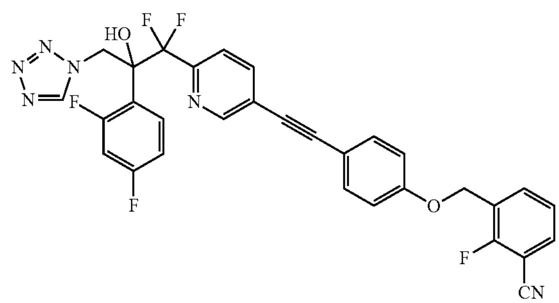 [SMILES: N#Cc1cccc(COc2ccc(C#Cc3ccc(C(F)(F)C(O)(Cn4cnnn4)c4ccc(F)cc4F)nc3)cc2)c1F] |
| 127 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.198 | 603 | Racemic | 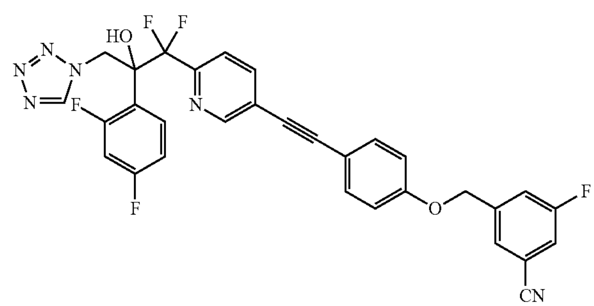 [SMILES: N#Cc1cc(F)cc(COc2ccc(C#Cc3ccc(C(F)(F)C(O)(Cn4cnnn4)c4ccc(F)cc4F)nc3)cc2)c1] |
| 128 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 1.893 | 461 | Racemic | 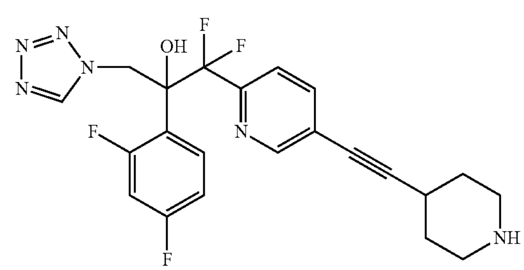 [SMILES: OC(Cn1cnnn1)(c1ccc(F)cc1F)C(F)(F)c1ccc(C#CC2CCNCC2)cn1] |
| 129 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.936 | 619 | Racemic | 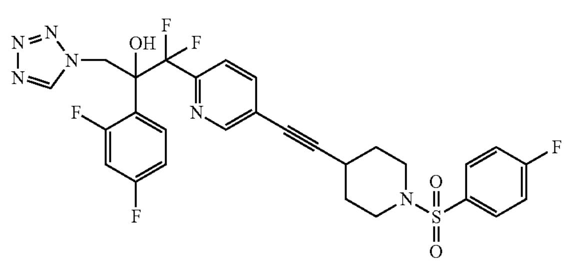 [SMILES: O=S(=O)(c1ccc(F)cc1)N1CCC(C#Cc2ccc(C(F)(F)C(O)(Cn3cnnn3)c3ccc(F)cc3F)nc2)CC1] |

| Example Number | HPLC Method | HPLC (RT) | MS (ESI) (M + H) | Stereochem./ Optical Rotation | Structure |
|---|---|---|---|---|---|
| 130 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.974 | 602 | Racemic | 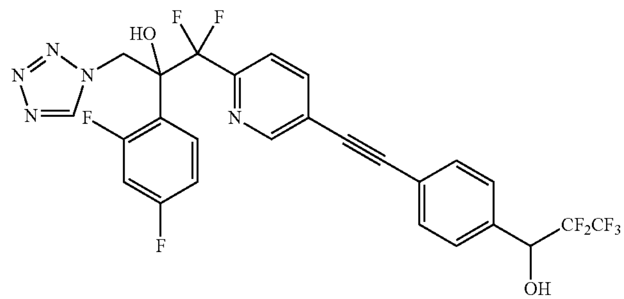 |
| 131 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.943 | 603 | Racemic | 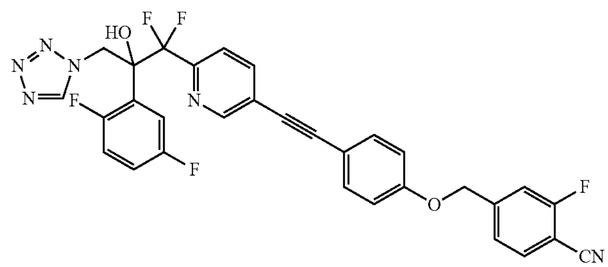 [SMILES: N#Cc1ccc(COc2ccc(C#Cc3ccc(C(F)(F)C(O)(Cn4cnnn4)c4cc(F)ccc4F)nc3)cc2)cc1F] |
| 132 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.335 | 619 | Racemic | 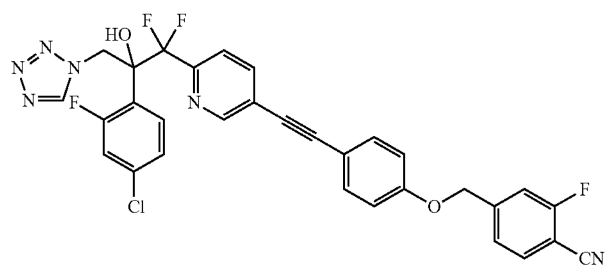 |
| 133 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 3.224 | 619 | Racemic | 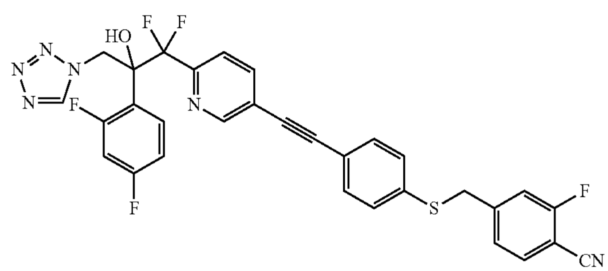 |
| 134 | Method A Column, Type, Size: Acquity BEH C-18 (50 × 2.1 mm, 1.7µ) Mobile Phase: Solvent A: Acetonitrile Solvent B: 0.025% TFA (Aq) Flow Rate: 0.50 mL/min | 2.674 | 635 | Racemic | 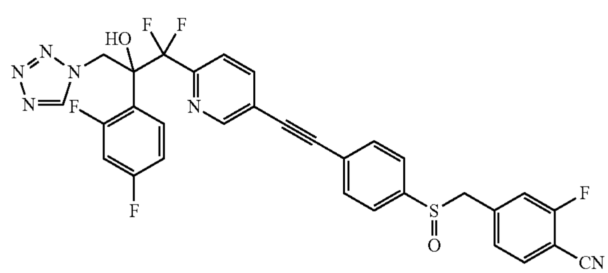 [SMILES: N#Cc1ccc(CS(=O)c2ccc(C#Cc3ccc(C(F)(F)C(O)(Cn4cnnn4)c4ccc(F)cc4F)nc3)cc2)cc1F] |

| Example Number | HPLC Method | HPLC (RT) | MS (ESI) (M + H) | Stereochem./ Optical Rotation | Structure |
|---|---|---|---|---|---|
| 135 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.811 | 649 (M − H)⁻ | Racemic | 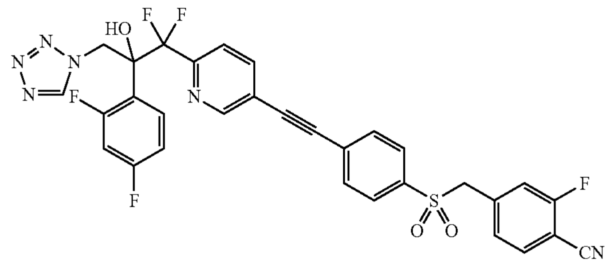 [SMILES: N#Cc1ccc(CS(=O)(=O)c2ccc(C#Cc3ccc(C(F)(F)C(O)(Cn4cnnn4)c4ccc(F)cc4F)nc3)cc2)cc1F] |
| 136 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.906 | 585 | Racemic | 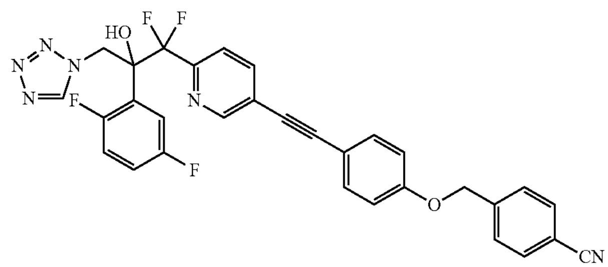 [SMILES: N#Cc1ccc(COc2ccc(C#Cc3ccc(C(F)(F)C(O)(Cn4cnnn4)c4cc(F)ccc4F)nc3)cc2)cc1] |
| 137 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.022 | 601 | Racemic | 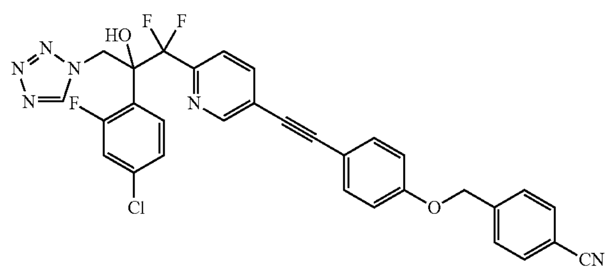 |
| 138 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 3.251 | 601 | Racemic | 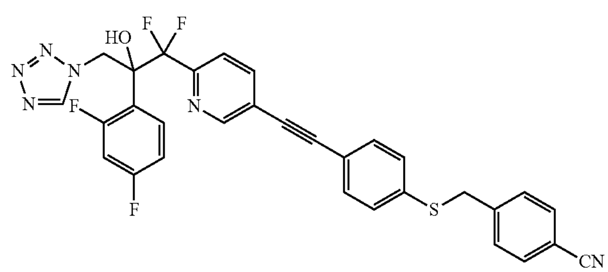 |
| 139 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.828 | 586 | Racemic | 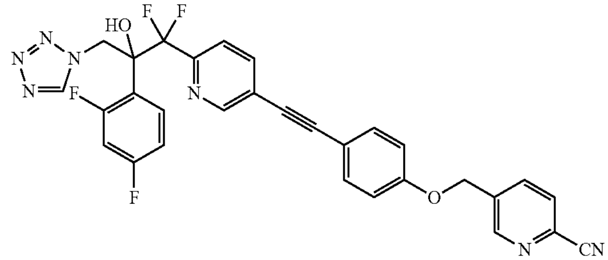 |

-continued

| Example Number | HPLC Method | HPLC (RT) | MS (ESI) (M + H) | Stereochem./ Optical Rotation | Structure |
| --- | --- | --- | --- | --- | --- |
| 140 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.447 | 665 (M)+ | — | 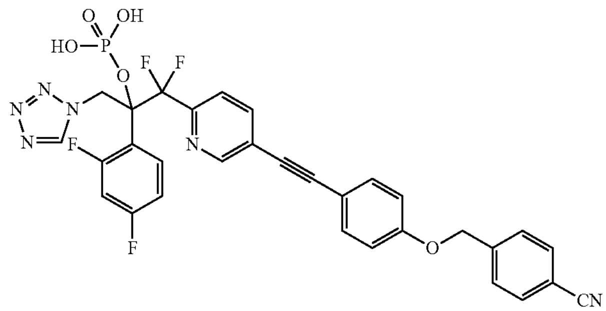 [SMILES: N#Cc1ccc(COc2ccc(C#Cc3ccc(C(F)(F)C(Cn4cnnn4)(OP(=O)(O)O)c4ccc(F)cc4F)nc3)cc2)cc1] |
| 141 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.752 | 611 | Racemic | 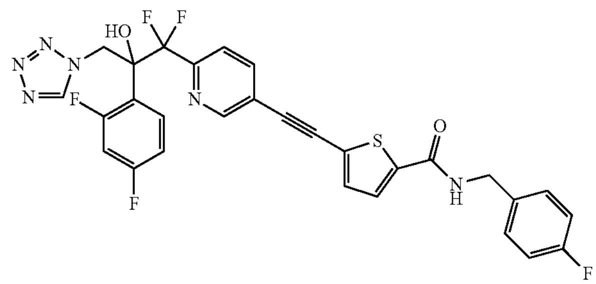 [SMILES: O=C(NCc1ccc(F)cc1)c1ccc(C#Cc2ccc(C(F)(F)C(O)(Cn3cnnn3)c3ccc(F)cc3F)nc2)s1] |
| 142 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.979 | 585 | Racemic | 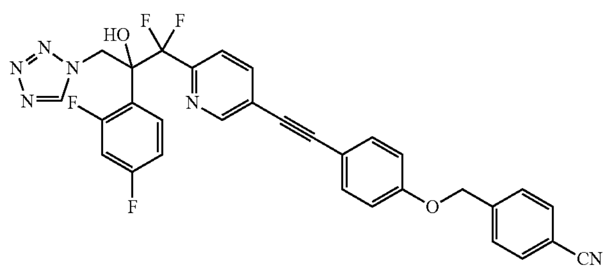 [SMILES: N#Cc1ccc(COc2ccc(C#Cc3ccc(C(F)(F)C(O)(Cn4cnnn4)c4ccc(F)cc4F)nc3)cc2)cc1] |
| 143 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.990 | 603 | Racemic | 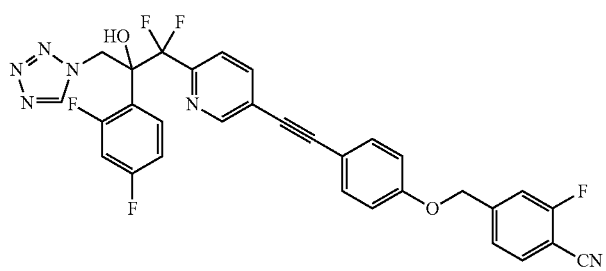 [SMILES: N#Cc1ccc(COc2ccc(C#Cc3ccc(C(F)(F)C(O)(Cn4cnnn4)c4ccc(F)cc4F)nc3)cc2)cc1F] |
| 144 | Method A Column, Type, Size: Acquity BEH C-18 (50 × 2.1 mm, 1.7μ) Mobile Phase: Solvent A: Acetonitrile Solvent B: 0.025% TFA (Aq) Flow Rate: 0.50 mL/min | 2.234 | 529 | (+) | 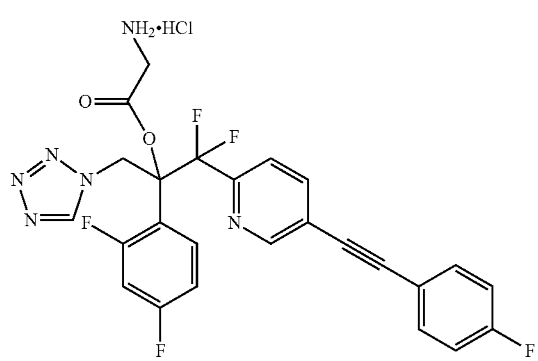 |

-continued

| Example Number | HPLC Method | HPLC (RT) | MS (ESI) (M + H) | Stereochem./ Optical Rotation | Structure |
| --- | --- | --- | --- | --- | --- |
| 145 | Method F Column, Type, Size: Eclipse XDB C-18 (150 × 4.63 mm, 5 μm) Mobile Phase A: ACN Mobile Phase B: 5 mM NH$_4$OAC Flow Rate: 1.0 mL/min | 8.670 | 600 | (+) | 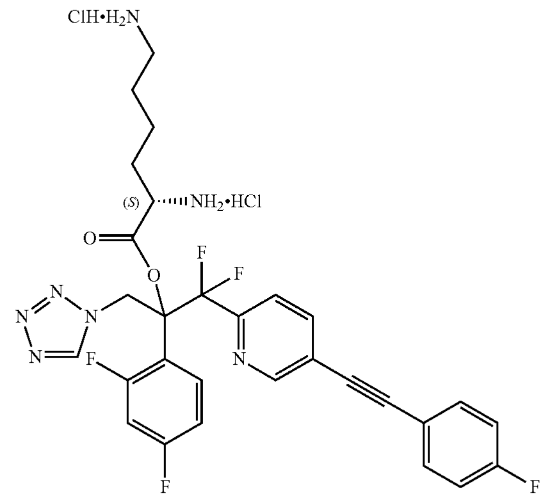 |
| 146 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 13.20 | 613 | Racemic | 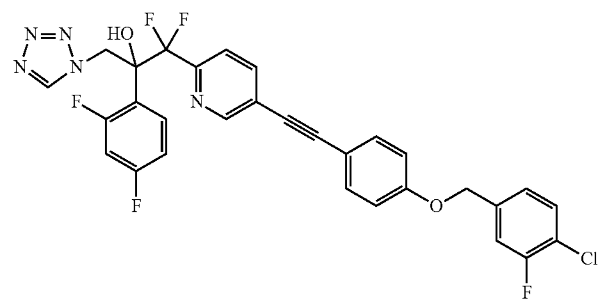 [SMILES: OC(Cn1cnnn1)(c1ccc(F)cc1F)C(F)(F)c1ccc(C#Cc2ccc(OCc3ccc(Cl)c(F)c3)cc2)cn1] |
| 147 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 19.90 | 636 | Racemic | 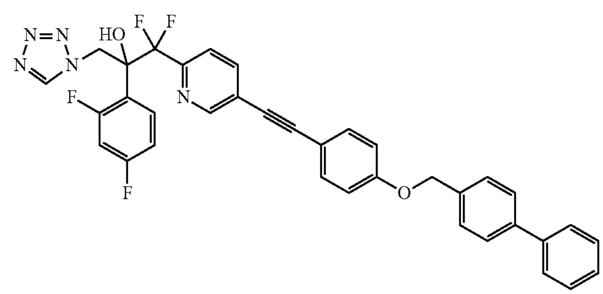 [SMILES: OC(Cn1cnnn1)(c1ccc(F)cc1F)C(F)(F)c1ccc(C#Cc2ccc(OCc3ccc(-c4ccccc4)cc3)cc2)cn1] |
| 148 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 12.30 | 574 | Racemic | 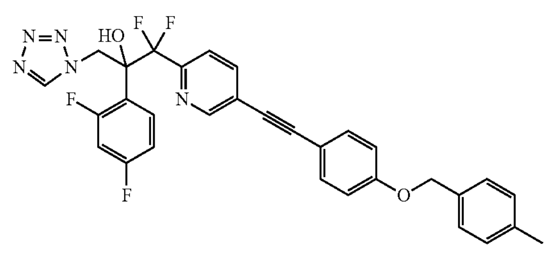 [SMILES: Cc1ccc(COc2ccc(C#Cc3ccc(C(F)(F)C(O)(Cn4cnnn4)c4ccc(F)cc4F)nc3)cc2)cc1] |

-continued

| Example Number | HPLC Method | HPLC (RT) | MS (ESI) (M + H) | Stereochem./ Optical Rotation | Structure |
|---|---|---|---|---|---|
| 149 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 16.90 | 588 | Racemic | 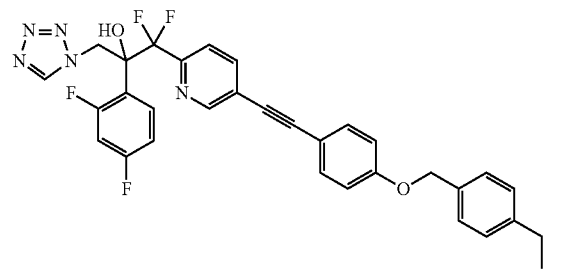 [SMILES: CCc1ccc(COc2ccc(C#Cc3ccc(C(F)(F)C(O)(Cn4cnnn4)c4ccc(F)cc4F)nc3)cc2)cc1] |
| 150 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 7.60 | 610 | Racemic | 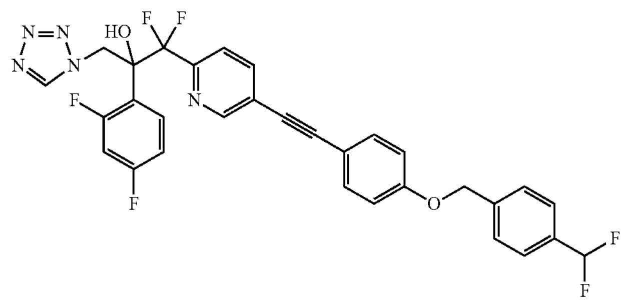 [SMILES: OC(Cn1cnnn1)(c1ccc(F)cc1F)C(F)(F)c1ccc(C#Cc2ccc(OCc3ccc(C(F)F)cc3)cc2)cn1] |
| (+)- 150 | Method N Column, Type, Size: Chiralpak IA (250 × 10 mm, 5 μm) Mobile Phase A: 15% EtOH Mobile Phase B: 30% IPA Mobile Phase C: 55% hexanes Flow Rate: 1.0 mL/min | 20.669 | 610 | [a]23/D = +12.0° (c 0.1 MeOH) | See above |
| 151 | Method M Column, Type, Size: Sunfire C-18 (150 × 4.6 mm, 5 μm) Mobile Phase A: ACN Mobile Phase B: 50 nM NH$_4$HCO2 Flow Rate: 1.0 mL/min | 21.20 | 628 | Racemic | 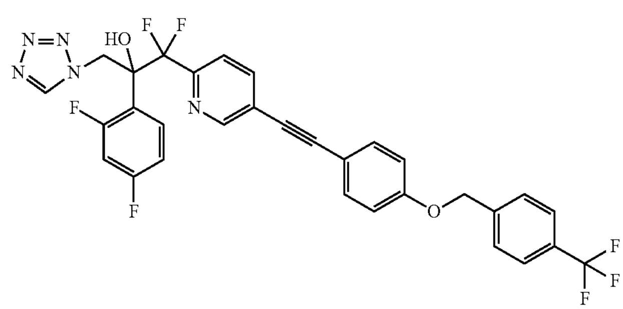 [SMILES: OC(Cn1cnnn1)(c1ccc(F)cc1F)C(F)(F)c1ccc(C#Cc2ccc(OCc3ccc(C(F)(F)F)cc3)cc2)cn1] |
| 152 | Method M Column, Type, Size: Sunfire C-18 (150 × 4.6 mm, 5 μm) Mobile Phase A: ACN Mobile Phase B: 50 mM NH$_4$HCO2 Flow Rate: 1.0 mL/min | 5.90 | 603 | Racemic | 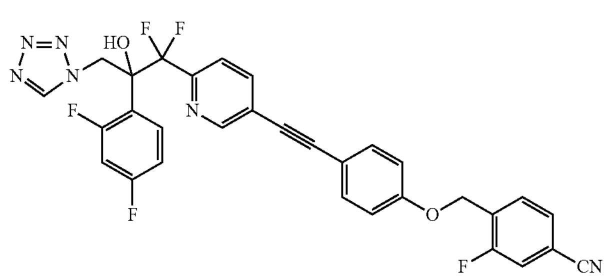 [SMILES: N#Cc1ccc(COc2ccc(C#Cc3ccc(C(F)(F)C(O)(Cn4cnnn4)c4ccc(F)cc4F)nc3)cc2)c(F)c1] |

-continued

| Example Number | HPLC Method | HPLC (RT) | MS (ESI) (M + H) | Stereochem./ Optical Rotation | Structure |
| --- | --- | --- | --- | --- | --- |
| 153 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 6.30 | 603 | Racemic | 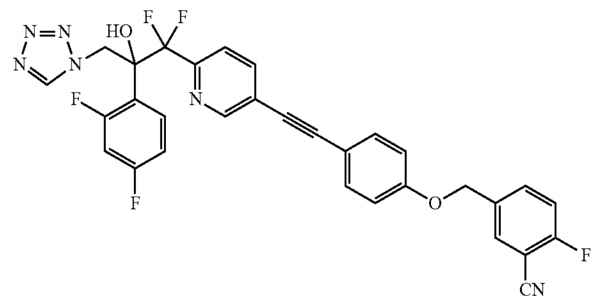 [SMILES: N#Cc1cc(COc2ccc(C#Cc3ccc(C(F)(F)C(O)(Cn4cnnn4)c4ccc(F)cc4F)nc3)cc2)ccc1F] |
| 154 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 6.30 | 626 | Racemic | 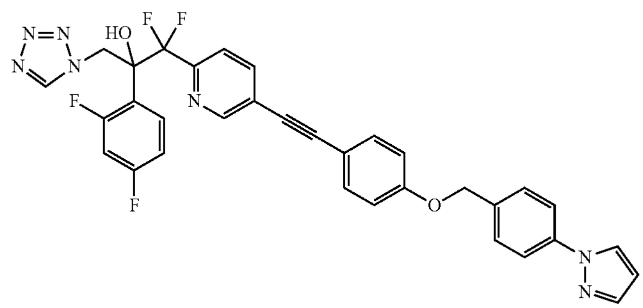 [SMILES: OC(Cn1cnnn1)(c1ccc(F)cc1F)C(F)(F)c1ccc(C#Cc2ccc(OCc3ccc(-n4cccn4)cc3)cc2)cn1] |
| 155 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 5.30 | 585 | Racemic | 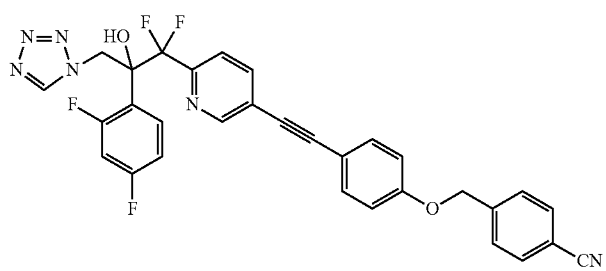 [SMILES: N#Cc1ccc(COc2ccc(C#Cc3ccc(C(F)(F)C(O)(Cn4cnnn4)c4ccc(F)cc4F)nc3)cc2)cc1] |
| 156 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 12.50 | 594 | Racemic | 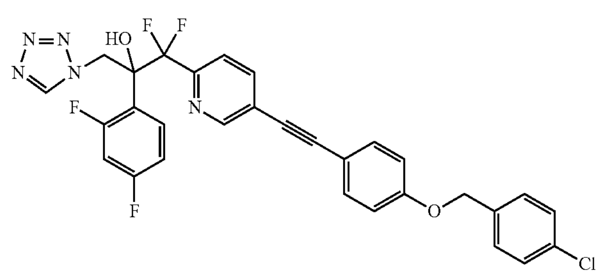 [SMILES: OC(Cn1cnnn1)(c1ccc(F)cc1F)C(F)(F)c1ccc(C#Cc2ccc(OCc3ccc(Cl)cc3)cc2)cn1] |
| 157 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 19.20 | 636 | Racemic | 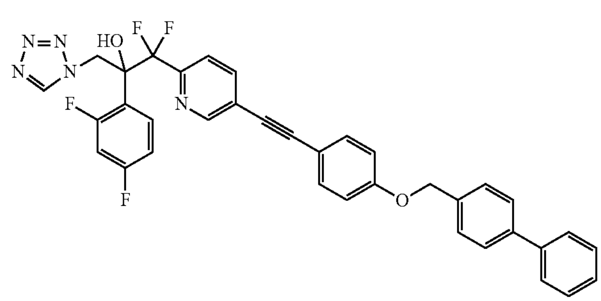 [SMILES: OC(Cn1cnnn1)(c1ccc(F)cc1F)C(F)(F)c1ccc(C#Cc2ccc(OCc3ccc(-c4ccccc4)cc3)cc2)cn1] |

-continued

| Example Number | HPLC Method | HPLC (RT) | MS (ESI) (M + H) | Stereochem./ Optical Rotation | Structure |
|---|---|---|---|---|---|
| 158 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 15.2 | 627 | | 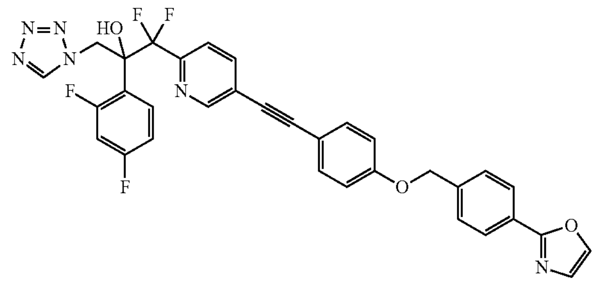 [SMILES: OC(Cn1cnnn1)(c1ccc(F)cc1F)C(F)(F)c1ccc(C#Cc2ccc(OCc3ccc(-c4ncco4)cc3)cc2)cn1] |
| 159 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 12.0 | 578 | Racemic | 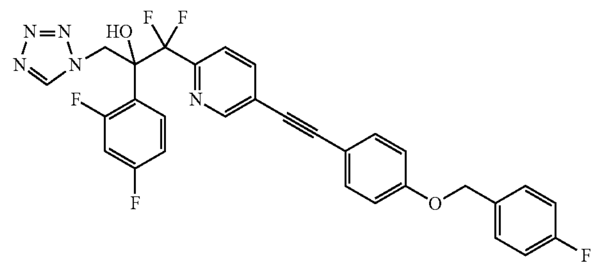 [SMILES: OC(Cn1cnnn1)(c1ccc(F)cc1F)C(F)(F)c1ccc(C#Cc2ccc(OCc3ccc(F)cc3)cc2)cn1] |
| 160 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 14.6 | 596 | Racemic | 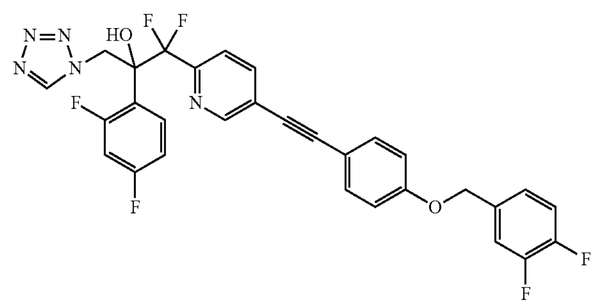 [SMILES: OC(Cn1cnnn1)(c1ccc(F)cc1F)C(F)(F)c1ccc(C#Cc2ccc(OCc3ccc(F)c(F)c3)cc2)cn1] |
| 161 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 20.1 | 610 | Racemic | 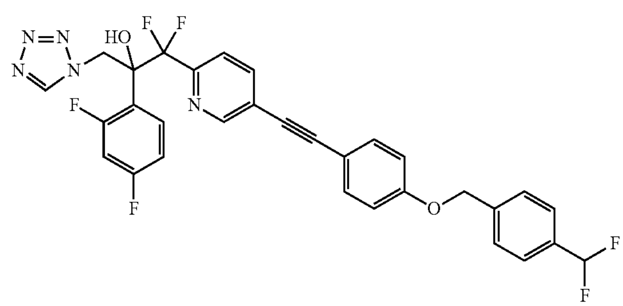 [SMILES: OC(Cn1cnnn1)(c1ccc(F)cc1F)C(F)(F)c1ccc(C#Cc2ccc(OCc3ccc(C(F)F)cc3)cc2)cn1] |
| 162 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 16.2 | 601 | Racemic | 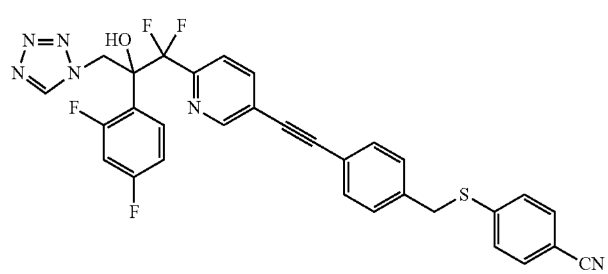 [SMILES: N#Cc1ccc(SCc2ccc(C#Cc3ccc(C(F)(F)C(O)(Cn4cnnn4)c4ccc(F)cc4F)nc3)cc2)cc1] |

-continued

| Example Number | HPLC Method | HPLC (RT) | MS (ESI) (M + H) | Stereo-chem./ Optical Rotation | Structure |
|---|---|---|---|---|---|
| 163 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 12.9 | 591 | Racemic | 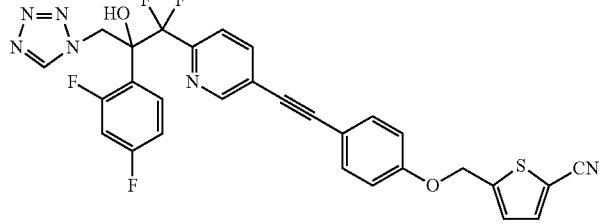 |
| 164 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 12.5 | 603 | Racemic | 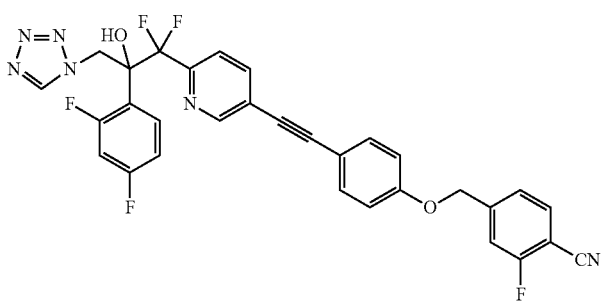 [SMILES: N#Cc1ccc(COc2ccc(C#Cc3ccc(C(F)(F)C(O)(Cn4cnnn4)c4ccc(F)cc4F)nc3)cc2)cc1F] |
| 165 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 38.0 | 613 | Racemic | 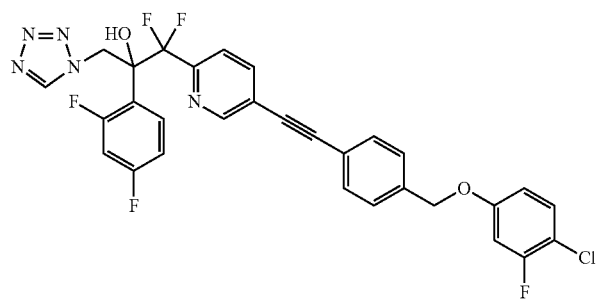 [SMILES: OC(Cn1cnnn1)(c1ccc(F)cc1F)C(F)(F)c1ccc(C#Cc2ccc(COc3ccc(Cl)c(F)c3)cc2)cn1] |
| 166 | Method M Column, Type, Size: Sunfire C-18 (150 × 4.6 mm, 5 μm) Mobile Phase A: ACN Mobile Phase B: 50 mM NH₄HCO2 Flow Rate: 1.0 mL/min | 13.9 | 585 | Racemic | 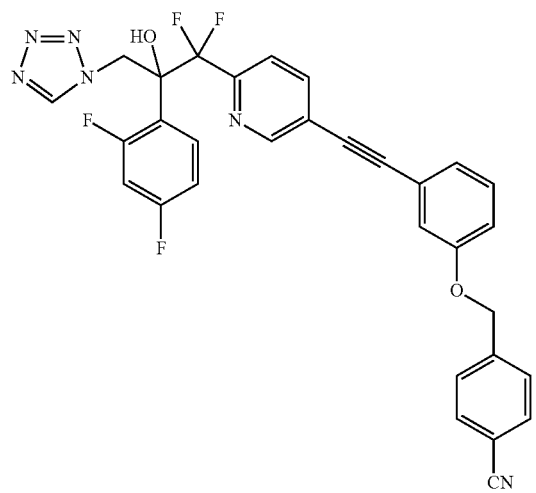 [SMILES: N#Cc1ccc(COc2cccc(C#Cc3ccc(C(F)(F)C(O)(Cn4cnnn4)c4ccc(F)cc4F)nc3)c2)cc1] |

Method Specifications

Method A:

Column, Type, Size:
Acquity BEH C-18
(50 × 2.1 mm, 1.7µ)
Mobile Phase:
Solvent A: Acetonitrile
Solvent B: 0.025% TFA (Aq)
Flow Rate: 0.50 mL/min

Method B:

Column, Type, Size:
ChiralPak IC, 250 × 4.6 mm, 5µ
Mobile Phase A: n-Hexane
Mobile Phase B: IPA
A:B:: 50:50
Flow Rate: 1.0 mL/min

Method C:

Column, Type, Size:
Acquity UPLC BEH C-18
(2.1 × 50 mm, 1.7µ)
Mobile Phase:
Solvent A: Acetonitrile
Solvent B: 0.025% TFA (Aq)
Flow Rate: 0.50 mL/min

Method D:

Column, Type, Size:
X-Terra RP-18
(50 × 4.6 mm, 5µm)
Mobile Phase A: ACN:THF (80:20)
Mobile Phase B: 0.1% TFA in water
Flow Rate: 1.0 mL/min

Method E:

Column, Type, Size:
Eclipse XDB C-18
(150 × 4.6 mm, 5.0 µm)
Mobile Phase A: ACN
Mobile Phase B: 0.1% Aq TFA
Flow Rate: 1.0 mL/min

Method F:

Column, Type, Size:
Eclipse XDB C-18
(150 × 4.63 mm, 5 µm)
Mobile Phase A: ACN
Mobile Phase B: 5 mM NH$_4$OAC
Flow Rate: 1.0 mL/min

Method G:

Column, Type, Size:
ChiralPak IC, 250 × 4.6 mm, 5µ
Mobile Phase A:
0.1% TEA in n-Hexane
Mobile Phase B: Ethanol
A:B:: 70:30
Flow Rate: 1.0 mL/min

Method H:

Column, Type, Size:
Luna C-18 (150 × 2.0 mm, 5.0 µm)
Mobile Phase A: ACN
Mobile Phase B: 0.1% TFA in water
Flow Rate: 1.0 mL/min

Method I:

Column, Type, Size:
ChiralPak IC, 250 × 4.6 mm, 5µ
Mobile Phase A: n-Hexane
Mobile Phase B: Ethanol
A:B:: 80:20
Flow Rate: 1.0 mL/min

Method J:

Column, Type, Size:
ChiralPak IA, 250 × 4.6 mm, 5µ
Mobile Phase A: n-Hexane
Mobile Phase B: Ethanol
A:B:: 75:25
Flow Rate: 1.0 mL/min

Method K:

Column, Type, Size:
ChiralPak IA, 250 × 4.6 mm, 5µ
Mobile Phase A:
0.1% DEA in n-Hexane
Mobile Phase B: Methanol
A:B:: 80:20
Flow Rate: 1.0 mL/min

Method L:

Column, Type, Size:
ChiralPak IC, 250 × 4.6 mm, 5 µm
Mobile Phase A:
0.1% DEA in n-Hexane
Mobile Phase B: Ethanol
A:B:: 60:40
Flow Rate: 1.0 mL/min

Method M:

Column, Type, Size:
Sunfire C-18
(150 × 4.6 mm, 5 µm)
Mobile Phase A: ACN
Mobile Phase B:
50 mM NH$_4$HCO2
Flow Rate: 1.0 mL/min

Method N:

Column, Type, Size:
Chiralpak IA (250 × 10 mm, 5 µm)
Mobile Phase A: 15% EtOH
Mobile Phase B: 30% IPA
Mobile Phase C: 55% hexanes
Flow Rate: 1.0 mL/min

Example 167

Metalloenzyme Activity

A. Minimum Inhibitory Concentration (MIC)

Compounds were assessed for their ability to inhibit the growth of common strains of fungus, *C. albicans* using a standardized procedure (CLSI M27-A2).

Stock solutions of the test compounds and standards were prepared in DMSO at 1600 µg/mL (*C. albicans*). Eleven, serial, one-half dilutions of compounds were prepared in 96-well plates in RPMI+MOPS. The assay concentration ranges were 1-0.001 µg/mL (*C. albicans*). Cell suspensions of *C. albicans* were prepared and added to each well at concentrations of approximately 3.7×10$^3$ colony-forming-units per milliliter (cfu/mL). All testing was in duplicate. The inoculated plates were incubated for approximately 48 h at 35±1° C. At the completion of incubation the wells of each plate were evaluated visually for the presence of fungal growth.

For fluconazole and the test compounds, the MIC was the concentration at which growth was significantly reduced (about 50% reduction). For voriconazole the MIC was the concentration which reduced *C. albicans* growth by 50% (per CLSI, M27-A2). For QC purposes *C. krusei* isolate ATCC 6258 (4.0×10$^3$ cfu/mL) was included in the VOR assay. This isolate did not exhibit trailing growth against voriconazole, therefore the MIC was the concentration at which growth was completely inhibited.

*A. fumigatus* MICs were determined at both 50% and 100% growth inhibition following CLSI guidelines at a concentration range of 64-0.062 µg/mL (CLSI M38-A2).

Results: Antifungal Activity

| Example | *Candida* MIC* | *Aspergillus* MIC |
|---|---|---|
| 2 | 0.004 | 8 |
| 5 | 0.016 | 8 |
| 9 | ≤0.001 | 0.5 |
| 101 | 0.25 | 2 |
| 108 | 0.062 | 4 |
| Voriconazole | 0.016 | 0.25 |

*Candida albicans* MIC50 (median inhibitory concentration) values expressed in ug/mL; *Aspergillus fumigatus* MIC50 values expressed in ug/mL.

Compounds of the present invention inhibit growth of *A. fumigatus* in a standard 4-day mouse model. For example, oral administration of Compound (−)-9 at 20 mg/kg each of 4 days reduced mouse kidney fungal burden 84% compared to control.

Compounds of the present invention inhibit growth of *Septoria* and *Puccinia* to protect plants from fungal infection (in vitro and in planta). For example, Compounds 2, 3, and 21 exhibit a range of MIC=0.25-1.0 ug/mL in a standard *Septoria tritici* MIC assay (ATCC 26517, CLSI protocol). Compounds of the present invention, for example Compound 2, provide protection from fungal growth when applied at 50 ppm in planta against both *Septoria* and *Puccinia* pathogens.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of formula (I) or salt thereof, wherein:

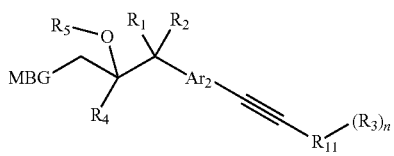

$R_1$ is halo;

$R_2$ is halo;

each $R_3$ is independently cyano, haloalkyl, alkoxy, haloalkoxy, hydroxy, amino, —$NR_6R_9$, —$SR_{10}$, —$C(O)R_{10}$, optionally substituted haloalkyl, optionally substituted arylalkoxy, —$C(O)NR_6R_7$, —CH(OH)-haloalkyl, optionally substituted alkyl, hydroxyalkyl, alkoxyalkyl, isocyano, cycloalkylaminocarbonyl, optionally substituted aryloxyalkyl, optionally substituted arylalkylthio, haloalkylthio, optionally substituted arylalkylsulfonyl, optionally substituted arylalkylsulfinyl, optionally substituted heteroarylalkoxy, optionally substituted arylthioalkyl, or haloalkylcarbonyl;

n is 0, 1, 2 or 3;

$R_4$ is aryl optionally substituted with 0, 1, 2 or 3 independent $R_8$;

$R_5$ is H, alkyl, phosphato, phosphito, alkoxyphosphato, or —C(O)alkyl optionally substituted with 1 or 2 amino;

$R_6$ is independently H or alkyl;

$R_7$ is independently H, optionally substituted alkyl, optionally substituted haloalkyl, or optionally substituted arylalkyl;

each $R_8$ is independently cyano, haloalkyl, alkoxy, halo, or haloalkoxy;

each $R_9$ is independently H, alkyl, —C(O)alkyl, —C(O)H, —C(O)haloalkyl, optionally substituted arylalkyl, or optionally substituted haloalkyl;

each $R_{10}$ is independently H, optionally substituted alkyl, optionally substituted aryl, optionally substituted heterocycloalkyl, or optionally substituted arylalkyl;

$Ar_2$ is

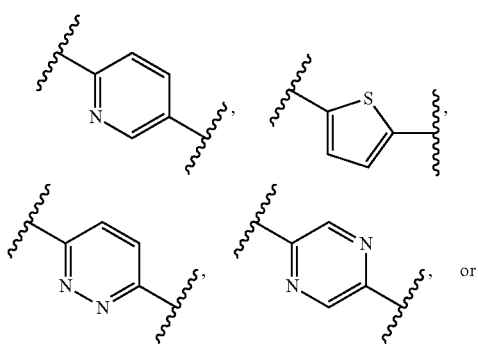

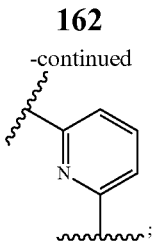

$R_{11}$ is phenyl, alkyl, thienyl, pyrrolyl, furanyl, pyridyl, —CH(OH)-alkyl, —CH(OH)-haloalkyl, arylalkyl, aryloxyalkyl, haloalkyl, haloalkoxyalkyl, indolyl, benzofuranyl, heterocycloalkyl, or

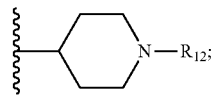

$R_{12}$ is $R_4$, —$C(O)R_4$, —$C(O)R_D$, —$SO_2R_4$;

MBG is optionally substituted tetrazolyl, optionally substituted triazolyl, optionally substituted oxazolyl, optionally substituted pyrimidinyl, optionally substituted thiazolyl, or optionally substituted pyrazolyl.

2. The compound of claim 1, wherein $R_1$ is fluoro.

3. The compound of claim 1, wherein $R_2$ is fluoro.

4. The compound of claim 1, wherein $R_1$ and $R_2$ are fluoro.

5. The compound of claim 1, wherein $R_4$ is phenyl optionally substituted with 0, 1, 2 or 3 independent $R_8$.

6. The compound of claim 1, wherein $R_4$ is phenyl optionally substituted with 0, 1, 2 or 3 independent halo.

7. The compound of claim 1, wherein $R_4$ is phenyl optionally substituted with 0, 1, 2 or 3 independent fluoro.

8. The compound of claim 1, wherein $R_4$ is 2,4-difluorophenyl.

9. The compound of claim 1, wherein $R_5$ is H.

10. The compound of claim 1, wherein $R_5$ is amino substituted acyl.

11. The compound of claim 1, wherein $R_5$ is phosphato.

12. The compound of claim 1, wherein:

$R_1$ is fluoro;

$R_2$ is fluoro;

$R_4$ is 2,4-difluorophenyl;

$R_5$ is H;

$Ar_2$ is

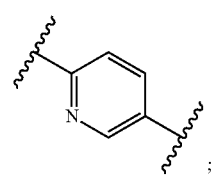 [SMILES: *c1ccc(*)nc1]

and

MBG is 1-tetrazolyl.

13. The compound of claim 12, wherein:

$R_{11}$ is phenyl, thienyl, arylalkyl, aryloxyalkyl, each optionally substituted with 0, 1, 2, or 3 independent $R_3$;

each $R_3$ is independently cyano, haloalkyl, haloalkoxy, optionally substituted arylalkoxy, haloalkylaminocarbonyl, optionally substituted arylalkylaminocarbonyl; and n is 1 or 2.

163

14. The compound of claim 12, wherein:
$R_{11}$ is phenyl, thienyl, arylalkyl, aryloxyalkyl, each optionally substituted with 0, 1, 2, or 3 independent $R_3$;
each $R_3$ is independently cyano, haloalkyl, haloalkoxy, optionally substituted arylalkoxy, haloalkylaminocarbonyl, optionally substituted arylalkylaminocarbonyl; and
n is 1.

15. The compound of claim 12, wherein:
$R_{11}$ is phenyl optionally substituted with 0, 1, 2, or 3 independent $R_3$;
each $R_3$ is independently cyano or haloalkyl; and
n is 1 or 2.

16. The compound of claim 12, wherein:
$R_{11}$ is thienyl optionally substituted with 0, 1, 2, or 3 independent $R_3$;
each $R_3$ is independently haloalkylaminocarbonyl, optionally substituted arylalkylaminocarbonyl; and
n is 1 or 2.

17. The compound of claim 1, which is one of:
2-(2,4-Difluorophenyl)-1,1-difluoro-1-(5-(phenylethynyl)pyridin-2-yl)-3-(1H-tetrazol-1-yl)propan-2-ol (1);
2-(2,4-Difluorophenyl)-1,1-difluoro-3-(1H-tetrazol-1-yl)-1-(5-((4-(trifluoromethyl)phenyl) ethynyl)pyridin-2-yl)propan-2-ol (5);
5-((6-(2-(2,4-difluorophenyl)-1,1-difluoro-2-hydroxy-3-(1H-tetrazol-1-yl)propyl)pyridin-3-yl) ethynyl)-N-(4-fluorobenzyl)thiophene-2-carboxamide (6);
4-((4-((6-(2-(2,4-difluorophenyl)-1,1-difluoro-2-hydroxy-3-(1H-tetrazol-1-yl) propyl)pyridin-3-yl) ethynyl) phenoxy)methyl)-2-fluorobenzonitrile (7);
4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (8);
2-(2,4-difluorophenyl)-1,1-difluoro-3-(1H-tetrazol-1-yl)-1-(5-((4-(2,2,2-trifluoro-1-hydroxyethyl)phenyl) ethynyl)pyridin-2-yl)propan-2-ol (9);
2-(2,4-Difluorophenyl)-1,1-difluoro-1-(5-((1-methyl-1H-pyrrol-3-yl)ethynyl)pyridin-2-yl)-3-(1H-tetrazol-1-yl)propan-2-ol (10);
4-(6-(2-(2,4-Difluorophenyl)-1,1-difluoro-2-hydroxy-3-(1H-tetrazol-1-yl)propyl)pyridin-3-yl)but-3-yn-2-ol (13);
2-(2,4-Difluorophenyl)-1,1-difluoro-3-(1H-tetrazol-1-yl)-1-(5-((5-(2,2,2-trifluoro-1-hydroxyethyl)thiophen-2-yl)ethynyl)pyridin-2-yl)propan-2-ol (14);
2-(2,4-Difluorophenyl)-1,1-difluoro-3-(1H-tetrazol-1-yl)-1-(5-((5-(2,2,2-trifluoro-1-hydroxy ethyl)furan-2-yl)ethynyl)pyridin-2-yl)propan-2-ol (16);
2-(2,4-Difluorophenyl)-1,1-difluoro-1-(5-((1-(4-fluorophenyl)piperidin-4-yl)ethynyl)pyridin-2-yl)-3-(1H-tetrazol-1-yl)propan-2-ol (19);
1-(5-((4-((4-Cyanobenzyl)oxy)phenyl)ethynyl)pyridin-2-yl)-2-(2,4-difluorophenyl)-1,1-difluoro-3-(1H-tetrazol-1-yl) propan-2-yl dihydrogen phosphate (20);
2-(2,4-difluorophenyl)-1-(5-(3,3-difluoroprop-1-ynyl)pyridin-2-yl)-1,1-difluoro-3-(1H-tetrazol-1-yl)propan-2-ol (23);
1-(5-((4-(difluoromethyl)phenyl)ethynyl)pyridin-2-yl)-2-(2,4-difluorophenyl)-1,1-difluoro-3-(1H-tetrazol-1-yl) propan-2-ol (26);
2-(2,4-difluorophenyl)-1,1-difluoro-3-(1-tetrazol-1-yl)-1-(5-(((5-(trifluoromethyl)thiophen-2-yl)ethynyl)pyridin-2-yl)propan-2-ol (30);
2-(2,4-difluorophenyl)-1,1-difluoro-3-(1H-tetrazol-1-yl)-1-(5-((4-(trifluoromethoxy)phenyl)ethynyl)pyridin-2-yl)propan-2-ol (34);

164

2-(2,4-difluorophenyl)-1,1-difluoro-1-(5-((5-methylthiophen-2-yl)ethynyl)pyridin-2-yl)-3-(1H-tetrazol-1-yl) propan-2-ol (38);
1-(5-((4-(1,1-difluoroethyl)phenyl)ethynyl)pyridin-2-yl)-2-(2,4-difluorophenyl)-1,1-difluoro-3-(1H-tetrazol-1-yl)propan-2-ol (39);
1-(5-((4-(difluoromethoxy)phenyl)ethynyl)pyridin-2-yl)-2-(2,4-difluorophenyl)-1,1-difluoro-3-(1H-tetrazol-1-yl)propan-2-ol (40);
2-(2,4-difluorophenyl)-1,1-difluoro-3-(1H-tetrazol-1-yl)-1-(5-((4-(trifluoromethylthio)phenyl)ethynyl)pyridin-2-yl)propan-2-ol (41);
1-(4-((6-(2-(2,4-difluorophenyl)-1,1-difluoro-2-hydroxy-3-(1H-tetrazol-1-yl)propyl)pyridin-3-yl)ethynyl)phenyl)ethanone (47);
2-(2,4-difluorophenyl)-1,1-difluoro-1-(5-((4-(hydroxymethyl)phenyl)ethynyl)pyridin-2-yl)-3-(1H-tetrazol-1-yl)propan-2-ol (50);
2-(2,4-difluorophenyl)-1,1-difluoro-1-(5-((4-(methoxymethyl)phenyl)ethynyl)pyridin-2-yl)-3-(1H-tetrazol-1-yl)propan-2-ol (51);
4-(6-(2-(2,4-difluorophenyl)-1,1-difluoro-2-hydroxy-3-(1H-tetrazol-1-yl)propyl)pyridin-3-yl)-1,1,1-trifluorobut-3-yn-2-ol (52);
1-(5-((5-(difluoromethyl)thiophen-2-yl)ethynyl)pyridin-2-yl)-2-(2,4-difluorophenyl)-1,1-difluoro-3-(1H-tetrazol-1-yl)propan-2-ol (54);
1-(5-((6-(2-(2,4-difluorophenyl)-1,1-difluoro-2-hydroxy-3-(1H-tetrazol-1-yl)propyl)pyridin-3-yl)ethynyl) thiophen-2-yl)-2,2,2-trifluoroethanone (55);
2-(2,4-difluorophenyl)-1,1-difluoro-3-(1H-tetrazol-1-yl)-1-(5-((1-(2,2,2-trifluoroethyl)-1H-pyrrol-3-yl)ethynyl) pyridin-2-yl)propan-2-ol (56);
2-(2,4-difluorophenyl)-1,1-difluoro-3-(1-tetrazol-1-yl)-1-(5-(3-(2,2,2-trifluoroethoxy)prop-1-ynyl)pyridin-2-yl) propan-2-ol (57);
2-(2,4-difluorophenyl)-1,1-difluoro-3-(1-tetrazol-1-yl)-1-(5-(thiophen-2-ylethynyl)pyridin-2-yl)propan-2-ol (58);
2-(2,4-difluorophenyl)-1,1-difluoro-1-(5-((4-(methylamino)phenyl)ethynyl)pyridin-2-yl)-3-(1H-tetrazol-1-yl)propan-2-ol (60);
2-(2,4-difluorophenyl)-1-(5-((4-(dimethylamino)phenyl) ethynyl)pyridin-2-yl)-1,1-difluoro-3-(1H-tetrazol-1-yl) propan-2-ol (62);
1-(5-((1H-pyrrol-3-yl)ethynyl)pyridin-2-yl)-2-(2,4-difluorophenyl)-1,1-difluoro-3-(1H-tetrazol-1-yl)propan-2-ol (63);
1-(5-((1-(difluoromethyl)-1H-pyrrol-3-yl)ethynyl)pyridin-2-yl)-2-(2,4-difluorophenyl)-1,1-difluoro-3(1H-tetrazol-1-yl)propan-2-ol (66);
N-(4-((6-(2-(2,4-difluorophenyl)-1,1-difluoro-2-hydroxy-3-(1H-tetrazol-1-yl)propyl)pyridin-3-yl)ethynyl)phenyl)formamide (68);
4-((6-(2-(2,4-difluorophenyl)-1,1-difluoro-2-hydroxy-3-(1H-tetrazol-1-yl)propyl)pyridin-3-yl)ethynyl)benzonitrile (69);
2-(2,4-difluorophenyl)-1,1-difluoro-1-(5-((4-isocyanophenyl)ethynyl)pyridin-2-yl)-3-(1H-tetrazol-1-yl) propan-2-ol (70);
3-((6-(2-(2,4-difluorophenyl)-1,1-difluoro-2-hydroxy-3-(1H-tetrazol-1-yl)propyl)pyridin-3-yl)ethynyl)benzonitrile (71);
1-(5-((5-(difluoromethyl)furan-2-yl)ethynyl)pyridin-2-yl)-2-(2,4-difluorophenyl)-1,1-difluoro-3-(1H-tetrazol-1-yl)propan-2-ol (76);

2-(2,4-difluorophenyl)-1,1-difluoro-3-(1H-tetrazol-1-yl)-1-(5-((5-(2,2,2-trifluoroethyl)thiophen-2-yl)ethynyl)pyridin-2-yl)propan-2-ol (77);

1-(5-((4-aminophenyl)ethynyl)pyridin-2-yl)-2-(2,4-difluorophenyl)-1,1-difluoro-3-(1H-tetrazol-1-yl)propan-2-ol (78);

N-(4-((6-(2-(2,4-difluorophenyl)-1,1-difluoro-2-hydroxy-3-(1H-tetrazol-1-yl)propyl)pyridin-3-yl)ethynyl)phenyl)-2,2,2-trifluoroacetamide (79);

2-(2,4-difluorophenyl)-1,1-difluoro-3-(1H-tetrazol-1-yl)-1-(5-((4-(2,2,2-trifluoroethylamino)phenyl)ethynyl)pyridin-2-yl)propan-2-ol (80);

4-((6-(2-(2,4-difluorophenyl)-1,1-difluoro-2-hydroxy-3-(1H-tetrazol-1-yl)propyl)pyridin-3-yl)ethynyl)phenol (81);

4-((6-(2-(2,4-difluorophenyl)-1,1-difluoro-2-hydroxy-3-(1H-tetrazol-1-yl)propyl)pyridin-3-yl)ethynyl)benzamide (82);

N-(4-((6-(2-(2,4-difluorophenyl)-1,1-difluoro-2-hydroxy-3-(1H-tetrazol-1-yl)propyl)pyridin-3-yl)ethynyl)phenyl)acetamide (84);

4-(3-(6-(2-(2,4-difluorophenyl)-1,1-difluoro-2-hydroxy-3-(1H-tetrazol-1-yl)propyl)pyridin-3-yl)prop-2-ynyloxy)benzonitrile (86);

1-(5-((1H-indol-5-yl)ethynyl)pyridin-2-yl)-2-(2,4-difluorophenyl)-1,1-difluoro-3-(1H-tetrazol-1-yl)propan-2-ol (87);

2-(2,4-difluorophenyl)-1,1-difluoro-1-(5-((4-(4-fluorobenzylamino)phenyl)ethynyl)pyridin-2-yl)-3-(1H-tetrazol-1-yl)propan-2-ol (88);

1-(5-(benzofuran-5-ylethynyl)pyridin-2-yl)-2-(2,4-difluorophenyl)-1,1-difluoro-3-(1H-tetrazol-1-yl)propan-2-ol (89);

2-(2,4-difluorophenyl)-1,1-difluoro-3-(1H-tetrazol-1-yl)-1-(5-((4-(2,2,2-trifluoroethyl)phenyl)ethynyl)pyridin-2-yl)propan-2-ol (90);

4-((6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)benzamide (91);

(4-((6-(2-(2,4-difluorophenyl)-1,1-difluoro-2-hydroxy-3-(1H-tetrazol-1-yl)propyl)pyridin-3-yl)ethynyl)phenyl)(pyrrolidin-1-yl)methanone (92);

2-(2,4-difluorophenyl)-1,1-difluoro-1-(5-((4-(4-fluorobenzyloxy)phenyl)ethynyl)pyridin-2-yl)-3-(1H-tetrazol-1-yl)propan-2-ol (93);

5-((6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)thiophene-2-carboxamide (94);

(4-((6-(2-(2,4-difluorophenyl)-1,1-difluoro-2-hydroxy-3-(1H-tetrazol-1-yl)propyl)pyridin-3-yl)ethynyl)piperidin-1-yl)(4-fluorophenyl)methanone (95);

1-(4-((6-(2-(2,4-difluorophenyl)-1,1-difluoro-2-hydroxy-3-(1H-tetrazol-1-yl)propyl)pyridin-3-yl)ethynyl)piperidin-1-yl)-2,2,2-trifluoroethanone (96);

2-(2,4-difluorophenyl)-1,1-difluoro-3-(1H-tetrazol-1-yl)-1-(5-((3-(2,2,2-trifluoroethoxy)phenyl)ethynyl)pyridin-2-yl)propan-2-ol (97);

3-(6-(2-(2,4-difluorophenyl)-1,1-difluoro-2-hydroxy-3-(1H-tetrazol-1-yl)propyl)pyridin-3-yl)ethynyl)-N-(2,2,2-trifluoroethyl)benzamide (98);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (100);

2-(2,4-difluorophenyl)-1,1-difluoro-3-(1H-tetrazol-1-yl)-1-(5-((4-(4-(trifluoromethoxy)benzyloxy)phenyl)ethynyl)pyridin-2-yl)propan-2-ol (101);

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)-3-fluorobenzonitrile (102);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-4-fluorobenzonitrile (103);

2-(2,4-difluorophenyl)-1,1-difluoro-3-(1H-tetrazol-1-yl)-1-(5-((4-(3-(trifluoromethoxy)benzyloxy)phenyl)ethynyl)pyridin-2-yl)propan-2-ol (104);

1-(5-((4-(2,4-difluorobenzyloxy)phenyl)ethynyl)pyridin-2-yl)-2-(2,4-difluorophenyl)-1,1-difluoro-3-(1H-tetrazol-1-yl)propan-2-ol (105);

1-(5-((4-(3,4-difluorobenzyloxy)phenyl)ethynyl)pyridin-2-yl)-2-(2,4-difluorophenyl)-1,1-difluoro-3-(1H-tetrazol-1-yl)propan-2-ol (106);

1-(5-((4-(4-chlorobenzyloxy)phenyl)ethynyl)pyridin-2-yl)-2-(2,4-difluorophenyl)-1,1-difluoro-3-(1H-tetrazol-1-yl)propan-2-ol (107);

1-(5-((4-(4-chloro-2-fluorobenzyloxy)phenyl)ethynyl)pyridin-2-yl)-2-(2,4-difluorophenyl)-1,1-difluoro-3-(1H-tetrazol-1-yl)propan-2-ol (108);

4-((4-((6-(2-(2,4-difluorophenyl)-1,1-difluoro-2-hydroxy-3-(1H-tetrazol-1-yl)propyl)pyridin-3-yl)ethynyl)phenoxy)methyl)-N-methylbenzamide (109);

6-((4-((6-(2-(2,4-difluorophenyl)-1,1-difluoro-2-hydroxy-3-(1H-tetrazol-1-yl)propyl)pyridin-3-yl)ethynyl)phenoxy)methyl)nicotinonitrile (110);

2-(2,4-difluorophenyl)-1,1-difluoro-3-(1H-tetrazol-1-yl)-1-(5-((4-(thiazol-2-ylmethoxy)phenyl)ethynyl)pyridin-2-yl)propan-2-ol (111);

5-((4-((6-(2-(2,4-difluorophenyl)-1,1-difluoro-2-hydroxy-3-(1H-tetrazol-1-yl)propyl)pyridin-3-yl)ethynyl)phenoxy)methyl)-2-fluorobenzonitrile (112);

1-(5-((4-(2,3-difluorobenzyloxy)phenyl)ethynyl)pyridin-2-yl)-2-(2,4-difluorophenyl)-1,1-difluoro-3-(1H-tetrazol-1-yl)propan-2-ol (113);

1-(5-(3-(4-(difluoromethyl)phenoxy)prop-1-ynyl)pyridin-2-yl)-2-(2,4-difluorophenyl)-1,1-difluoro-3-(1H-tetrazol-1-yl)propan-2-ol (118);

5-((6-(2-(2,4-difluorophenyl)-1,1-difluoro-2-hydroxy-3-(1H-tetrazol-1-yl)propyl)pyridin-3-yl)ethynyl)-N-(3-fluorobenzyl)thiophene-2-carboxamide (119);

N-(3-cyanobenzyl)-5-((6-(2-(2,4-difluorophenyl)-1,1-difluoro-2-hydroxy-3-(1H-tetrazol-1-yl)propyl)pyridin-3-yl)ethynyl)thiophene-2-carboxamide (120);

N-(4-cyanobenzyl)-5-((6-(2-(2,4-difluorophenyl)-1,1-difluoro-2-hydroxy-3-(1H-tetrazol-1-yl)propyl)pyridin-3-yl)ethynyl)thiophene-2-carboxamide (121);

5-((6-(2-(2,4-difluorophenyl)-1,1-difluoro-2-hydroxy-3-(1H-tetrazol-1-yl)propyl)pyridin-3-yl)ethynyl)-N-(4-(trifluoromethyl)benzyl)thiophene-2-carboxamide (122);

(5-((6-(2-(2,4-difluorophenyl)-1,1-difluoro-2-hydroxy-3-(1H-tetrazol-1-yl)propyl)pyridin-3-yl)ethynyl)thiophen-2-yl)(morpholino)methanone (123);

(5-((6-(2-(2,4-difluorophenyl)-1,1-difluoro-2-hydroxy-3-(1H-tetrazol-1-yl)propyl)pyridin-3-yl)ethynyl)thiophen-2-yl)(pyrrolidin-1-yl)methanone (124);

5-((6-(2-(2,4-difluorophenyl)-1,1-difluoro-2-hydroxy-3-(1H-tetrazol-1-yl)propyl)pyridin-3-yl)ethynyl)-N-(4-(methylsulfonyl)benzyl)thiophene-2-carboxamide (125);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-2-fluorobenzonitrile (126);

3-((4-((6-(2-(2,4-difluorophenyl)-1,1-difluoro-2-hydroxy-3-(1H-tetrazol-1-yl)propyl)pyridin-3-yl)ethynyl)phenoxy)methyl)-5-fluorobenzonitrile (127);

2-(2,4-difluorophenyl)-1,1-difluoro-1-(5-(piperidin-4-ylethynyl)pyridin-2-yl)-3-(1H-tetrazol-1-yl)propan-2-ol (128);

2-(2,4-difluorophenyl)-1,1-difluoro-1-(5-((1-(4-fluorophenylsulfonyl)piperidin-4-yl)ethynyl)pyridin-2-yl)-3-(1H-tetrazol-1-yl)propan-2-ol (129);

1-(4-((6-(2-(2,4-difluorophenyl)-1,1-difluoro-2-hydroxy-3-(1H-tetrazol-1-yl)propyl)pyridin-3-yl)ethynyl)phenyl)-2,2,3,3,3-pentafluoropropan-1-ol (130);

4-((4-((6-(2-(2,5-difluorophenyl)-1,1-difluoro-2-hydroxy-3-(1H-tetrazol-1-yl)propyl)pyridin-3-yl)ethynyl)phenoxy)methyl)-2-fluorobenzonitrile (131);

4-((4-((6-(2-(4-chloro-2-fluorophenyl)-1,1-difluoro-2-hydroxy-3-(1H-tetrazol-1-yl)propyl)pyridin-3-yl)ethynyl)phenoxy)methyl)-2-fluorobenzonitrile (132);

4-((4-((6-(2-(2,4-difluorophenyl)-1,1-difluoro-2-hydroxy-3-(1H-tetrazol-1-yl)propyl)pyridin-3-yl)ethynyl)phenylthio)methyl)-2-fluorobenzonitrile (133);

4-((4-((6-(2-(2,4-difluorophenyl)-1,1-difluoro-2-hydroxy-3-(1H-tetrazol-1-yl)propyl)pyridin-3-yl)ethynyl)phenylsulfinyl)methyl)-2-fluorobenzonitrile (134);

4-((4-((6-(2-(2,4-difluorophenyl)-1,1-difluoro-2-hydroxy-3-(1H-tetrazol-1-yl)propyl)pyridin-3-yl)ethynyl)phenylsulfonyl)methyl)-2-fluorobenzonitrile (135);

4-((4-((6-(2-(2,5-difluorophenyl)-1,1-difluoro-2-hydroxy-3-(1H-tetrazol-1-yl)propyl)pyridin-3-yl)ethynyl)phenoxy)methyl)benzonitrile (136);

4-((4-((6-(2-(4-chloro-2-fluorophenyl)-1,1-difluoro-2-hydroxy-3-(1H-tetrazol-1-yl)propyl)pyridin-3-yl)ethynyl)phenoxy)methyl)benzonitrile (137);

4-((4-((6-(2-(2,4-difluorophenyl)-1,1-difluoro-2-hydroxy-3-(1H-tetrazol-1-yl)propyl)pyridin-3-yl)ethynyl)phenylthio)methyl)benzonitrile (138);

5-((4-((6-(2-(2,4-difluorophenyl)-1,1-difluoro-2-hydroxy-3-(1H-tetrazol-1-yl)propyl)pyridin-3-yl)ethynyl)phenoxy)methyl)picolinonitrile (139);

1-(5-((4-(4-cyanobenzyloxy)phenyl)ethynyl)pyridin-2-yl)-2-(2,4-difluorophenyl)-1,1-difluoro-3-(1H-tetrazol-1-yl)propan-2-yl dihydrogen phosphate (140);

5-((6-(2-(2,4-difluorophenyl)-1,1-difluoro-2-hydroxy-3-(2H-tetrazol-2-yl)propyl)pyridin-3-yl)ethynyl)-N-(4-fluorobenzyl)thiophene-2-carboxamide (141);

4-((4-((6-(2-(2,4-difluorophenyl)-1,1-difluoro-2-hydroxy-3-(2H-tetrazol-2-yl)propyl)pyridin-3-yl)ethynyl)phenoxy)methyl)benzonitrile (142);

4-((4-((6-(2-(2,4-difluorophenyl)-1,1-difluoro-2-hydroxy-3-(2H-tetrazol-2-yl)propyl)pyridin-3-yl)ethynyl)phenoxy)methyl)-2-fluorobenzonitrile (143);

1-(5-((4-(4-chloro-3-fluorobenzyloxy)phenyl)ethynyl)pyridin-2-yl)-2-(2,4-difluorophenyl)-1,1-difluoro-3-(1H-tetrazol-1-yl)propan-2-ol (146);

1-(5-((4-(biphenyl-4-ylmethoxy)phenyl)ethynyl)pyridin-2-yl)-2-(2,4-difluorophenyl)-1,1-difluoro-3-(1H-tetrazol-1-yl)propan-2-ol (147);

2-(2,4-difluorophenyl)-1,1-difluoro-1-(5-((4-(4-methylbenzyloxy)phenyl)ethynyl)pyridin-2-yl)-3-(1H-tetrazol-1-yl)propan-2-ol (148);

2-(2,4-difluorophenyl)-1-(5-((4-(4-ethylbenzyloxy)phenyl)ethynyl)pyridin-2-yl)-1,1-difluoro-3-(1H-tetrazol-1-yl)propan-2-ol (149);

1-(5-((4-(4-(difluoromethyl)benzyloxy)phenyl)ethynyl)pyridin-2-yl)-2-(2,4-difluorophenyl)-1,1-difluoro-3-(1H-tetrazol-1-yl)propan-2-ol (150);

(+)-1-(5-((4-(4-(difluoromethyl)benzyloxy)phenyl)ethynyl)pyridin-2-yl)-2-(2,4-difluorophenyl)-1,1-difluoro-3-(1H-tetrazol-1-yl)propan-2-ol ((+)-150);

2-(2,4-difluorophenyl)-1,1-difluoro-3-(1H-tetrazol-1-yl)-1-(5-((4-(4-(trifluoromethyl)benzyloxy)phenyl)ethynyl)pyridin-2-yl)propan-2-ol (151);

4-(4-((6-(2-(2,4-difluorophenyl)-1,1-difluoro-2-hydroxy-3-(1H-tetrazol-1-yl)propyl)pyridin-3-yl)ethynyl)benzyloxy)-3-fluorobenzonitrile (152);

5-(4-((6-(2-(2,4-difluorophenyl)-1,1-difluoro-2-hydroxy-3-(1H-tetrazol-1-yl)propyl)pyridin-3-yl)ethynyl)benzyloxy)-2-fluorobenzonitrile (153);

1-(5-((4-(4-(1H-pyrazol-1-yl)benzyloxy)phenyl)ethynyl)pyridin-2-yl)-2-(2,4-difluorophenyl)-1,1-difluoro-3-(1H-tetrazol-1-yl)propan-2-ol (154);

4-(4-((6-(2-(2,4-difluorophenyl)-1,1-difluoro-2-hydroxy-3-(1H-tetrazol-1-yl)propyl)pyridin-3-yl)ethynyl)benzyloxy)benzonitrile (155);

1-(5-((4-((4-chlorophenoxy)methyl)phenyl)ethynyl)pyridin-2-yl)-2-(2,4-difluorophenyl)-1,1-difluoro-3-(1H-tetrazol-1-yl)propan-2-ol (156);

1-(5-((4-((biphenyl-4-yloxy)methyl)phenyl)ethynyl)pyridin-2-yl)-2-(2,4-difluorophenyl)-1,1-difluoro-3-(1H-tetrazol-1-yl)propan-2-ol (157);

2-(2,4-difluorophenyl)-1,1-difluoro-1-(5-((4-(4-(oxazol-2-yl)benzyloxy)phenyl)ethynyl)pyridin-2-yl)-3-(1H-tetrazol-1-yl)propan-2-ol (158);

2-(2,4-difluorophenyl)-1,1-difluoro-1-(5-((4-((4-fluorophenoxy)methyl)phenyl)ethynyl)pyridin-2-yl)-3-(1H-tetrazol-1-yl)propan-2-ol (159);

1-(5-((4-((3,4-difluorophenoxy)methyl)phenyl)ethynyl)pyridin-2-yl)-2-(2,4-difluorophenyl)-1,1-difluoro-3-(1H-tetrazol-1-yl)propan-2-ol (160);

1-(5-((4-((4-(difluoromethyl)phenoxy)methyl)phenyl)ethynyl)pyridin-2-yl)-2-(2,4-difluorophenyl)-1,1-difluoro-3-(1H-tetrazol-1-yl)propan-2-ol (161);

4-(4-((6-(2-(2,4-difluorophenyl)-1,1-difluoro-2-hydroxy-3-(1H-tetrazol-1-yl)propyl)pyridin-3-yl)ethynyl)benzylthio)benzonitrile (162);

5-((4-((6-(2-(2,4-difluorophenyl)-1,1-difluoro-2-hydroxy-3-(1H-tetrazol-1-yl)propyl)pyridin-3-yl)ethynyl)phenoxy)methyl)thiophene-2-carbonitrile (163);

4-(4-((6-(2-(2,4-difluorophenyl)-1,1-difluoro-2-hydroxy-3-(1H-tetrazol-1-yl)propyl)pyridin-3-yl)ethynyl)benzyloxy)-2-fluorobenzonitrile (164);

1-(5-((4-((4-chloro-3-fluorophenoxy)methyl)phenyl)ethynyl)pyridin-2-yl)-2-(2,4-difluorophenyl)-1,1-difluoro-3-(1H-tetrazol-1-yl)propan-2-ol (165);

4-((3-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (166).

18. A composition comprising a compound of claim 1 and a pharmaceutically acceptable carrier.

19. The compound of claim 1, which is one of:
4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (8); or
4-((4-((6-(2-(2,4-difluorophenyl)-1,1-difluoro-2-hydroxy-3-(1H-tetrazol-1-yl) propyl)pyridin-3-yl) ethynyl) phenoxy)methyl)-2-fluorobenzonitrile (7).

20. A compound that is 4-((4-((6-(2-(2,4-difluorophenyl)-1,1-difluoro-2-hydroxy-3-(1H-tetrazol-1-yl)propyl)pyridin-3-yl)ethynyl)phenoxy)methyl)benzonitrile (8), or salt thereof.

21. A compound that is 4-((4-((6-(2-(2,4-difluorophenyl)-1,1-difluoro-2-hydroxy-3-(1H-tetrazol-1-yl) propyl)pyridin-3-yl) ethynyl) phenoxy)methyl)-2-fluorobenzonitrile (7), or salt thereof.

* * * * *